US008518062B2

(12) United States Patent
Cole et al.

(10) Patent No.: US 8,518,062 B2
(45) Date of Patent: Aug. 27, 2013

(54) DEVICES AND METHODS FOR FORMING MAGNETIC ANASTOMOSES BETWEEN VESSELS

(75) Inventors: David H. Cole, San Mateo, CA (US);
Darin C. Gittings, Sunnyvale, CA (US);
Stephen L. Olson, Sunnyvale, CA (US);
Dean F. Carson, Mountain View, CA (US); Michael L. Reo, Redwood City, CA (US); Keke Lepulu, Redwood City, CA (US); A. Adam Sharkawy, Union City, CA (US)

(73) Assignee: Medtronic, Inc., Minneapolis, MN (US)

( * ) Notice: Subject to any disclaimer, the term of this patent is extended or adjusted under 35 U.S.C. 154(b) by 4030 days.

(21) Appl. No.: 10/299,582

(22) Filed: Nov. 18, 2002

(65) Prior Publication Data
US 2006/0282106 A1 Dec. 14, 2006

Related U.S. Application Data

(63) Continuation-in-part of application No. 09/915,226, filed on Jul. 23, 2001, now Pat. No. 6,802,847, which is a continuation-in-part of application No. 09/638,805, filed on Aug. 12, 2000, now Pat. No. 6,719,768, which is a continuation-in-part of application No. 09/562,599, filed on Apr. 29, 2000, now Pat. No. 6,352,543.

(60) Provisional application No. 60/255,635, filed on Dec. 13, 2000.

(30) Foreign Application Priority Data

Sep. 16, 2002 (WO) ...................... PCT/US02/29485

(51) Int. Cl.
*A61B 17/08* (2006.01)
(52) U.S. Cl.
USPC ........................................... 606/153
(58) Field of Classification Search
USPC .............. 606/8, 151–153; 285/9.1, 312, 317, 285/320
See application file for complete search history.

(56) References Cited

U.S. PATENT DOCUMENTS 2,793,057 A * 5/1957 McGugin ........................ 285/9.1
2,912,263 A * 11/1959 Christy .......................... 285/371

(Continued)

FOREIGN PATENT DOCUMENTS
DE 29513195 12/1996
DE 29713335 7/1997

(Continued)

OTHER PUBLICATIONS

Certified translation of USSR Inventor's certificate—SU 1179978 A.*

(Continued)

*Primary Examiner* — Thomas McEvoy

(57) ABSTRACT

An anastomosis device has first and second components which each having first and second parts. The first and second components are magnetically attracted to one another. The device forms a throughhole when in use. The first parts of the first and second components are positioned radially outward from the second parts relative to the longitudinal axis with the first parts of the first and second components contacting one another and being magnetically attracted to one another. The second parts of the first and second components also being magnetically attracted to one another and are separated by the vessel walls.

12 Claims, 89 Drawing Sheets

(56) References Cited

U.S. PATENT DOCUMENTS

| | | |
|---|---|---|
| 2,953,970 A | 9/1960 | Maynard |
| 3,041,697 A | 7/1962 | Budreck |
| 3,254,650 A | 6/1966 | Collito |
| 3,254,651 A | 6/1966 | Collito |
| 3,372,443 A | 3/1968 | Daddona, Jr. |
| 3,519,187 A | 7/1970 | Kapitanov et al. |
| 3,727,658 A | 4/1973 | Eldridge, Jr. |
| 3,774,615 A | 11/1973 | Lim et al. |
| 3,952,334 A | 4/1976 | Bokros et al. |
| 3,952,726 A * | 4/1976 | Hennig et al. .................. 600/30 |
| 3,986,493 A | 10/1976 | Hendren, III |
| 4,118,806 A | 10/1978 | Porier et al. |
| 4,154,226 A | 5/1979 | Hennig et al. |
| 4,210,132 A | 7/1980 | Perlin |
| 4,217,664 A | 8/1980 | Faso |
| 4,258,705 A | 3/1981 | Sorensen et al. |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,397,311 A | 8/1983 | Kanshin et al. |
| 4,503,568 A | 3/1985 | Madras |
| 4,523,592 A | 6/1985 | Daniel |
| 4,534,761 A | 8/1985 | Raible |
| 4,553,542 A | 11/1985 | Schenck |
| 4,577,631 A | 3/1986 | Kreamer |
| 4,593,693 A | 6/1986 | Schenck |
| 4,607,637 A | 8/1986 | Berggren et al. |
| 4,624,255 A | 11/1986 | Schenck et al. |
| 4,624,257 A | 11/1986 | Berggren et al. |
| 4,636,205 A * | 1/1987 | Steer .............................. 604/338 |
| 4,657,019 A | 4/1987 | Walsh et al. |
| 4,665,906 A | 5/1987 | Jervis |
| 4,679,546 A | 7/1987 | van Waalwijk van Doorn et al. |
| 4,721,109 A | 1/1988 | Healey |
| 4,747,407 A | 5/1988 | Liu et al. |
| 4,784,646 A | 11/1988 | Feingold |
| 4,809,713 A | 3/1989 | Grayzel |
| 4,837,114 A | 6/1989 | Hamada et al. |
| 4,861,330 A | 8/1989 | Voss |
| 4,889,120 A | 12/1989 | Gordon |
| 4,899,744 A | 2/1990 | Fujitsuka et al. |
| 4,904,256 A | 2/1990 | Yamaguchi |
| 4,907,591 A | 3/1990 | Vasconcellos et al. |
| 4,917,087 A | 4/1990 | Walsh |
| 4,917,090 A | 4/1990 | Berggren et al. |
| 4,917,091 A | 4/1990 | Berggren et al. |
| 4,917,778 A | 4/1990 | Takada et al. |
| 4,935,080 A | 6/1990 | Hassell et al. |
| 5,013,411 A | 5/1991 | Minowa et al. |
| 5,015,238 A | 5/1991 | Solomon et al. |
| 5,089,006 A | 2/1992 | Stiles |
| 5,119,983 A | 6/1992 | Green et al. |
| 5,156,619 A | 10/1992 | Ehrenfeld |
| 5,178,634 A | 1/1993 | Martinez |
| 5,192,289 A | 3/1993 | Jessen |
| 5,211,683 A | 5/1993 | Maginot |
| 5,217,474 A | 6/1993 | Zacca et al. |
| 5,234,447 A | 8/1993 | Kaster et al. |
| 5,250,060 A | 10/1993 | Carbo et al. |
| 5,275,891 A | 1/1994 | Tagaya et al. |
| 5,304,220 A | 4/1994 | Maginot |
| 5,314,468 A | 5/1994 | Martinez |
| 5,316,595 A | 5/1994 | Hamada et al. |
| 5,330,486 A | 7/1994 | Wilk |
| 5,336,233 A | 8/1994 | Chen |
| 5,366,462 A | 11/1994 | Kaster et al. |
| 5,395,311 A | 3/1995 | Andrews |
| 5,411,508 A | 5/1995 | Bessler et al. |
| 5,425,763 A | 6/1995 | Stemmann |
| 5,441,507 A | 8/1995 | Wilk |
| 5,443,497 A | 8/1995 | Venbrux |
| 5,456,712 A | 10/1995 | Maginot |
| 5,456,714 A | 10/1995 | Owen |
| 5,464,449 A | 11/1995 | Ryan et al. |
| 5,478,354 A | 12/1995 | Tovey et al. |
| 5,507,629 A | 4/1996 | Jarvik |
| 5,522,834 A | 6/1996 | Fonger et al. |
| 5,556,405 A | 9/1996 | Lary |
| 5,571,167 A | 11/1996 | Maginot |
| 5,595,562 A | 1/1997 | Grier |
| 5,611,689 A | 3/1997 | Stemmann |
| 5,626,601 A | 5/1997 | Gershony et al. |
| 5,643,340 A | 7/1997 | Nunokawa |
| 5,669,918 A | 9/1997 | Balazs et al. |
| 5,676,670 A | 10/1997 | Kim |
| 5,681,260 A | 10/1997 | Ueda et al. |
| 5,690,656 A | 11/1997 | Cope et al. |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,725,544 A | 3/1998 | Rygaard |
| 5,725,553 A | 3/1998 | Moenning |
| 5,758,663 A | 6/1998 | Wilk et al. |
| 5,797,920 A | 8/1998 | Kim |
| 5,817,113 A | 10/1998 | Gifford, III et al. |
| 5,824,061 A * | 10/1998 | Quijano et al. ............... 623/1.13 |
| 5,830,224 A | 11/1998 | Cohn et al. |
| 5,868,763 A | 2/1999 | Spence et al. |
| 5,868,765 A * | 2/1999 | Wells-Roth .................. 606/155 |
| 5,895,404 A | 4/1999 | Ruiz |
| 5,904,147 A | 5/1999 | Conlan et al. |
| 5,906,579 A | 5/1999 | Vander Salm et al. |
| 5,916,226 A | 6/1999 | Tozzi |
| 5,968,089 A | 10/1999 | Krajicek |
| 5,997,467 A | 12/1999 | Connolly |
| 6,068,637 A | 5/2000 | Popov et al. |
| 6,074,416 A | 6/2000 | Berg et al. |
| 6,099,542 A | 8/2000 | Cohn et al. |
| 6,113,612 A | 9/2000 | Swanson et al. |
| 6,152,937 A | 11/2000 | Peterson et al. |
| 6,173,715 B1 | 1/2001 | Sinanan et al. |
| 6,179,849 B1 | 1/2001 | Yencho et al. |
| 6,187,020 B1 | 2/2001 | Zegdi et al. |
| 6,190,353 B1 | 2/2001 | Makower et al. |
| 6,206,913 B1 | 3/2001 | Yencho et al. |
| 6,241,743 B1 | 6/2001 | Levin et al. |
| 6,293,955 B1 | 9/2001 | Houser et al. |
| 6,296,604 B1 | 10/2001 | Garibaldi et al. |
| 6,352,543 B1 | 3/2002 | Cole |
| 6,419,681 B1 | 7/2002 | Vargas et al. |
| 6,428,550 B1 | 8/2002 | Vargas et al. |
| 6,491,705 B2 | 12/2002 | Gifford et al. |
| 6,558,400 B2 | 5/2003 | Deem et al. |
| 6,565,581 B1 | 5/2003 | Spence et al. |
| 6,575,168 B2 | 6/2003 | LaFontaine et al. |
| 6,579,311 B1 | 6/2003 | Makower |
| 6,616,675 B1 | 9/2003 | Evard et al. |
| 6,632,229 B1 | 10/2003 | Yamanouchi |
| 6,652,540 B1 | 11/2003 | Cole et al. |
| 6,802,847 B1 | 10/2004 | Carson et al. |
| 6,932,827 B2 | 8/2005 | Cole |
| 7,214,234 B2 | 5/2007 | Rapacki et al. |
| 7,232,449 B2 | 6/2007 | Sharkawy et al. |
| 7,241,300 B2 | 7/2007 | Sharkawy et al. |
| 2002/0143347 A1 | 10/2002 | Cole |
| 2002/0193782 A1 | 12/2002 | Ellis et al. |
| 2003/0014061 A1 | 1/2003 | Houser et al. |
| 2003/0014063 A1 | 1/2003 | Houser et al. |
| 2003/0065345 A1 | 4/2003 | Weadock |
| 2003/0167064 A1 | 9/2003 | Whayne |
| 2004/0215214 A1 | 10/2004 | Crews |
| 2005/0021059 A1 | 1/2005 | Cole |
| 2005/0080439 A1 | 4/2005 | Carson |
| 2005/0192603 A1 | 9/2005 | Cole |
| 2006/0161244 A1 | 7/2006 | Seguin |
| 2006/0282106 A1 | 12/2006 | Cole |
| 2007/0010834 A1 | 1/2007 | Sharkawy |
| 2007/0250084 A1 | 10/2007 | Sharkawy |

FOREIGN PATENT DOCUMENTS

| | | |
|---|---|---|
| FR | 2760627 | 9/1998 |
| RU | 1769863 | 10/1992 |
| RU | 2123300 | 12/1998 |
| SU | 736966 | 5/1980 |
| SU | 1025420 | 6/1983 |
| SU | 1179978 | 9/1985 |
| SU | 1438738 | 11/1988 |
| SU | 2018266 | 3/1989 |
| SU | 1537228 | 1/1990 |
| SU | 1595534 | 9/1990 |
| SU | 1629040 | 2/1991 |
| SU | 1635966 | 3/1991 |
| SU | 1277452 | 6/1991 |
| SU | 1708313 | 1/1992 |
| SU | 1361753 | 4/1992 |
| SU | 1725851 | 4/1992 |
| SU | 1766383 | 10/1992 |
| WO | WO 81/00668 | 3/1981 |
| WO | WO 97/12555 | 4/1997 |
| WO | WO 97/13463 | 4/1997 |
| WO | WO 97/27897 | 8/1997 |
| WO | WO 97/31578 | 9/1997 |
| WO | WO 98/40036 | 9/1998 |
| WO | WO 99/40851 | 8/1999 |
| WO | WO 99/62415 | 12/1999 |
| WO | WO 99/63894 | 12/1999 |
| WO | WO 00/09040 | 2/2000 |
| WO | WO 00/24339 | 5/2000 |
| WO | WO 00/27312 | 5/2000 |
| WO | WO 00/32241 | 6/2000 |
| WO | WO 00/33770 | 6/2000 |
| WO | WO 00/69364 | 11/2000 |
| WO | WO 00/74579 | 12/2000 |
| WO | WO 01/39672 | 6/2001 |
| WO | WO 01/82803 | 11/2001 |
| WO | WO 02/09594 | 2/2002 |
| WO | WO 02/19946 | 3/2002 |
| WO | WO 02/39878 | 5/2002 |
| WO | WO 02/094108 | 11/2002 |

OTHER PUBLICATIONS

Aharinejad S.H., et al., *Microvascular Corrosion Casting in Scanning Electron Microscopy. Technique and Applications,* Springer—Verlag/Wien, New York, pp. 12-23, 25, 28-39, 63-73, 75-81.

Ahn CY, Shaw WW, Berns S, et al., "Clinical Experience With the 3M Microvascular Coupling Anastomotic Device in 100 Free-Tissue Transfers," *Plastic and Reconstructive Surgery,* Jun. 1994;93(7):1481-84.

Angelini E, et al., "Corrosion under Static and Dynamic Conditions of Alloys Used for Magnetic Retention in Dentistry," *J Prosthet Dent,* 1991; 65:848-53.

ASM Metals Reference Book, Third Edition, Copyright 1993, p. 355.

Attai, et al., *Aortic Valve Replacement in the Presence of Hufnagel Valve in the Descending Aorta,* J. Thoracic Cardiovas. Surg., 1974, 68(1):112-115.

Attanasio SA, et al., "Corrosion of Rapidly Solidified Neodymion-Iron-Boron (Nd-Fe-B) Permanent Magnets and Protection via Sacrificial Zinc Coatings," *Material Science and Engineering,* 1995; A198:25-34.

Bala H, et al., "Effect of Impurities on the Corrosion Behavior of Neomydium," *Journal of Applied Electrochemistry,* 1993; 23(10):1017-1024.

Beppu, et al., *A Computerized Control System for Cardiopulmonary Bypass,* J. Thoracic Cardiovas. Surg., 1995, 109(3):428-438.

Bjork VO, Iert T, Landou C., "Angiographic changes in Internal Mammary Artery and Saphenous Vein Grafts, Two Weeks, One Year and Five Years After Coronary Bypass Surgery," *Scand J Thor Cardiovasc Surg,* 1981; 15:23-30.

Bondemark, et al., "Long-term effects of orthodontic magnets on human buccal mucosa—a clinical, histological and immunohistochemical study," *Eur J Orthod,* 20(3): Jun. 1998, pp. 211-218.

Bondemark, et al., "Orthodontic Rare Earth Magnets—in Vitro Assessment of Cytotoxicity," *British Journal of Orthodontia,* vol. 21, No. 4, Nov. 1994, pp. 335-341.

Bornemisza G, Furka I., "Nonsuture Vascular Anastomosis," *Acta Chirurgica Academiae Scientiarium Hungaricae, Tomus,* 1971; 12(1):49-56.

Bourassa MG, Fisher LD, Campeau L, et al., "Long-Term Fate if Bypass Grafts: The Coronary Artery Surgery Study (CASS) and Montreal Heart Institute Experiences," *Circ,* Dec. 1985; 72(suppl V):71-77.

Brochure for "Neomax, Rare Earth Magnets," pp. 31-33, undated.

Buffolo E, de Andrade JCS, Branco JNR, et al., "Coronary Artery Bypass Grafting Without Cardiopulmonary Bypass," *Ann Thorac Surg,* 1996; 61:63-6.

Casanova R, Herrera GA, Vasconez EB, et al, "Microarterial Sutureless Sleeve Anastomosis Using a Polymeric Adhesive: An Experimental Study," *J Reconstr Microsurg,* Apr. 1987; 3(3):201-7.

Cha, et al., *Silent Coronary Artery-Left Ventricular Fistula: A Disorder of the Thebesian System?,* Angiology, 1978; 29(2):169-173.

Cheng CW, Cheng FT, Man HC, "Improvement of protective coatings on Nd-Fe-B magnet by pulse nickel plating," *Journal of Applied Physics,* Jun. 1, 1998; 83(11):6417-6419.

Cheng CW, et al., "Magnetic and Corrosion Characteristics of Nd-Fe-B Magnet with Various Surface Coatings," *IEEE Transactions on Magnetics,* 1997; 33(5):3910-3912 and CD-10.

Cope, "Creation of Compression Gastroenterostomy by Means of the Oral, Percutaneous, or Surgical Introduction of Magnets: Feasibility Study in Swine," *Journal of Vascular and Interventional Radiology,* vol. 6, No. 4, Jul.-Aug. 1995, pp. 539-545.

Cope, "Evaluation of Compression of Cholecystogastric and Cholecystojejunal Anastomoses in Swine after Peroral and Surgical Introduction of Magnets," *Journal of Vascular and Interventional Radiology,* vol. 6, No. 4, Jul.-Aug. 1995, pp. 546-552.

Cope, "Stent Placement of Gastroenteric Anastomoses Formed by Magnetic Compression," *Journal of Visceral Intervention,* vol. 10, No. 10, Nov.-Dec. 1999, pp. 1379-1386.

Dake, et al., *Transluminal Placement of Endovascular Stent-Grafts for the Treatment of Descending Thoracic Aortic Aneurysms,* New England J. Med., 1994, 331(2):1729-1.

David JL, Limet R, "Antiplatelet Activity of Clopidogrel in Coronary Artery Bypass Graft Surgery Patients," *Thromb Haemost,* Nov. 1999; 82(5):417-21.

DeLacure MD, Kuriakose MA, Spies AL, "Clinical Experience in End-to-Side Venous Anastomosis With a Microvascular Anastomotic Coupling Device in Head and Neck Reconstruction," *Arch Otolaryngol Head Neck Surg,* Aug. 1999; 125:869-72.

Detweiler MB, Detweiler JG, Fenton J, et al., "Sutureless and Reduced Suture Anastomosis of Hollow Vessels with Fibrin Glue: A Review," *J Invest Surg,* Sep. 1999; 12(5):245-62.

Dormer KJ, Gan RZ, Santo R, "Middle Ear Titanium Transducer," *Society for Biomaterials,* Sixth World Biomaterials Congress Transactions; 2000: 1272.

Eckstein FS, Bonilla LF, Meyer B, et al., "Sutureless mechanical anastomosis of a saphenous vein graft to a coronary artery with a new connector device," *Lancet,* vol. 357, Mar. 24, 2001, pp. 931-932.

Endo K, et al., "Effects of Titanium Nitride Coatings on Surface and Corrosion Characteristics on Ni-Ti Alloy," *Dental Materials Journal,* 1994; 13(2):228-39.

Esformes, et al., "Biological Effects of Magnetic Fields Generated with CoSm Magnets," *Bull Hosp Jt Dis Orthop Inst,* 1981; 41 pp. 81-87.

Evans RD, et al., "Effect of Corrosion Products (neodymium Iron Boron) on Oral Fibroblast Proliferation," *J of Applied Biomater,* 1995; 6(3):199-202.

Frey RR, Bruschke AVG, Vermeulen Fee, "Serial Angiographic Evaluation 1 Year and 9 Years After Aorata-Coronary Bypass," *J Thorac Cardiovasc Surg,* 1984; 87(2):167-74.

Fuestel, et al., "Kontinente Kolostomie durch Magnetverschluss," *Dtsch. Med. Wschr.* 100 (1975), pp. 1063-1064 (includes English Abstract).

Fukumura, et al., "Development of a Magnetically Operated Artificial Urethral Sphincter," *ASAIO Journal,* 1993, pp. M283-M287.

Goldman S, Copeland J, Moritz T, et al., "Improvement in Early Saphenous Vein Graft Patency After Coronary Artery Bypass Surgery With Antiplatelet Therapy: Results of a Veterans Administration Cooperative Study," *Circulation,* Jun. 1988; 77(6):1324-32.

Goldman S, et al., "Starting aspirin therapy after operation—effects on early graft patency," *Circulation*, 1991; 84:520-526.

Goldman S, Zadina K, Krasnicka B, et al., "Predictors of Graft Patency 3 Years After Coronary Artery Bypass Graft Surgery," *J Am Coll Cardiol*, Jun. 1997; 29(7):1563-8.

Goy JJ, Kaufman U, Goy-Eggenberger D, et al., "A Prospective Randomized Trial Comparing Stenting to Internal Mammary Artery Grafting for Proximal, Isolated de novo Left Anterior Coronary Artery Stenosis: The SIMA Trial, Stenting vs. Internal Mammary Artery," *Mayo Clin Proc*, Nov. 2000; 75(11):1116-23.

Grieb B, "New Corrosion Resistant Materials Based on Neodym-Iron-Boron," *Intermag Conference*, 1997; CD-08.

Group Arnold, The Magnetic Products Group of SPS Technologies, "Neodymium Magnets," Website: www.grouparnold.com, 4 pages (2008).

Gundry SR, Black K, Izuntani H, "Sutureless Coronary Artery Bypass with Biologic Glued Anastomosis: Preliminary in Vivo and in Vitro Results," *J Thorac Cardiovasc Surg*, Sep. 2000; 120(3):473-77.

Guyton RA, McClenathan JH, Michaelis LL, "A Mechanical Device for Sutureless Aorta-Saphenous Vein Anastomosis," *Ann Thorac Surg*, Oct. 1979; 28(4):342-5.

Heijmen RH, Borst C, van Dalen R, et al., "Temporary Luminal Arteriotomy Seal: II. Coronary Artery Bypass Grafting on the Beating Heart," *Ann Thorac Surg*, 1998; 66:471-6.

Heijmen RH, Hinchliffe P, Borst C, et al., "A Novel One-Shot Anastomotic Stapler Prototype for the Coronary Bypass Grafting on the Beating Heart: Feasibility on the Pig," *J Thorac and Cardiovasc Surg*, Jan. 1999; 117(1):117-25.

Ilia, R., *Coronary Angiography in Dextrocardia, Catheterization Cardio. Diag.*, 1991, 24 p. 150.

Jamieson, S.W., *Aortocoronary Saphenous Vein Bypass Grafting*, Operative Surgery, 4th Edition, pp. 454-470.

Jansen, et al., "Clinical Applications of Magnetic Rings in Colorectal Anastomosis," *Surgery, Gynecology & Obstetrics*, vol. 153, Oct. 1981, pp. 537-545.

Kajiya, et al., *Mechanical Control of Coronary Arter Inflow and Vein Outflow*, Jap. Cir. J., 1989, 53:431-438.

Kanshin, et al., "A Goal-Oriented Local Approach to the Prevention of Postoperative Purulent Complications," 1991, pp. 24-27 (English abstract is provided).

Kanshin, et al., "Sutureless anastomoses in gastrointestinal surgery with and without steady magnetic field," *Arkh Patol*, 1978; 40(8):56-61 (with English Abstract).

Kitsugi A, et al., "The Corrosion Behavior of Nd2Fe14B and SmCo5 Magnets," *Dental Materials Journal*, 1992; 11(2):119-29.

Konerding MA, et al., "Scanning Electron Microscopy of Corrosion Casting in Medicine," *Scanning Microscopy*, 1991; 5(3):851-865.

Ku NC, et al., "Enhanced corrosion Resistance of NdFeB Type Permanent Magnet Coated by a Dual Layer of Either Ti/Al or Ni/Al Intermetallics," *IEEE Transactions on Magnetics*, 1997; 33(5):3913-5.

Ku NC, Qin C-D, Yu CC and Ng DHL, "Corrosion Reisstance of NdFeB magnets coated by Al," *IEEE Transactions on Magnetics*, Sep. 1996; 32(5):4407-4409.

Lamestschwandter A, et al., "Scanning Electron Microscopy of Vascular Corrosion Casts—Technique and Applications: Updated Review," *Scanning Microscopy*, 1990; 4(4):889-941.

Louagie, et al., *Operative Risk Assessment in Coronary Artery Bypass Surgery*, 1990-1993: *Evaluation of Perioperative Variables*, Thorac. Cardiovasc. Surg., 1995, 43:134-141.

Lytle BW, Loop FD, Cosgrove DM, et al., "Long-Term (5 to 12 Years) Serial Studies of Internal Mammary Artery and Saphenous Vein Coronary Bypass Grafts." *J Thorac and Cardiovasc Surg*, Feb. 1985; 89(2):248-58.

Magnet Sales and Manufacturing Company, Inc., "Neodymium Iron Boron," Website: www.magnetsales.com, 4 pages (2008).

Mattox DE, Wozniak JJ, "Sutureless Vascular Anastomosis with Biocompatible Heat-Shrink Tubing," *Arch Otolaryngol Head Neck Surg*, Nov. 1991; 117:1260-4.

Minowa T, Yoshikawa M, Honshima M, "Improvement of the corrosion resistance on Nd-Fe-B magnet with nickel plating," *IEEE Transactions on Magnetics*, Sep. 1989; 25(5):3776-3778.

Myshkin, et al., "Use of Permanent Magnets in Sutureless Anastomoses," 1987, pp. 47-52 (English translation is provided).

Nataf P, Hinchliffe P, Manzo S, et al., "Facilitated Vascular Anastomoses: The One-Shot Device," *Ann Thorac Surg*, 1998; 66:1041-4.

Nataf P, Kirsch W, Hill AC, et al., "Nonpentrating Clips for Coronary Anastomosis," *Ann Thorac Surg*, 1997; 63:S135-7.

Noar JH, Whab A, Evans RD, Wojcik AG, "The durability of parylene coatings on neodymiumiron-iron-boron magnets," *Eur J Orthod,*, Dec. 1999; 21(6):685-93.

Obora, et al., "Nonsuture Microvascular Anastomosis Using Magnet Rings: Preliminary Report," *Surg. Neurol.*, vol. 9, Feb. 1978, pp. 117-120.

Obora, et al., "Nonsuture Microvascular Anastomosis using Magnetic Rings," *Neurol Med Chir* , May 20, 1980 (5) pp. 497-505. (English translation is provided.).

Paz MA, Lupon J, Bosch X, et al., "Predictors of Early Saphenous Vein Aortocoronary Bypass Graft Occlusion. The GESIC Study Group," *Ann Thorac Surg*, Nov. 1993; 56(5):1101-6.

Pirusyan, et al., "Some Regularities of Tissue Squeezing and Regeneration Under Formation of "unstitch" Anastomoses of the Alimentary Canal's Hollow Organs," 1979, pp. 13-17 (includes English abstract).

Pourbaix M, "Electrochemical Corrosion of Metallic Biomaterials," *Biomaterials*, 1984; 5:122-34.

Puskas JD, Wright CE, Ronson RS, et al., "Clinical Outcomes and Angiographic Patency in 125 Consecutive Off-Pump Coronary Bypass Patients," *The Heart Surgery Forum* #999-95310, May 1999; 2(3):216-21.

Reddy, et al., *Multiple Coronary Arteriosystemic Fistulas*, Amer. J. Cardiol., 1974, 33:304-306.

Riess, Friedrich-Christian, et al., "Clinical Experience with the CorLink Device for Proximal Anastomosis of the Saphenous Vein to the Aorata: A Clinical Prospective, and Randomized Study," *The Heart Surgery Forum*, #2002-71002, 5(4), 2002:345-353.

Rueland D, Schomacher PR, Mueller KM, et al., "Experimental Studies With a New Sutureless Anastomic Flange," *Trans AM Soc Artif Intern Organs*, 1979; 25:339-43.

Ryhanen J, et al., "Biocompatibility of Nickel-Titanium Shape Memory Metal and Its Corrosion Behavior in Human Cell Cultures," *JBMR*, 33 1997; 451-7.

Sanz G, Pajaron A, Algria E, et al., "Prevention of Early Aortocoronary Bypass Occlusion by Low-Dose Aspirin and Dipyridamole," *Circulation*, Sep. 1990; 82(3):765-73.

Sastri, et al., *Coronary Artery Left Ventricular Fistula*, Chest, 1975, 68(5):735-736.

Scheltes JS, Heikens M, Pistecky PV, et al., "Assessment of Patented Coronary End-to-Side Anastomotic Devices Using Micromechanical Bonding," *Ann Thorac Surg*, Jul. 2000; 70(1):218-21.

Segal, et al., *Alterations of Phasic Coronary Artery Flow Velocity in Humans During Percutaneous Coronary Angioplasty*, JACC, 1992, 20(2):276-286.

Seides SF, Borer JS, Kent KM, et al., "Long-Term Anatomic Fate of Coronary-Artery Bypass Grafts and Functional Status of Patients Five Years after Operation," *N Engl J Med*, 1978; 298(22):1213-17.

Senftle F, et al., "Electrolytic Corrosion of Gold and the Formation of Au2(SO4)3 in Concentrated Sulfuric Acid," *Journal of the Electrochemical Society*, 1985; 129-30.

Sethi GK, Copeland JG, Goldman S, et al., "Implications of Preoperative Administration of Aspirin in Patients Undergoing Coronary Artery Bypass Grafting. Department of Veterans Affairs Cooperative Study on Antiplatelet Therapy," *J Am Coll Cardiol*, Jan. 1990; 15(1):15-20.

Souza DSR, Bomfim V, Skoglund H, et al., "High Early Patency Saphenous Vein Graft for Coronary Artery Bypass Havested with Surrounding Tissue," *Ann Thorac Surg*, 2001; 71:797-800.

Stepanov, et al., "The treatment of intestinal fistulae in children by applying a by-pass anastomosis using magnetic devices," *Khirugiia (Mosk)*, Nov.-Dec. 1992, pp. 11-12 (English abstract is provided).

Stevens, et al., *Port-Access Coronary Artery Bypass Grafting: A Proposed Surgical Method*, J. Thorac. J. Cardiovasc. Surg., 1996, 111(3):567-573.

Sugiura T., "Magnetic Compression Anastomosis of the Vascular System in Experimental Dog Models," 211, p. S141, 1 page English abstract and 12 page slide show.

Supplementary Partial European Search Report from European Patent Application No. 01959718.6 dated Jan. 7, 2005.

Takenaka H, Esato K, Ohara M, et al., "Sutureless Anastomosis of Blood Vessels Using Cyanoacrylate Adhesives," *Surg Today*, 1992; 22(1):46-54.

Thierry B, et al., "Effect of Surface Treatment and Sterilization Processes on the Corrosion Behavior of NiTi Shape Memory Alloy," *JBMR*, 51(4), 2000; 685-93.

von Segesser, L.K., *Arterial Grafting for Myocardial Revascularization*, 1990, pp. 3-140.

Weissberg D, Schwartz P, Goetz RH, Nonsuture End-to-Side Anastomoses of Small Blood Vessels, *Surgery, Gynecology & Obstetrics*, Aug. 1966; 341-46.

Werker P, Kon M, "Review of Facilitated approaches to Vascular Anastomosis Surgery," *Ann Thorac Surg*, 1997; 63:S122-7.

Whiffen JD, Boake WC, Gott VL, "Vessel Patency Following Nonsuture Anastomosis with Intravascular Rings," *Arch Surg*, Dec. 1965; 91(6):939-41.

Willman CJ, et al., "Corrosion Characteristics of RE-Fe-B Permanent Magnets," *J Appl Phys*, 1987; 61(8):3766-3768.

Yamagata S, Carter LP, Handa H, et al., "Experimental Studies in Nonsuture End-to-Side Microvascular Anastomosis," *Neurol Med Chiro* (Tokyo), 1981; 21:701-08.

Yanase, "An Experimental Study on Traumatic Changes in Microvessels Produced by Pressure Clamping," *Aust N.Z. J. Surg*, vol. 50-No. 4, Aug. 1980, pp. 423-428.

Zegdi R, Martinod E, Fabre O, et al., "Video-Assisted Replacement of Bypass Grafting of the Descending Thoracic Aorta With a New Sutureless Vascular Prostahesis: An Experimental Study," *J Vasc Surg*, 1999; 30:320-4.

\* cited by examiner

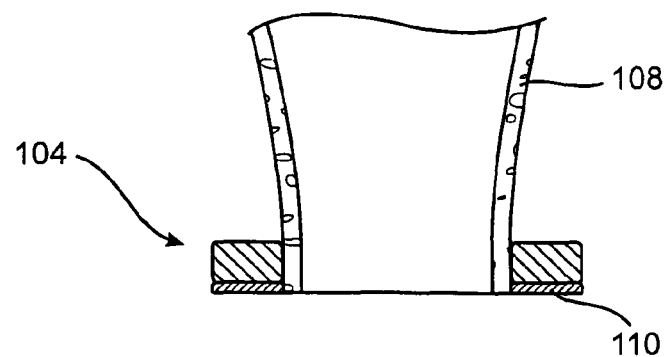
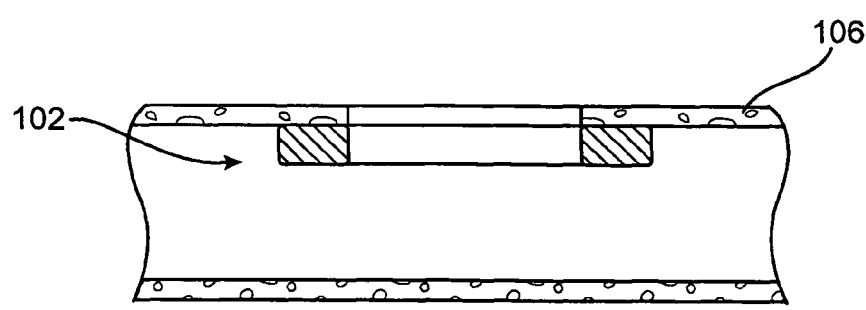
FIG. 10C
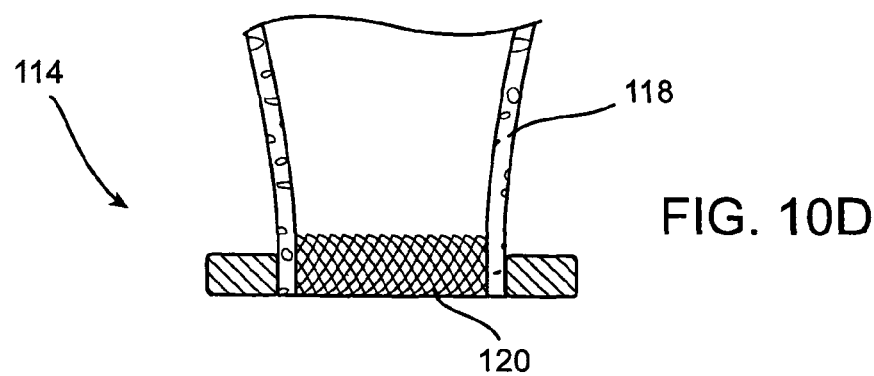
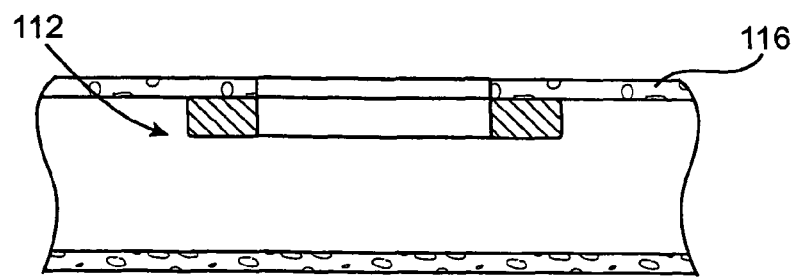
FIG. 10D

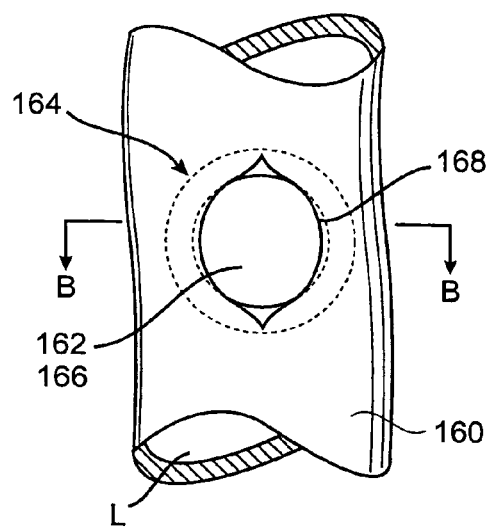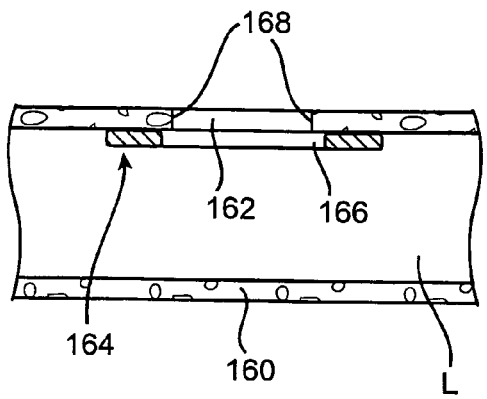
FIG. 17A    FIG. 17B
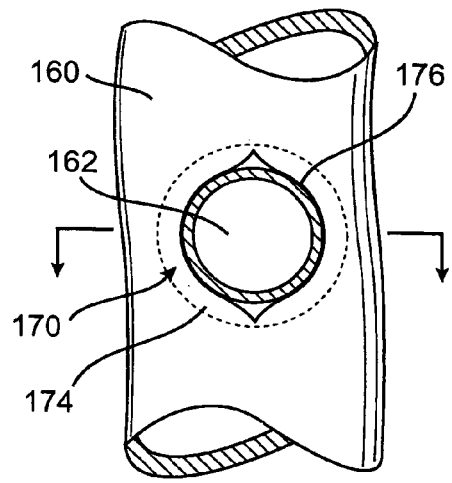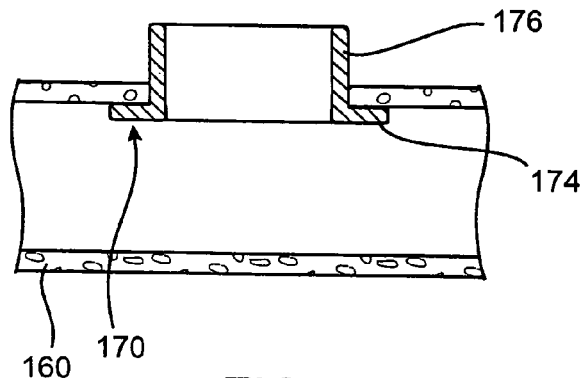
FIG. 18A    FIG. 18B

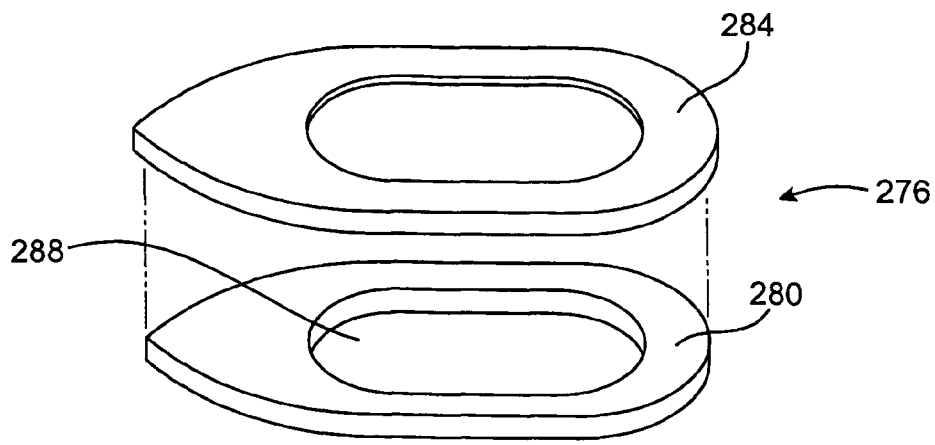
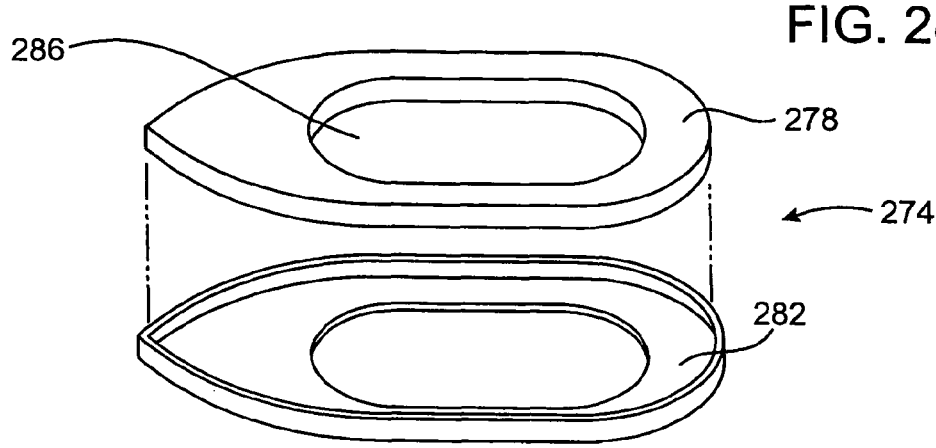
FIG. 28
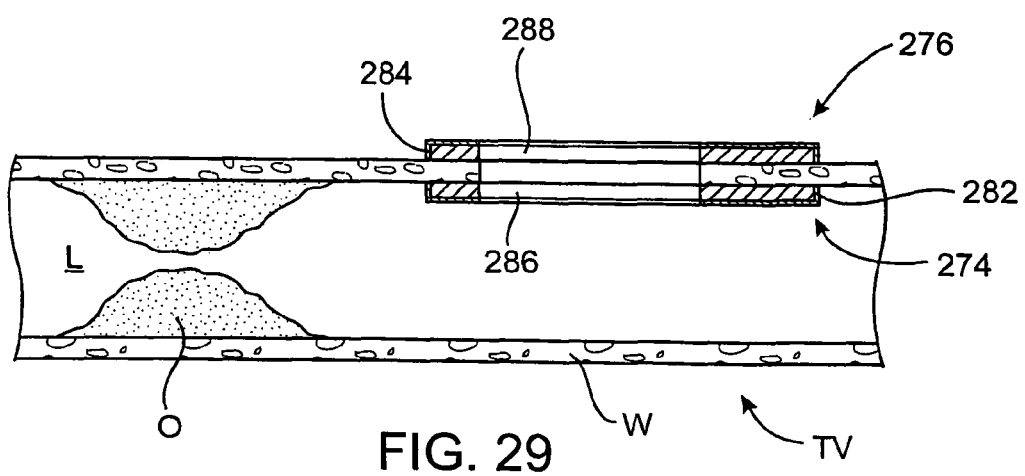
FIG. 29

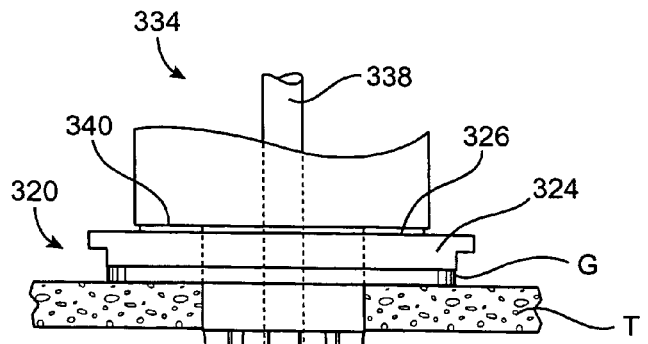
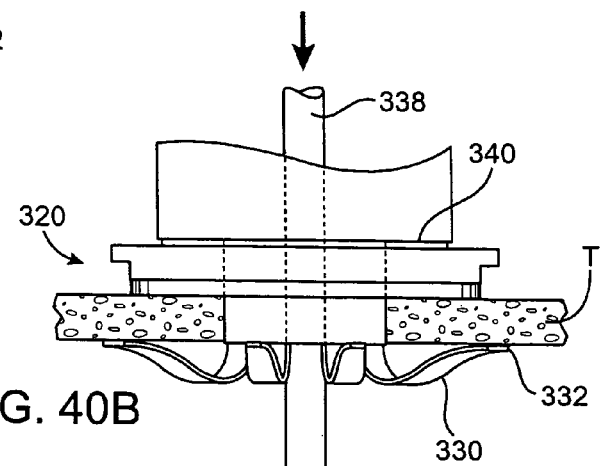
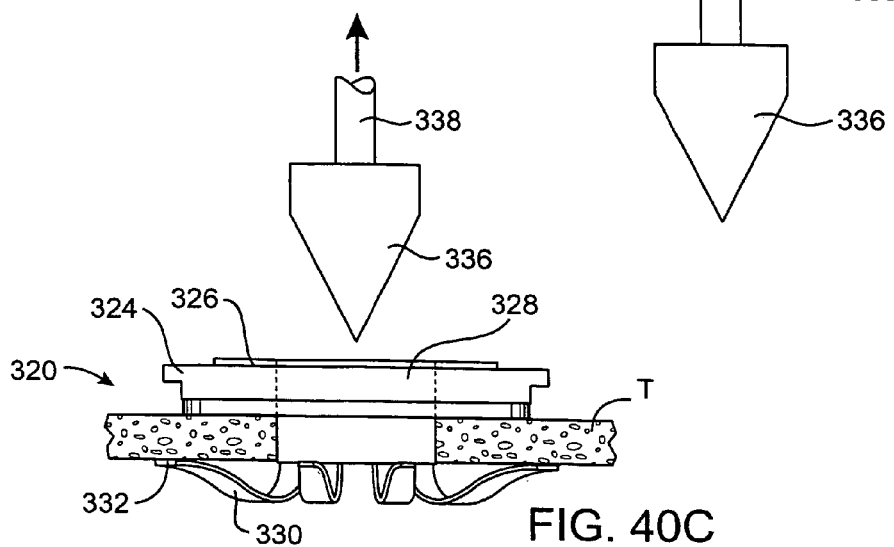
FIG. 40A
FIG. 40B
FIG. 40C

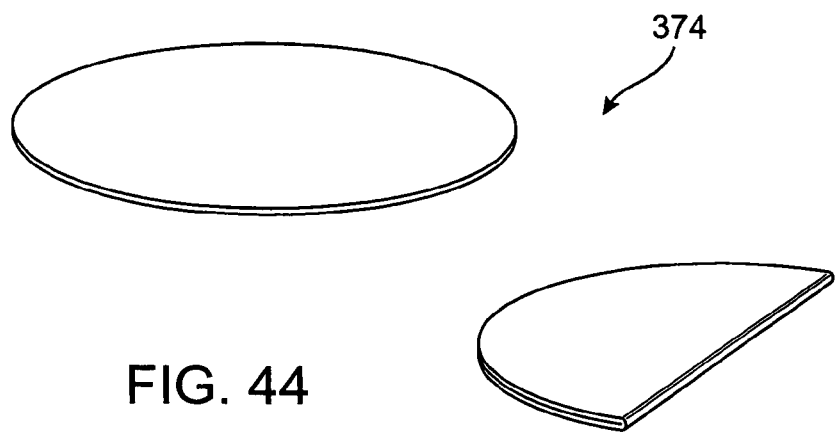
FIG. 44
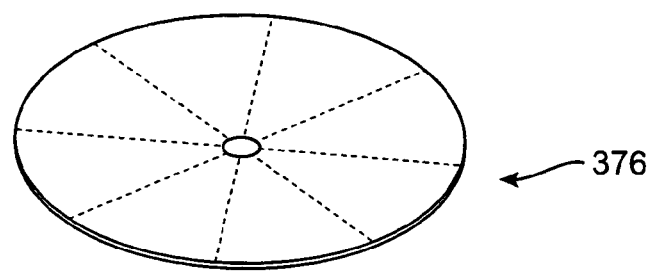
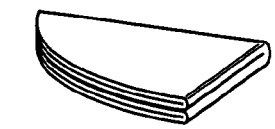
FIG. 45A
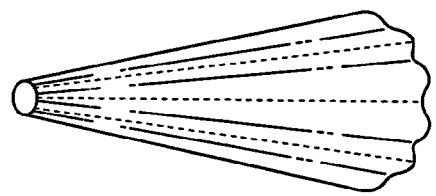
FIG. 45B
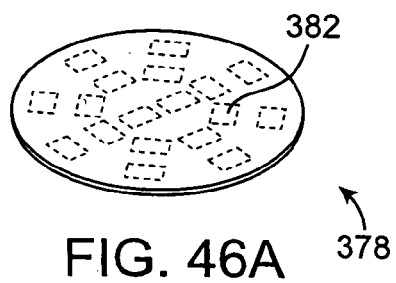
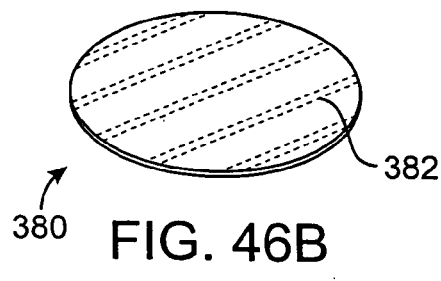
FIG. 46A      FIG. 46B

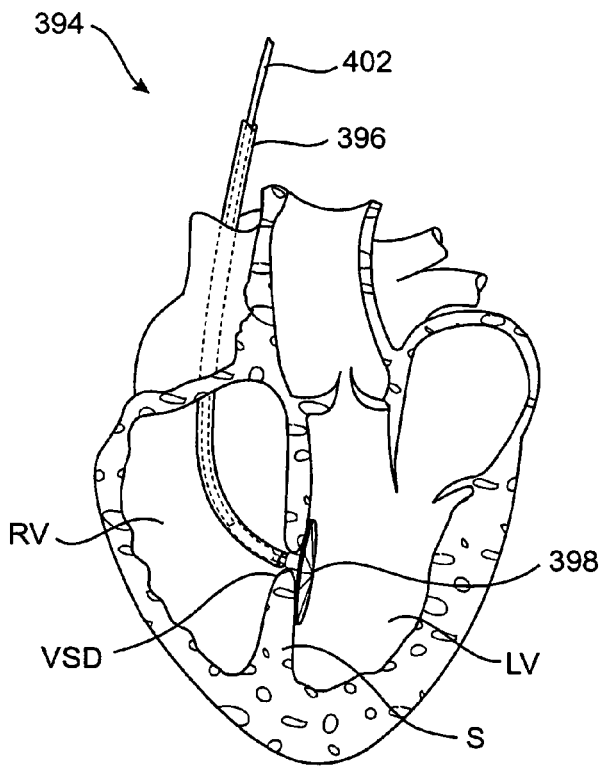
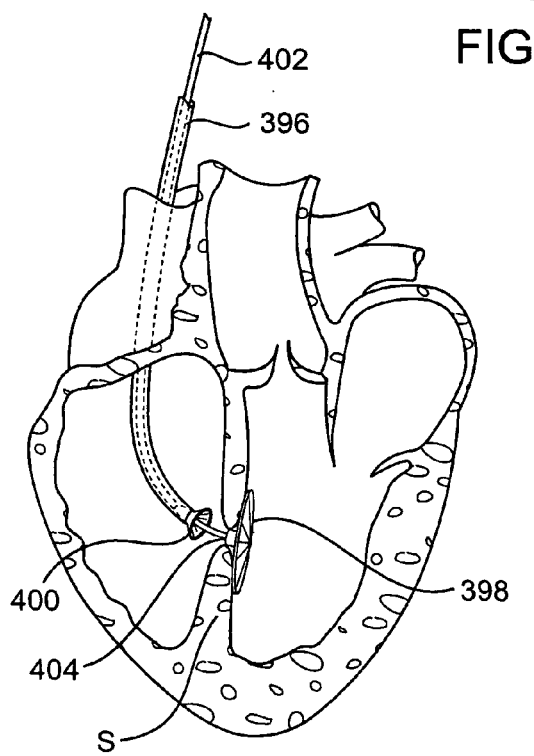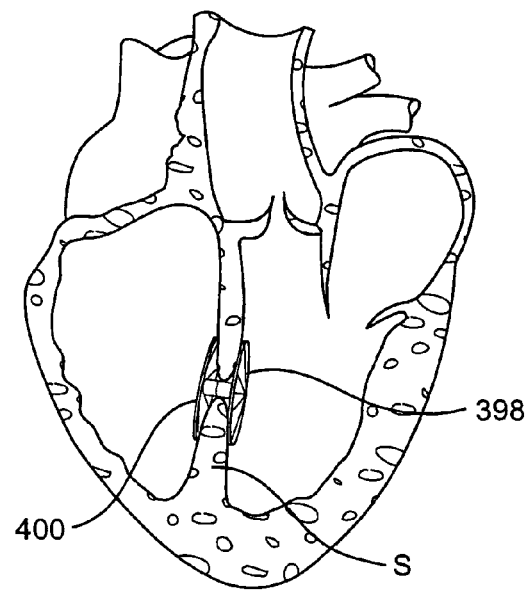
FIG. 48A
FIG. 48B  FIG. 48C

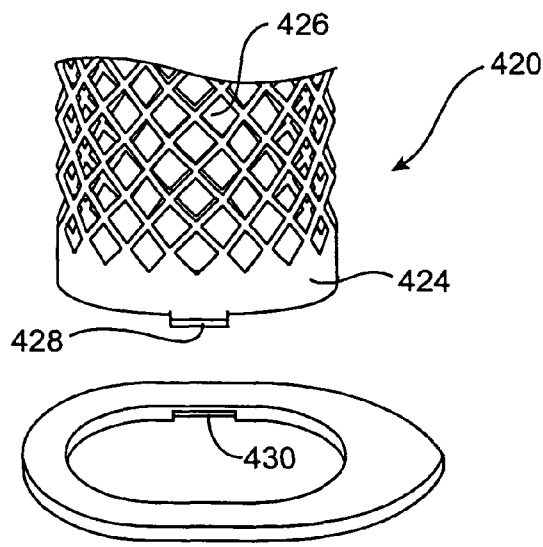
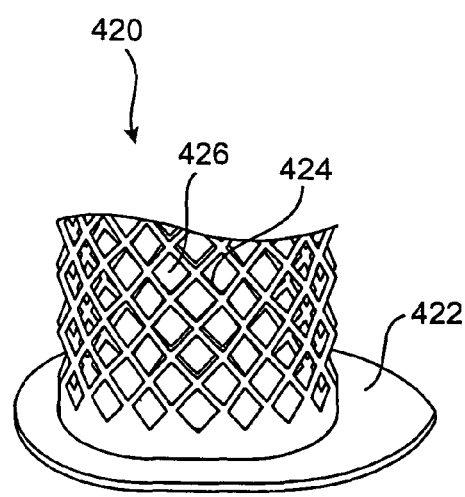
FIG. 49A
FIG. 49B
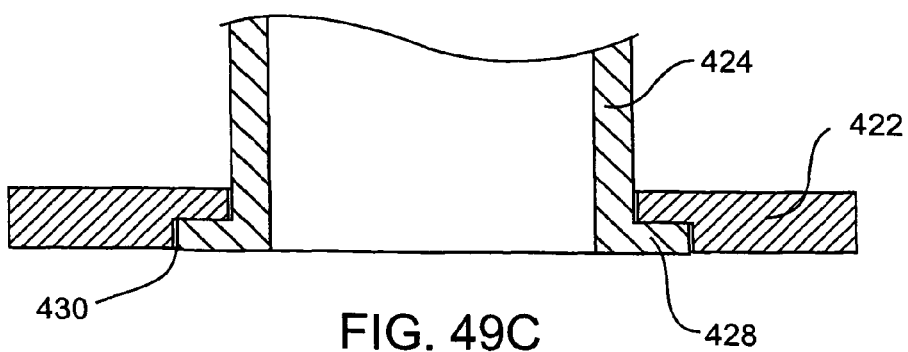
FIG. 49C

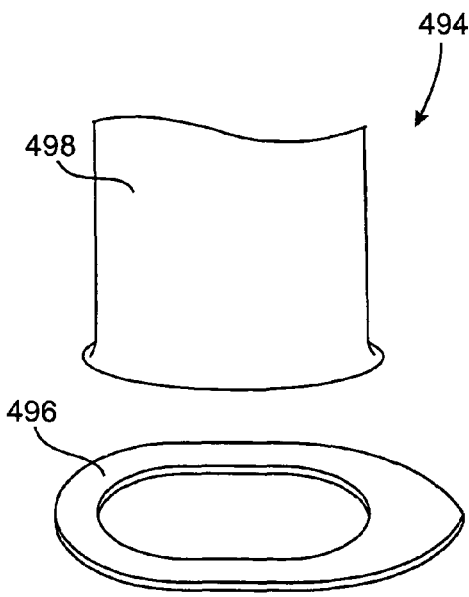
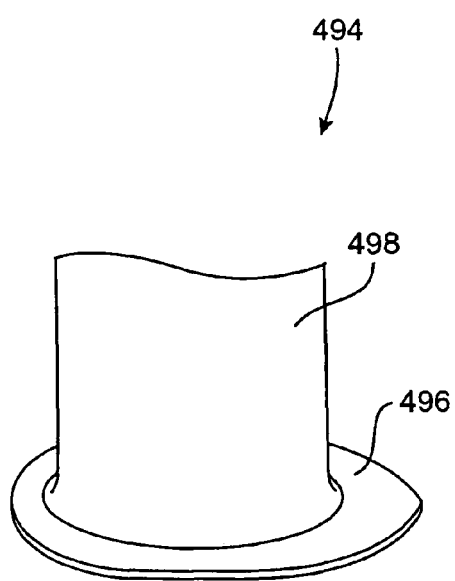
FIG. 55A FIG. 55B
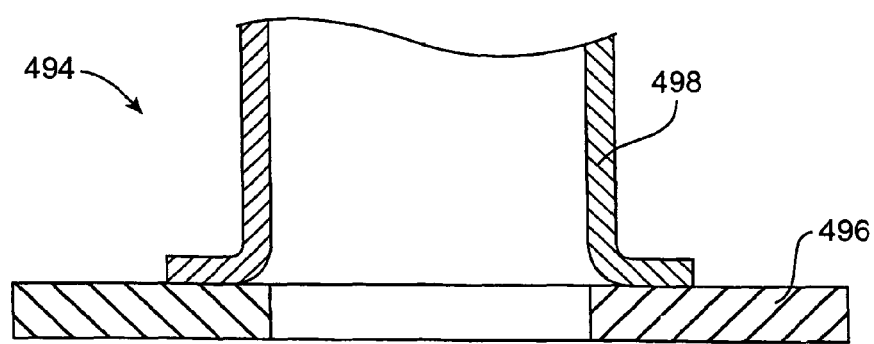
FIG. 55C

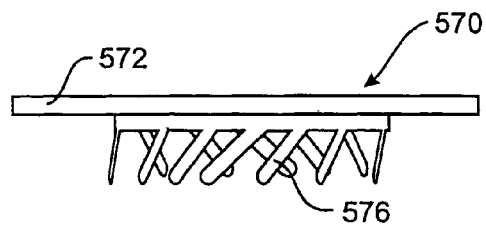
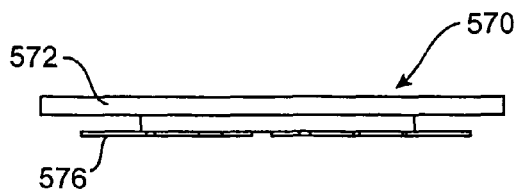
FIG. 63A
FIG. 63B
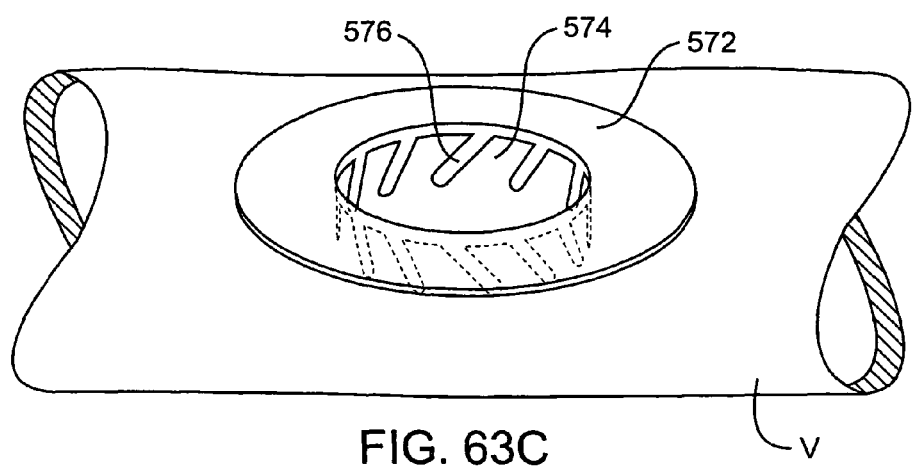
FIG. 63C
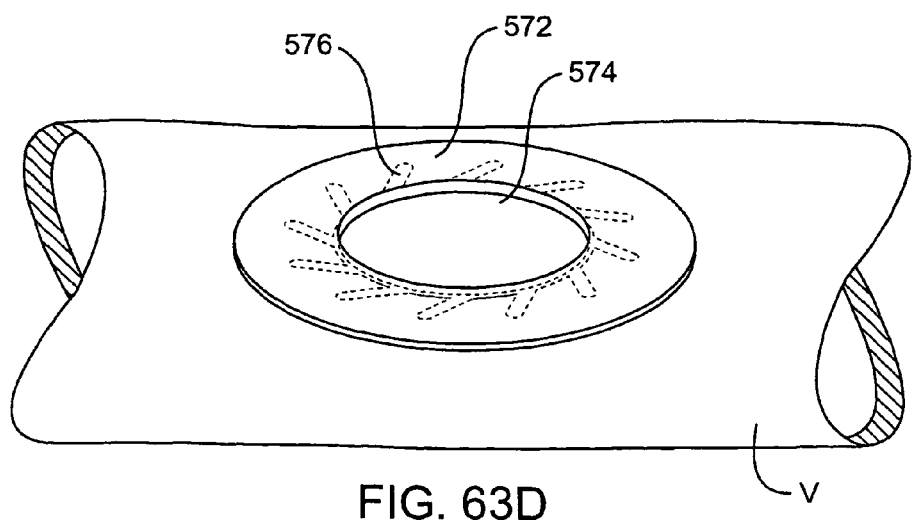
FIG. 63D

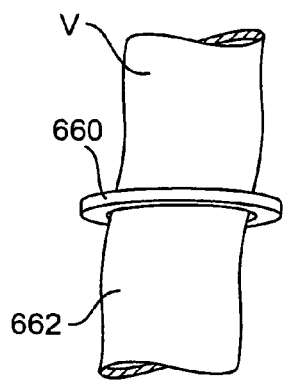
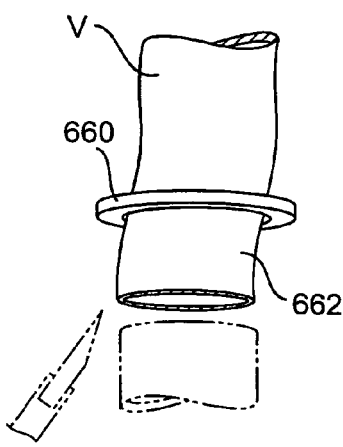
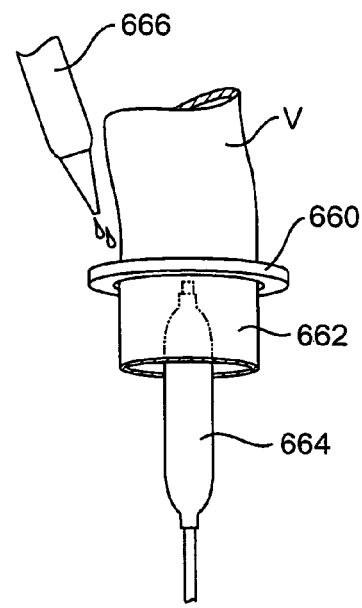
FIG. 72A
FIG. 72B
FIG. 72C
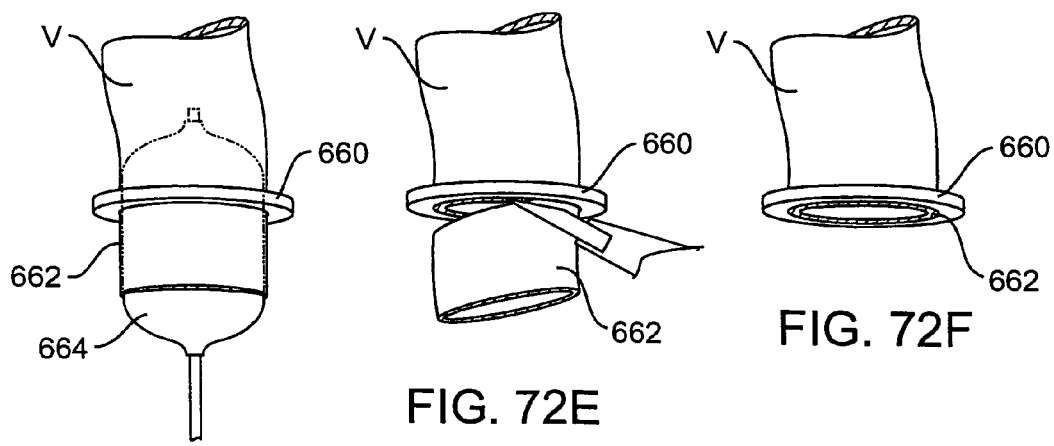
FIG. 72D
FIG. 72E
FIG. 72F

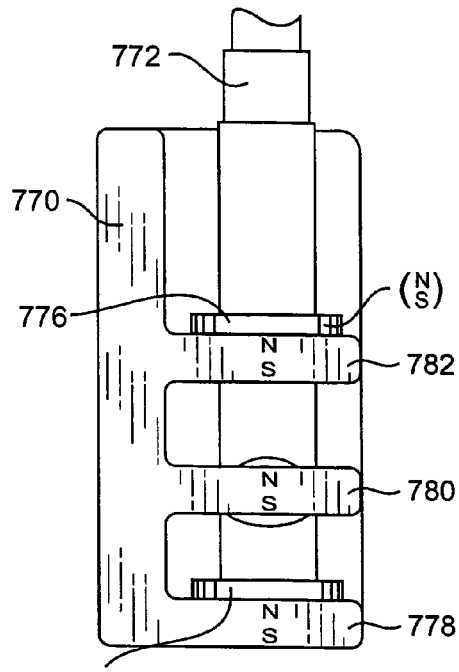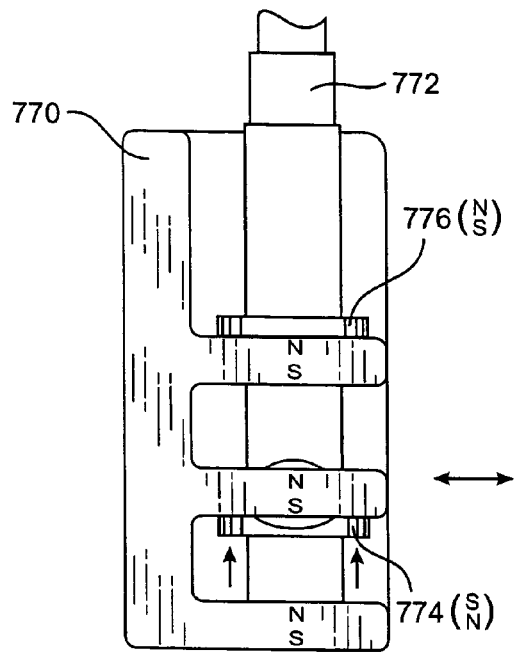
FIG. 83A   FIG. 84A
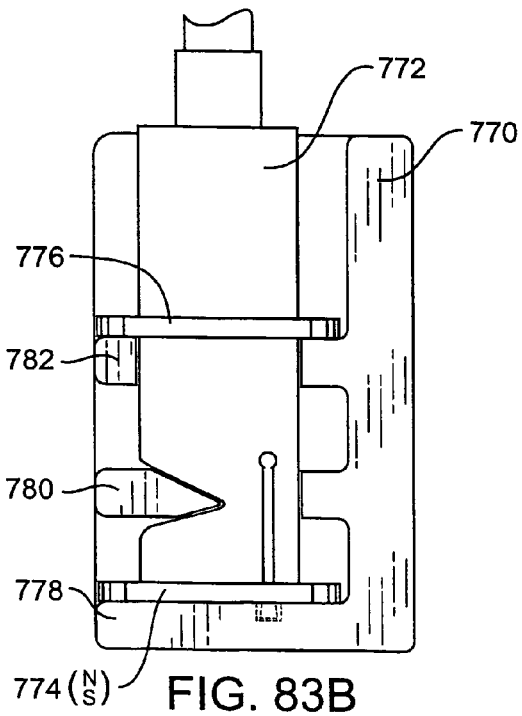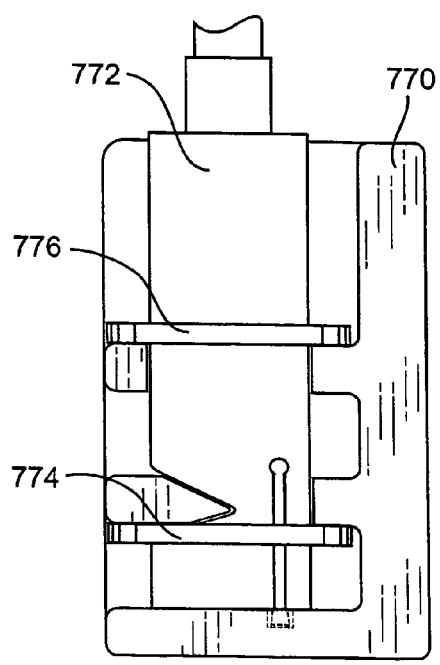
FIG. 83B   FIG. 84B

DEVICES AND METHODS FOR FORMING MAGNETIC ANASTOMOSES BETWEEN VESSELS

CROSS-REFERENCE TO RELATED APPLICATIONS

The present application is a continuation-in-part of application Ser. No. 09/915,226, filed Jul. 23, 2001 now U.S. Pat. No. 6,802,847, which is a continuation-in-part of application Ser. No. 09/638,805, filed Aug. 12, 2000 now U.S. Pat. No. 6,719,768, which is a continuation-in-part of application Ser. No. 09/562,599, filed Apr. 29, 2000 now U.S. Pat. No. 6,352,543. This application also claims priority from provisional application Ser. No. 60/255,635, filed Dec. 13, 2000, application Ser. No. 09/851,400, filed May 7, 2001 and PCT application no. PCT/US02/29485, filed Sep. 16, 2002. The entire disclosure of each of the above-referenced patent applications is expressly incorporated herein by reference.

BACKGROUND OF THE INVENTION

1. Field of the Invention

The invention relates to forming anastomoses between hollow anatomical bodies, such as blood vessels. More particularly, the invention relates to using magnetic force to form anastomoses between such vessels while attempting to minimize the amount of material that is located in the blood flow path.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue to search, with varying degrees of success, for new and improved manners of treating cardiovascular disease.

Coronary artery disease is currently treated by interventional procedures such as percutaneous transluminal coronary angioplasty (PTCA), coronary stenting and atherectomy, as well as surgical procedures including coronary artery bypass grafting (CABG). The goal of these procedures is to reestablish or improve blood flow through occluded (or partially occluded) coronary arteries, and is accomplished, for example, by enlarging the blood flow lumen of the artery or forming a bypass that allows blood to circumvent the occlusion. What procedure(s) is used typically depends on the severity and location of the blockage. CABG is typically performed when interventional procedures have been unsuccessful or, for one reason or another, are not available options for a given patient. When successful, these procedures restore flow within the treated vessel(s) and feed blood to myocardial tissue that had previously been insufficiently perfused.

Another proposed treatment places the target vessel, e.g., a coronary artery, in direct fluid communication with a heart chamber containing blood, for example, the left ventricle. Blood flows from the ventricle into a conduit that is in fluid communication with the artery; as such, this treatment may be described as a ventricular bypass procedure. Benefits of this procedure include obviating the need to manipulate the aorta, for example, as is done when a side-biting clamp is used in a typical CABG procedure to create a proximal anastomosis between the bypass graft and the aorta.

The most challenging aspect of CABG (as well as many other procedures that requiring forming an anastomosis) is connecting the graft vessel to the target vessel in a secure, fluid-tight manner. This is conventionally done by hand using suture that is passed through the tissue of the two vessels to create a handsewn connection. The small diameter of coronary vessels (typically 1 mm to 4 mm) makes creating these handsewn anastomoses highly technical and time consuming. The difficulty in forming the sutured anastomosis is exacerbated when access to the target vessel is restricted or limited as compared to open-chest CABG, for example, as in minimally invasive or percutaneous procedures. A number of other medical procedures also require the attachment of hollow anatomical bodies (by sewing or otherwise) and therefore involve the same or similar considerations, for instance, treating peripheral vascular disease or injury and creating arteriovenous shunts.

Many various anastomotic couplings have been proposed in the art, although none has performed well enough to receive any significant level of acceptance in the field. Exemplary problems experienced by some of these couplers include damage to the graft or target vessel wall, for instance, due to piercing, penetrating or overly compressing the tissue, and failure to produce repeatable results. Additionally, producing an anastomotic coupler that creates and maintains a patent connection has been somewhat elusive and hard to achieve.

One coupling technology with promising results based on early clinical success is Ventrica, Inc.'s MVP™ (Magnetic Vascular Positioner) anastomotic connector system. The reader's attention is directed to U.S. Pat. No. 6,352,543 to Cole, which discloses various magnetic connector configurations Accordingly, there is a need in the art for methods and devices for forming a reliable anastomosis between hollow bodies in a relatively quick, easy and repeatable manner.

SUMMARY OF THE INVENTION

According to one embodiment, a method for securing a magnetic anastomotic component to a hollow body is provided and includes steps of providing an anastomotic component capable of producing or being attracted by a magnetic field, the component having an opening, positioning a placement member in a first configuration within a lumen of a hollow body at a selected location, the placement member being capable of producing or being attracted by a magnetic field, and using magnetic attraction between the anastomotic component and the placement member to position the component at a selected location. The anastomotic component is secured to the hollow body, the placement member is changed from the first configuration to a second configuration and then removed from the lumen of the hollow body.

According to another embodiment, a method for securing a magnetic anastomotic to a blood vessel having a lumen includes steps of placing an anastomotic component having an opening adjacent a blood vessel having a lumen, the anastomotic component capable of producing or being attracted by a magnetic field, providing a plurality of separate attachment members each of which is configured to be engaged with the anastomotic component, and securing the anastomotic component to the blood vessel by using the separate attachment members.

According to another embodiment, a method for adhesively securing a magnetic anastomotic component to an end of a hollow body having a lumen is provided. This method includes steps of providing an anastomotic component capable of producing or being attracted by a magnetic field, the component having an opening adapted to be placed in communication with a lumen of a hollow body, applying adhesive to at least one of the anastomotic component and the hollow body adjacent an end of the hollow body, and using the adhesive to secure the anastomotic component to the hollow body adjacent the end of the hollow body.

According to yet another embodiment, a method for securing a magnetic anastomotic component to an end of a hollow body having a lumen is provided and includes steps of providing an anastomotic component including first and second portions, at least one of the first and second portions being capable of producing or being attracted by a magnetic field, positioning the first portion of the anastomotic component within a lumen of a hollow body, positioning the second portion of the anastomotic component at least partially around the exterior of the hollow body, and allowing the first and second portions to compress the tissue of the hollow body to secure the anastomotic component to the hollow body.

According to still another embodiment, a method for checking a seal between an anastomotic component and a blood vessel to which the anastomotic component is secured is provided. This method includes steps of providing an anastomotic component capable of producing or being attracted by a magnetic field, the anastomotic component having an opening, attaching the anastomotic component to a blood vessel in fluid communication with the lumen of the blood vessel, using a cover to block the opening in the anastomotic component, the cover being capable of producing or being attracted by a magnetic field, and using magnetic attraction to maintain a seal between the cover and the anastomotic component and prevent blood from exiting through the opening in the anastomotic component, whereby any blood that does leak may be attributed to leaking at the attachment between the anastomotic component and the hollow body.

According to yet another embodiment, a method for confirming the proper orientation of a magnetic anastomotic component is provided. This method includes steps of providing a delivery device supporting at least one anastomotic component having an opening, the anastomotic component being capable of producing a magnetic field, providing a fixture including at least one portion that is magnetized according to a selected polarity and movable to a location adjacent the anastomotic component, and using the fixture to determine whether the anastomotic component is oriented properly on the delivery device.

According to another embodiment, a magnetic anastomotic component is provided having a first portion with an opening adapted to be placed in communication with a lumen of a hollow body, and a second portion attached to the first portion and including an expandable tubular body configured to be attached to an end of the hollow body. The first and second portions are disposed generally transverse to each other and at least one of them is capable of producing or being attracted by a magnetic field.

According to another embodiment, a magnetic anastomotic component is provided and has an annular body and a plurality of separate attachment members each of which may be selectively engaged with the annular body to secure it to a hollow body. At least one of the annular body and the attachment members is capable of producing or being attracted to a magnetic field.

According to still another embodiment, a device for checking the seal between an anastomotic component and a hollow body to which it is secured is provided. The device includes an expandable structure with a substantially fluid-impervious surface and material capable of producing or being attracted by a magnetic field. The expandable structure may be magnetically attached to a magnetic or ferromagnetic anastomotic component secured to a hollow body by placing the fluid-impervious surface over the component to block flow. The expandable structure is expanded to break the magnetic attraction between the magnetic material and the component.

According to yet another embodiment, a device having first and second components is provided. The second component is magnetically attracted to the first component. The first and second components form a throughhole to provide fluid communication between a first vessel and a second vessel with the throughhole having a longitudinal axis. The first component has a first part and a second part with the first and second parts configured to compress a wall of the first vessel with the first part being forced toward the second part in a first direction. The second component is magnetically attracted to the first component in a second direction in order to couple the first and second components together with the first and second directions being generally non-parallel.

According to another embodiment, a method of forming an anastomosis between a first vessel and a second vessel using a first component and a second component magnetically attracted to one another is provided. The first component has a first part and a second part. At least a portion of the second part is introduced into the first vessel. The first and second parts are moved together to compress a wall of the first vessel with the first part positioned against an outer wall of the first vessel. The second component is also coupled to the second vessel. The first and second components are then moved together so that the first and second components are magnetically coupled together with the components forming a throughhole to provide fluid communication between the first and second vessels. The first and second parts compress the wall of the first vessel in a first direction while the second component is magnetically attracted to the first component in a direction not parallel to the first direction.

According to still another embodiment, a method of forming an anastomosis between a first vessel and a second vessel is provided using first and second components each having first and second parts. The first and second components are coupled to the first and second vessels, respectively, by compressing the walls of the vessels between the first and second parts. The components are then moved together so that the first and second components are magnetically attracted to one another to couple the first and second vessels together. The first parts of the components are magnetically attracted to one another and the second parts of the components compress the first and second vessels together.

According to still another embodiment, an anastomotic device is provided including first and second components each having first and second parts. The first and second components are magnetically attracted to one another. The first and second components form a throughhole when magnetically coupled together with the throughhole having a longitudinal axis. The first parts of the components are positioned radially outward from the second parts relative to the throughhole. The first parts of the components contact one another and are magnetically attracted to one another. The second parts of the first and second components are also magnetically attracted to one another.

According to yet another embodiment, a method of forming an anastomosis between first and second vessels is provided using first and second components each having a first part and a second part. The components are coupled to the vessels by compressing the walls of the vessels between the first and second parts. The first and second components are moved together so that the first and second components are attracted to one another to couple the first and second vessels together. The first parts of the components contact one another and are magnetically attracted to one another while positioned entirely outside a blood flow path formed by the components to prevent blood from contacting the first parts of the components.

BRIEF DESCRIPTION OF THE DRAWING FIGURES

Other features, aspects, benefits and advantages of the invention will be appreciated from the following detailed description of exemplary embodiments thereof taken in conjunction with the following Figures, wherein:

FIG. 10C is a section view similar to FIG. 10A but showing an alternative attachment between a hollow body and an anastomotic securing component;

FIG. 10D is a section view similar to FIG. 10C showing another alternative attachment between the hollow body and a securing component;

FIG. 17A is a plan view of one of the hollow bodies and securing components shown in FIG. 12;

FIG. 17B is a longitudinal sectional view of the hollow body and securing component shown in FIG. 17A;

FIG. 18A is a plan view of the hollow body of FIGS. 17A-17B and a securing component constructed according to an alternative embodiment of the invention;

FIG. 18B is a longitudinal sectional view of the hollow body and securing component shown in FIG. 18A;

FIG. 28 is an exploded perspective view of two devices which are constructed according to another embodiment of the invention and are adapted to be coupled to tissue using magnetic force for forming a magnetic port in a hollow body having a lumen;

FIG. 29 is a sectional view taken through a vessel having a lumen, wherein the devices shown in FIG. 28 are coupled to the tissue of the vessel wall;

FIGS. 40A-40C are elevation views sequentially showing the device of FIGS. 36A-39C being deployed in a vessel having a lumen;

FIG. 44 is a perspective view sequentially showing a flexible magnetic component constructed according to one embodiment of the invention being collapsed;

FIGS. 45A-45B are perspective views illustrating a flexible magnetic component constructed according to one embodiment of the invention in its expanded and collapsed orientations, respectively.

Figure 46C:
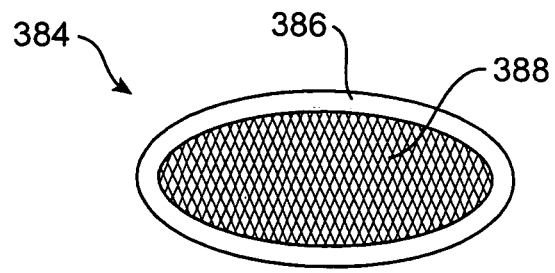
FIG. 46C is a perspective view of a flexible component with a magnetic core constructed according to yet another embodiment of the invention, the component being adapted to substantially or completely close an opening in tissue or another component.
Figure 46D:
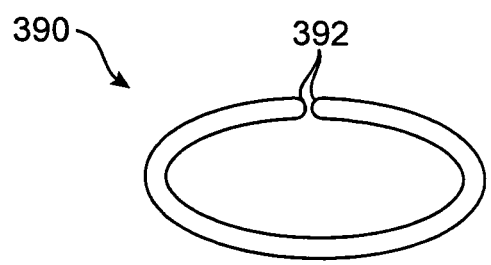
FIG. 46D is a perspective view of an alternative flexible magnetic component with a construction similar to the component of FIG. 46C but having an opening for placement in communication with the lumen of a vessel.
Figure 46E:
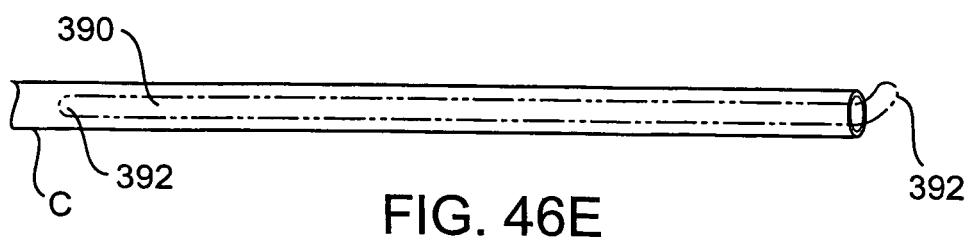
FIGS. 46A-46B shows alternative flexible magnetic components constructed according to additional embodiments of the invention.
Figure 47A:
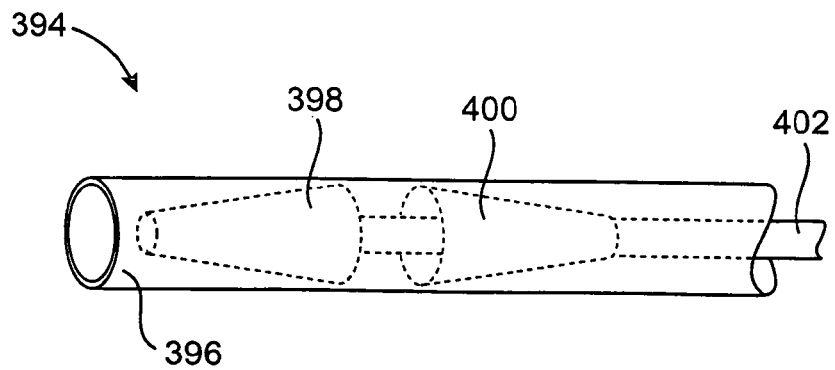
Figure 47B:
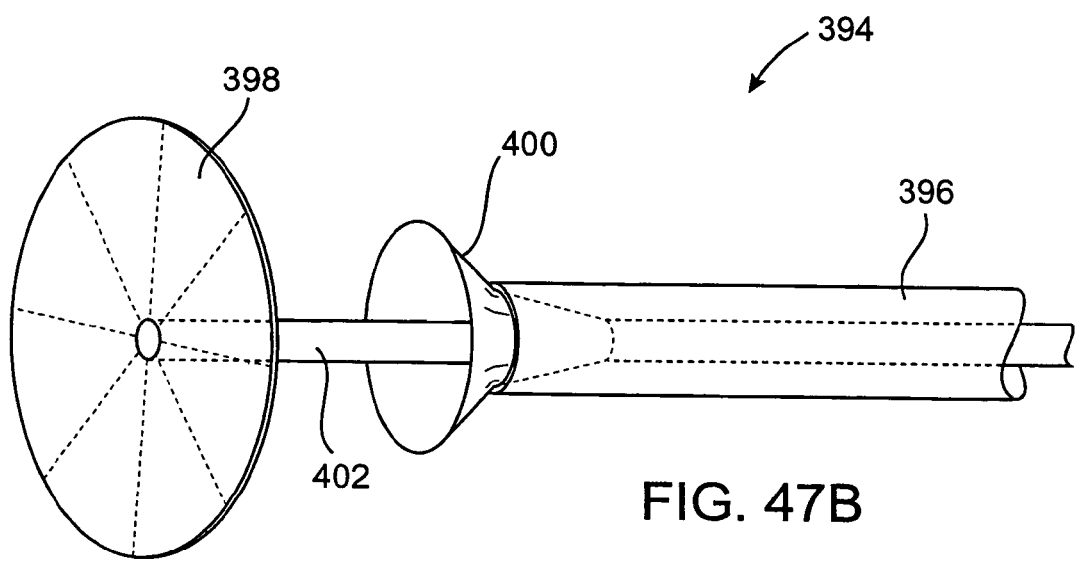
Figure 47C:
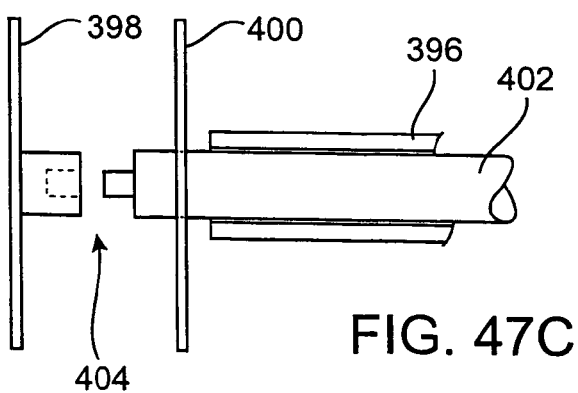

FIG. 46E schematically illustrates and exemplifies delivering the component shown in FIG. 46D in a low profile manner by way of a catheter or sheath;

FIGS. 47A-47B are perspective views showing a device constructed according to another embodiment of the invention for closing openings in tissue in a restrained position for delivery and a partially deployed position, respectively;

FIG. 47C is a fragmentary side elevation view of the device shown in FIGS. 47A-47B but with the device fully deployed; and FIGS. 48A-48C are elevation views sequentially showing the device of FIGS. 47A-47C being used to close a ventricular septal defect.

Figure 50A:
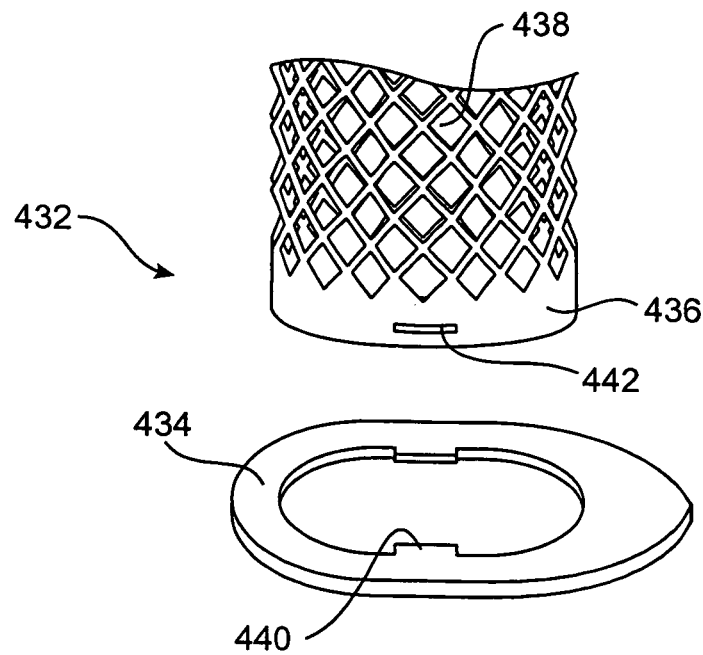
Figure 50B:
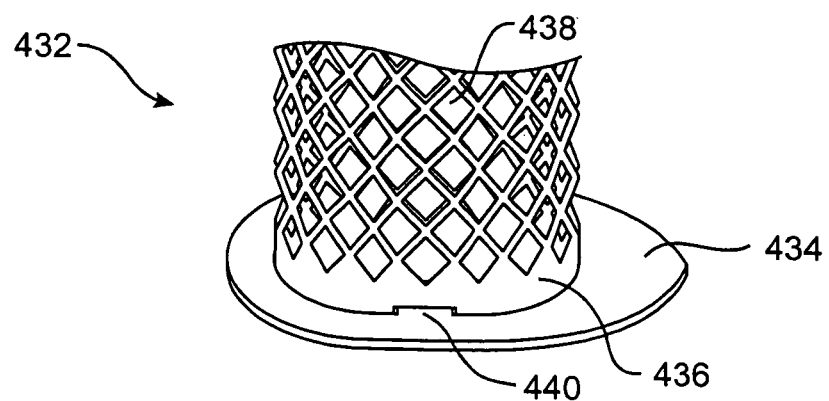
Figure 51A:
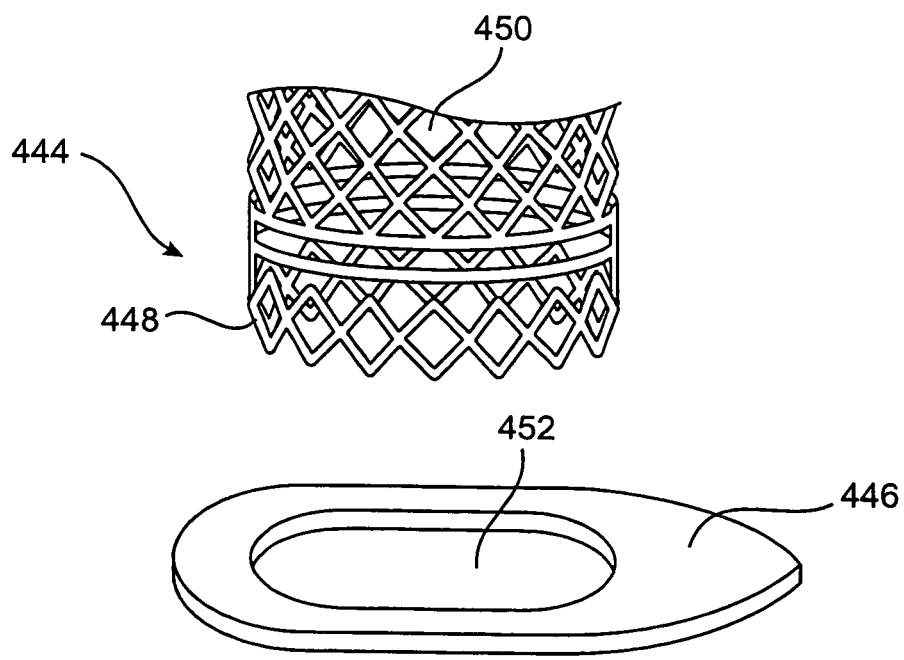
Figure 51B:
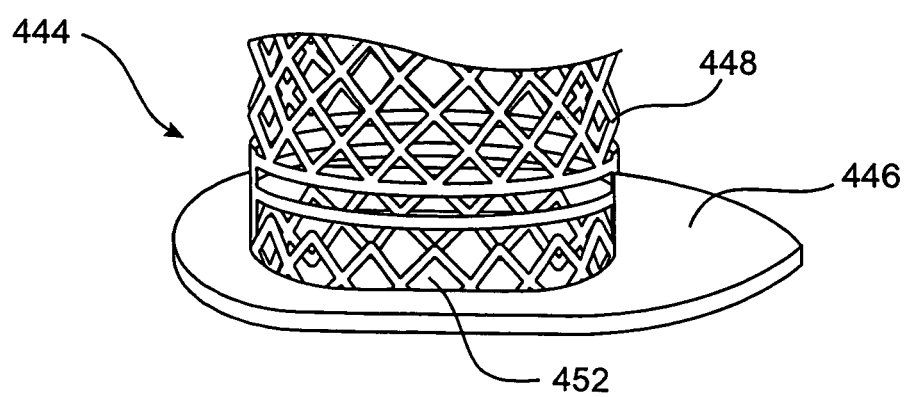
Figure 52A:
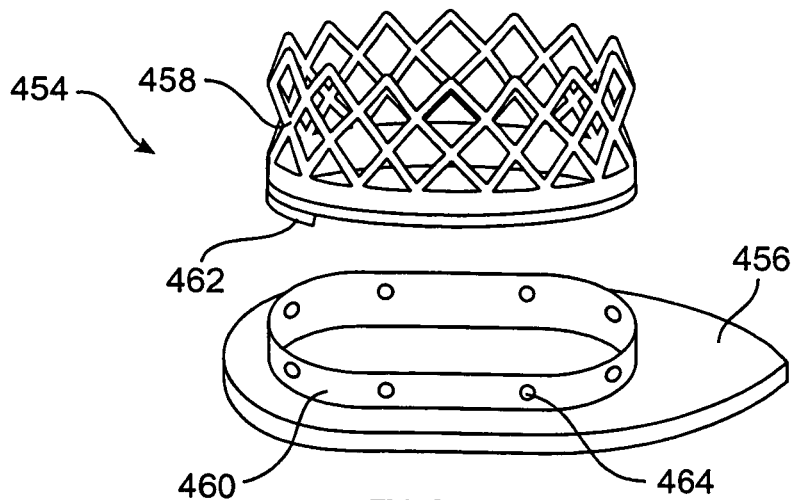
Figure 52B:
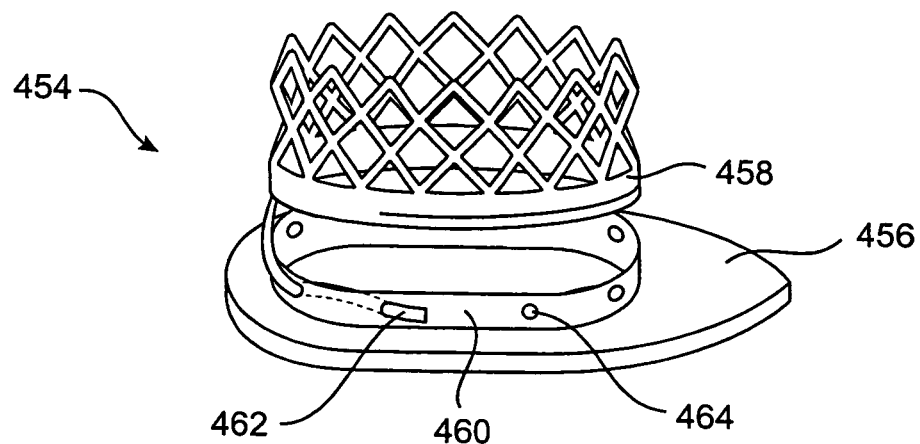
Figure 52C:
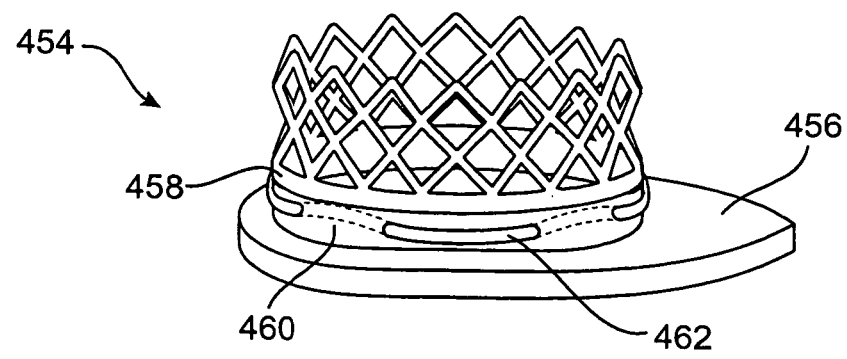
Figure 53A:
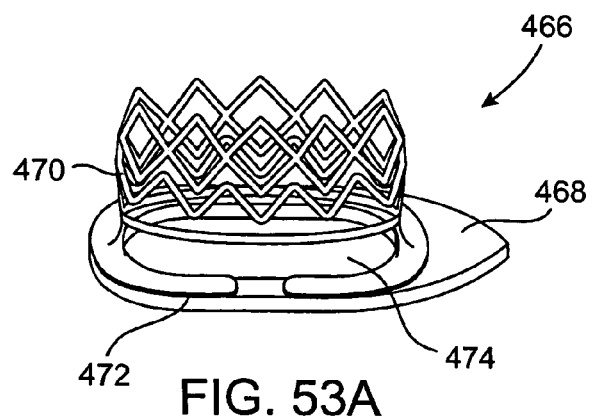
Figure 53B:
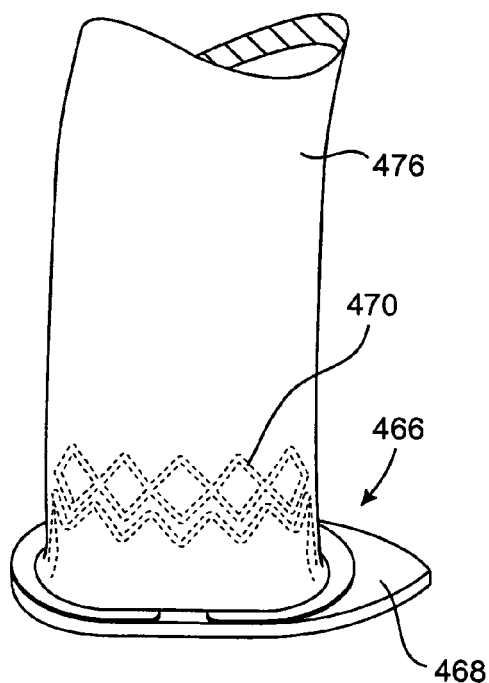
Figure 53C:
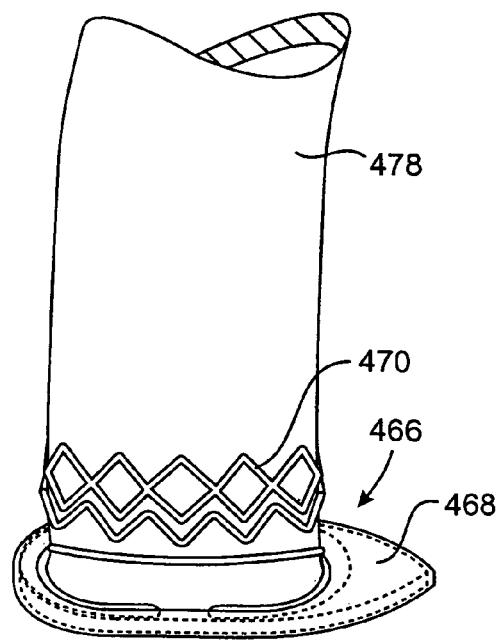
Figure 54A:
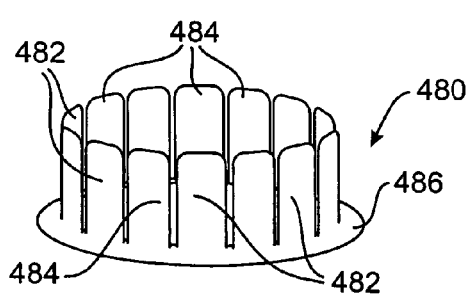
Figure 54B:
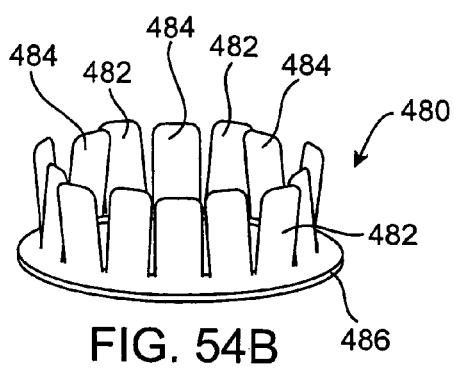
Figure 54C:
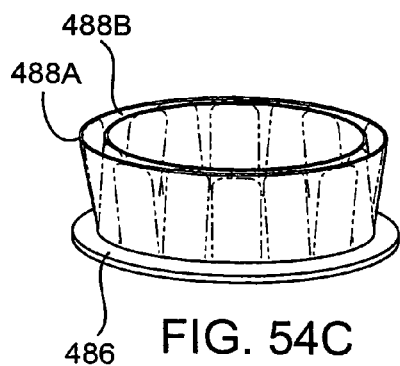
Figure 54D:
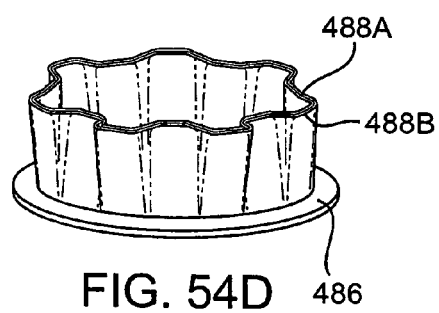
Figure 54E:
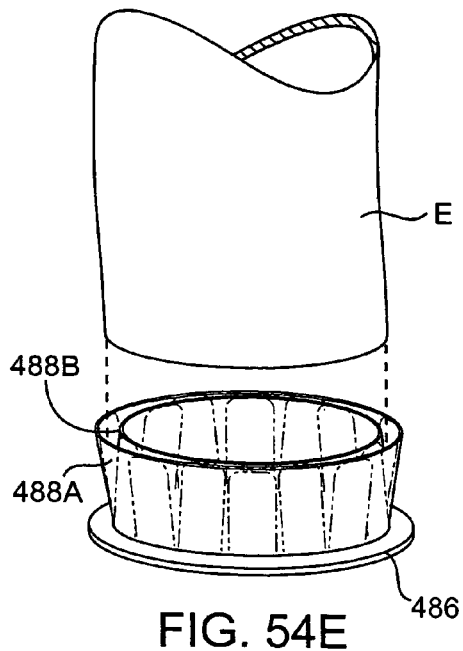
Figure 54F:
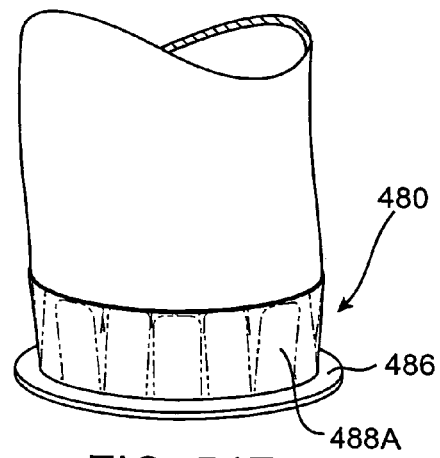
Figure 56A:
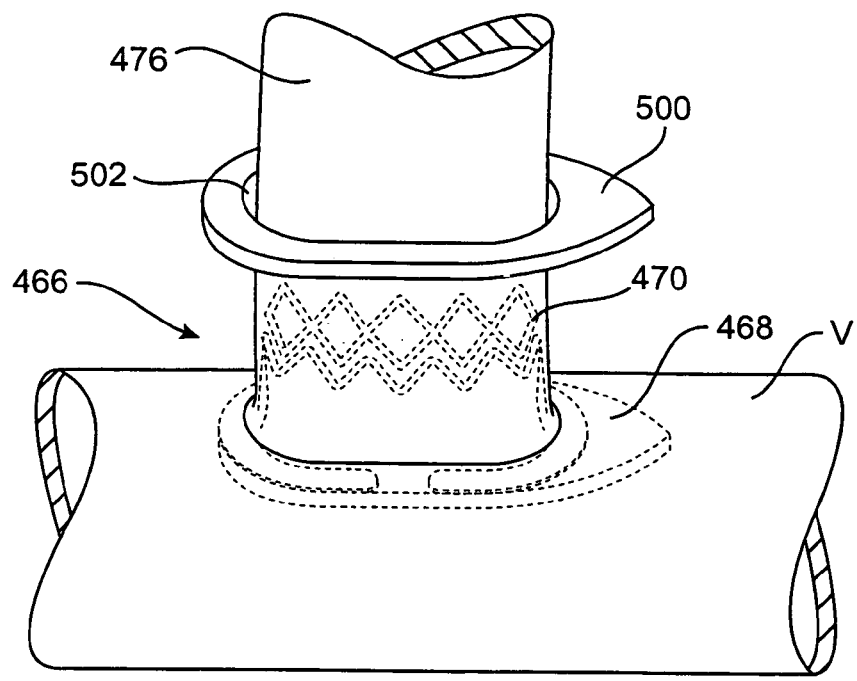
Figure 56B:
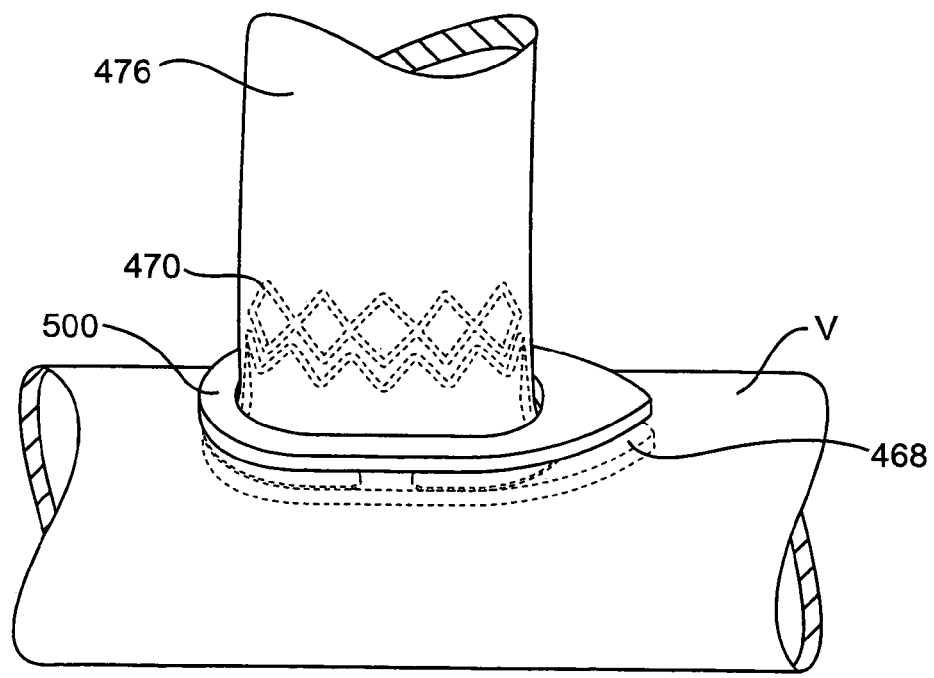
Figure 57A:
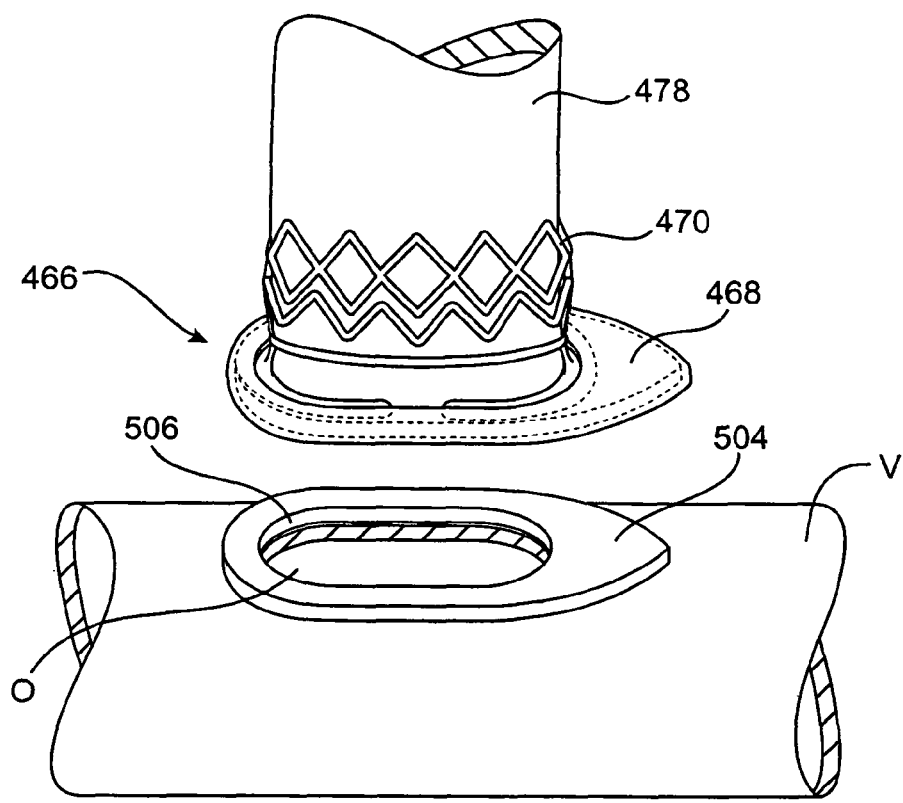
Figure 57B:
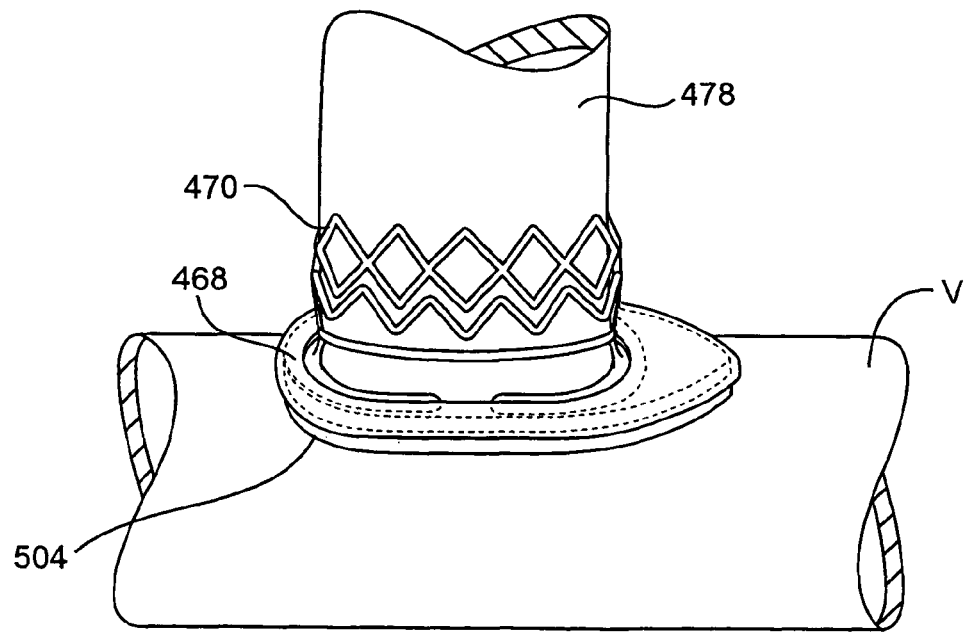
Figure 58A:
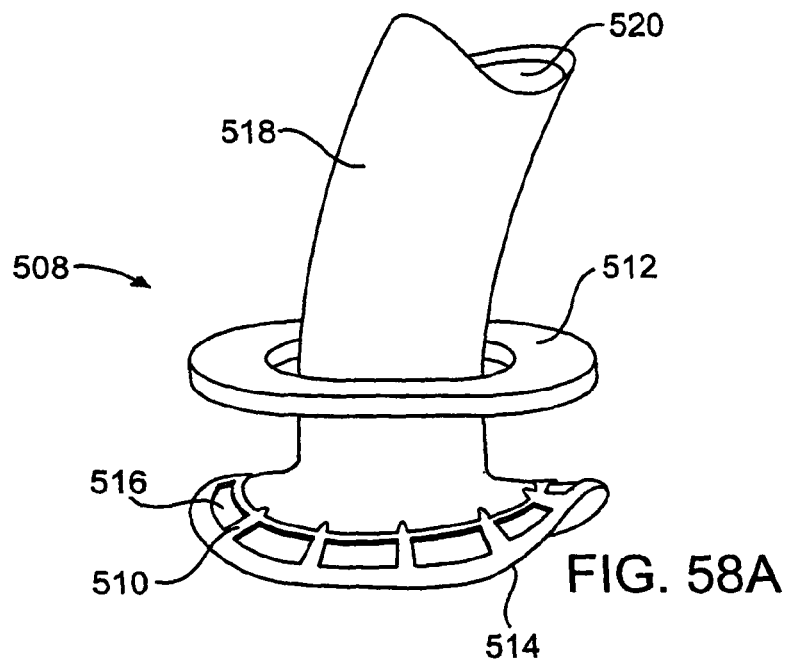
Figure 58B:
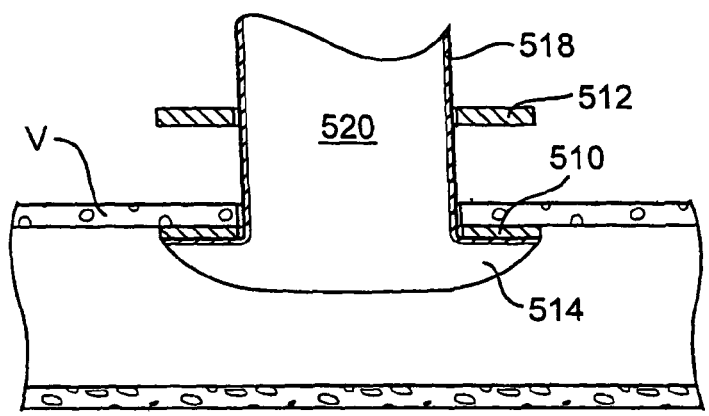
Figure 58C:
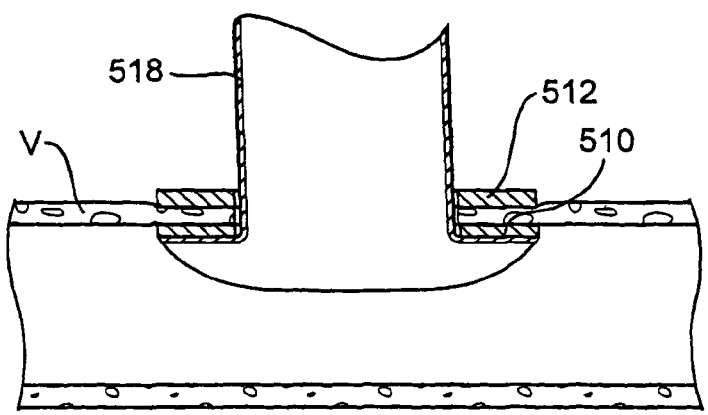
Figure 59A:
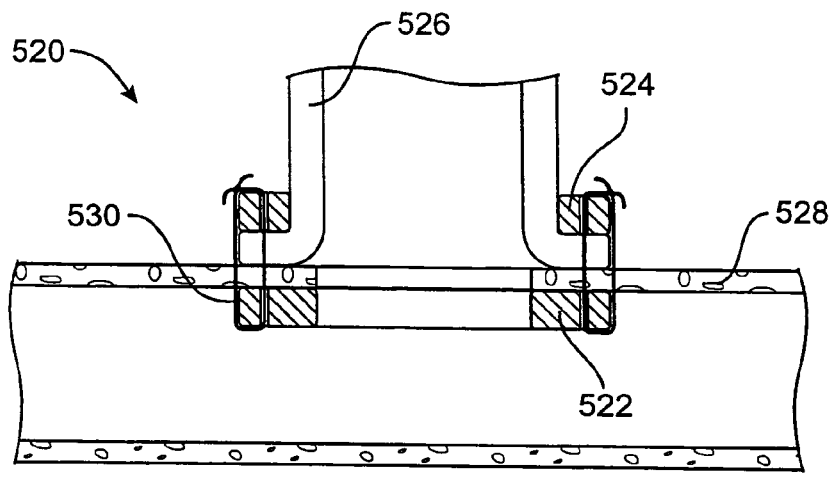
Figure 59B:
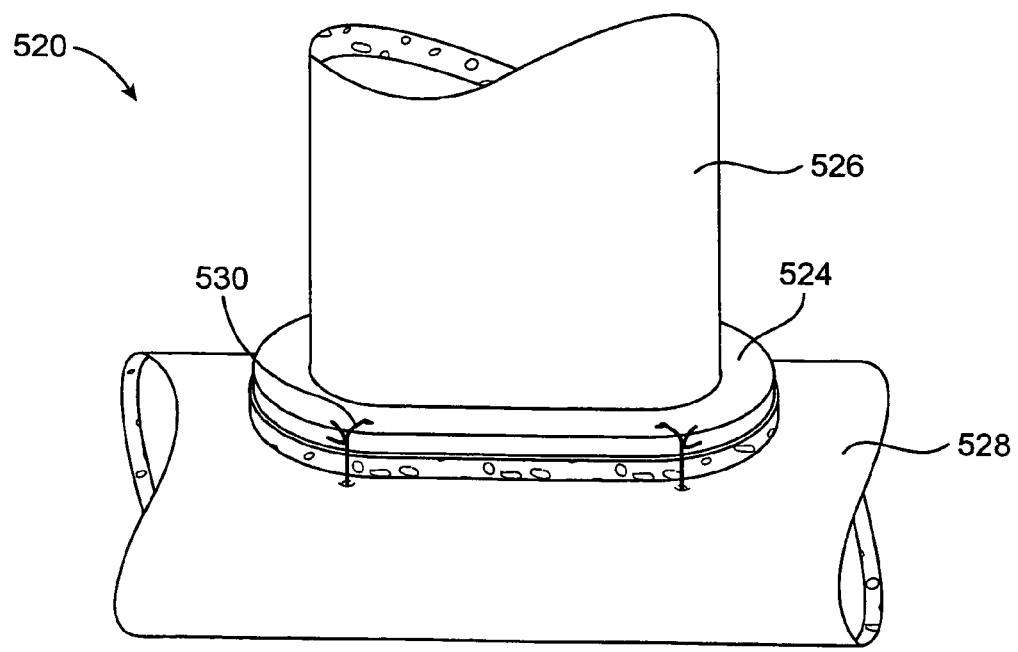
Figure 60A:
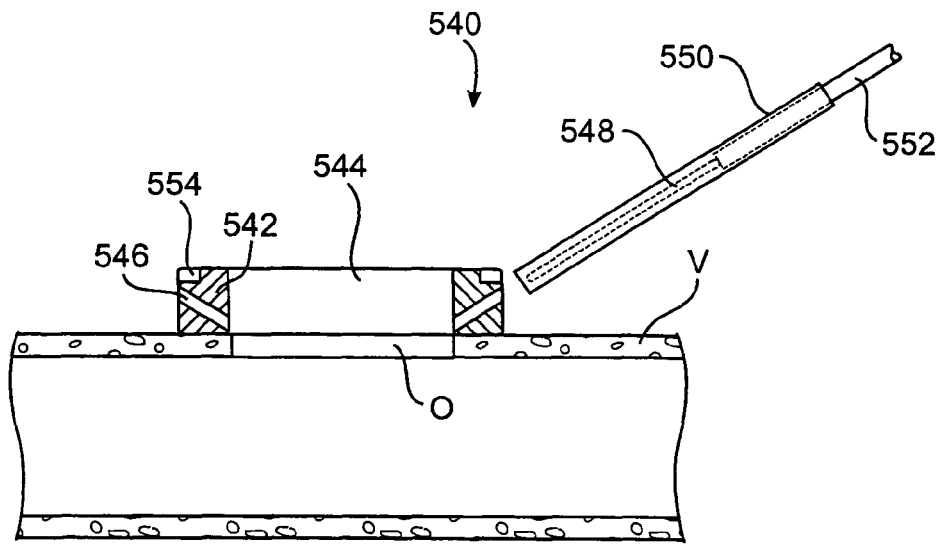
Figure 60B:
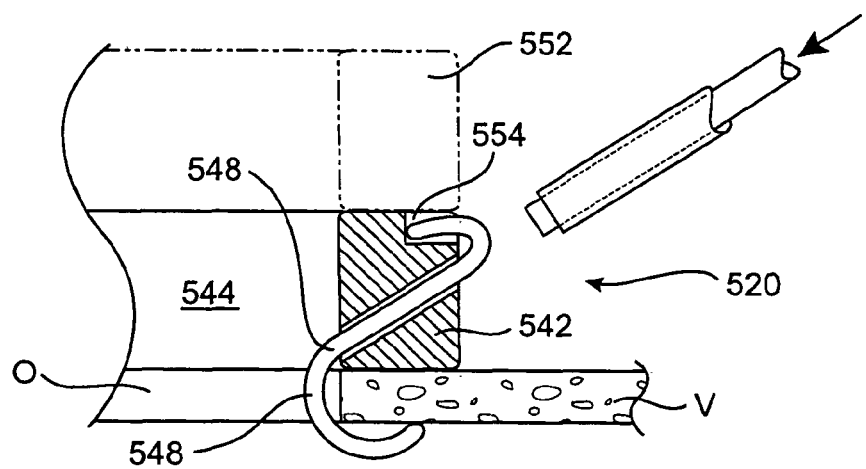
Figure 60C:
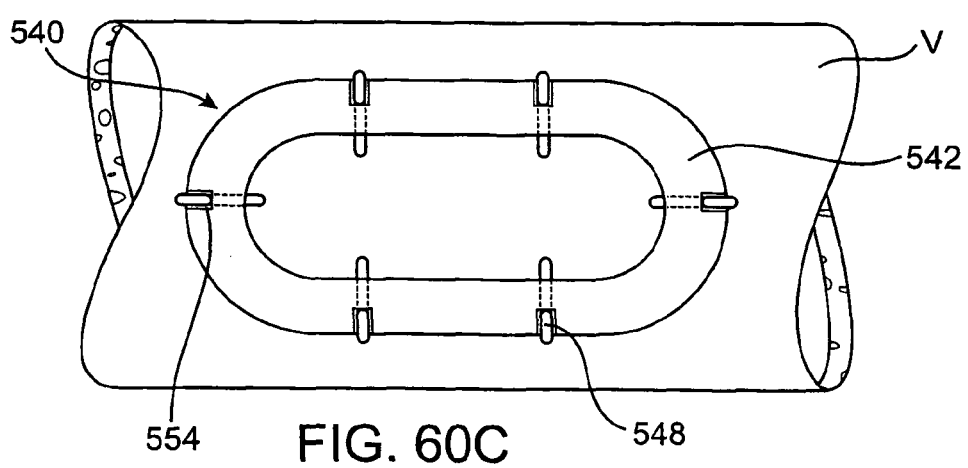
Figure 61A:
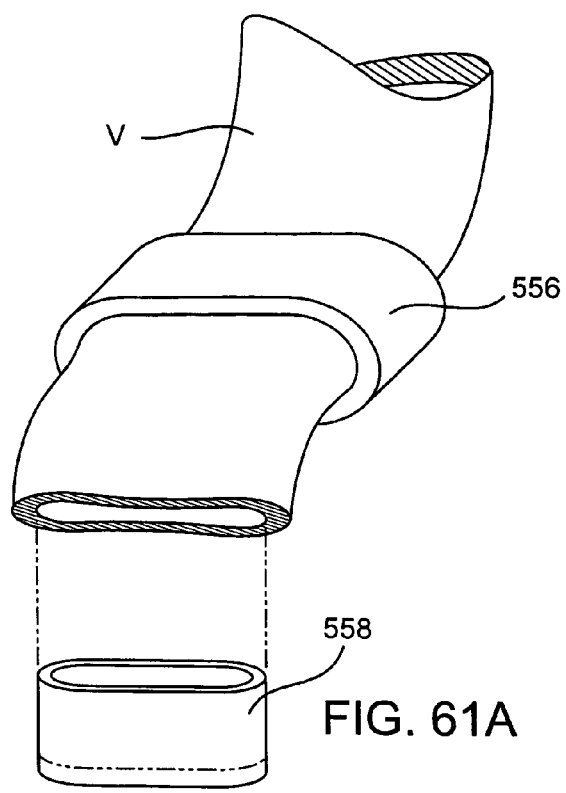
Figure 61B:
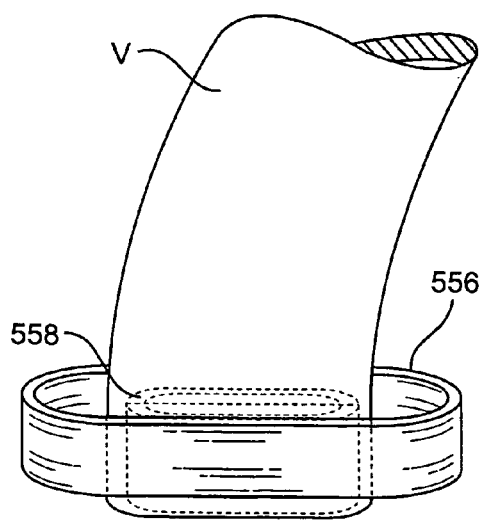
Figure 61C:
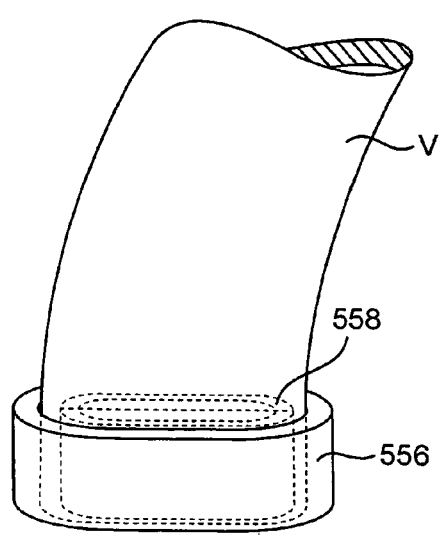
Figure 62A:
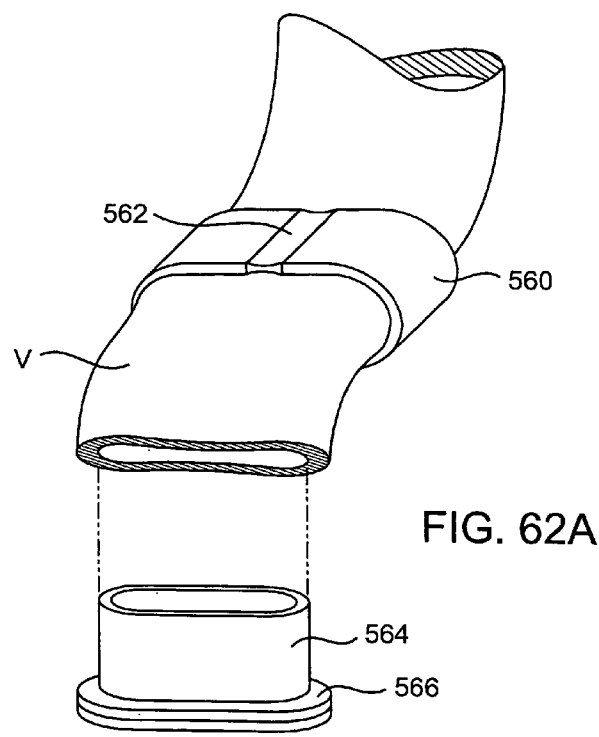
Figure 62B:
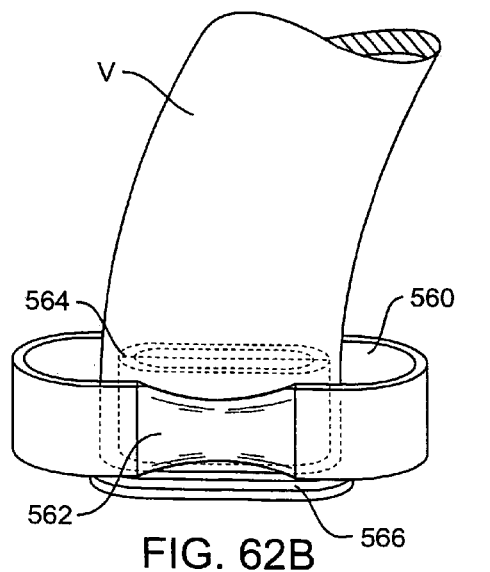
Figure 62C:
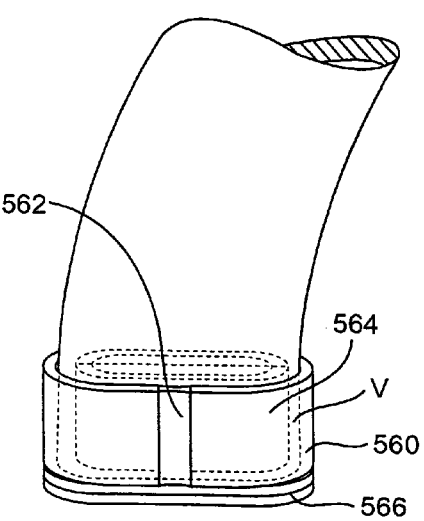
Figure 64A:
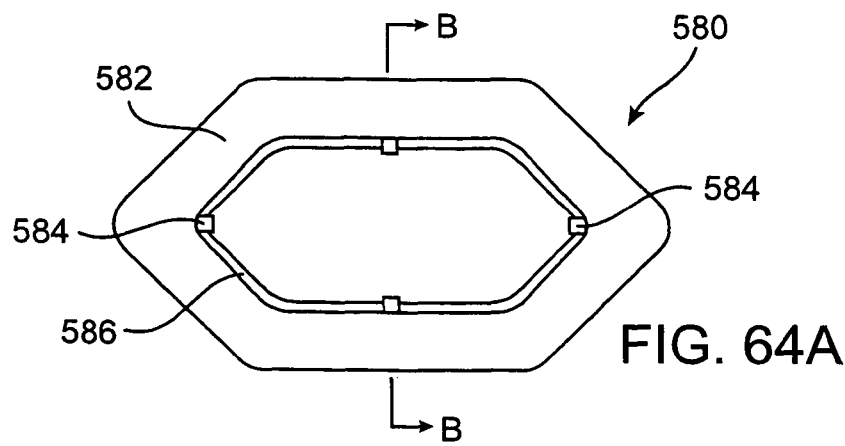
Figure 64B:
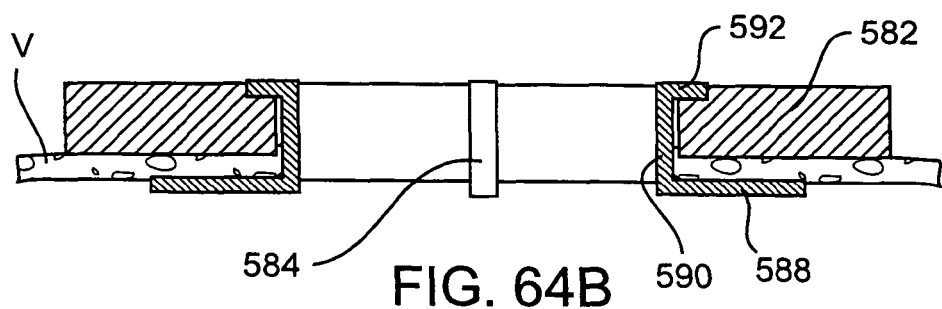
Figure 65A:
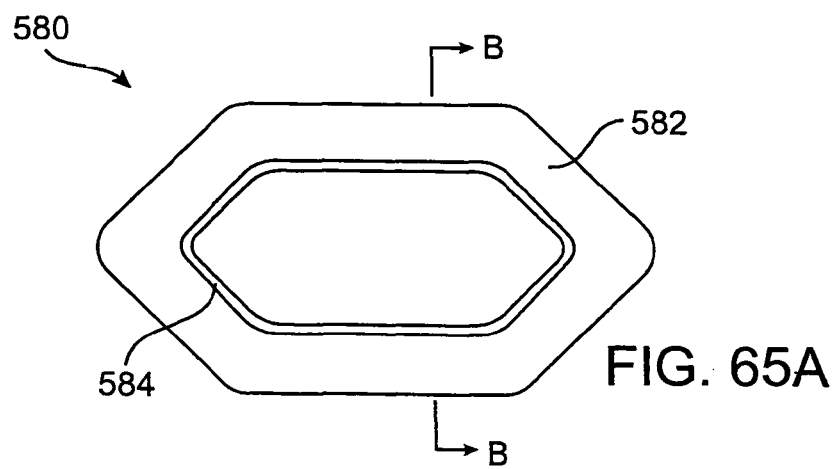
Figure 65B:
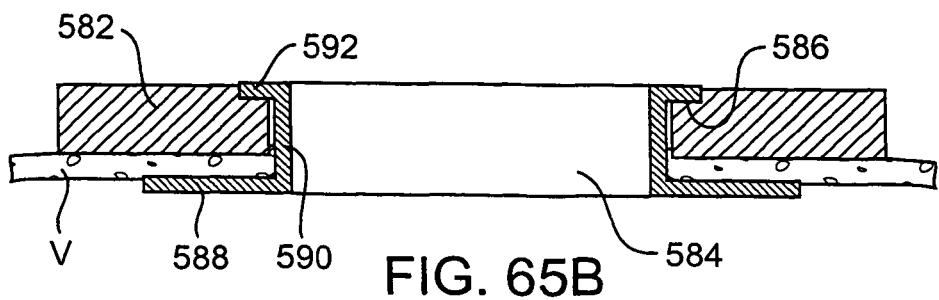
Figure 66A:
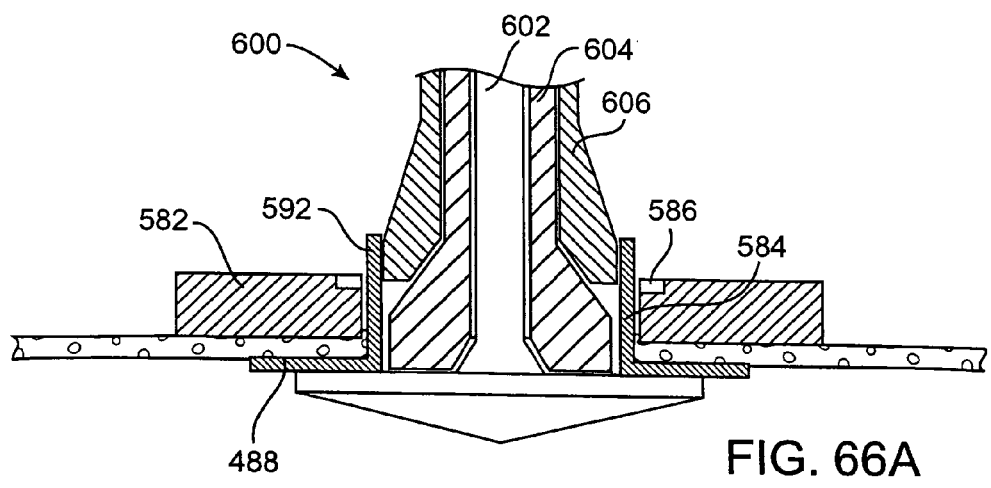
Figure 66B:
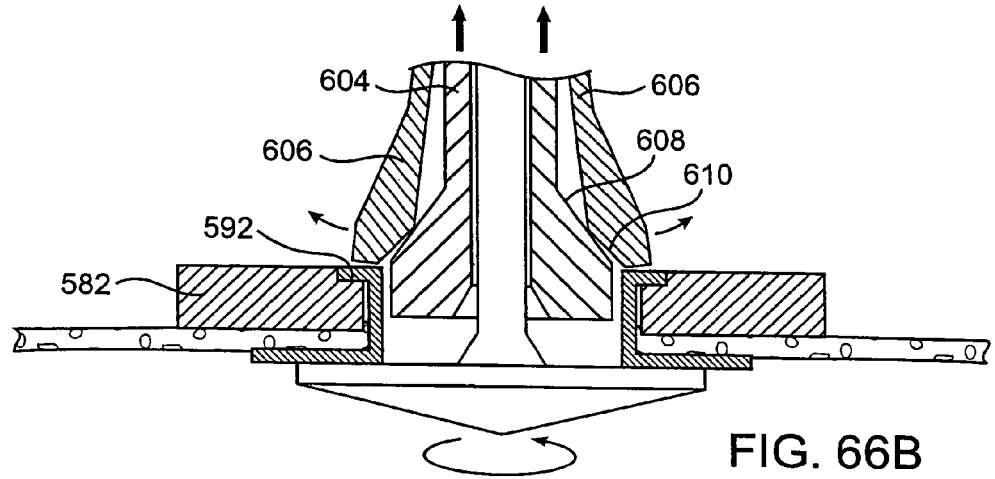
Figure 66C:
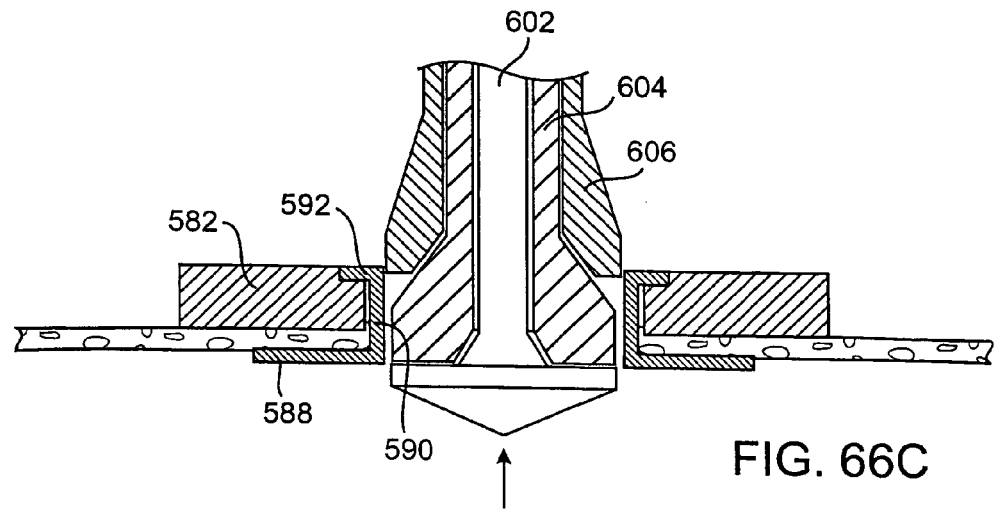
Figure 67A:
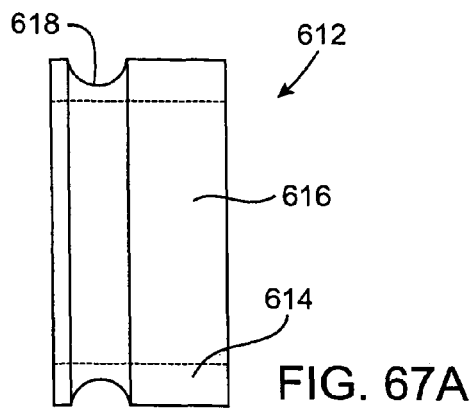
Figure 67B:
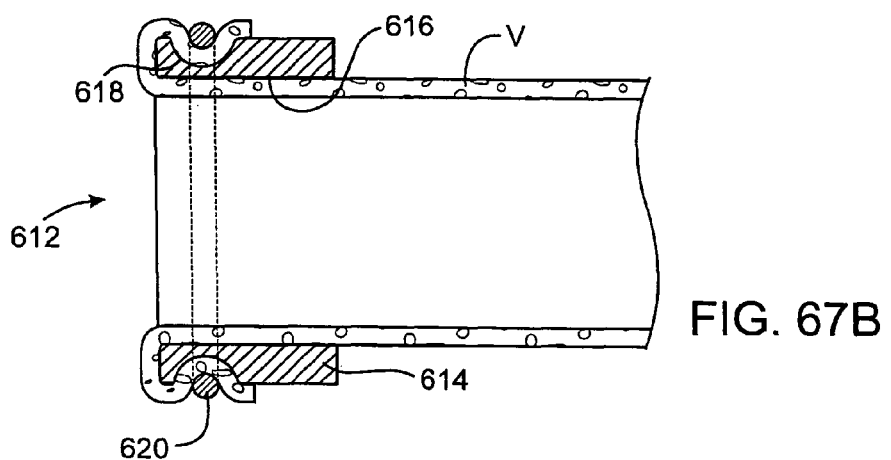
Figure 67C:
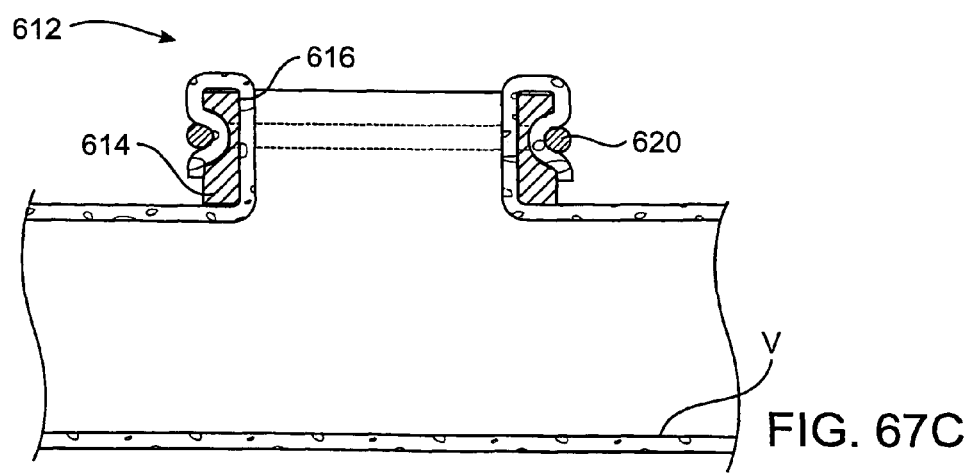
Figure 68A:
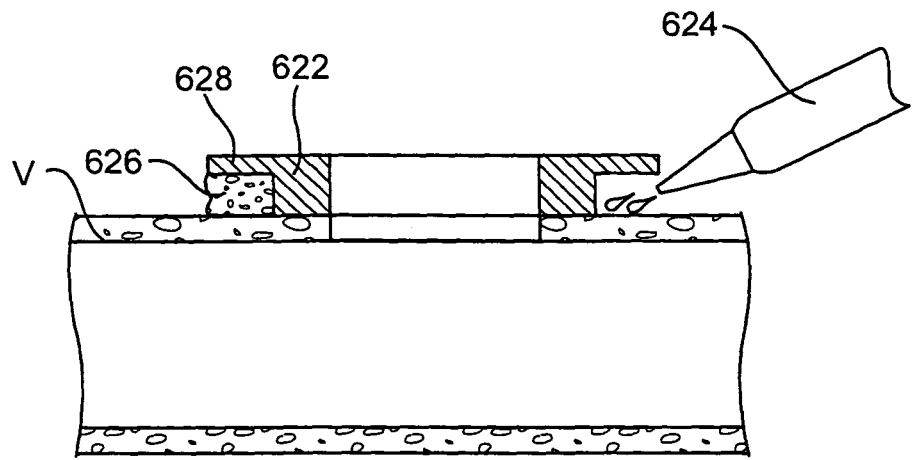
Figure 68B:
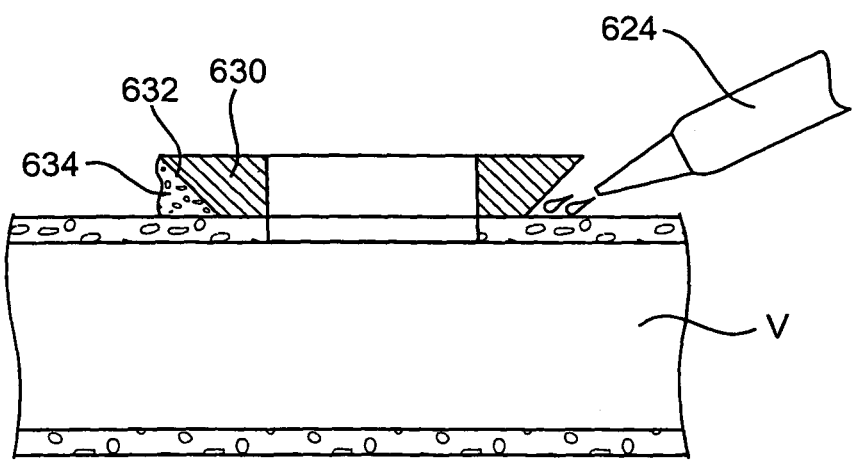
Figure 69A:
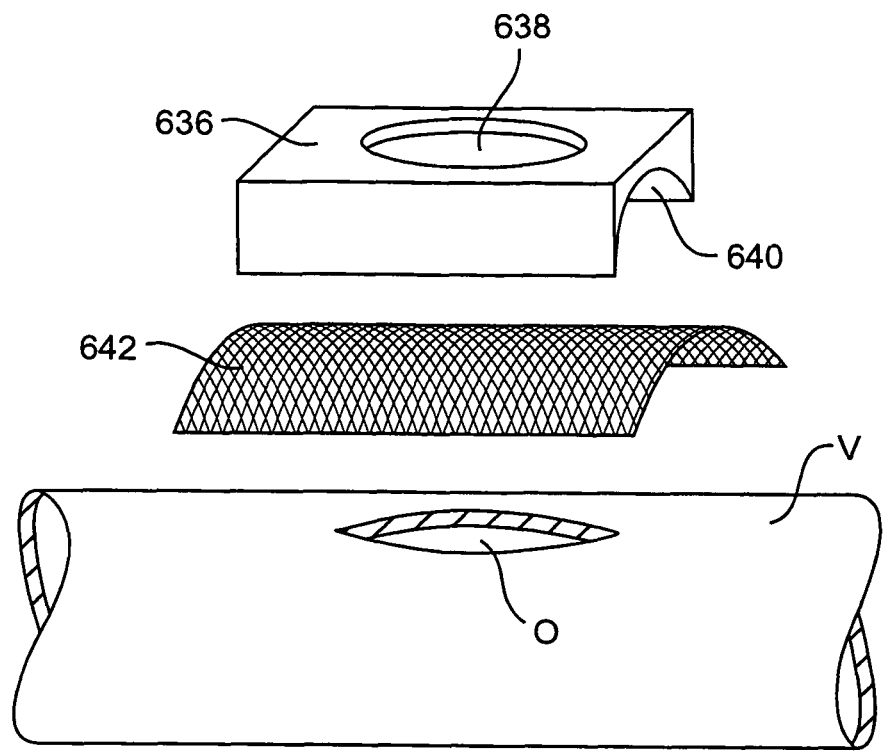
Figure 69B:
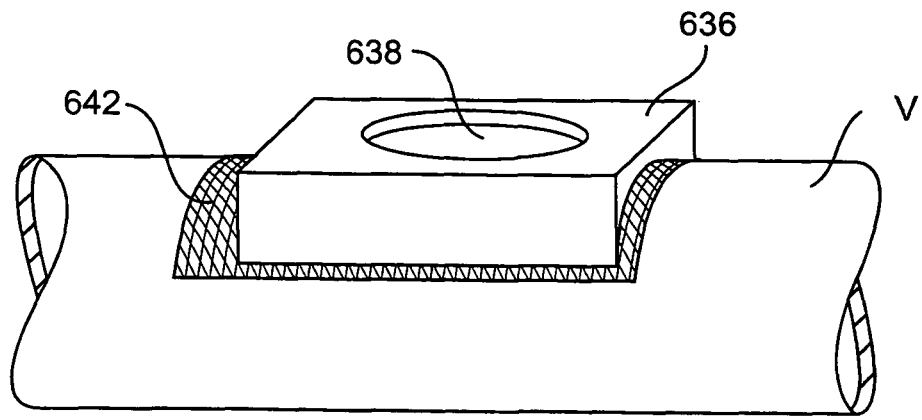
Figure 70:
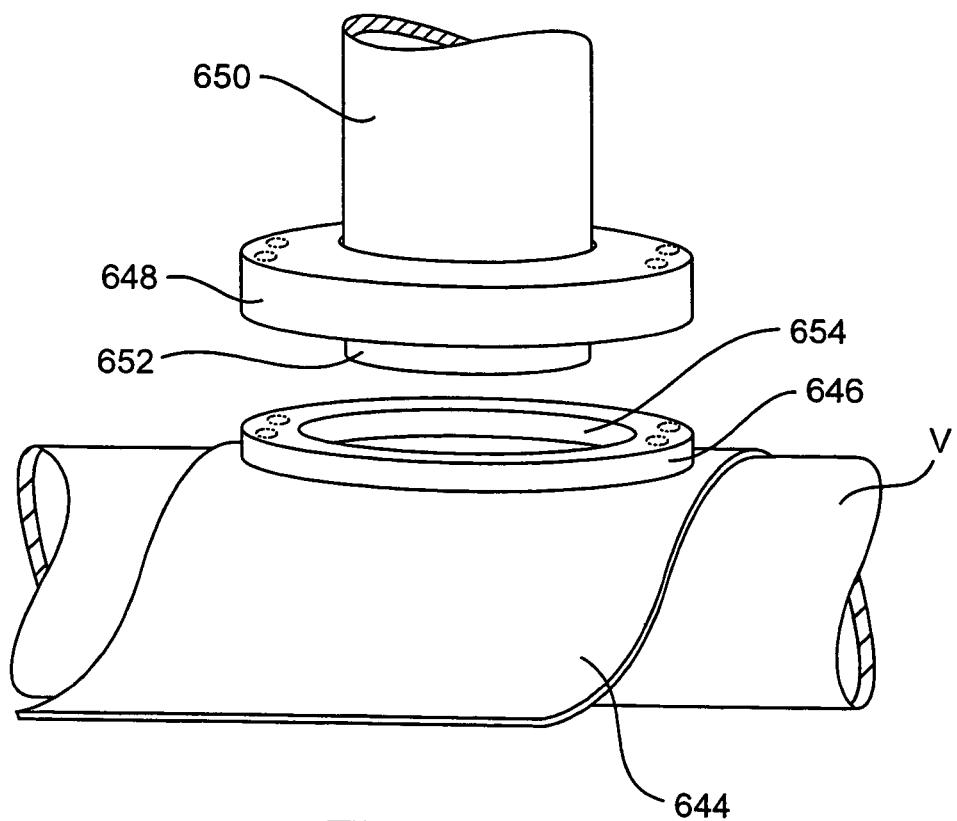
Figure 75A:
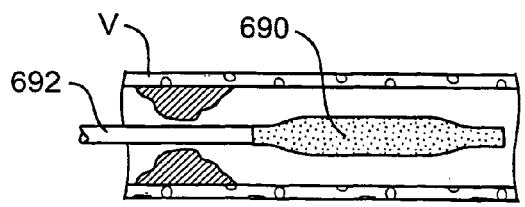
Figure 76A:
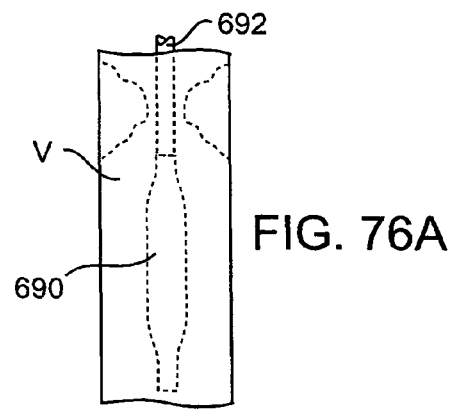
Figure 75B:
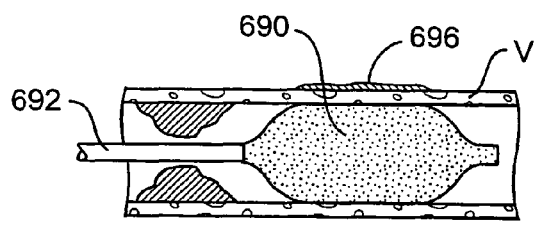
Figure 76B:
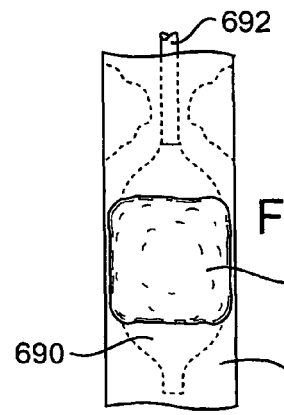
Figure 75C:
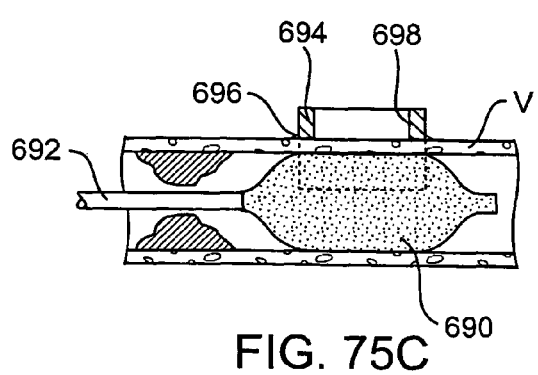
Figure 76C:
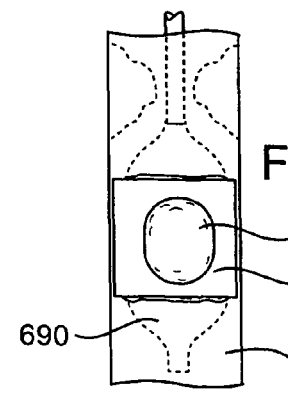
Figure 75D:
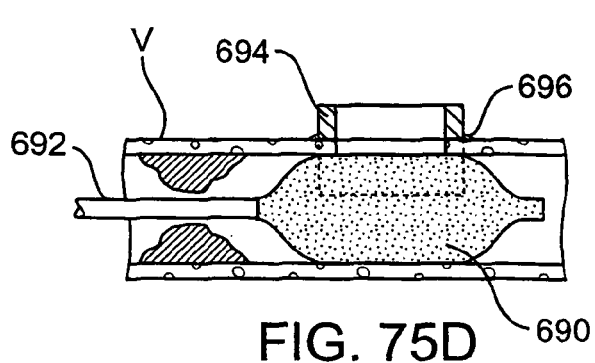
Figure 76D:
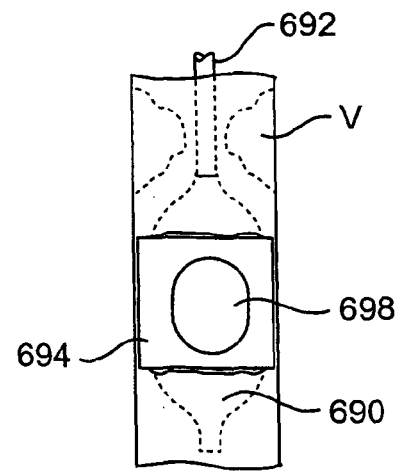
Figure 77:
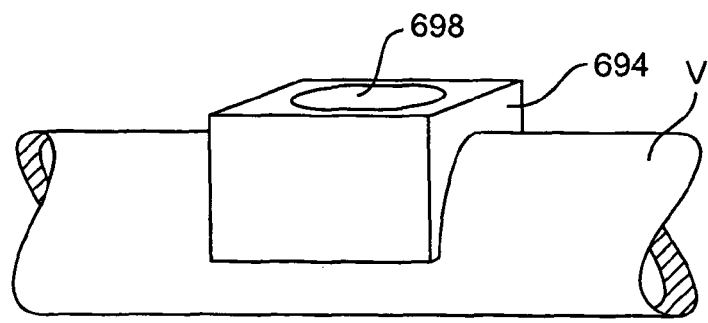
Figure 78A:
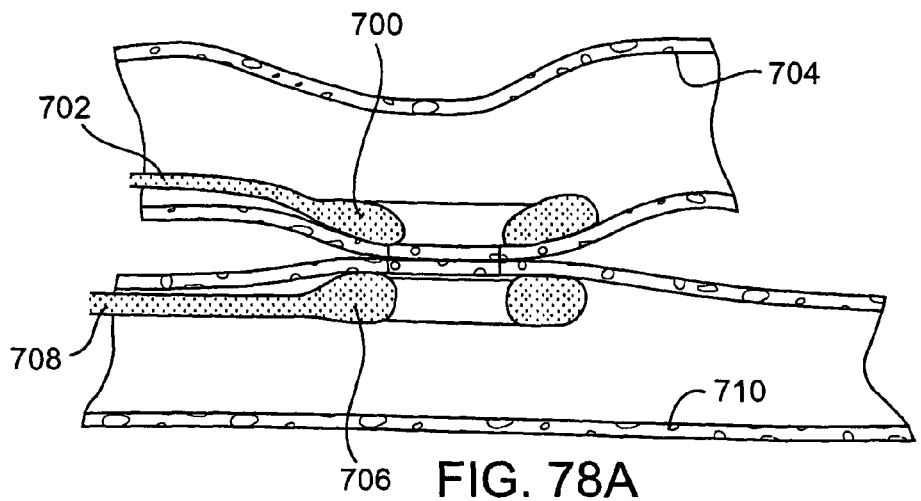
Figure 78B:
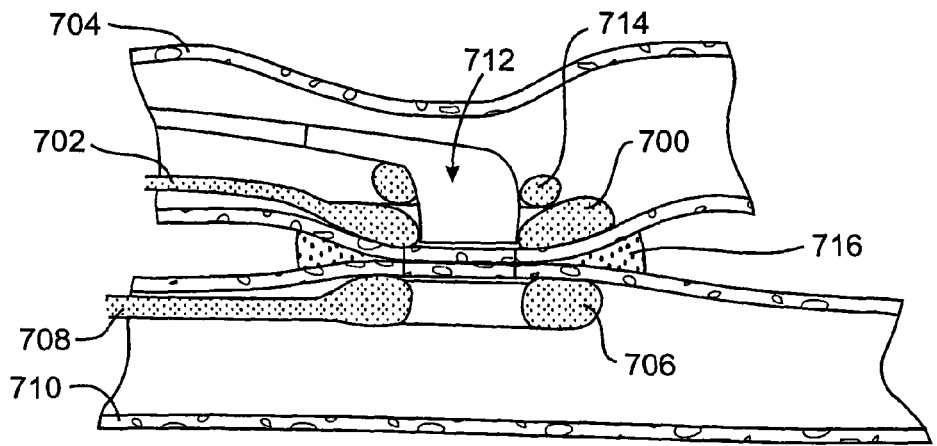
Figure 78C:
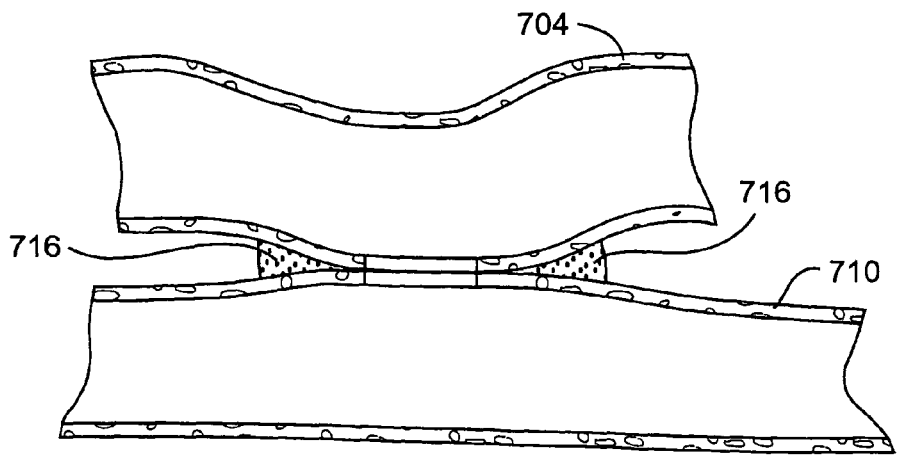
Figure 79A:
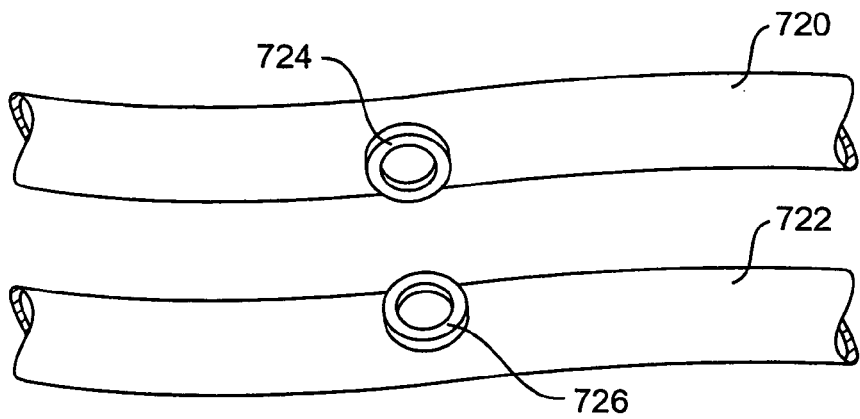
Figure 79B:
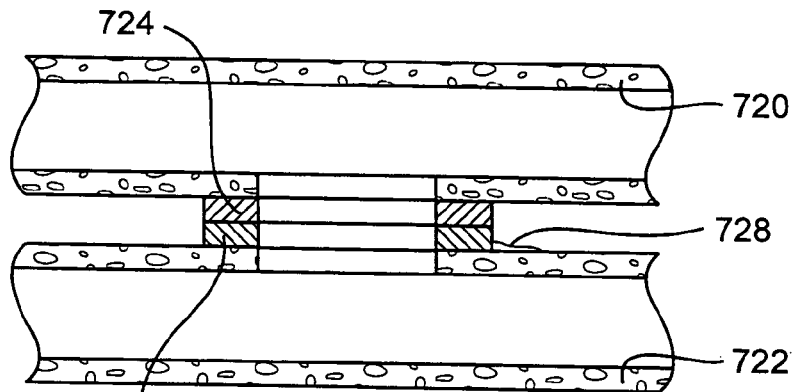
Figure 79C:
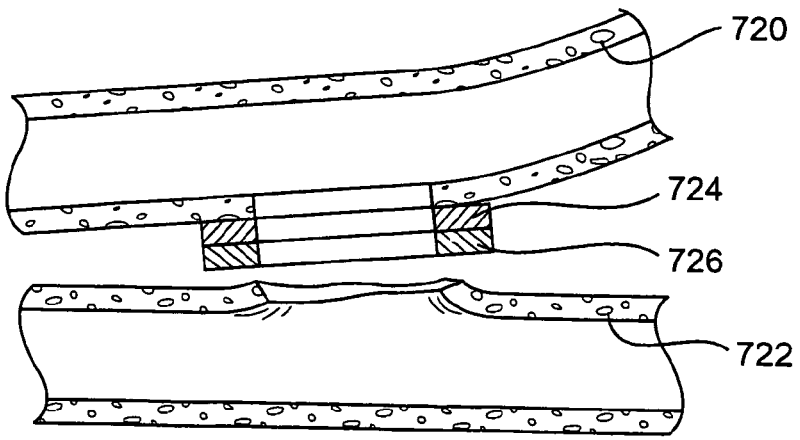
Figure 80A:
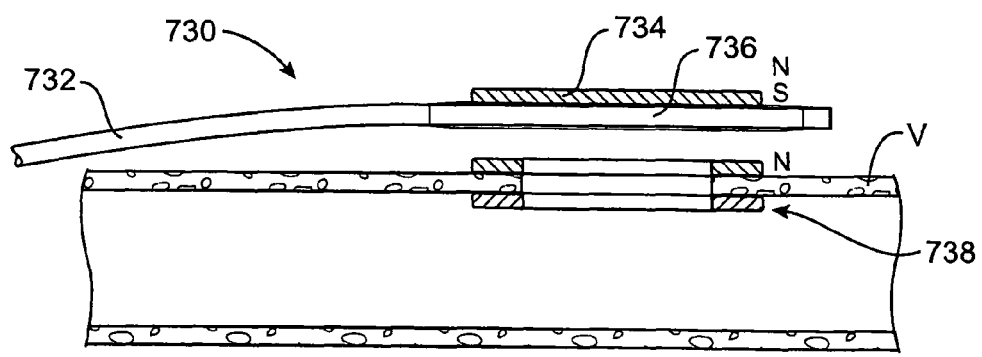
Figure 80B:
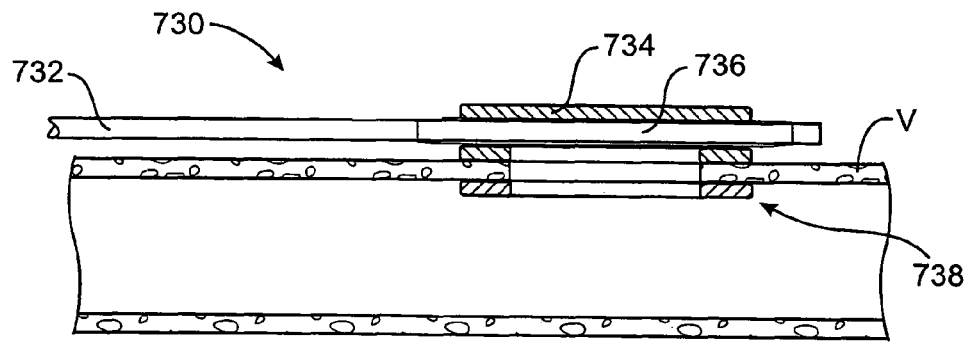
Figure 80C:
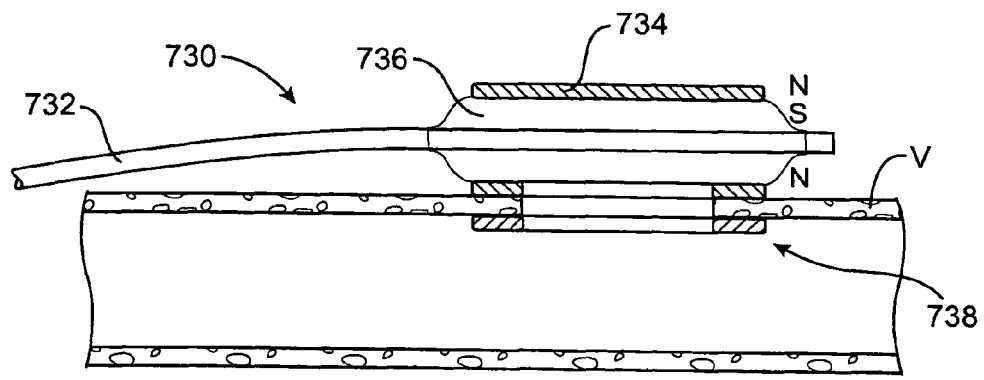
Figure 81A:
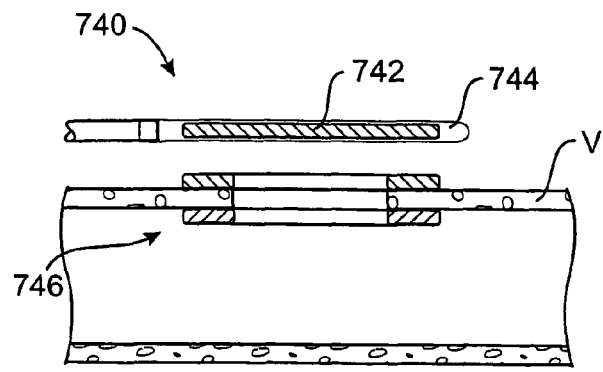
Figure 81B:
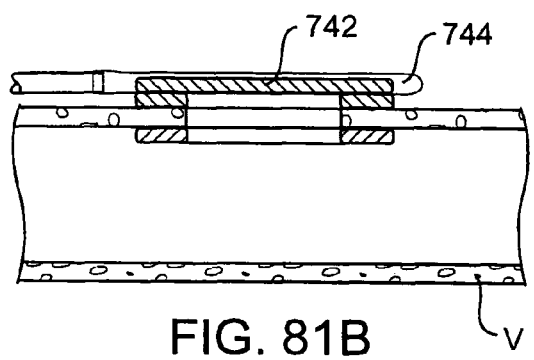
Figure 81C:
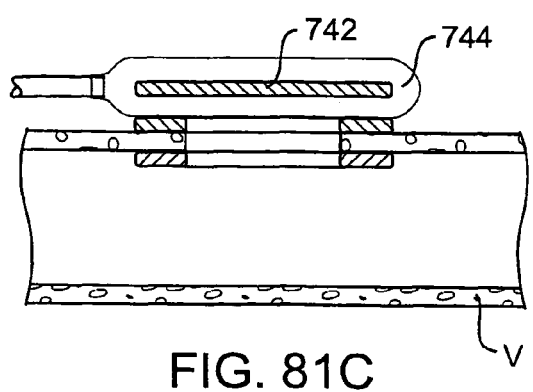
Figure 81D:
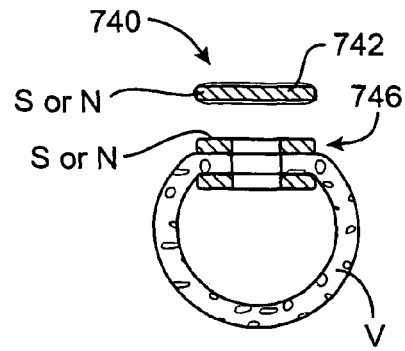
Figure 81E:
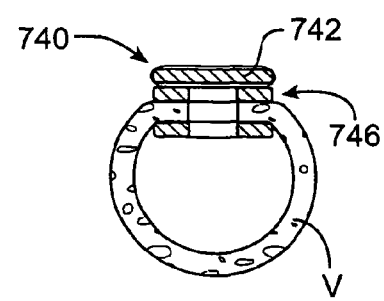
Figure 81F:
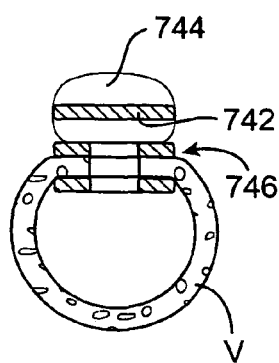
Figure 82A:
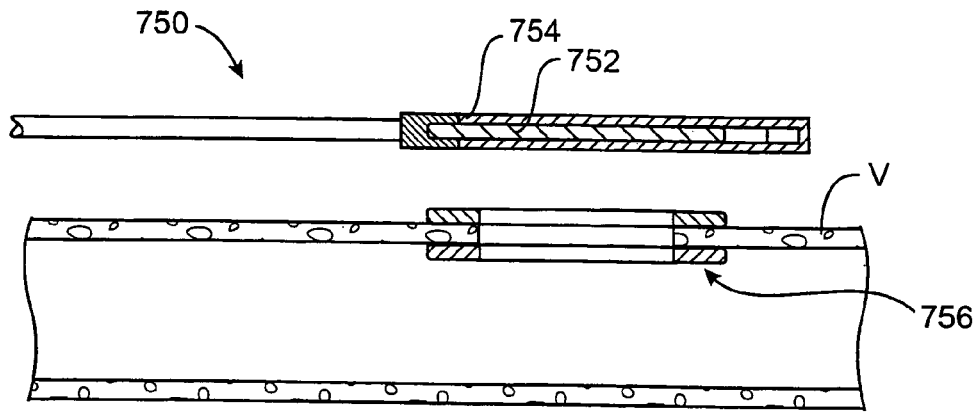
Figure 82B:
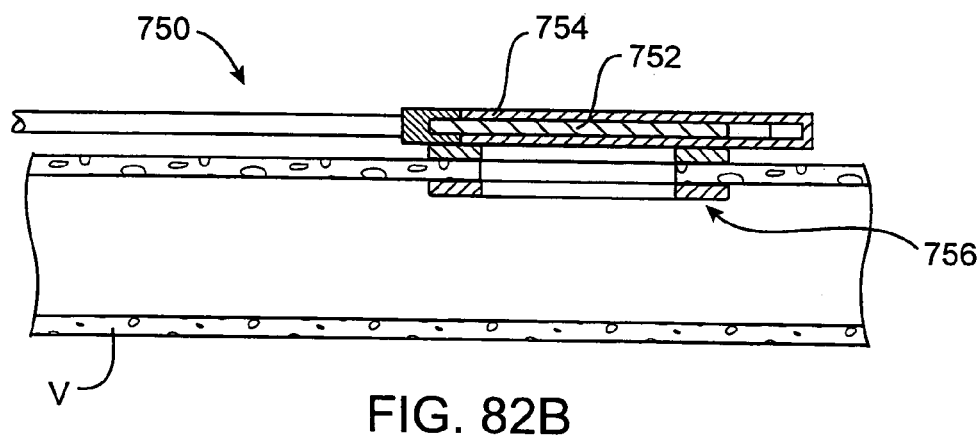
Figure 82C:
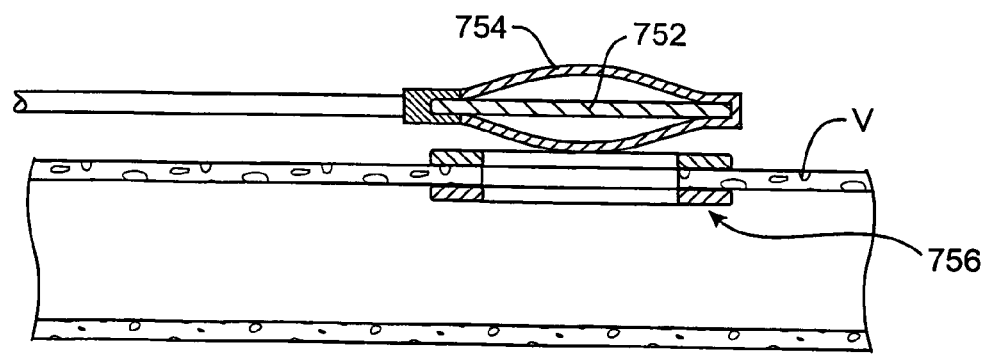
Figure 85A:
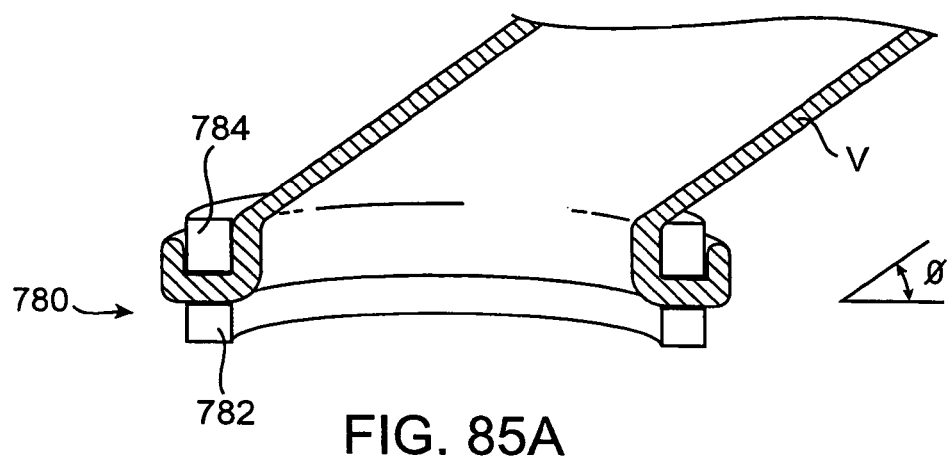
Figure 85B:
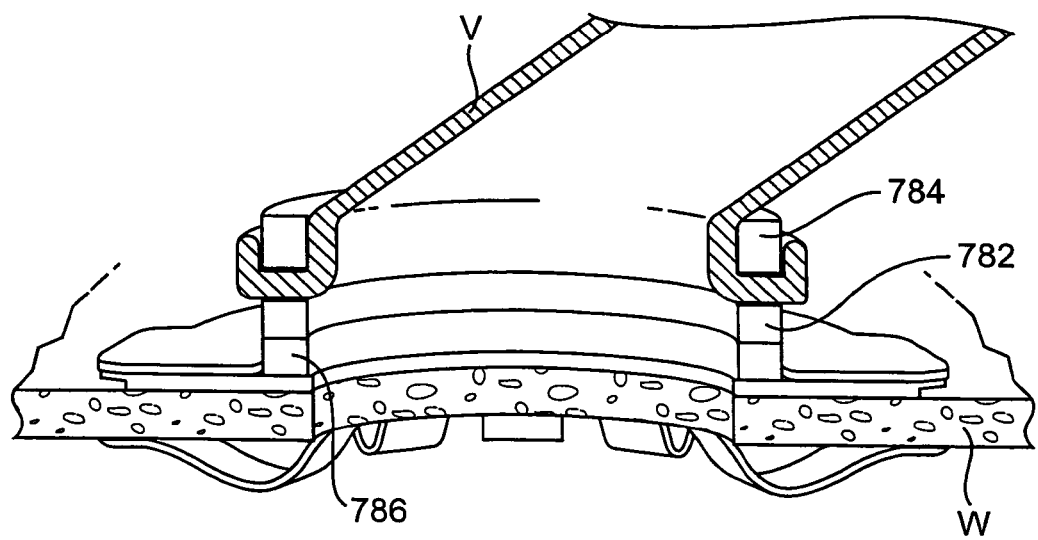
Figure 86A:
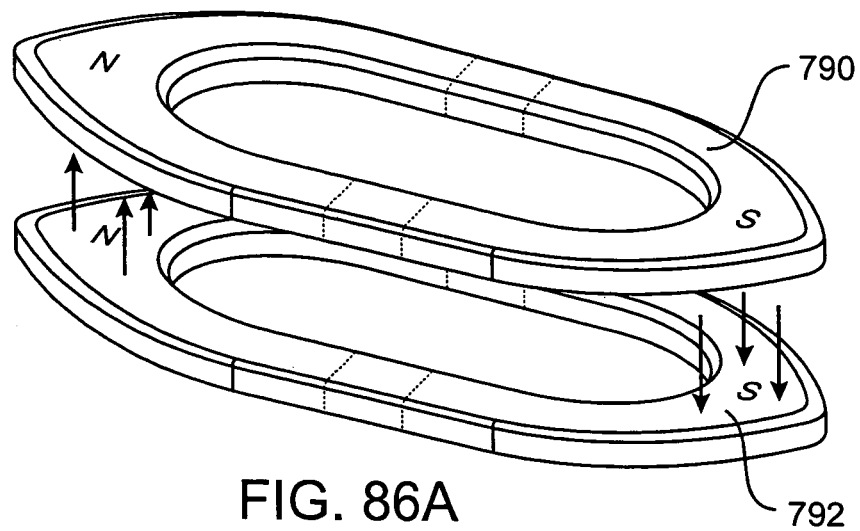
Figure 86B:
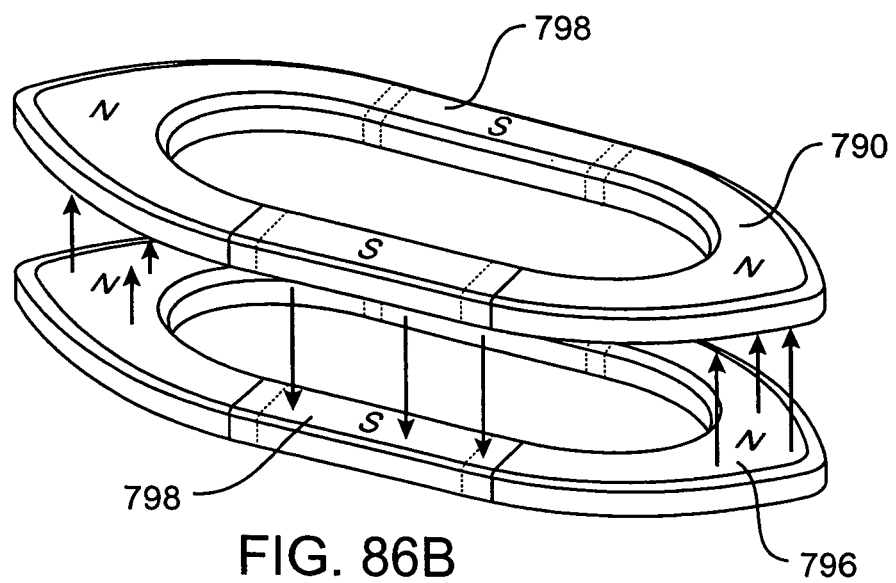
Figure 87:
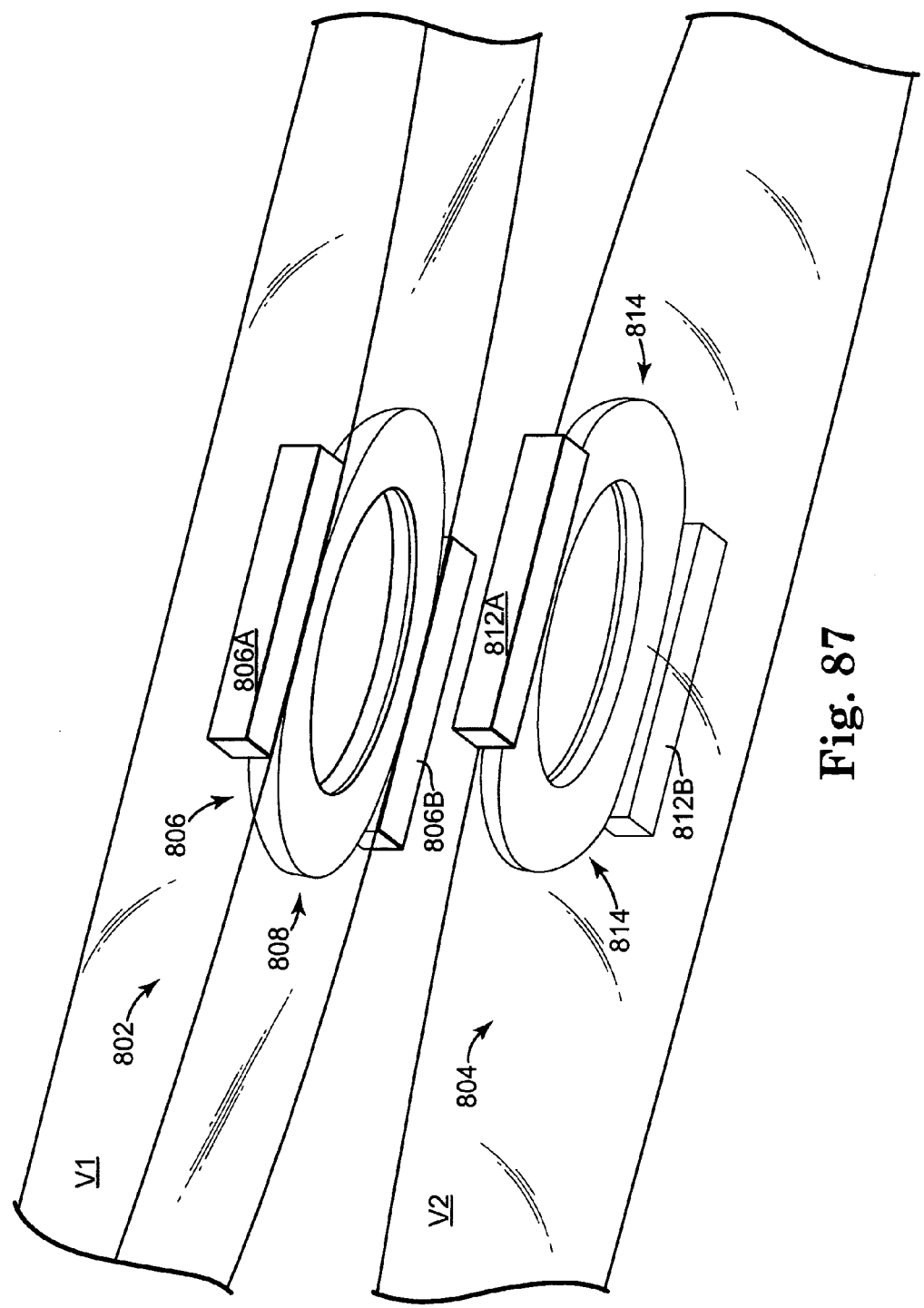
Figure 88:
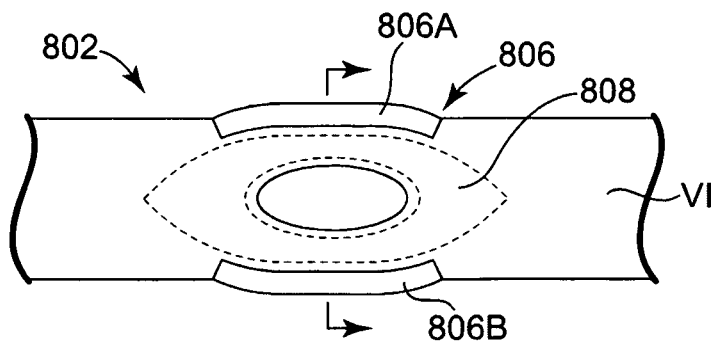
Figure 89:
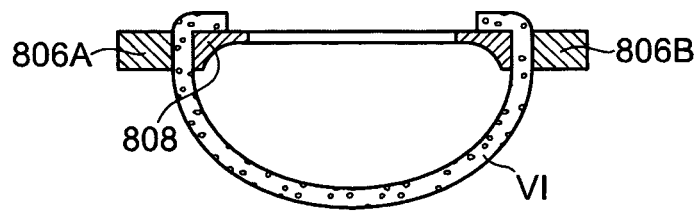
Figure 90:
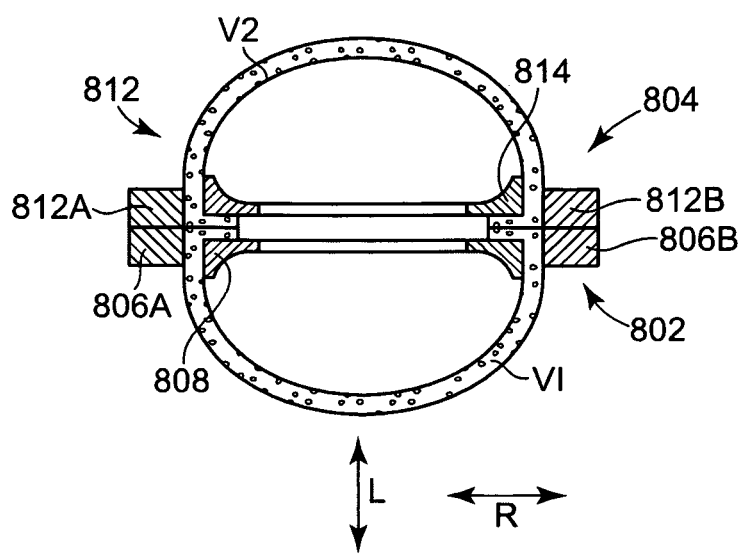
Figure 91:
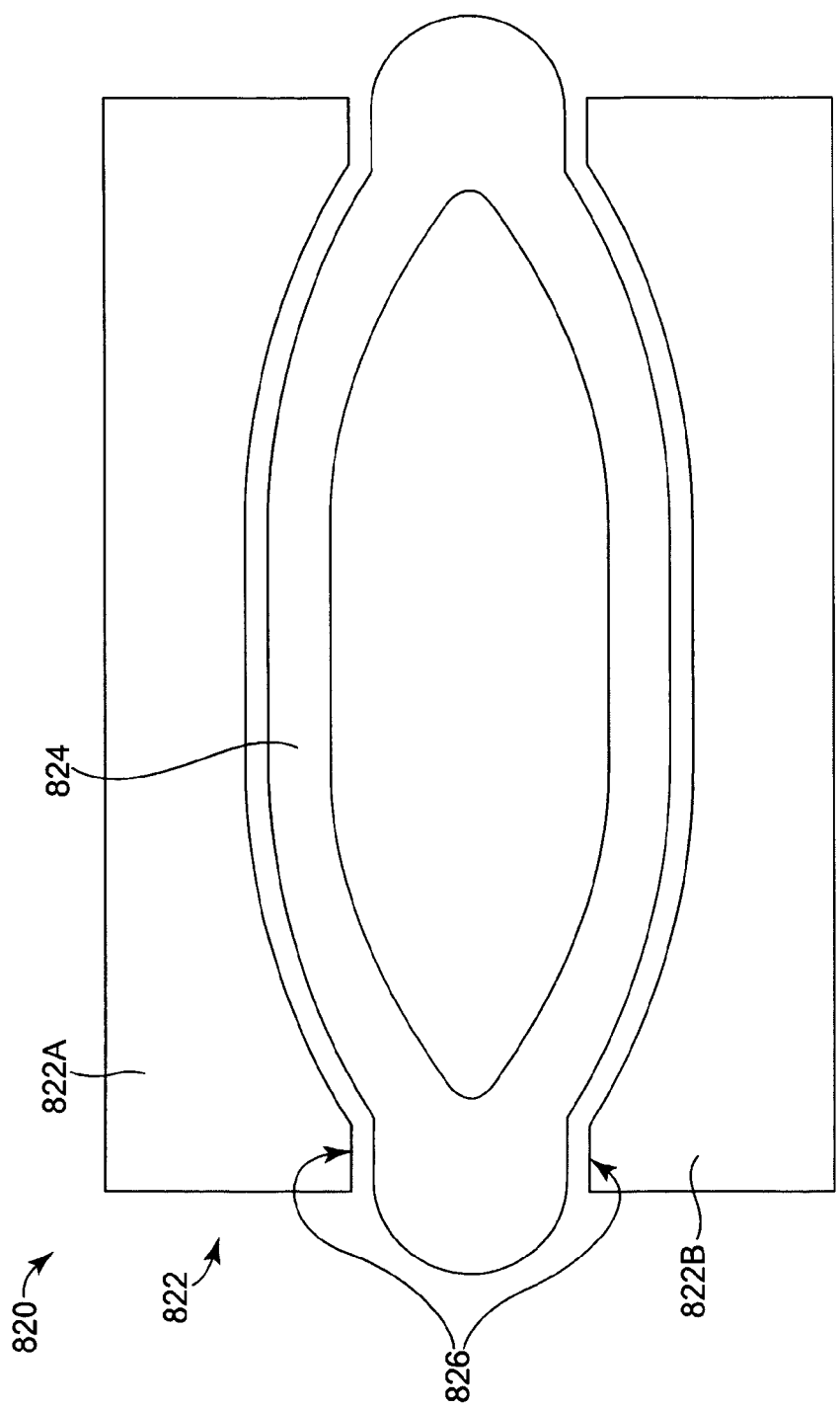
Figure 92:
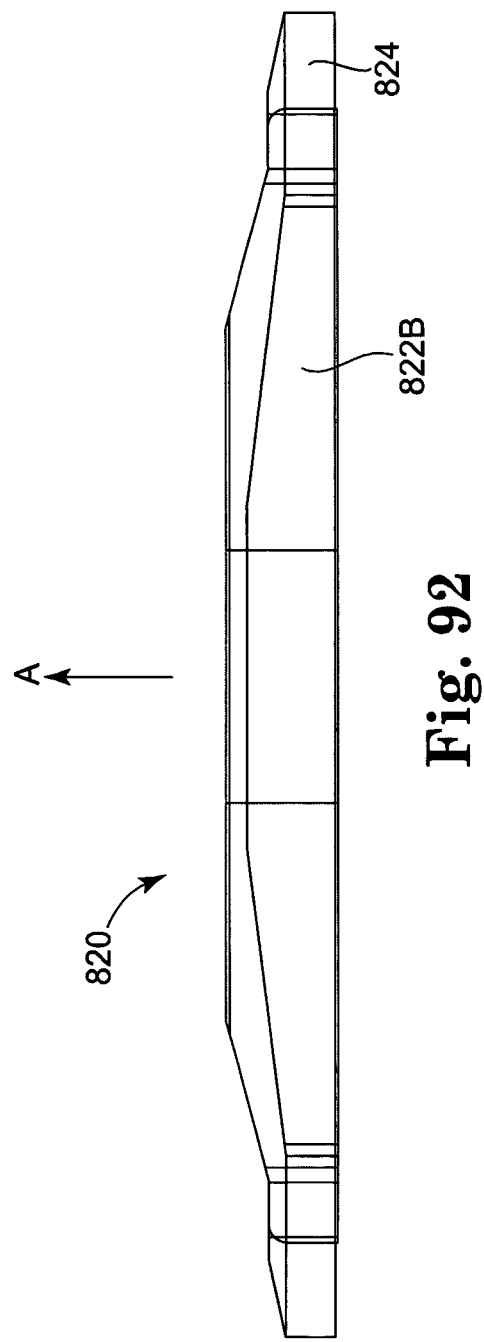
Figure 93:
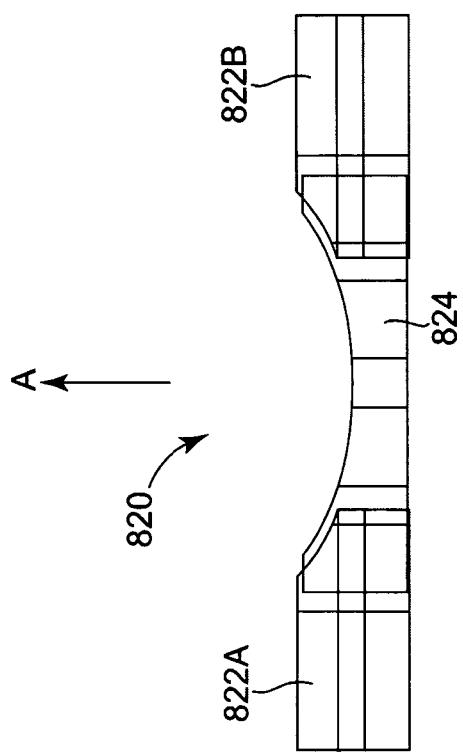
Figure 94:
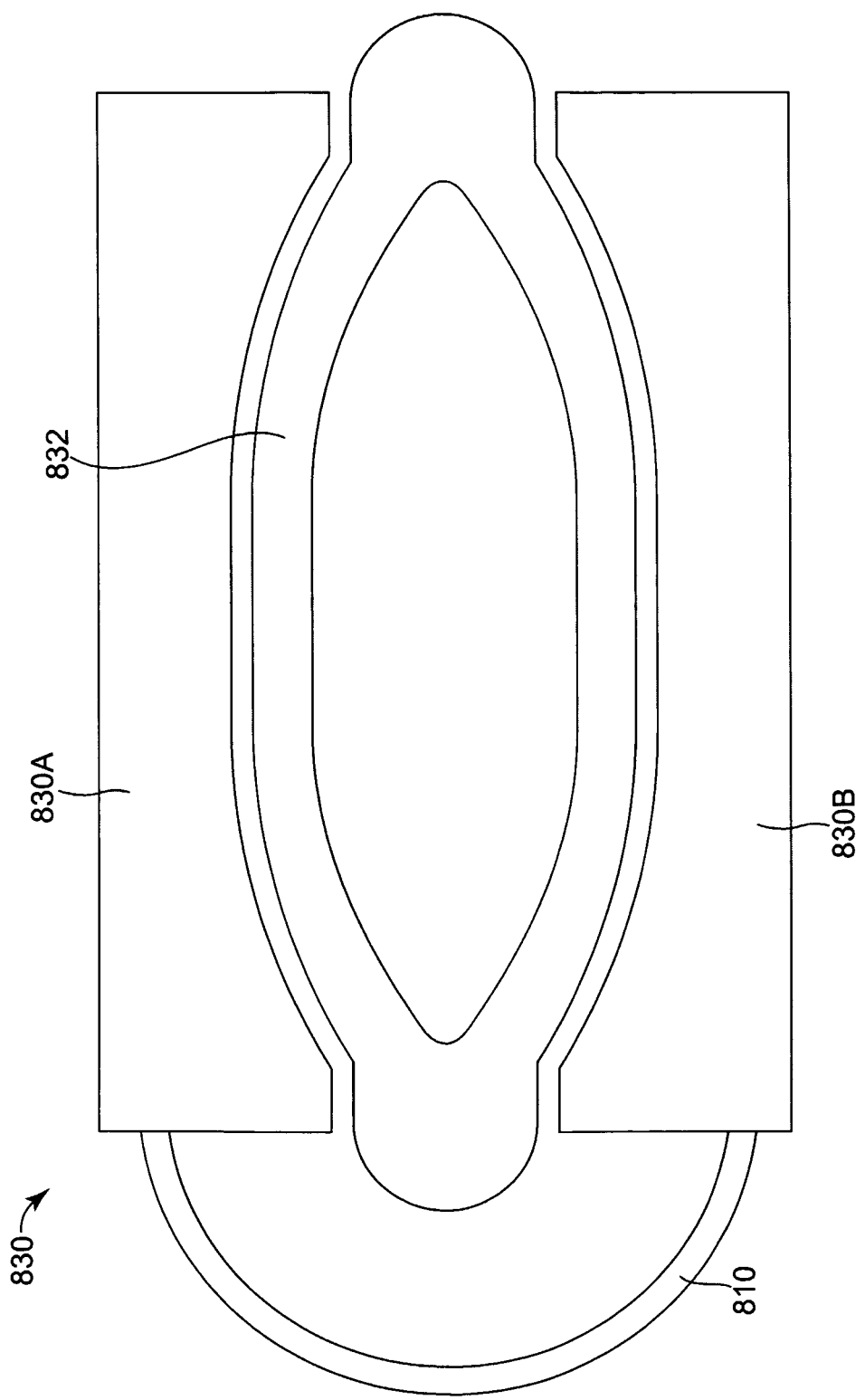
Figure 101:
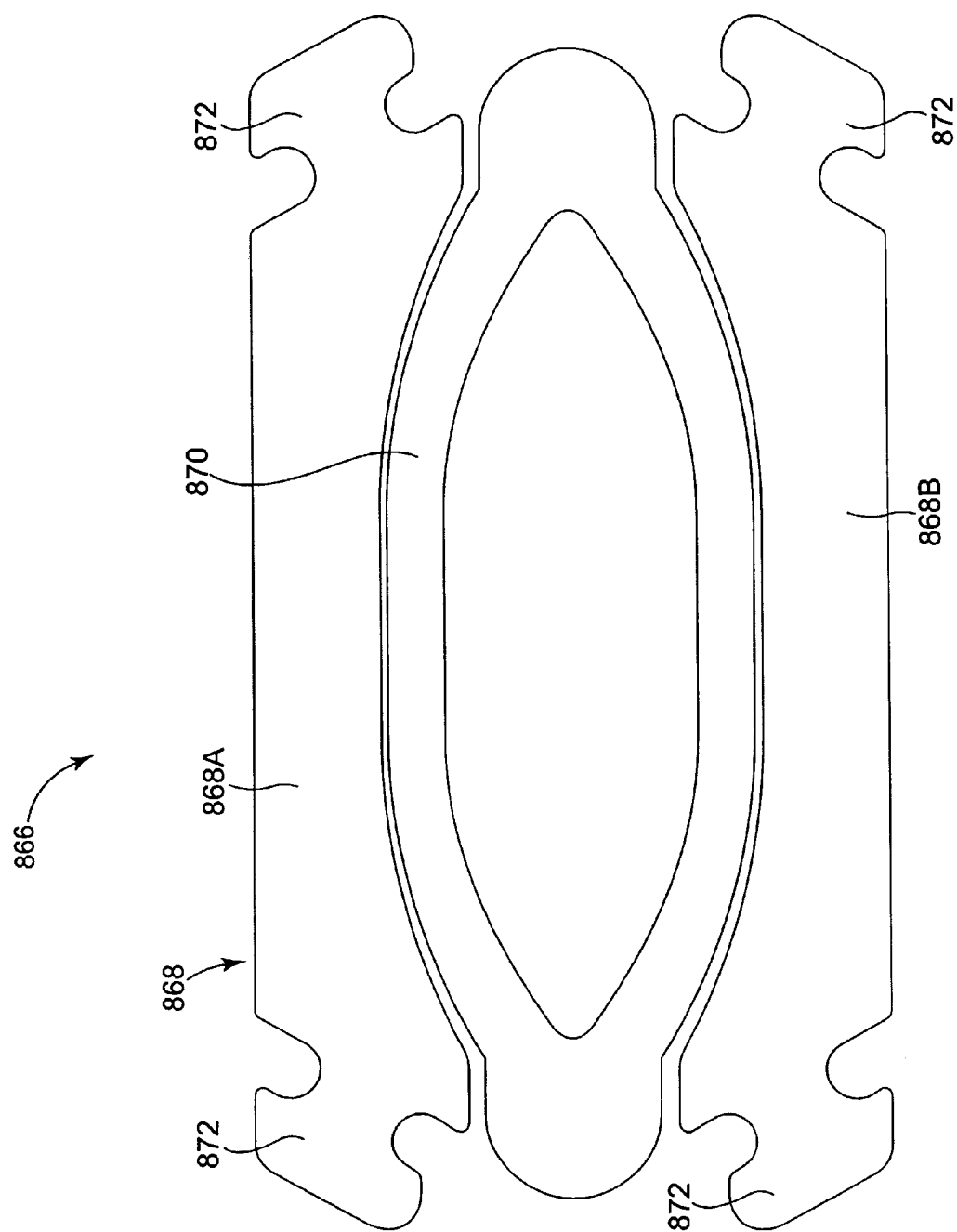
Figure 102:
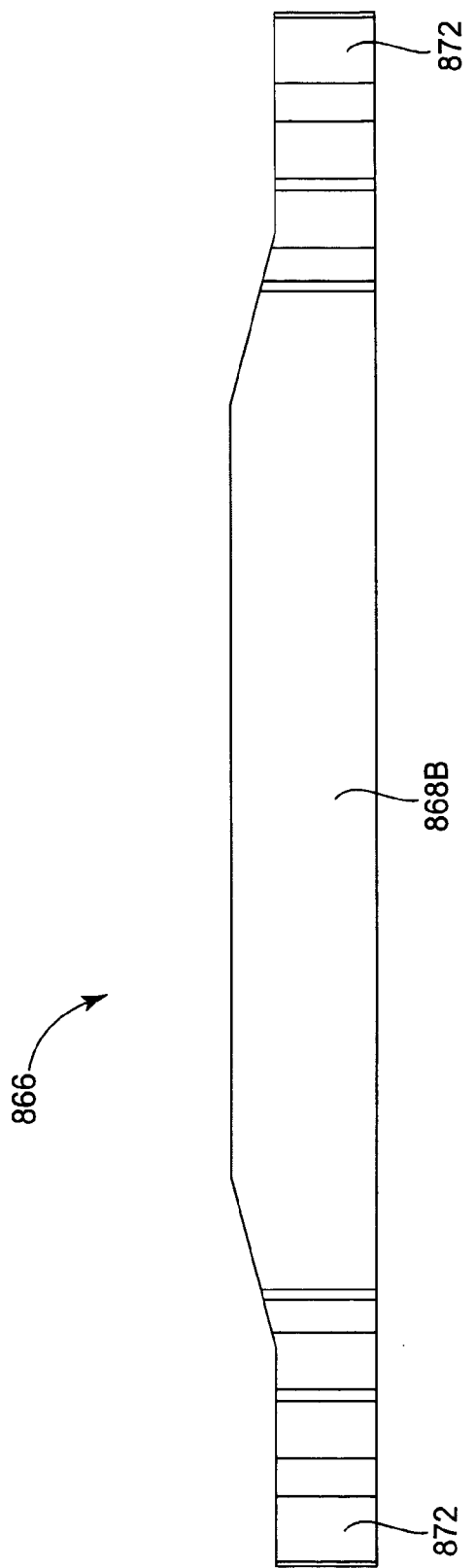
Figure 103:
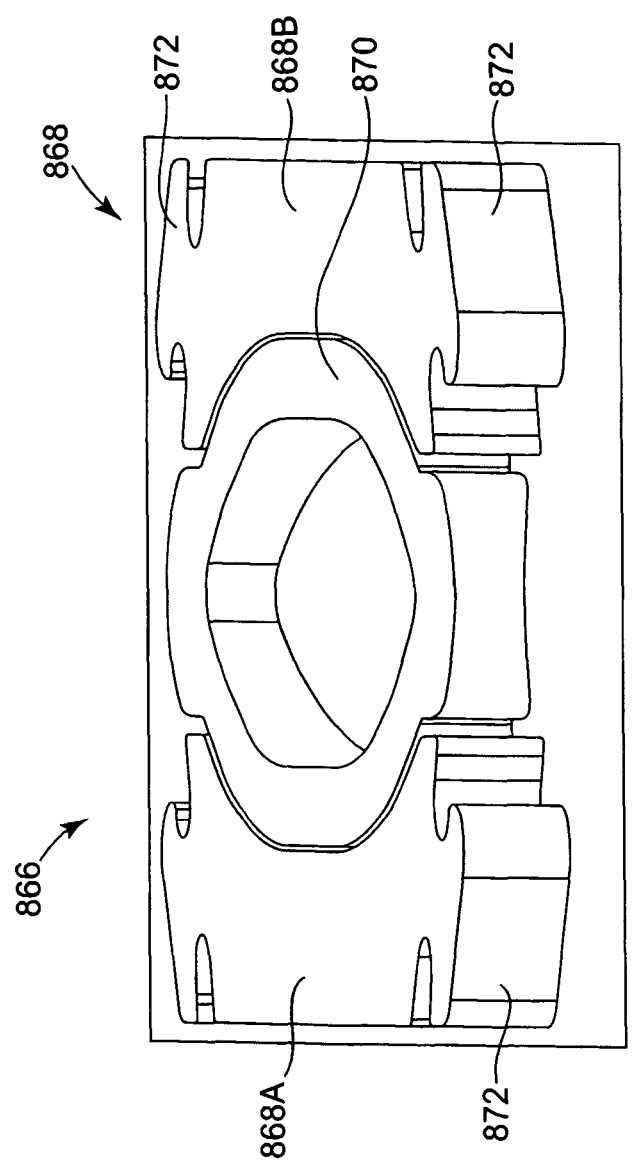
Figure 104:
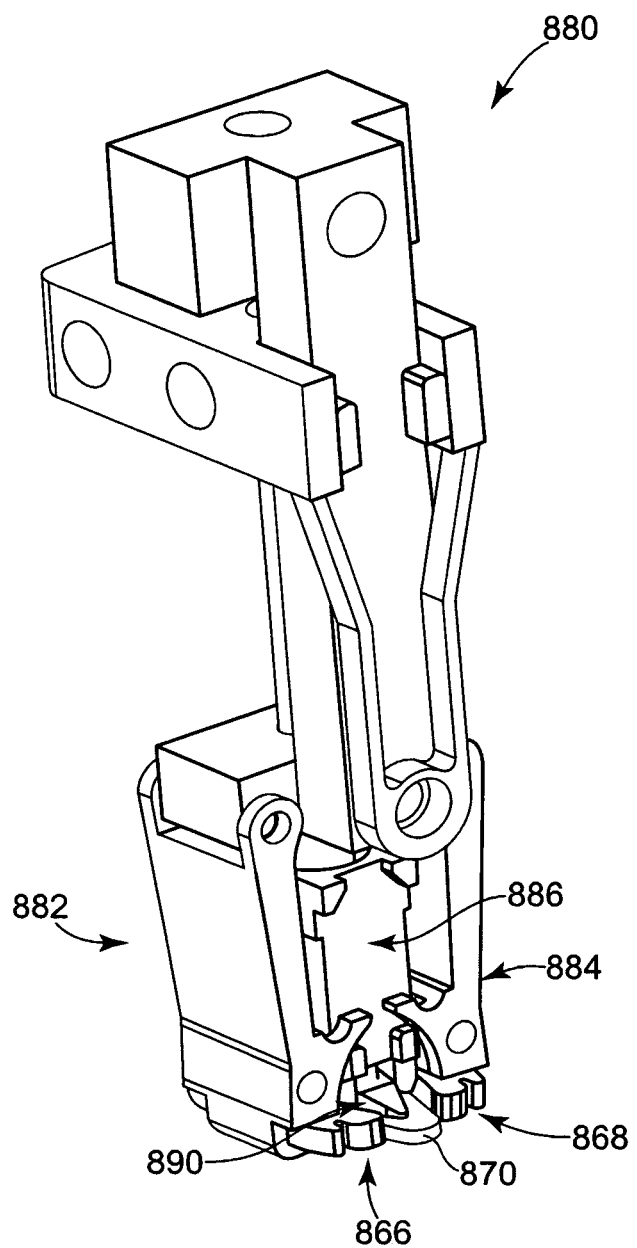
Figure 105:
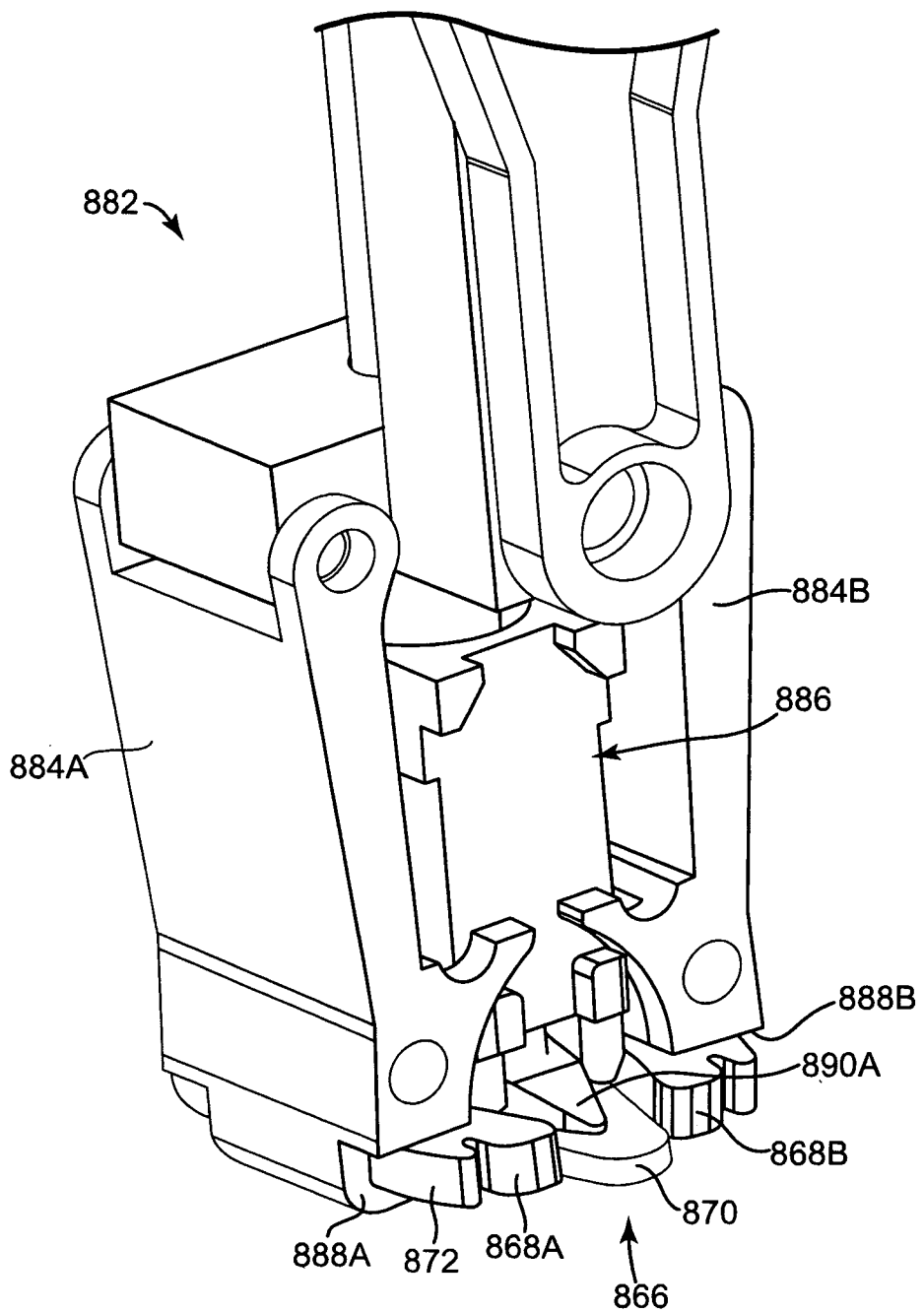
Figure 106:
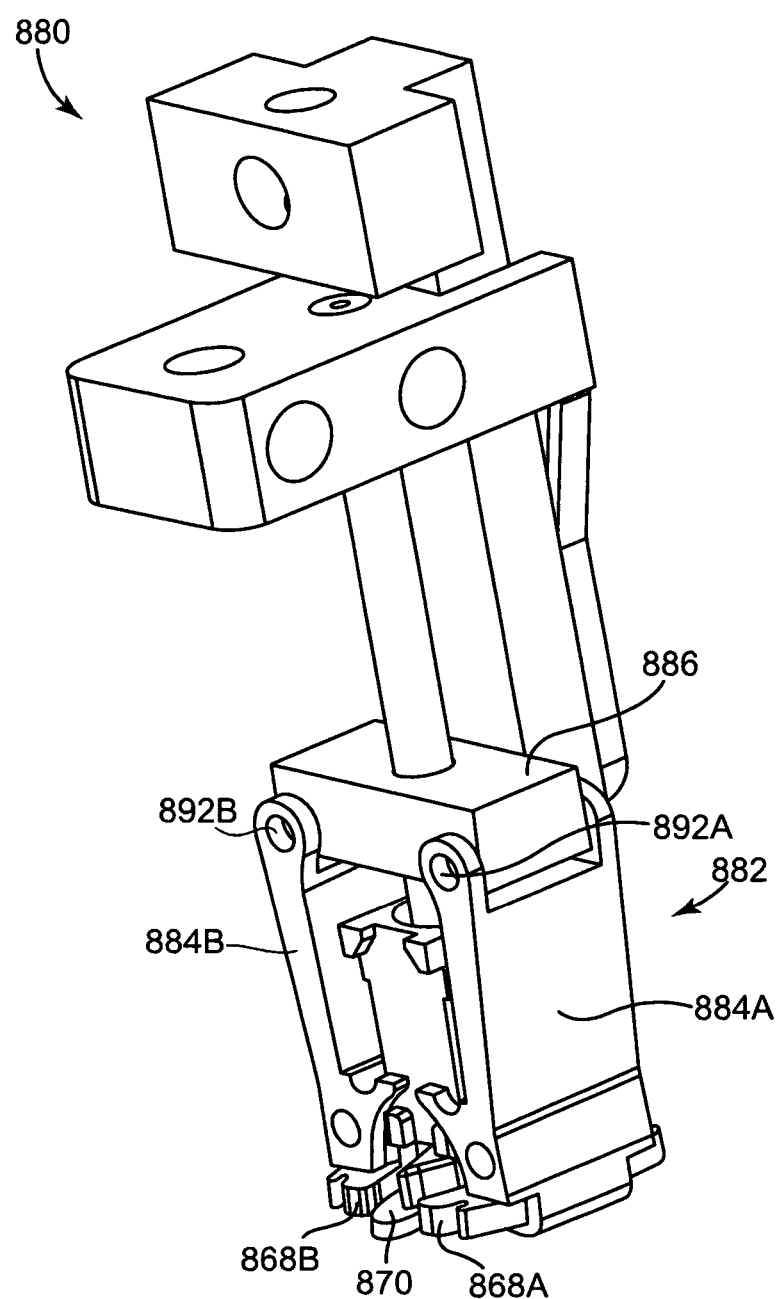
Figure 107:
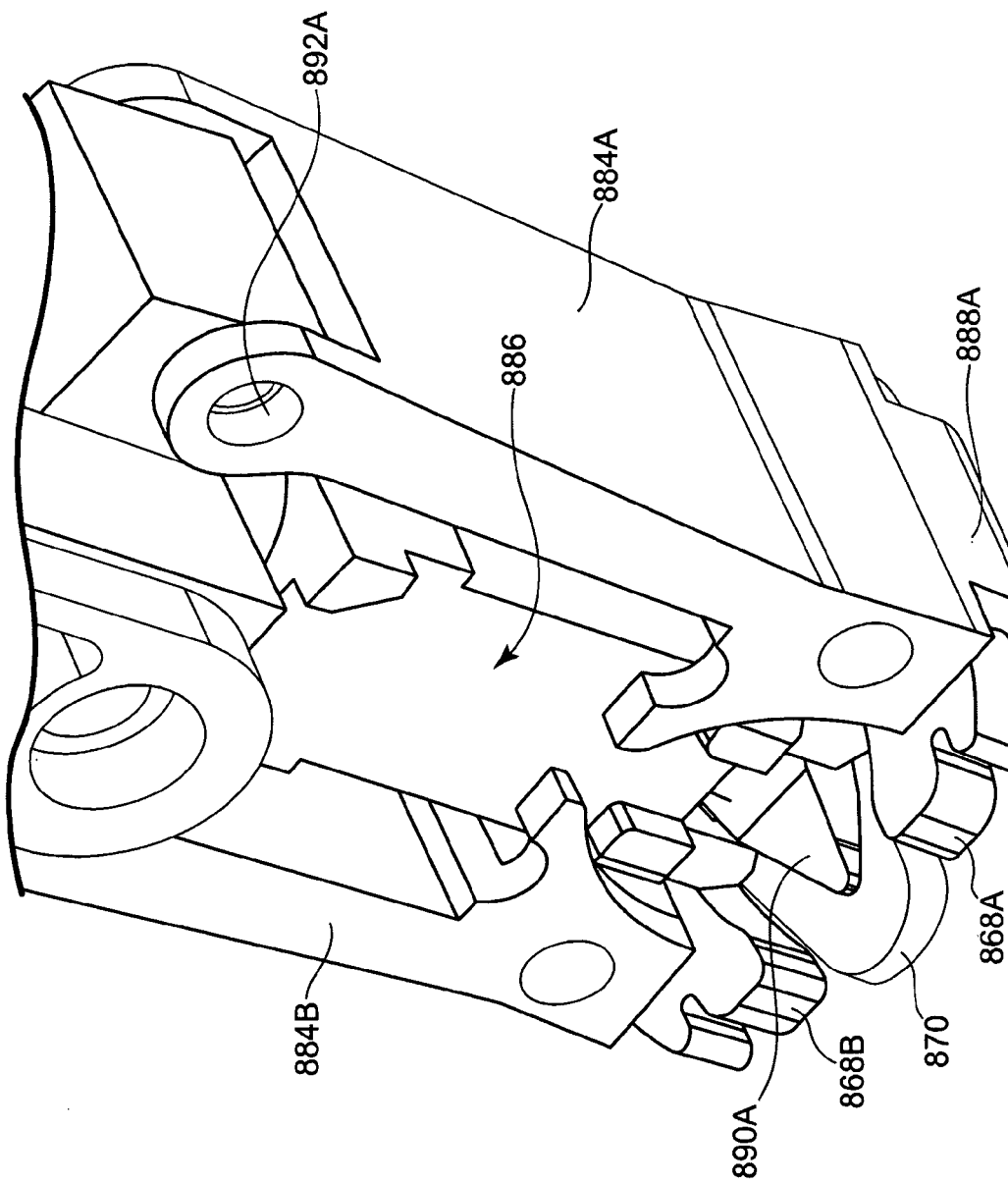
Figure 108:
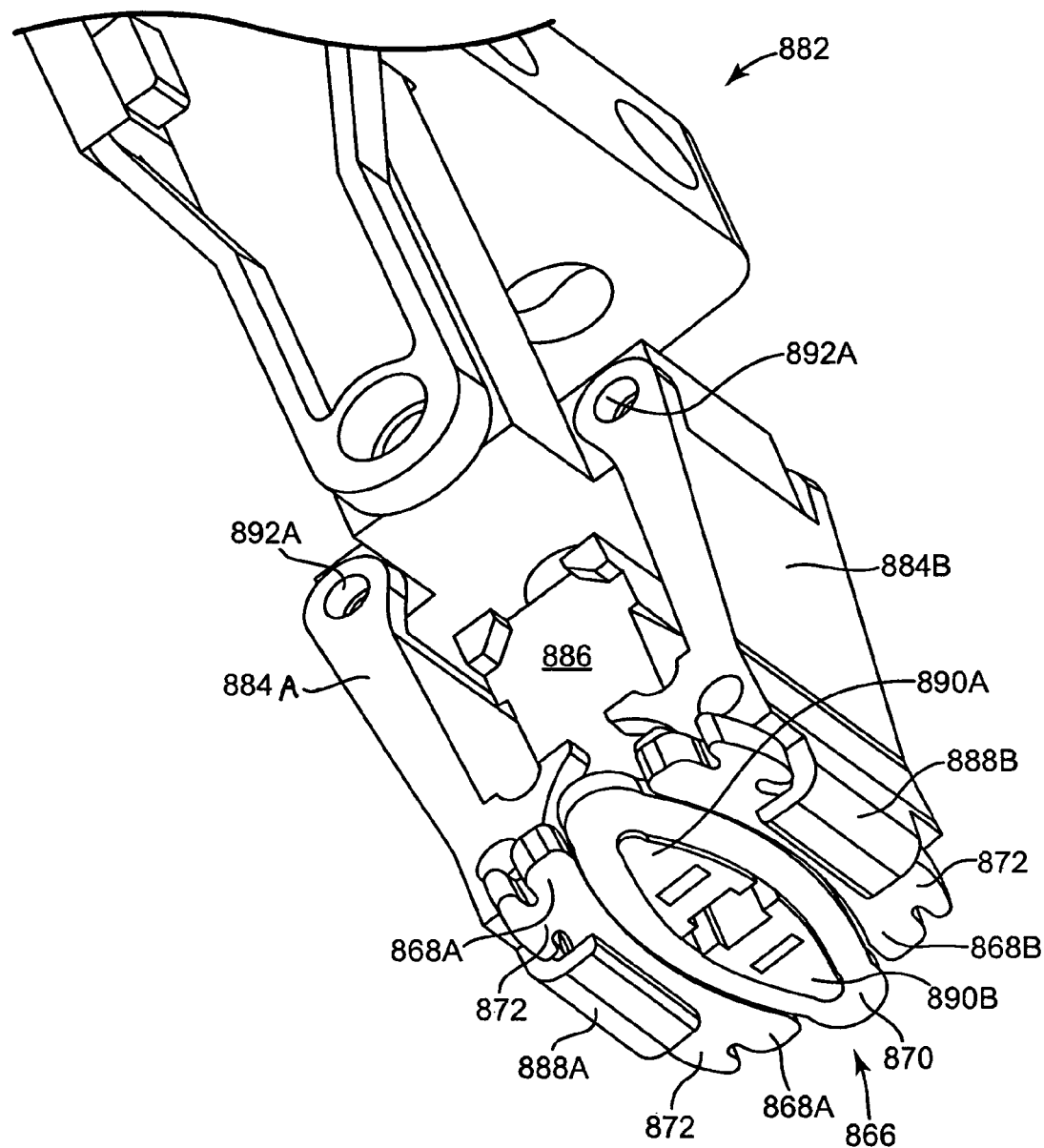
Figure 109:
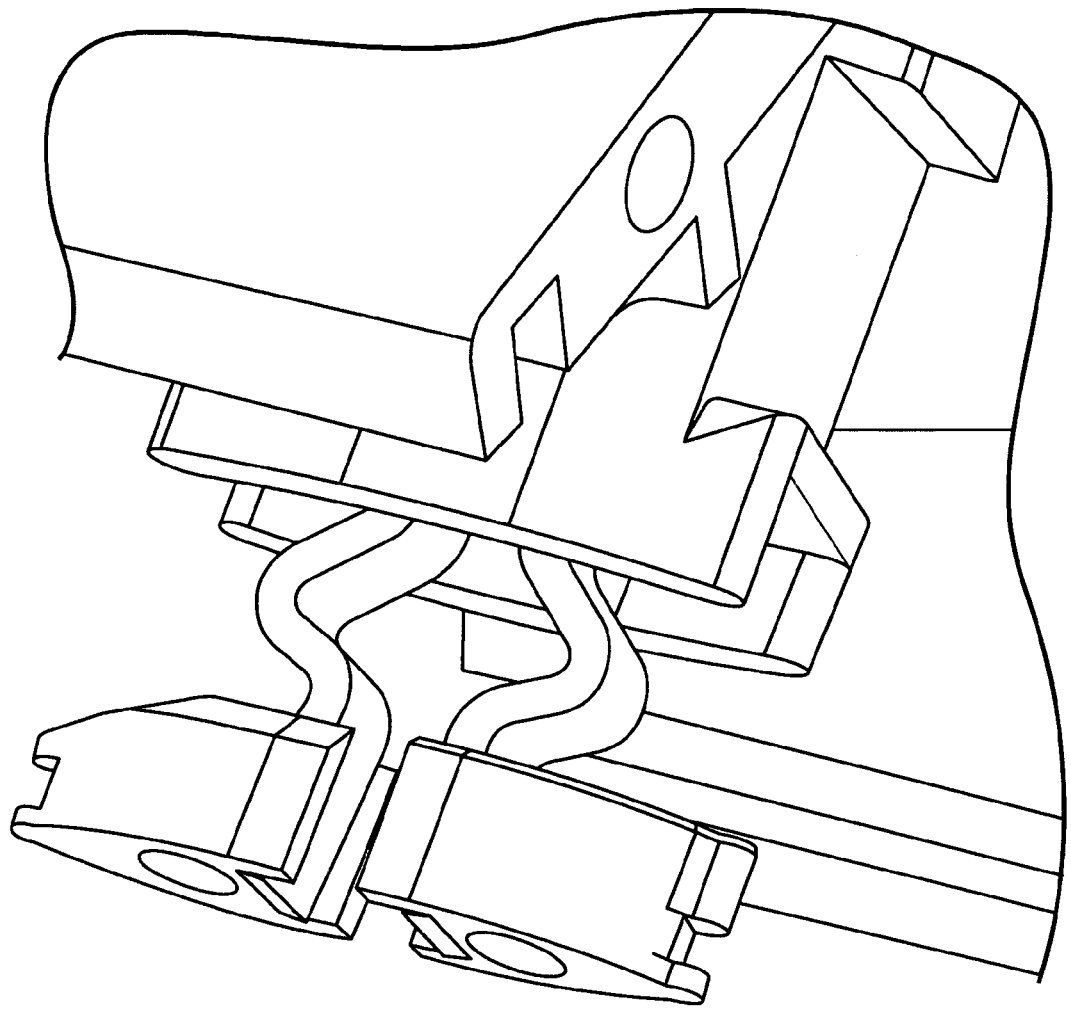
Figure 110:
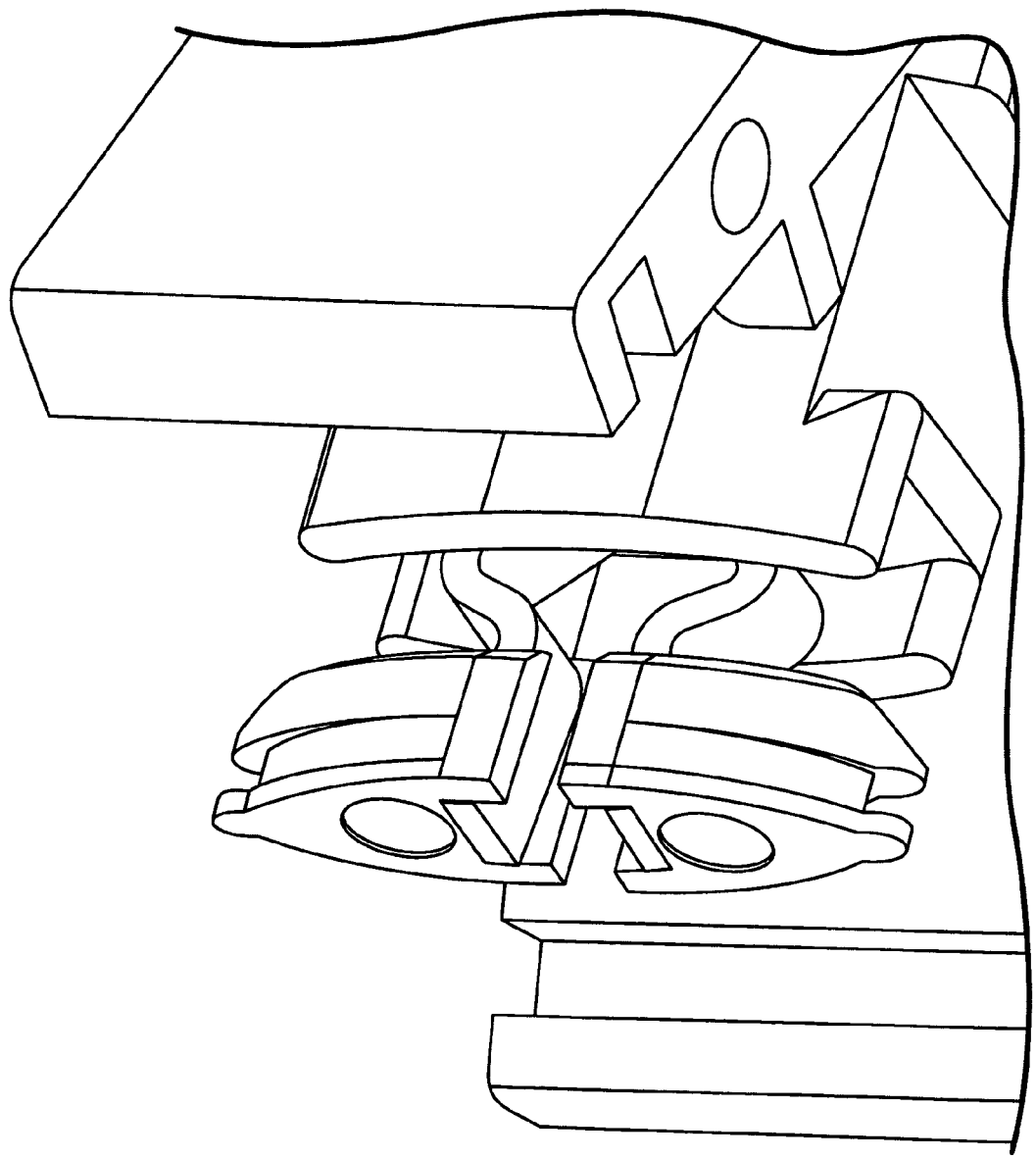

FIGS. 49A-49B are, respectively, exploded and assembled perspective views of a magnetic anastomotic component constructed according to one embodiment of the invention;

FIG. 49C is sectional view taken along line C-C in FIG. 49B;

FIGS. 50A-50B are, respectively, exploded and assembled perspective views of a magnetic anastomotic component constructed according to another embodiment of the invention;

FIGS. 51A-51B are, respectively, exploded and assembled perspective views of a magnetic anastomotic component constructed according to yet another embodiment of the invention;

FIGS. 52A-52C are perspective views sequentially showing the formation of a magnetic anastomotic component constructed according to still another embodiment of the invention;

FIG. 53A is a perspective view of a magnetic anastomotic component including an attachment portion constructed according to one embodiment of the invention;

FIG. 53B is a perspective view of the magnetic anastomotic component shown in FIG. 53A with the attachment portion coupled to a vessel;

FIG. 53C is a perspective view of the magnetic anastomotic component shown in FIG. 53A with the attachment portion coupled to a vessel in an alternative manner;

FIGS. 54A-54D are perspective views of a magnetic anastomotic component including an attachment portion constructed according to another embodiment of the invention;

FIGS. 54E-54F are perspective views showing the magnetic anastomotic component illustrated in FIGS. 54A-54D being secured to a vessel;

FIGS. 55A-55B are, respectively, exploded and assembled perspective views of a magnetic anastomotic component constructed according to one embodiment of the invention;

FIG. 55C is a sectional view taken along line C-C in FIG. 49B;

FIGS. 56A-56B are perspective views showing the anastomotic component illustrated in FIG. 5B being magnetically secured to a vessel;

FIGS. 57A-57B are perspective views showing the anastomotic component illustrated in FIG. 5C being magnetically secured to a vessel;

FIGS. 58A-58C are, respectively, a perspective view and sectional views sequentially showing an anastomotic component constructed according to another embodiment of the invention being secured to a vessel magnetically and mechanically;

FIGS. 59A-59B are, respectively, sectional and perspective views showing an anastomotic component constructed according to another embodiment of the invention being secured to a vessel mechanically;

FIGS. 60A-60B are sectional views showing an anastomotic component constructed according to another embodiment of the invention being secured to a vessel mechanically;

FIG. 60C is a plan view of the anastomotic component shown in FIG. 60B secured to the vessel;

FIGS. 61A-61C are perspective views sequentially showing an anastomotic component constructed according to another embodiment of the invention being secured to a vessel mechanically;

FIGS. 62A-62C are perspective views sequentially showing an anastomotic component constructed according to yet another embodiment of the invention being secured to a vessel mechanically;

FIGS. 63A-63B are side elevation views respectively showing a magnetic anastomotic component constructed according to another embodiment of the invention in restrained and unrestrained configurations;

FIGS. 63C-63D are perspective views showing the magnetic anastomotic component illustrated in FIGS. 63A-63B being secured to a hollow body;

FIG. 64A is a plan view of a magnetic anastomotic component constructed according to another embodiment of the invention secured to a vessel mechanically;

FIG. 64B is a sectional view taken along line B-B in FIG. 64A;

FIG. 65A is a plan view of a magnetic anastomotic component constructed according to yet another embodiment of the invention secured to a vessel mechanically;

FIG. 65B is a sectional view taken along line B-B in FIG. 65A;

FIGS. 66A-66C are perspective views sequentially showing a delivery device being used to mechanically secure a magnetic anastomotic component constructed according to another embodiment of the invention to a vessel;

FIG. 67A is an elevation view of a magnetic anastomotic component constructed according to another embodiment of the invention;

FIGS. 67B-67C are sectional views showing the component illustrated in FIG. 67A secured to, respectively, an end and side wall of a vessel;

FIGS. 68A-68B are sectional views showing magnetic anastomotic components constructed according to alternative embodiments of the invention being adhesively secured to a vessel;

FIGS. 69A-69B are perspective views sequentially showing a magnetic anastomotic component constructed according to another embodiment of the invention being adhesively secured to a vessel;

FIG. 70 is a perspective view of a magnetic anastomotic component constructed according to yet another embodiment of the invention to a vessel;

FIGS. 71A-71D show an internal magnet being used to align an outer magnet;

FIGS. 72A-72F are perspective views sequentially showing a magnetic anastomotic component constructed according to another embodiment of the invention being adhesively secured to an end of a vessel;

FIGS. 73A-73D are sectional views sequentially showing a magnetic anastomotic being adhesively secured to the wall of a vessel according to another embodiment of the invention;

FIGS. 74A-74D are sectional views sequentially showing a magnetic anastomotic being adhesively secured to the wall of a vessel according to still another embodiment of the invention;

FIGS. 75A-75D are sequential sectional views showing a magnetic anastomotic being adhesively secured to the wall of a vessel according to one embodiment of the invention;

FIGS. 76A-76D are sequential plan views corresponding to FIGS. 75A-75D;

FIG. 77 is a perspective view corresponding to FIGS. 75D and 76D;

FIGS. 78A-78C are sectional views sequentially showing the creation of a side-to-side anastomosis using magnetism according to another embodiment of the invention;

FIG. 79A is a perspective view of two vessels provided with respective anastomotic components;

FIG. 79B is a sectional view showing the two vessels joined by a side-to-side anastomosis;

FIG. 79C is a sectional view of the anastomosis shown in FIG. 79B illustrating one of the components being separated from its associated vessel;

FIGS. 80A-80C are sectional views illustrating a device constructed according to one embodiment of the invention being used to check the seal at a junction between an anastomotic component and a vessel;

FIGS. 81A-81C are sectional views illustrating a device constructed according to another embodiment of the invention being used to check the seal at a junction between an anastomotic component and a vessel;

FIGS. 81D-81F are transverse sectional views of the device illustrated in FIGS. 81A-81C;

FIGS. 82A-82C are sectional views illustrating a device constructed according to yet another embodiment of the invention being used to check the seal at a junction between an anastomotic component and a vessel;

FIGS. 83A-83B are, respectively, front and side elevation views of a device constructed according to one embodiment of the invention for confirming proper orientation of a magnetic anastomotic component, the component being shown correctly mounted on a delivery device;

FIGS. 84A-84B are, respectively, front and side elevation views of the device shown in FIGS. 83A-83B showing the magnetic anastomotic component incorrectly mounted on the delivery device;

FIG. 85A is a sectional view of a magnetic anastomotic component constructed according to another embodiment of the invention attached to a vessel in an angled fashion;

FIG. 85B is a sectional view of an anastomosis formed between the vessel and magnetic anastomotic component of FIG. 85A and a second component secured to a second vessel;

FIG. 86A is a perspective view of a two-pole magnetic anastomotic component constructed according to one embodiment of the invention; and FIG. 86B is a perspective view of a three-pole magnetic anastomotic component constructed according to another embodiment of the invention;

FIG. 87 is a perspective view showing first and second anastomotic components constructed according to another embodiment of the invention, the components being secured to first and second vessels, respectively;

FIG. 88 is an upper plan view showing the second component and vessel of FIG. 87;

FIG. 89 is a transverse sectional view taken along a line connecting the arrows shown in FIG. 88;

FIG. 90 is a transverse sectional view showing the first and second anastomotic components coupled together to form an anastomosis between the first and second vessels;

FIGS. 91-93 are, respectively, plan, side elevation and end elevation views of an anastomotic component constructed according to yet another embodiment of the invention, the component including a first, intravascular part and a second, extravascular part, the second part having two portions;

FIG. 94 shows the anastomotic component of FIG. 91 modified to include a connection between the two portions of the second, extravascular part of the component;

FIGS. 95-100 show various alternative cross-sectional profiles which may be incorporated into the two portions of the second, extravascular part of the anastomotic component;

FIG. 101 is a plan view of an anastomotic component constructed according to another embodiment of the invention which is similar to the embodiment shown in FIGS. 91-94, but includes securing tabs on the two portions of the second, extravascular part of the component;

FIG. 102 is a side elevation view of the anastomotic component shown in FIG. 101;

FIG. 103 is a perspective view of the anastomotic component shown in FIGS. 101 and 102;

FIG. 104 is a perspective view of a delivery device constructed according to one embodiment of the invention for securing the inventive anastomotic components to a vessel;

FIG. 105 is an enlarged view of the distal end of the delivery device shown in FIG. 104, wherein an anastomotic component of the invention is shown mounted on the device;

FIG. 106 is a perspective view of the delivery device shown in FIGS. 104 and 105, viewed from a different direction;

FIG. 107 is an enlarged view of the distal end of the delivery device as shown in FIG. 106 with the anastomotic component mounted thereon;

FIG. 108 is a bottom perspective view of the delivery device shown in FIGS. 104-107, wherein the two portions of the second part of the anastomotic component are spaced apart from the first part of the component;

FIG. 109 is an additional bottom perspective view of the delivery device and anastomotic component; and FIG. 110 is a bottom perspective view of the delivery device with the two portions of the second part of the anastomotic component moved from the position of FIG. 108 to a position adjacent the first part of the component.

DETAILED DESCRIPTION OF PREFERRED EMBODIMENTS

Figure 1:
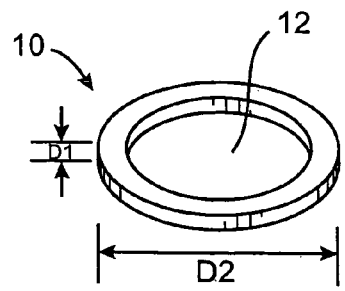
FIGS. 1-5 are perspective views of anastomotic securing components constructed according to various embodiments of the invention.

FIGS. 1-5 illustrate several exemplary embodiments of anastomotic securing components constructed according to the invention for use in forming an anastomosis between first and second hollow bodies. FIG. 1 shows a securing component 10 with an annular body and an opening 12 defined by the body. The component 10 is generally plate-shaped and circular in plan view with a constant (or substantially constant) thickness and width around its perimeter. The securing component 10 is sized and configured to be placed adjacent an opening of a first hollow body that has been prepared for anastomosis to a second hollow body. A second securing component would be placed adjacent an opening of the second hollow body for making the anastomotic connection.

Figure 2:
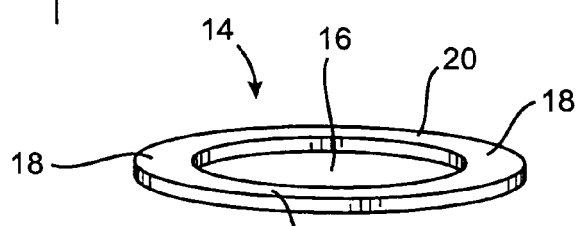
Figure 3:
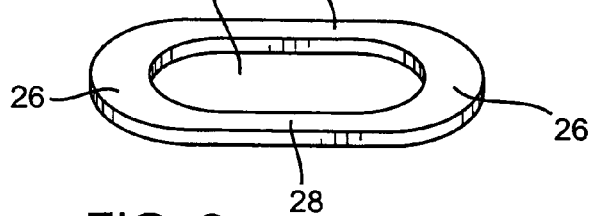
Figure 4:
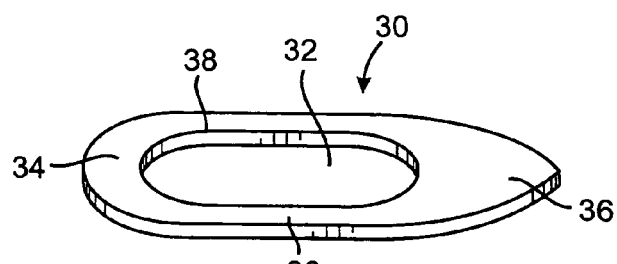

FIG. 2 shows an elliptical anastomotic securing component 14 with an opening 16. The securing component 14 is generally plate-shaped and the opening 16 is configured to provide the securing component 14 with larger end portions 18 than side portions 20. FIG. 3 shows a racetrack-shaped securing component 22 with an opening 24. As in securing component 14, the opening 24 provides securing component 22 with larger end portions 26 than side portions 28. FIG. 4 shows a securing component 30 with an opening 32, two end portions 34, 36 and two side portions 38. The securing component 30 has a generally racetrack-shaped configuration; however, the end portion 36 is larger than the end portion 34 which provides the component 30 with an asymmetric configuration. Stated otherwise, the opening 32 is not centrally located with respect to the body of the component 30, unlike the openings 12, 16 and 24 of respective securing components 10, 14 and 22 shown in FIGS. 1-3. Also, the end 36 provides a tapered leading edge for easier introduction into a hollow body such as blood vessel.

It will be understood that the specific shape and size of the securing components may be varied from the exemplary configurations depicted in FIGS. 1-4. For example, the thickness or width of the securing component may vary along all or part of the body of the component. The anastomotic securing components of the invention are preferably, though not necessarily, plate-shaped, i.e., a first dimension D1 of the component is less than a second dimension D2 of the component (FIG. 1). Typically, the lesser dimension corresponds to a thickness of the component while the larger dimension corresponds to a width or length of the component (or diameter in the case of FIG. 1). Minimizing the thickness of the securing component may be desirable for applications in which one or more components are placed within the lumen of a relatively small hollow body, e.g., a coronary artery, to reduce the amount of foreign material in the bloodstream and minimize flow impedance.

It will be noted that the securing components shown in FIGS. 1-4 are generally flat; however, they could instead be curved or arcuate, or comprise a combination of flat and curved sections. Additionally, in the illustrated and preferred construction the shape of each securing component substantially corresponds to the opening therein. That is, the securing component and its opening preferably have complementary configurations (e.g., elliptical component, elliptical opening). Nevertheless, the securing component could have a non-complementarily-shaped opening. Finally, while each of the illustrated securing components includes only one opening, more than one opening could be used if desired.

According to preferred embodiments of the invention the anastomotic securing components are formed of or have incorporated therein a material capable of producing a magnetic field that acts to maintain the components in a desired positional relationship. The magnetic field results in the securing components maintaining the first and second hollow bodies in a desired position so as to be in fluid-tight communication. The anastomotic component preferably has magnetic properties and may comprise permanent magnetic, ferro- or ferrimagnetic, or electromagnetic materials or assemblies.

Figure 5:
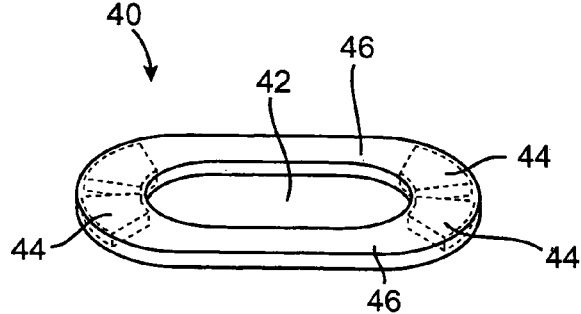

Each of the securing components shown in FIGS. 1-4 is formed substantially entirely of a suitable, magnetic field-producing material such that magnetic force may be generated over the entire area of the component. FIG. 5 shows an alternative embodiment wherein a securing component 40, which has an opening 42 and a racetrack-shaped configuration similar to securing component 22 of FIG. 3, has defined portions capable of producing a magnetic field. Specifically, the securing component 40 includes magnetic field-producing members 44 located at discrete areas which, in the illustrated embodiment, are at the ends of the component. The remaining areas 46 may thus be formed of a different material. It will be recognized that the members 44 could be located at alternative (or additional) areas of the securing component 40. An exemplary reason for providing the securing component 40 with areas 46 is to allow the use of a rigid magnetic material for the members 44 while still permitting the component to be partially or completely collapsed, for example, for delivery through a small incision or port, trocar, catheter, cannula, etc., by folding the areas 46.

Suitable materials that may be used to form an anastomotic securing component that is capable of producing a magnetic field include NdFeB (Neodymium Iron Boron), SmCo (Samarium Cobalt), and Alnico (Aluminum Nickel Cobalt). NdFeB is currently preferred for its force characteristics. The amount of force exerted will depend on various factors including the materials used, the size of the magnets and the number of magnets. In addition, different applications will call for different force ranges. For instance, it may be desirable to minimize the force as much as possible while still achieving a fluid-tight and secure attachment when treating small diameter blood vessels. As an example, in anastomosing coronary vessels, it is preferred to use anastomotic securing components that produce magnetic force in the area of less than 0.25 lbs, and more preferably approximately 0.15 lbs or less.

Figure 6:
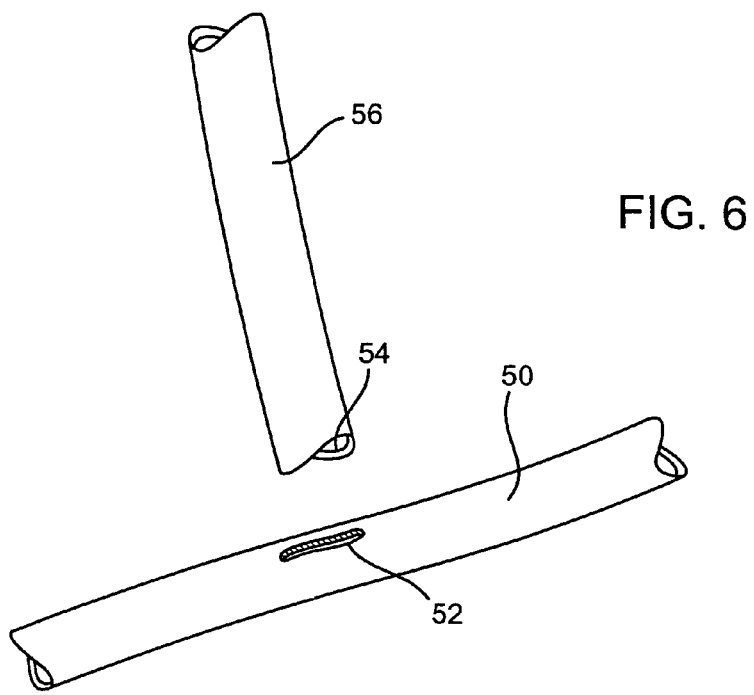
FIG. 6 is a perspective view showing two hollow bodies adapted to be joined in communication via an end-to-side anastomosis.
Figure 7:
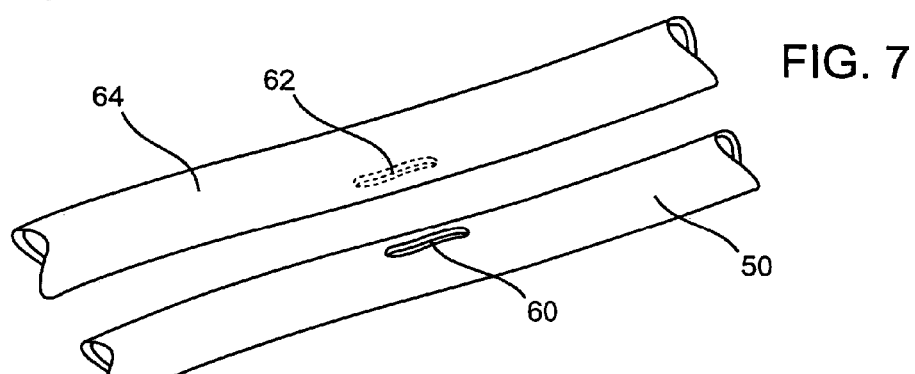
FIG. 7 is a perspective view showing two hollow bodies adapted to be joined in communication via a side-to-side anastomosis.
Figure 8:
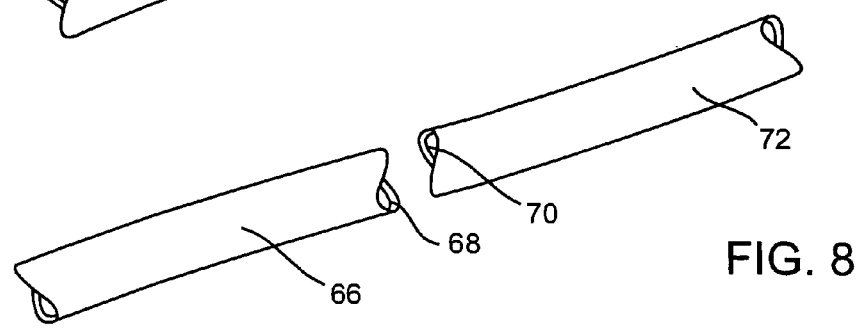
FIG. 8 is a perspective view showing two hollow bodies adapted to be joined in communication via an end-to-end anastomosis.

FIGS. 6-8 depict first and second hollow bodies that have been prepared for anastomosis in three different manners. FIG. 6 shows a first hollow body 50 with an opening 52 that is adapted to be joined to an opening 54 of a second hollow body 56 to form an end-to-side anastomosis. The completed anastomosis places the lumens of the respective hollow bodies in communication. The opening 52 is formed in the wall of the first hollow body 50, for example, by incising or punching the tissue of the wall, while the opening 54 is defined by an end of the second hollow body 56. FIG. 7 shows a first hollow body 58 with an opening 60 adapted to be joined to an opening 62 of a second hollow body 64, thereby forming a side-to-side anastomosis that places their lumens in communication. The openings 60, 62 are formed in the walls of the hollow bodies 58, 64, for example, as described above regarding opening 52. FIG. 8 shows a first hollow body 66 with an opening 68 adapted to be joined to an opening 70 of a second hollow body 72 to form an end-to-side anastomosis. Each opening 68, 70 is defined by an end its associated hollow body 66, 72.

The incision or other opening in the hollow body is preferably sized so as to cooperate with the magnetic anastomotic component(s) being used. For example, a gauge (not shown) may be placed along the vessel and used as a guide to form an incision having the correct length. A plurality of gauges, for example, each comprising a small rod with a handle to facilitate laying the rod along the vessel wall, may be provided for use with different anastomotic components and vessels.

Figure 9:
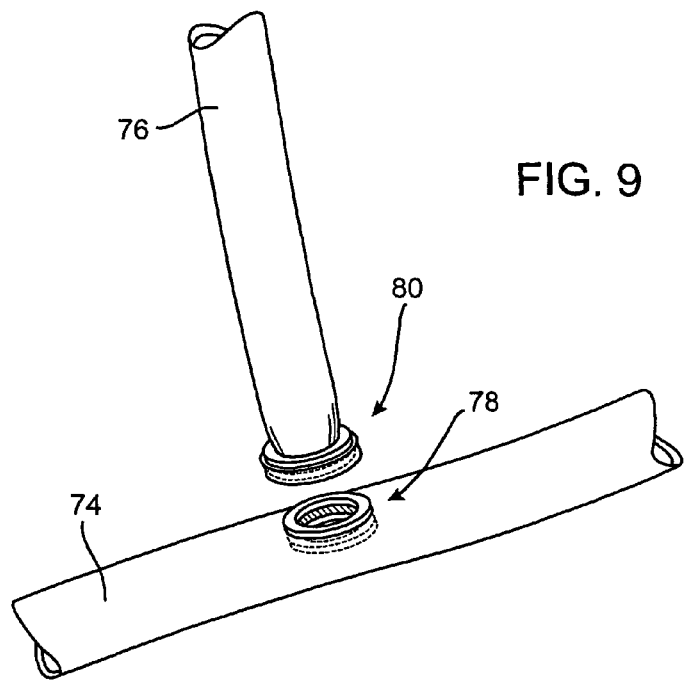
FIG. 9 is a perspective view of the two hollow bodies shown in FIG. 6 along with an anastomotic system including anastomotic securing components constructed according to one embodiment of the invention.
Figure 9A:
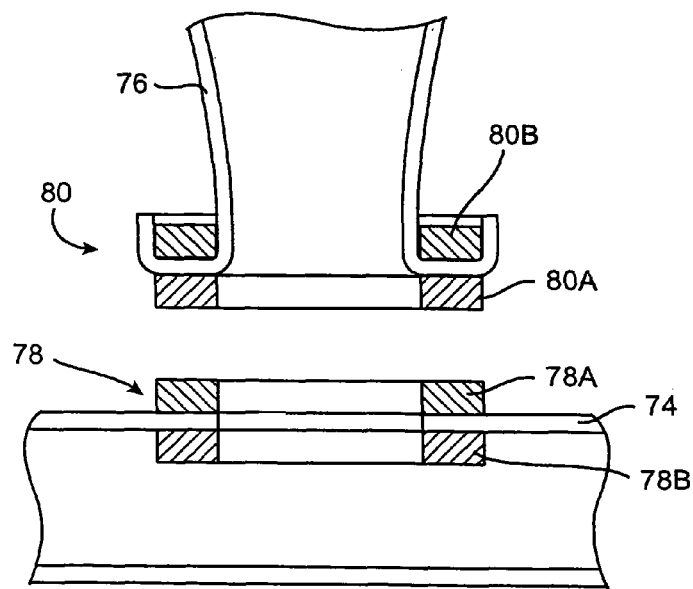
FIG. 9A is a sectional view taken along line A-A in FIG. 9.

FIGS. 9 and 9A show first and second hollow bodies 74, 76 respectively provided with first and second anastomotic securing components 78, 80 which are used to create an exemplary end-to-side anastomosis according to one embodiment of the invention. As shown best in FIG. 9A, the securing component 78 includes two members 78A, 78B disposed on opposite surfaces of a wall of the first hollow body 74. The securing component 80 includes two members 80A, 80B disposed on opposite surfaces of an everted end of the second hollow body 76. The members forming each securing component 76, 78 may be held in a desired and preferably fixed relative position by magnetic force, with magnetic force also being used to hold the two securing components in position. The securing components 78, 80 are moved together from the position of FIG. 9A to create a fluid-tight anastomosis.

Figure 10A:
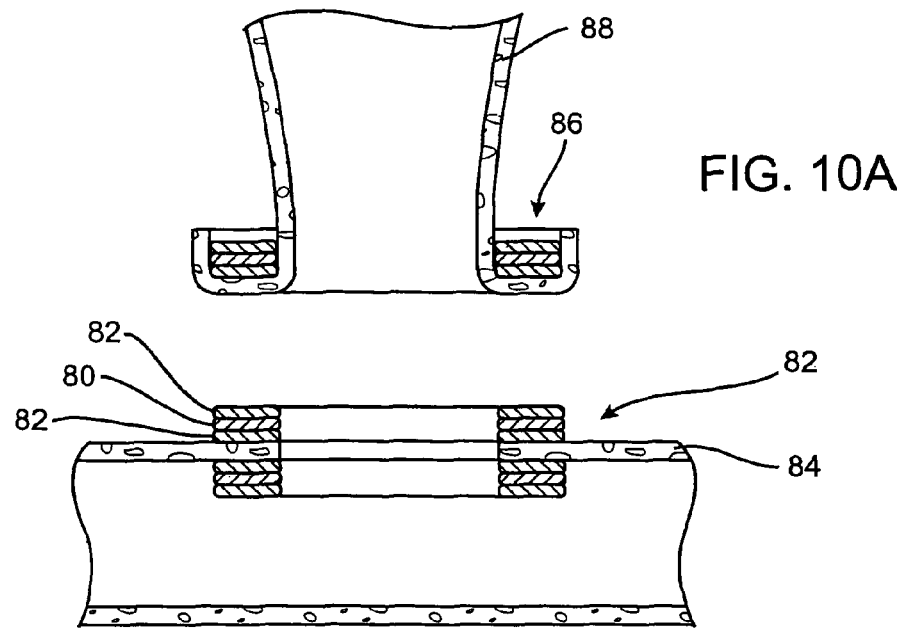
FIG. 10A is a section view similar to FIG. 9A but including alternative anastomotic securing components used to join the two hollow bodies.

FIGS. 10A-10D depict additional end-to-side anastomoses formed according to other embodiments of the invention. FIG. 10A shows a first securing component 82 coupled to a first hollow body 84 and a second securing component 86 coupled to a second hollow body 88. The securing components 82, 86 have a laminated structure comprising one layer of material capable of producing a magnetic field disposed between two outer layers of different material. In order to produce a magnetic field the components may comprise, for example, permanent magnetic, ferromagnetic, ferrimagnetic or electromagnetic materials or assemblies. Some exemplary materials that may be used include metals, polymers, ceramics, etc.

One example of this embodiment of the invention comprises a securing component having a middle layer of permanent magnetic material (e.g., NdFeB) and two outer layers of ferromagnetic material (e.g., 300 or 400 series stainless steel). The outer layers may be attached to the middle layer by suitable adhesive or magnetic force. One specific example of a securing component constructed according to this embodiment comprises a 0.008" thick inner magnetic layer and two 0.001" thick outer stainless steel layers. It will be understood that this aspect of the invention may be practiced using other materials or assemblies.

A benefit of a laminated construction is that it allows the thickness of the magnetic layer to be reduced because the other layer(s) will provide the assembly with the necessary strength and integrity, even if the magnetic layer is very thin (which typically makes the brittle magnet more easily fractured). In the above example, the steel layers may be very thin yet still able to absorb the load, e.g., the tensile forces that arise during movement of the hollow body or adjacent tissue. The particular overall dimensions of the securing component, as well as the dimensions of individual layer (or layers if a multilayer construction is used) will of course depend on the application. (As examples, for the securing component 22 shown in FIG. 3, the thickness is preferably less than 0.040", and more preferably less than 0.020", e.g., approximately 0.015" or even less, e.g., 0.008".)

The ability to form a very thin securing component allows formation of an anastomosis between relatively small hollow bodies, e.g., coronary blood vessels. Further, the anastomosis can be formed between blood-carrying hollow bodies with one or more of the securing components located in the blood flow path while minimizing the foreign material exposed to blood.

Figure 10B:
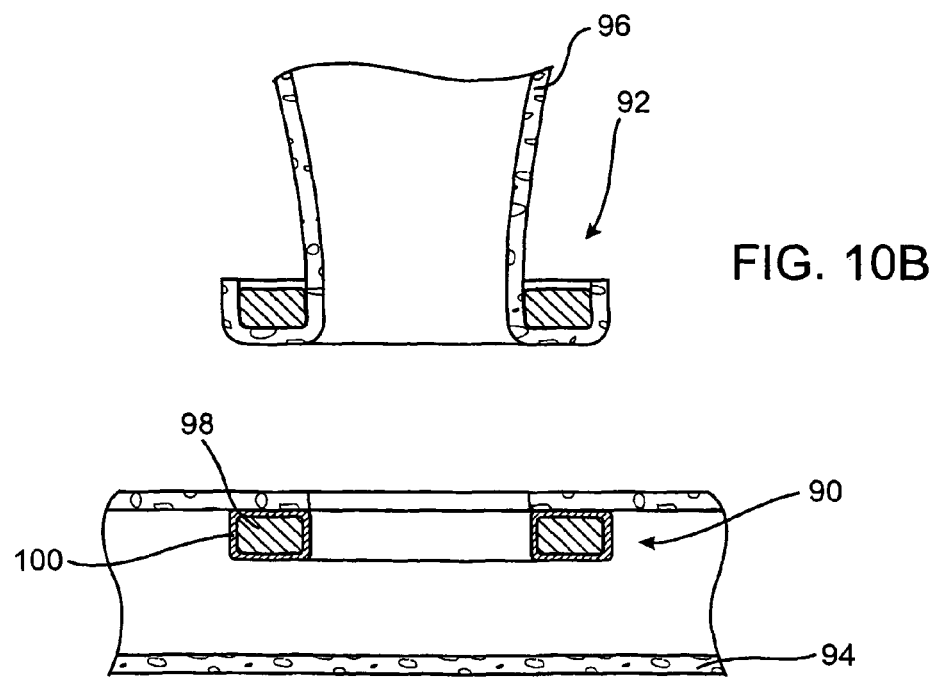
FIG. 10B is a section view similar to FIG. 10A including other alternative anastomotic securing components for joining the two hollow bodies.

FIG. 10B shows first and second securing components 90, 92 coupled to first and second hollow bodies 94, 96. The first securing component 90 comprises a single member 98 positioned within the lumen of the first hollow body 94 against the interior surface of the wall of the body adjacent an opening therein. The member 98 has a coating 100 substantially, and preferably completely, surrounding its exterior surface. It may be desirable in some applications to apply a suitable coating, or alternatively, a suitable surface treatment, to all or part of the anastomotic securing component. For example, if the first hollow body 94 represents a blood vessel such as a coronary or peripheral artery, the securing component 90 will be exposed to the blood flow path. As such, depending on the material used to the form the member 98, it may be desirable or necessary to coat or otherwise treat its surface to promote better thrombogenicity and/or improve flow past the anastomosis site. Some exemplary materials that may be used to coat or otherwise treat an anastomotic securing component constructed according to the invention include Gold, Platinum, Titanium Nitride, Parylene, Silicone, Urethane, Epoxy, Teflon and Polypropylene.

FIG. 10C shows an embodiment wherein first and second securing components 102, 104 are coupled to first and second hollow bodies 106, 108. Each component 102, 104 comprises a single member formed, as explained above, of a magnetic, ferromagnetic, or electromagnetic material. This embodiment, instead of everting an end of one of the hollow bodies 106, 108, provides the first securing component 102 with a portion 110 configured to attach the end of the first hollow body 106. The portion 110 may take various forms, for example, a DACRON® suture ring or bioadhesive. It will be recognized that the portion for attaching the hollow body may be located at different areas of the second securing component 104 than shown in FIG. 10C.

FIG. 10D shows an embodiment of the invention similar to that of FIG. 10C with first and second securing components 112, 114 coupled to first and second hollow bodies 116, 118. The means for attaching the first securing component 112 to the first hollow body 116 in this embodiment comprises an expandable member 120, such as a stent, disposed within the lumen of the first hollow body. The member 120 forces the end of the first hollow body 116 against the first securing component 112 to attach the elements in a fluid-tight fashion. It will be appreciated that the embodiments of FIGS. 10C and 10D are only two of the various ways in which a securing component may be coupled to a hollow body with everting tissue of the hollow body.

Figure 11A:
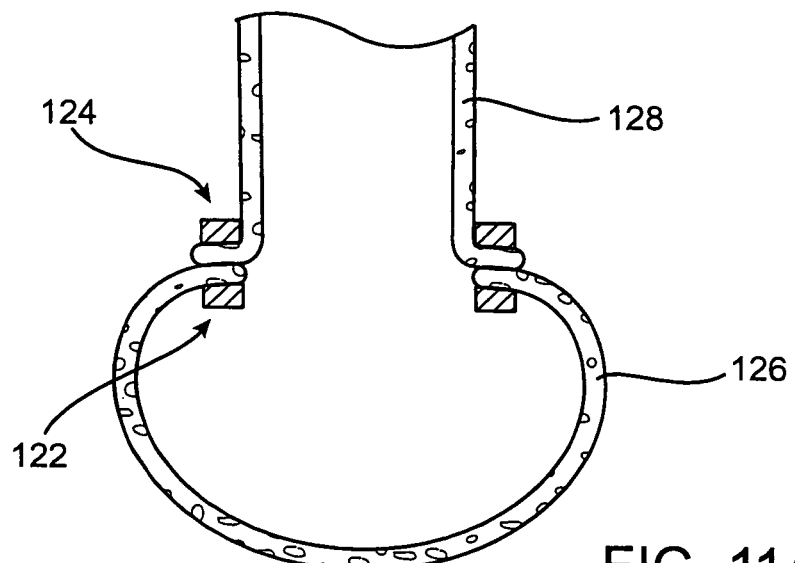
FIG. 11A is a transverse sectional view taken through an end-to-side anastomosis formed according to one embodiment of the invention.
Figure 11B:
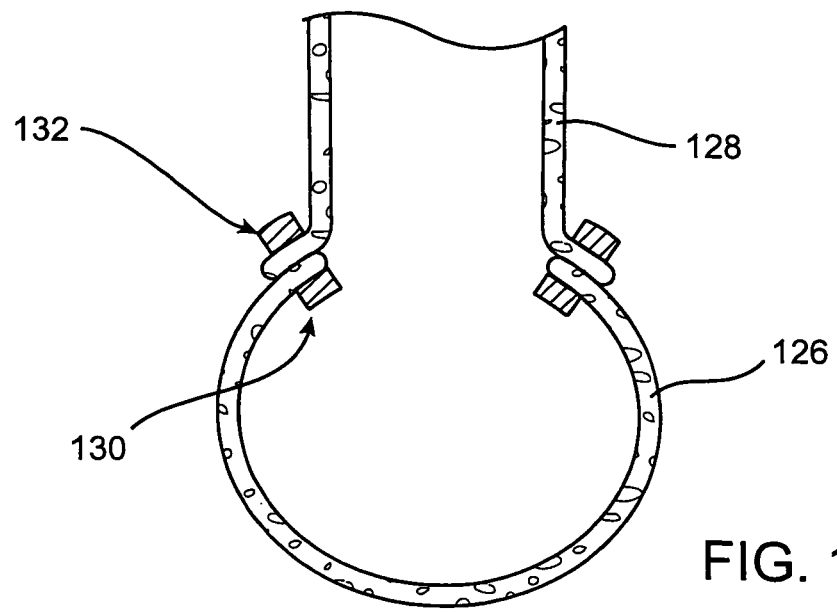
FIG. 11B is a transverse sectional view taken through an end-to-side anastomosis formed according to another embodiment of the invention.

FIG. 11A is a transverse sectional view taken through an end-to-side anastomosis created by first and second securing components 122, 124 which are positioned adjacent openings of first and second hollow bodies 126, 128. The securing components 122, 124 are plate-shaped (as described above) and generally flat. FIG. 11B shows first and second securing components 130, 132 constructed according to an alternative embodiment of the invention positioned adjacent the openings of first and second hollow bodies 126, 128. The securing components 130, 132 are also plate-shaped but, rather than being generally flat, are arcuate or curved. As can be seen, the curvature of the securing components 130, 132 maintains the first hollow body 126 in a substantially round configuration as compared to the more flattened-out shape it assumes when used with the flat securing components 122, 124.

The arcuate securing components 130, 132 preferably have complementarily or substantially complementarily radii of curvature to provide an even distribution of force and good sealing. The securing components of the invention could, however, have different degrees of curvature, the curvature of each being either constant or changing over the body of the component. Also, while the illustrated securing components 130, 132 extend over approximately 120°, other configurations that extend between 0° and 360° could be used if desired, for example, 180°. Finally, while FIGS. 11A and 11B show, respectively, a pair of flat components and a pair of arcuate components, the securing components of each pair used to create the anastomosis may have dissimilar configurations to varying degrees.

Figure 12:
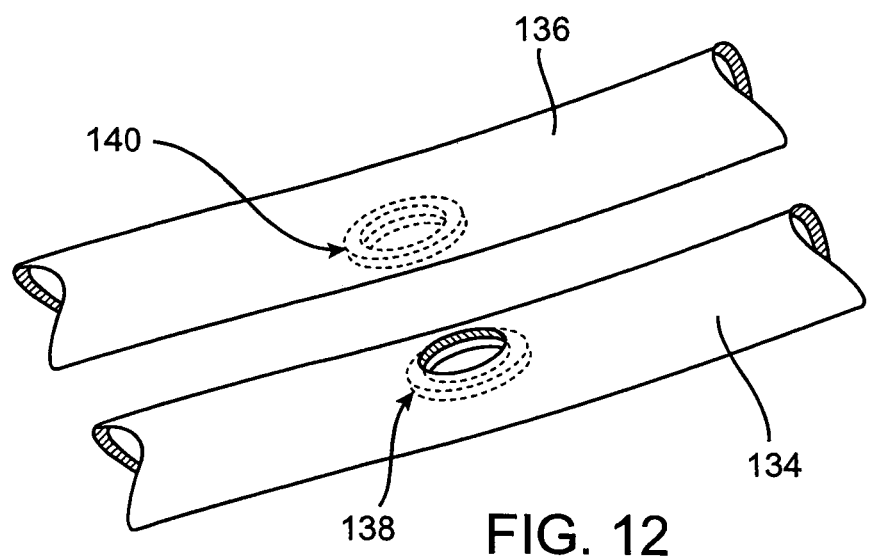
FIG. 12 is a perspective view showing two hollow bodies provided with anastomotic securing components constructed according to one embodiment of the invention, the two bodies adapted to be joined via a side-to-side anastomosis.
Figure 13:
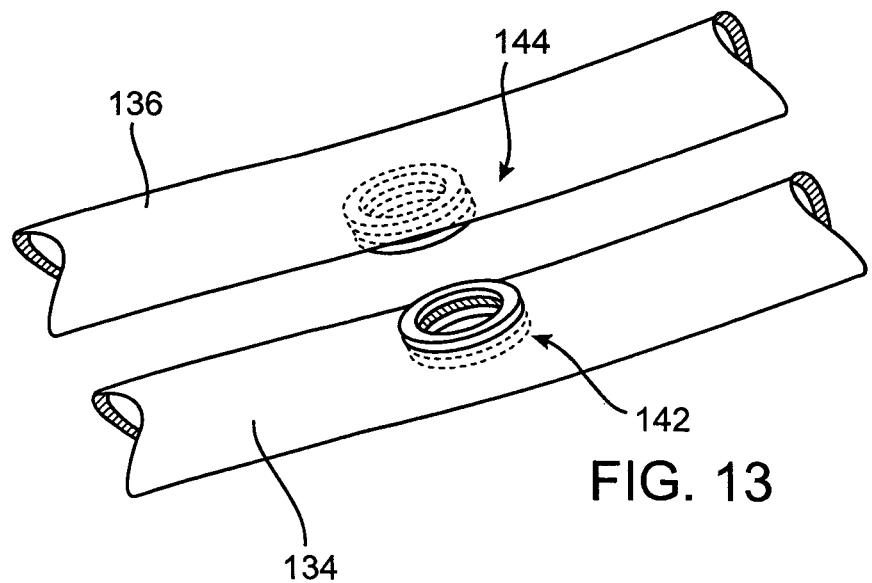
FIG. 13 is a perspective view showing the two hollow bodies of FIG. 12 provided with anastomotic securing components constructed according to another embodiment of the invention.
Figure 14A:
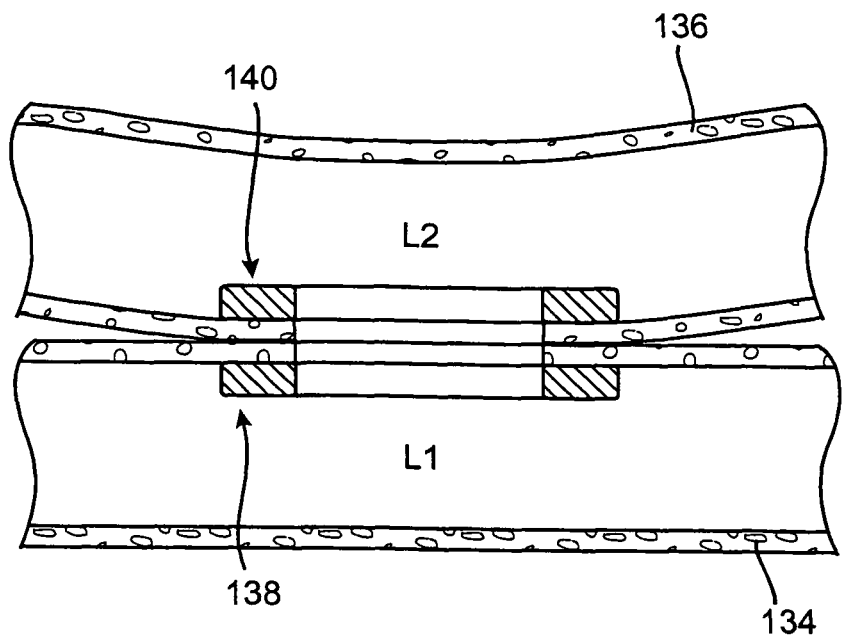
FIG. 14A is a longitudinal sectional view taken through the side-to-side anastomosis formed according to the embodiment shown in FIG. 12.
Figure 14B:
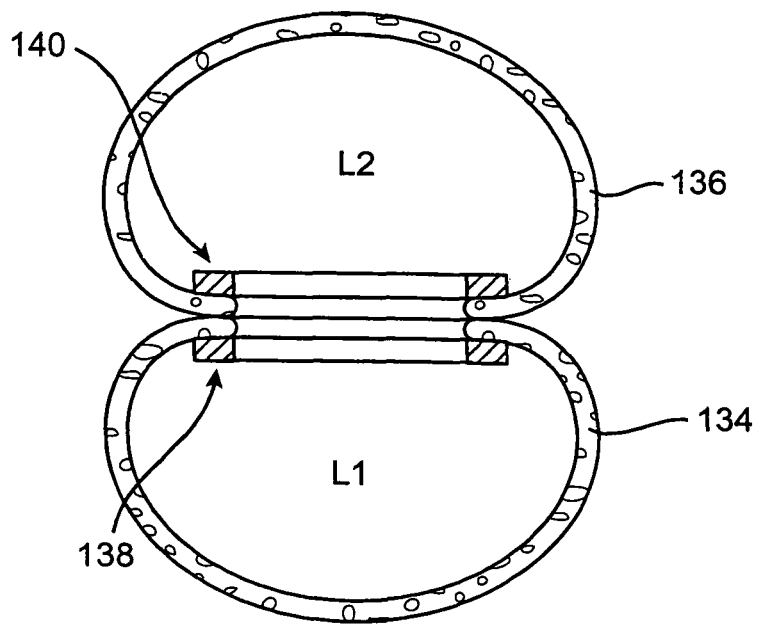
FIG. 14B is a transverse sectional view taken through the side-to-side anastomosis formed according to the embodiment shown in FIG. 12.

FIGS. 12 and 13 show other embodiments of the invention wherein first and second hollow bodies 134, 136 are respectively provided with securing components in order to create an end-to-side anastomosis. The embodiment of FIG. 12 utilizes first and second securing components 138, 140 respectively positioned adjacent openings in the hollow bodies 134, 136. Each securing component 134, 136 includes a single member that may comprise one or more materials and one or more layers, as described above. The components may be fixed by adhesive or other means or remain in position via magnetic force, as explained above. The securing components 138, 140 are positioned through openings formed in the wall of the hollow bodies 134, 136 and are located within the respective lumens L1, L2 thereof, as shown in FIGS. 14A and 14B. Once joined the components 138, 140 form a fluid-tight anastomosis that places the first and second hollow bodies 134, 136 in communication. If the hollow bodies 134, 136 are blood (or other fluid) carrying structures, the anastomosis places them in fluid communication and provides a fluid-tight seal.

The embodiment of FIG. 13 uses first and second securing components 142, 144 which are respectively positioned adjacent openings in the hollow bodies 134, 136 so as to be partially disposed within the lumens thereof. The opening in each hollow body may be a surgical incision or a punched hole. Each securing component 142, 144 includes a pair of members, and each member may comprise one or more materials and one or more layers. One member of each securing component 142, 144 is positioned within the lumen of its hollow body while the other member of the securing component is positioned on the exterior of the hollow body with tissue in between.

Figure 15:
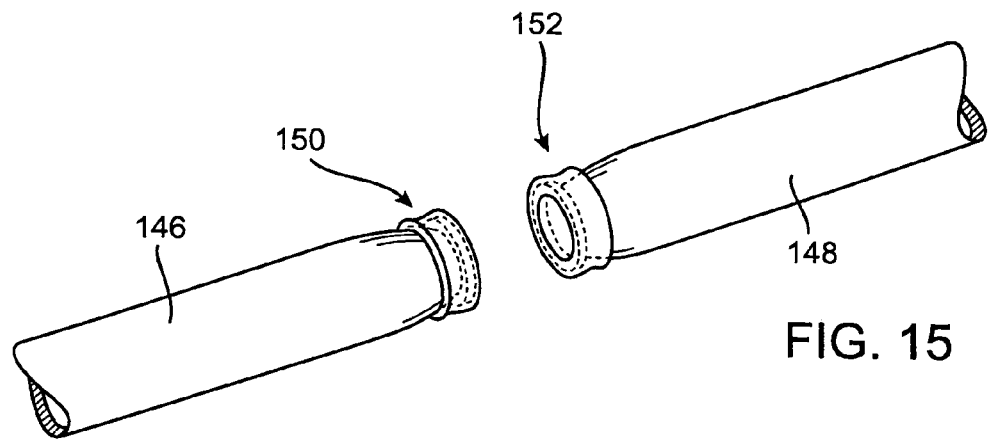
FIG. 15 is a perspective view showing two hollow bodies provided with anastomotic securing components constructed according to one embodiment of the invention, the two bodies adapted to be joined via an end-to-end anastomosis.
Figure 16:
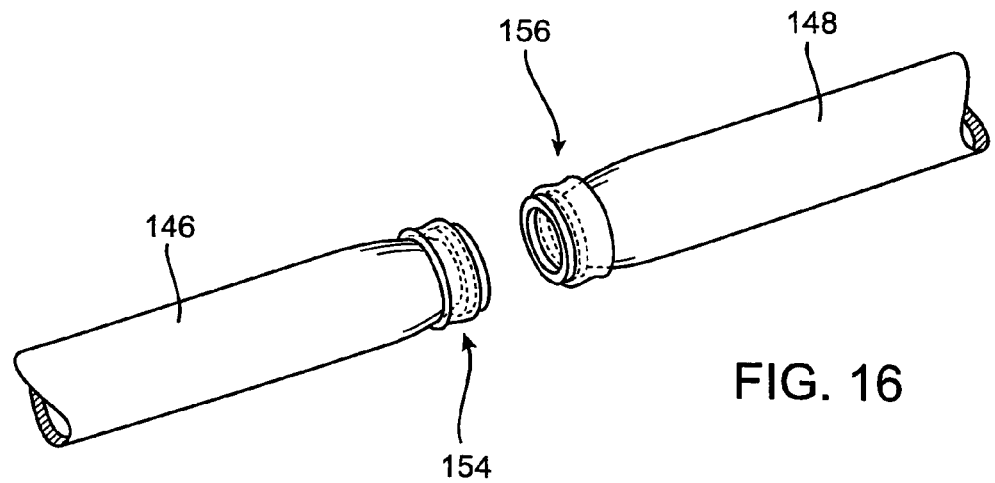
FIG. 16 is a perspective view showing the two hollow bodies of FIG. 15 provided with anastomotic securing components constructed according to another embodiment of the invention.

FIGS. 15 and 16 show further embodiments of the invention wherein first and second hollow bodies 146, 148 are respectively provided with first and second anastomotic securing components in order to create an end-to-end anastomosis. FIG. 15 shows first and second securing components 150, 152 positioned adjacent respective openings of the hollow bodies 146, 148, each opening being defined by an end of a hollow body and extending into the lumen thereof.

Each securing component 150, 152 includes a single member that may be constructed as described above. An end of each hollow body 146, 148 is passed through the opening defined in by a respective securing component and then is everted over the exterior of the component. As a result, joining the first and second securing components 150, 152 in end-to-end fashion places the everted ends of the hollow bodies 146, 148 in sealed contact. In a case where the hollow bodies are natural blood vessels, such an anastomosis places the intimal surfaces of the vessels in contact.

The embodiment of FIG. 16 includes first and second securing components 154, 156 positioned adjacent the openings of hollow bodies 146, 148, respectively. The securing components 154, 156 each comprise a pair of members constructed as described above. The first securing component 154 includes one member 154A positioned around the exterior of the first hollow body 146 (with the end thereof everted), and another member 154B positioned around the opening defined by the end of the hollow body 146, the members 154A, 154B being held in place by magnetic force. The second securing component 156 has the same or a similar construction and includes members 156A, 156B which are positioned adjacent the end of the second hollow body 148. In the embodiments of FIGS. 15-16 the securing components are not located within the lumen of either hollow body and thus are not exposed to fluid or other substances contained therein or moving therethrough.

Another embodiment of the invention will be described with reference to FIGS. 17A-17B. FIG. 17A shows a hollow body 160 with an opening 162 and an anastomotic securing component 164 positioned adjacent the opening. The securing component 164 is positioned within the lumen L of the hollow body 160 and has an opening 166. The opening 166 is aligned with the opening 162 in the wall of the body 160 as shown. In some instances, for example, when the securing component is forced through an incision in the wall, the tissue defining the opening 162 may move over the opening 166 of the securing component 164, as shown in FIG. 17B. As indicated by reference numeral 168 in FIG. 17B, this reduces the effective area of the securing component 164 that is available to communicate with a second hollow body to which the hollow body 160 is anastomosed (not shown).

FIGS. 18A-18B show the hollow body 160 with the opening 162 of FIGS. 17A-17B, however, a securing component 170 constructed according to another embodiment of the invention is positioned adjacent the opening 162. The securing component 170 has an opening 172 and has a feature for maintaining the opening 162 open to flow. The securing component 170 comprises a flange 174 and an extension 176 coupled thereto (or formed integrally therewith). As can be seen, the extension 174 prevents tissue defining or adjacent the opening 162 of hollow body 160 from migrating or springing back after delivery to reduce the cross-sectional flow area of the securing component 170.

Figure 19A:
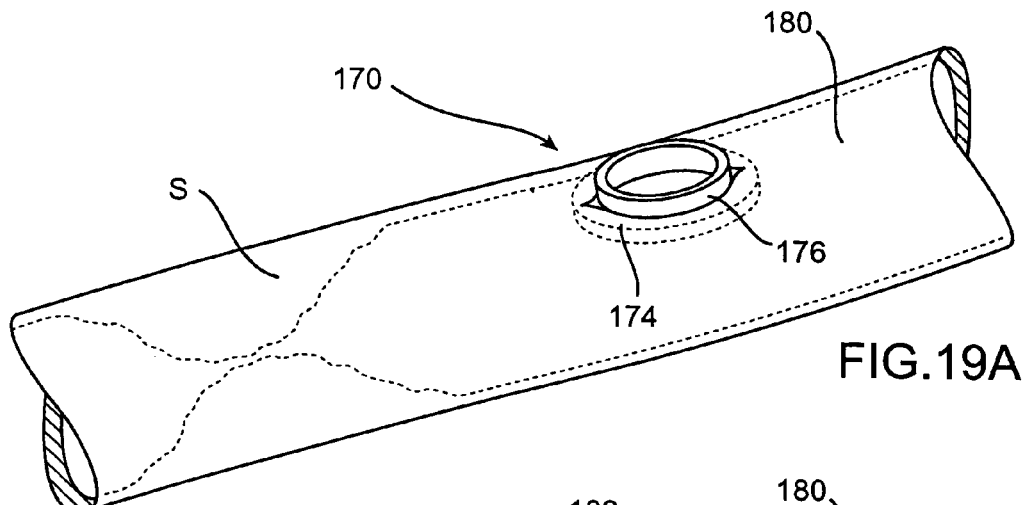
FIG. 19A is a perspective view of the anastomotic securing component shown in FIGS. 18A-18B, the component positioned in an opening in a hollow body having an occluded lumen.
Figure 19B:
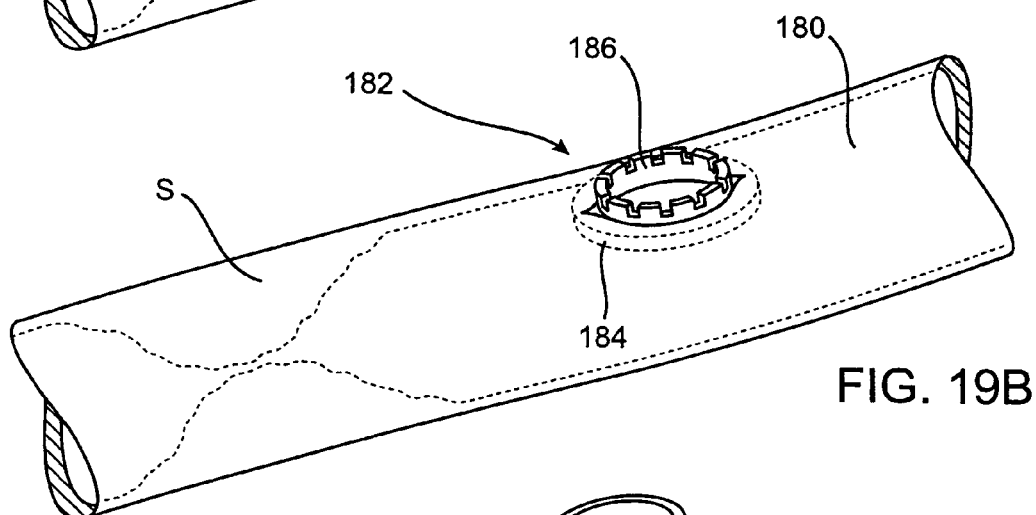
FIGS. 19B-19C show anastomotic securing components constructed according to further alternative embodiments of the invention, the components being shown positioned in the hollow body of FIG. 19A.
Figure 19C:
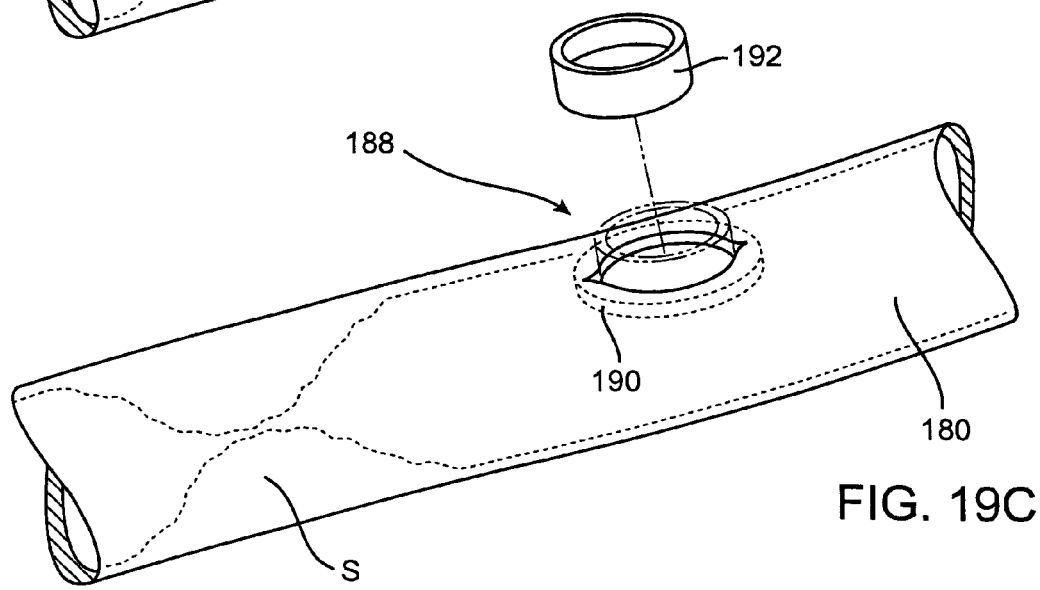

FIGS. 19A-19C show a hollow body 180 which may, for example, represent a patient's coronary or peripheral artery the lumen of which is stenosed at S. In FIG. 19A, the hollow body 180 is provided with the anastomotic securing component 170 of FIGS. 18A-18B by coupling the securing component to an opening in the wall of the artery, thereby forming a site for creating an end-to-side or side-to-side anastomosis. In FIG. 19B, the hollow body 180 is provided with an alternatively configured anastomotic securing component 182 which includes a flange 184 and a discontinuous or segmented extension 186 passing all or partly through the opening in the wall of the hollow body. FIG. 19C shows a securing component 188 with a multi-part construction including a flange 190 and a separate extension 192 which is received in the opening of the hollow body 180. It should be understood that these are only a few of the various constructions that may be employed in practicing this aspect of the invention.

Figure 20A:
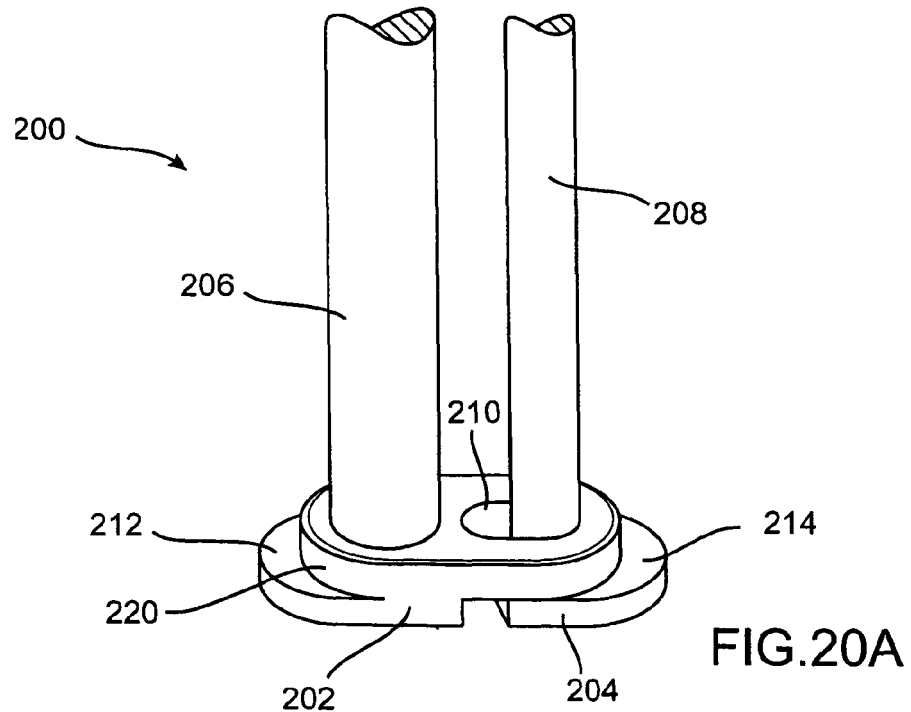
FIG. 20A is a perspective view of a delivery device constructed to one embodiment of the invention, the device being shown in a first position.

The anastomotic securing components of the invention may be delivered and deployed in various ways. FIGS. 20A-20B and 21A-21B depict somewhat schematically an exemplary delivery device 200 including a first portion 202 operatively coupled to a second portion 204. The first portion 202 is fixed to a shaft 206 while the second portion 204 is fixed to shaft 208 passing through a slot 210 in the portion 202. The first portion 202 defines a support ledge 212 and the second portion 202 similarly defines a support ledge 214. FIG. 20A shows the device 200 in a first position for retaining an anastomotic securing component of the invention. This position is shown in FIG. 21A wherein the ledges 212, 214 support a securing component 216 with the opening 218 of the component surrounding a boss 220 that extends upwardly from the ledges. The boss 220 is preferably used to help align the securing component on the support ledges 212, 214 and, if used in an application with an opening formed in a side wall of a hollow body, to restrain the surrounding tissue during placement.

Figure 20B:
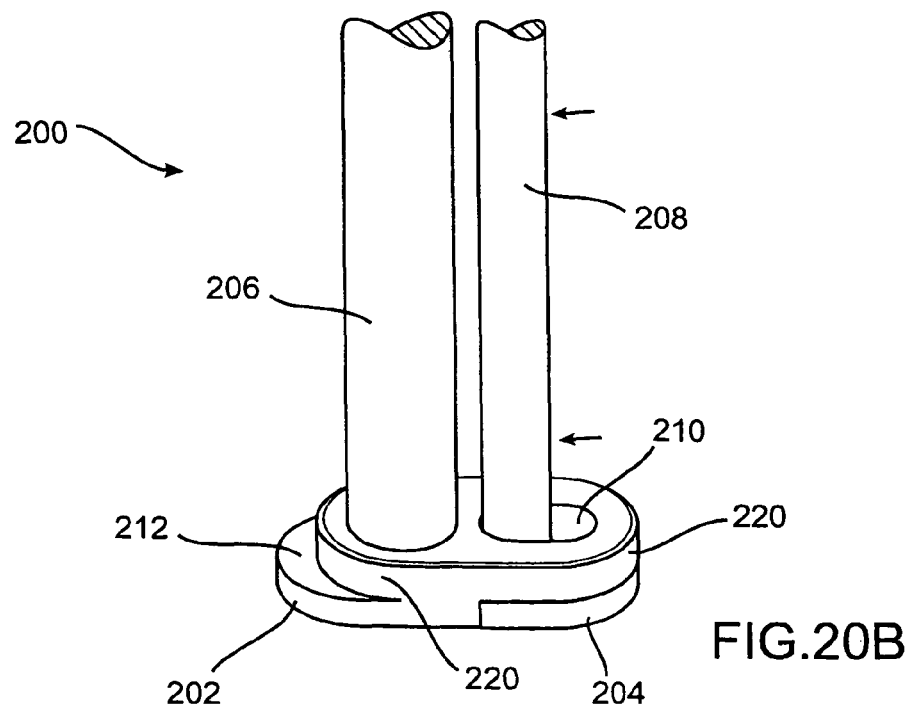
FIG. 20B is a perspective view of the delivery device shown in FIG. 20A, the device being shown in a second position.
Figure 21A:
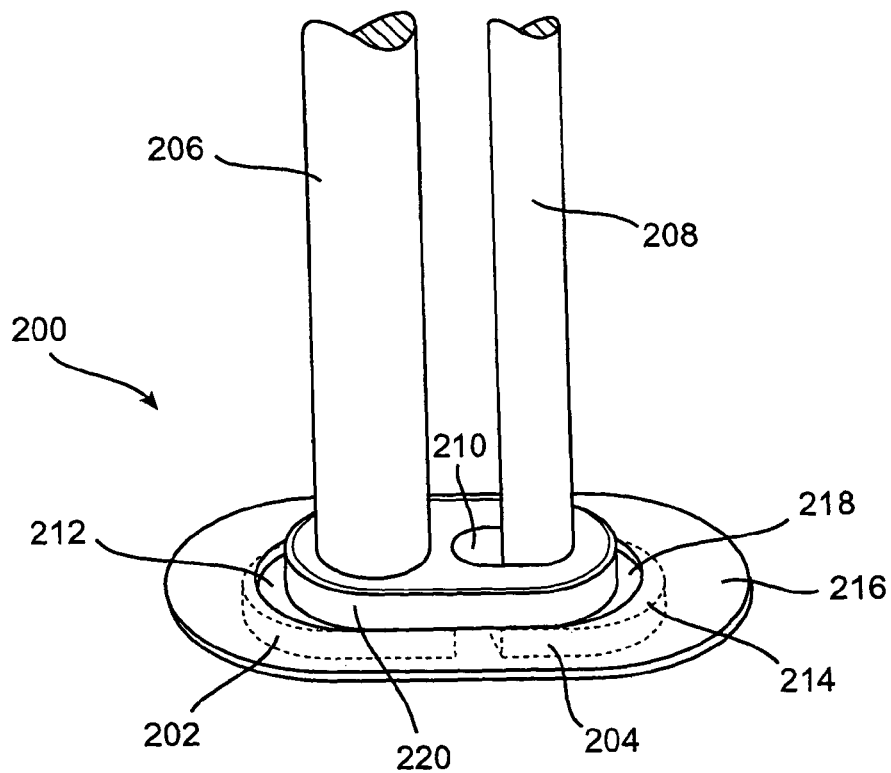
FIG. 21A is a perspective view of the delivery device shown in FIG. 20A with a securing component constructed to one embodiment of the invention mounted thereon, the delivery device being shown in the first position.
Figure 21B:
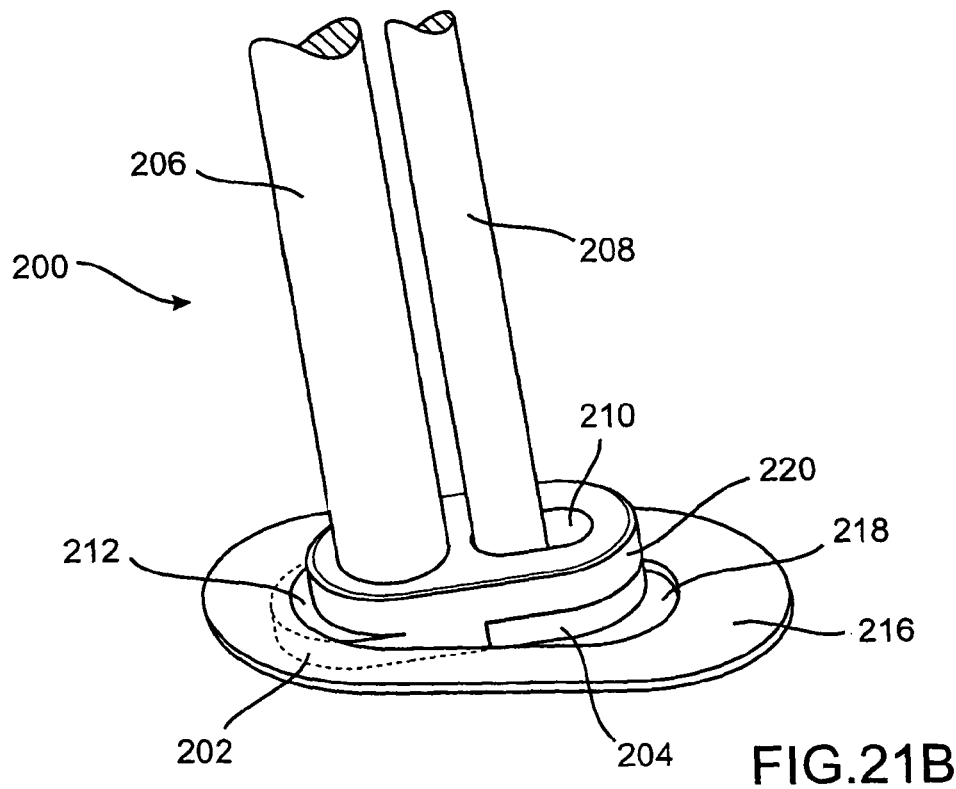
FIG. 21B is a perspective view of the delivery device shown in FIG. 21A, wherein the device is shown in the second position as it is being manipulated to release the securing component.

FIGS. 20B and 21B show the device 200 after it has been moved to a second position from the position of FIGS. 20A and 21A. This is achieved by moving the shaft 208 in the direction of the arrows to slide the second portion 204 with respect to the first portion 202, which moves the support ledge 214 within the opening 218 of the anastomotic securing component 216 (FIG. 21B). This allows the user to separate the device 200 from the securing component 216 once the latter has been positioned at the desired location. As shown, depending on the relative dimensions and shapes of the respective components it may be necessary to rock or otherwise manipulate the device 200 relative to the securing component 216 in order to separate them.

It will be understood that the illustrated delivery device 200 is only one possible device suitable for use in placing the anastomotic securing components of the invention, and that it may be modified or replaced with a different delivery device or system. For example, the delivery device 200 could be altered so that both support ledges 212, 214 are moved with respect to the boss 220 (if used) in order to move fully out of contact with and release the securing component. Any suitable material(s) may be used to construct the delivery device 200, it being appreciated using magnetic or ferromagnetic materials may result in magnetic interaction with the securing components, which may be desired to facilitate delivery of the components. The delivery device could also be constructed of nonmagnetic or ferromagnetic materials such as titanium, polymers, etc.

Figure 22A:
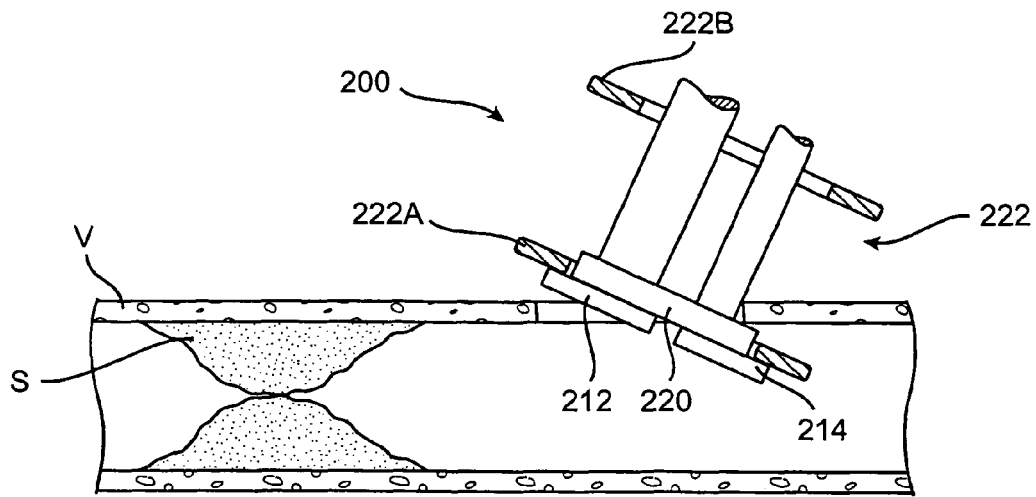
FIGS. 22A-22F are sectional views schematically illustrating the delivery device shown in FIGS. 20A-20B being used to deploy anastomotic securing components to form an end-to-side anastomosis according to one embodiment of the invention.

For sake of example, the creation of an anastomosis using the delivery device 200 and first and second securing components of the invention will be described with respect to FIGS. 22A-22F. FIG. 22A shows the delivery device 200 with a first securing component 222 comprising two members 222A, 222B, the former member being supported by the ledges 212, 214 of the device 200 while the latter member is held above the ledges (e.g., by magnetic attraction to the device 200). The member 222A is being inserted into an opening in the wall of a blood vessel V with a stenosis S. The member 222A may be shaped or otherwise treated to ease insertion into the vessel lumen; for example, the leading edge of the member 222A may be formed as shown in the embodiment of FIG. 5.

Figure 22B:
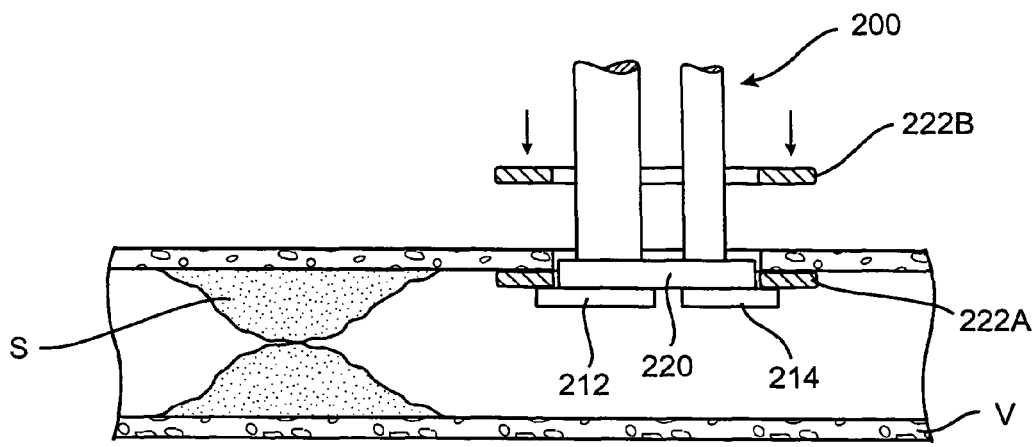
Figure 22C:
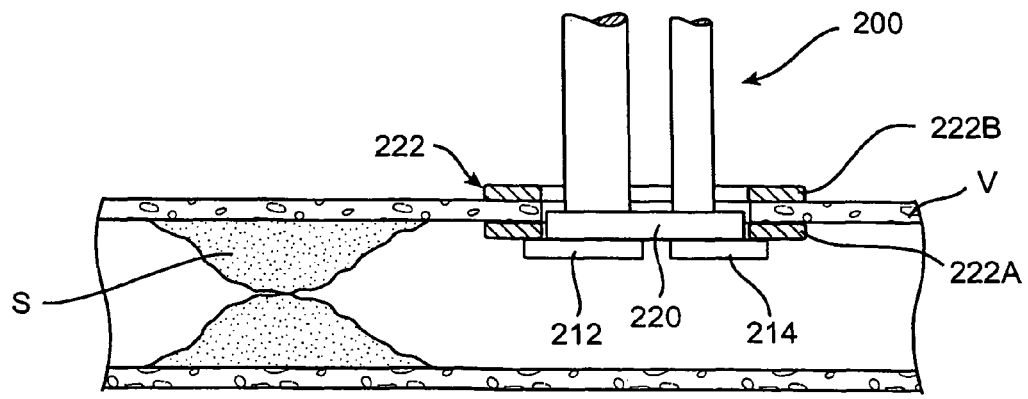
Figure 22D:
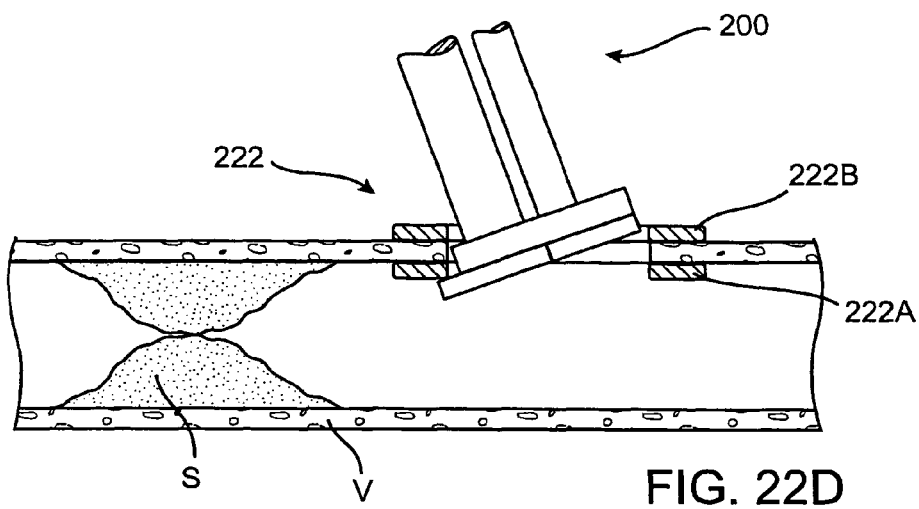
Figure 22E:
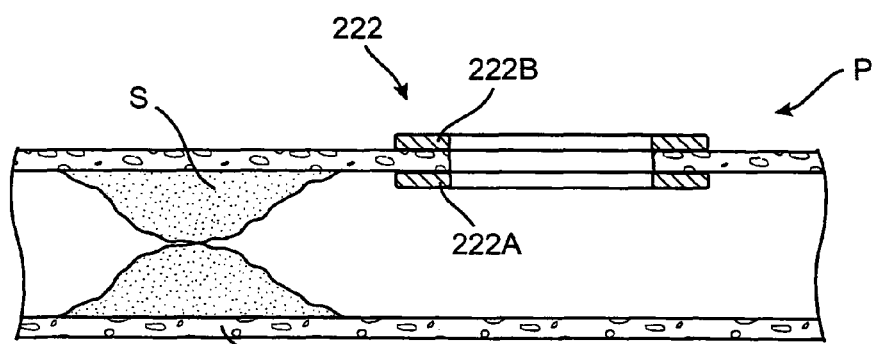

FIG. 22B shows the one member 222A of securing component 222 positioned against the interior surface of the wall of the vessel and the other member 222B being moved toward the vessel wall. FIG. 22C shows the members 222A, 222B in position with the delivery device 200 remaining. FIG. 22D shows the device 200 being removed through first securing component 222, and FIG. 22E shows the securing component 222 remaining in the vessel wall to form what may be characterized as a magnetic port P. The securing component(s) may be provided with a surface treatment, such as coatings, roughened or treated areas, or mechanical projections, to enhance engagement with the wall of the hollow body.

Figure 22F:
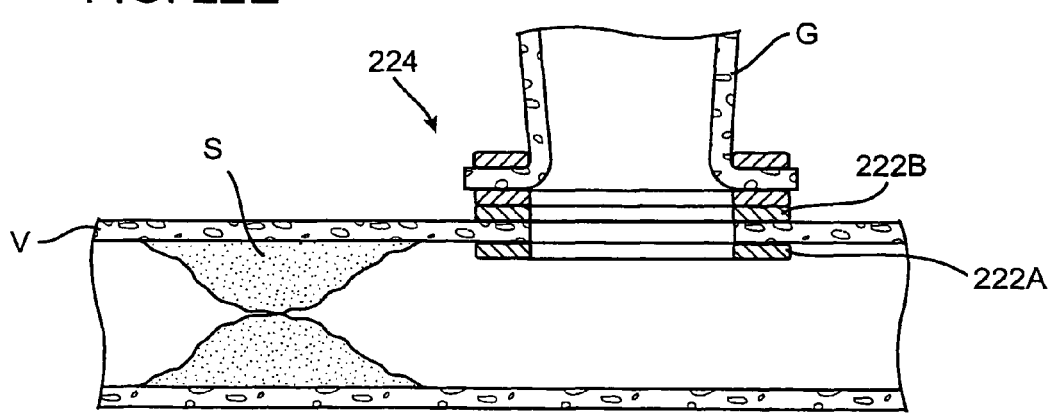

The illustrated securing component 222 defines the magnetic port P and produces a magnetic field that may be used to couple another vessel to the port. In FIG. 22F, a graft vessel G provided with a second securing component 224 (which itself includes two members) is anastomosed to the port P with magnetic force holding the first and second securing components 222, 224 in a desired relative position. The invention may also be practiced using means for fixing the relative distance between the first and second securing components, for example, to prevent tissue being forced or squeezed from the space between the components due to the application of the magnetic force over time. Such means could comprise projections that extend directly between the components and act as a stop, or an intermediate element coupled to the components to restrain them against further movement. It will be recognized that forming a magnetic port according to the invention may also be used in non-vascular applications, as well as applications not requiring an anastomosis to another vessel, for example, to provide an access to an area of a patient's body.

Figure 23:
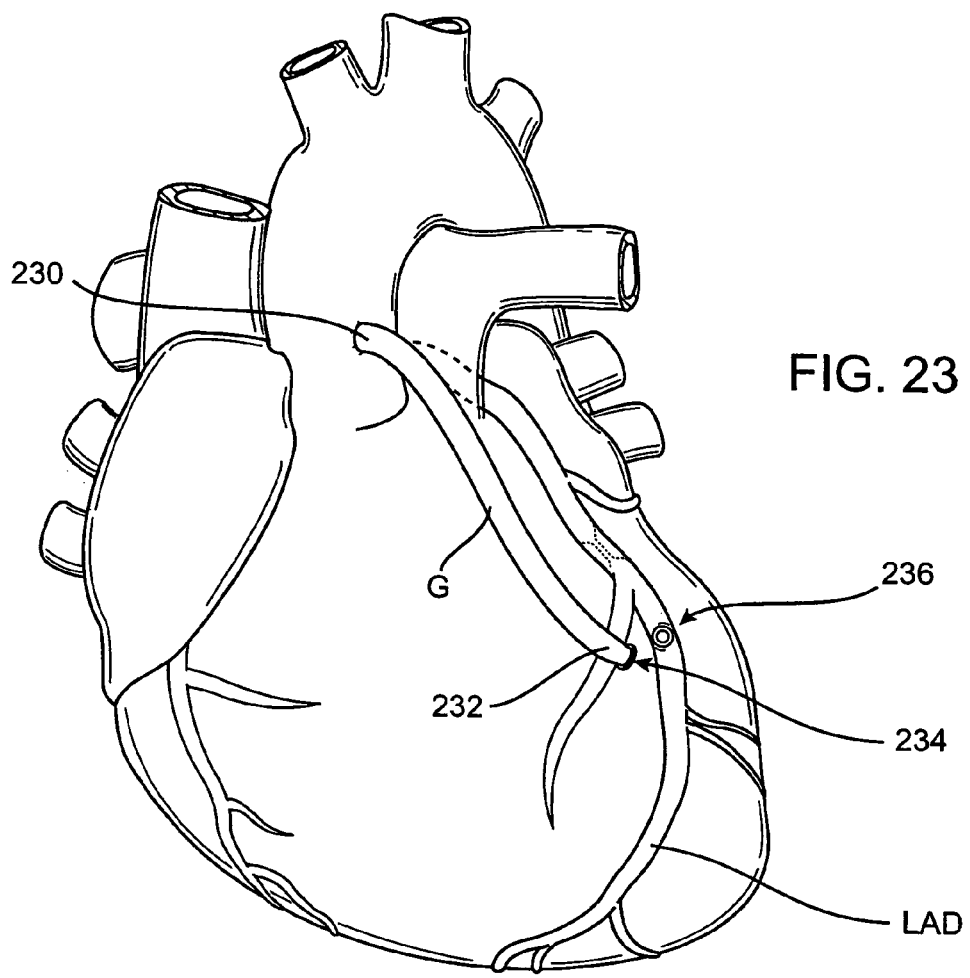
FIG. 23 is a perspective view of an exemplary application according to one embodiment of the invention.
Figure 23A:
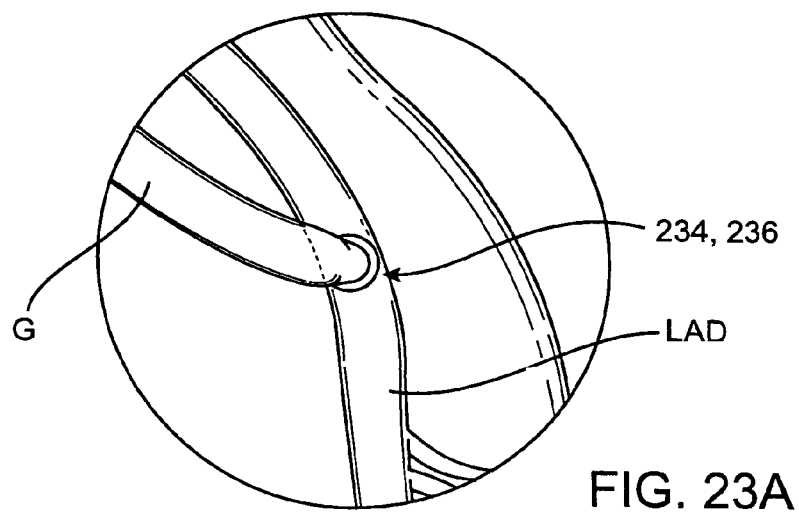
FIG. 23A is an enlarged view of a portion of the embodiment of FIG. 23 but showing a completed anastomosis.

Several exemplary applications of the invention will be described with reference to FIGS. 23-23A, 24-24A and 23-25A. FIG. 23 is an anterior view of a human heart with a graft vessel G having one end 230 attached to the aorta, e.g., by a sutured anastomosis, and another end 232 prepared to be anastomosed to an occluded LAD. One securing component 234 is coupled to the end 232 of the graft G by any of the methods described above, and another securing component 236 is coupled to the LAD adjacent an opening therein. The securing components 234, 236 are formed (at least in part) of materials capable of producing a magnetic field so that they may be attached as shown in FIG. 23A, thereby placing the graft G in fluid communication with the lumen of the LAD. The graft G could alternatively be attached to the aorta by an anastomotic system constructed according to the invention.

Figure 24:
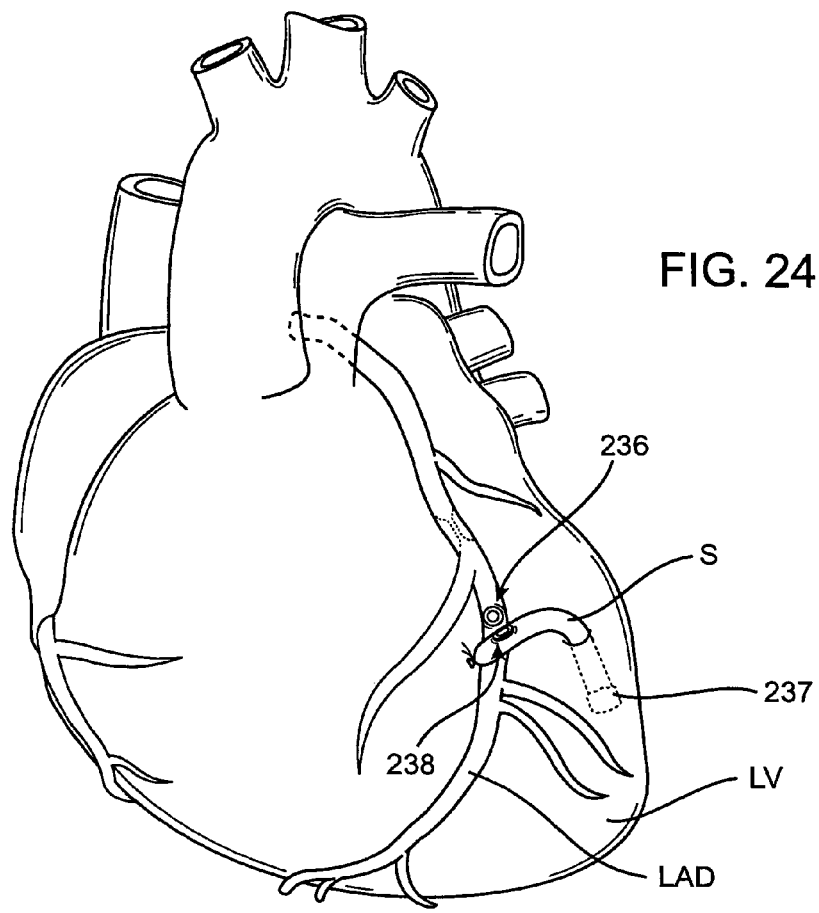
FIG. 24 is a perspective view of another exemplary application according to another embodiment of the invention.
Figure 24A:
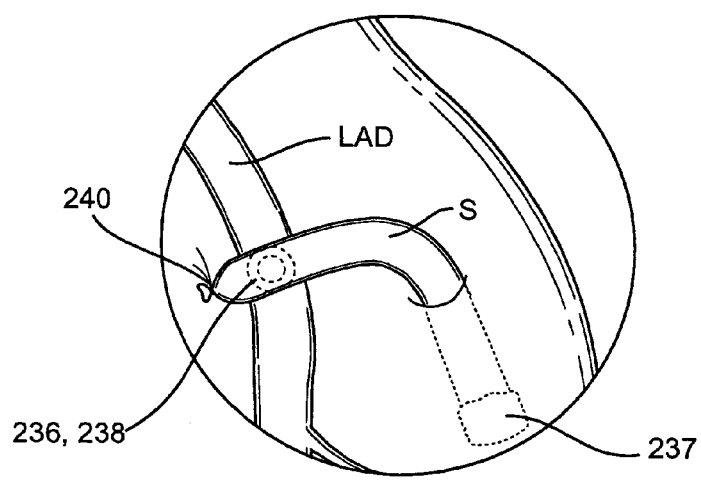
FIG. 24A is an enlarged view of a portion of the embodiment of FIG. 24 but showing a completed anastomosis.

FIG. 24 shows another exemplary application of the invention applied to the heart shown in FIG. 23. A ventriculocoronary shunt S has one end 237 placed in the myocardium in fluid communication with the left ventricle LV. The shunt S is provided with a securing component 238 adjacent its other end while the LAD is provided with the securing component 236 of FIG. 23. The shunt S is adapted to be coupled to the LAD via a side-to-side anastomosis, therefore the securing component 238 is positioned in an opening in the side wall of the shunt (and the free end of the shunt is tied off at 240). FIG. 24A shows the completed anastomosis once the securing components 236, 238 have been coupled and remain in position via the magnetic field produced according to the teachings of the invention.

Figure 25:
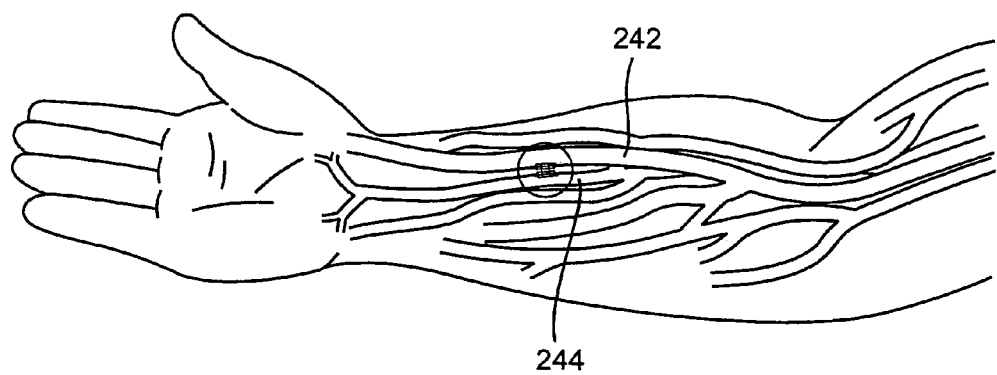
FIG. 25 is a perspective view of an exemplary application according to still another embodiment of the invention.
Figure 25A:
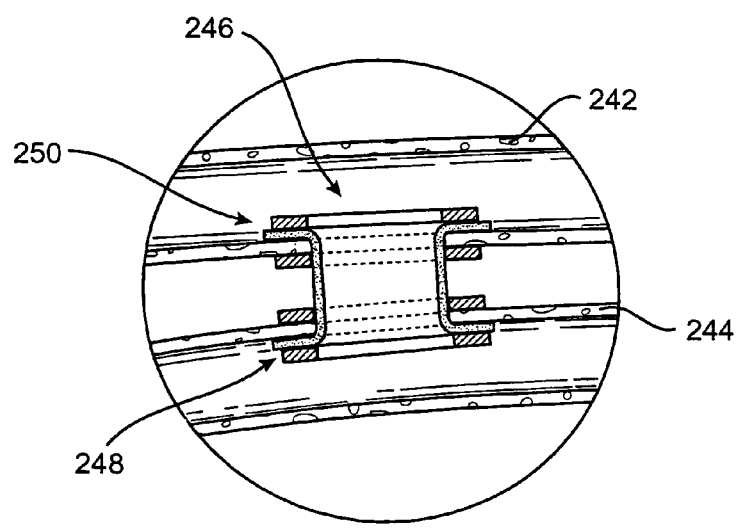
FIG. 25A is an enlarged view of a portion of the embodiment of FIG. 25 but showing a completed AV shunt with two anastomoses.

FIGS. 25-25A illustrate yet another example of the many different applications of the invention, namely, the creation of an AV shunt. FIG. 25 shows a patient's arm including a number of the blood vessels located therein. An artery 242 is shown disposed in relatively close proximity to a vein 244. AV shunts are often created between an artery and vein in order to provide a site for repeatedly accessing a patient's vascular system, for example, to treat dialysis patients. The shunt itself is typically formed of synthetic graft material and can withstand repeated needle sticks much better than a natural vein. An AV shunt 246 is created between the artery 242 and vein 244 by forming a side-to-side anastomosis using first and second securing components 248, 250. The shunt 246 is preferably formed of ePTFE, DACRON® or another suitable synthetic graft material.

It should be appreciated that the applications of FIGS. 23-23A, 24-24A and 23-25A represent several of many different uses for the invention. Other applications for the invention include, for example, neurological, urological and gastrointestinal procedures. As a further example, the invention could be used to form an anastomosis with an existing CABG graft that has partially or completely occluded over time, for instance, by placing the anastomotic securing components in the graft distal to the occlusion. In short, it will be recognized that the invention may be modified in varying degrees from the preferred embodiments illustrated and described specifically herein.

As noted above, it will be recognized that the invention may be used in many different procedures, for example, femoral-femoral, femoral-popliteal, femoral-tibial, iliofemoral, axillary-femoral, subclavian-femoral, aorticbifemoral, aorto-iliac, aorto-profunda femoris and extra-anatomic bypasses. In sum, the invention may be used to create an anastomosis with many different vessels, including, without limitation, the renal arteries, mesenteric vessel, inferior mesenteric artery, eroneal trunk, peroneal and tibial arteries.

Figure 26A:
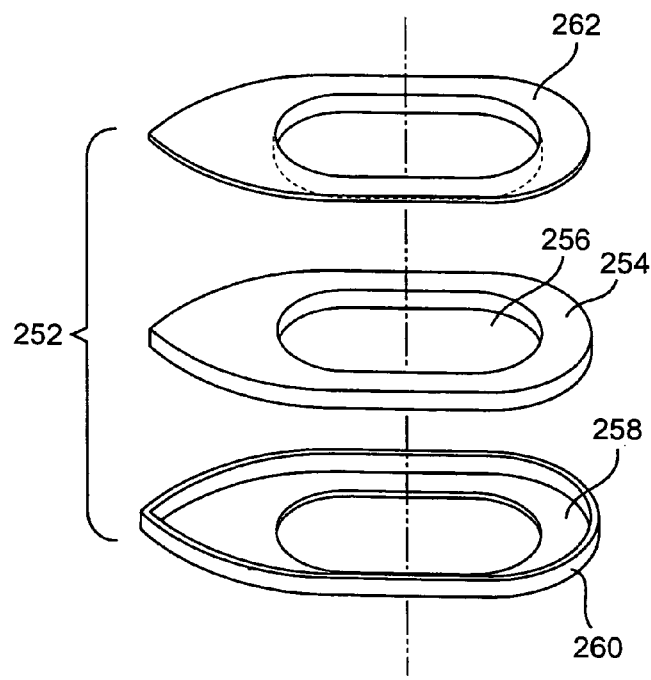
FIGS. 26A-26B are exploded perspective views of a device constructed according to one embodiment of the invention for forming a magnetic port in a hollow body having a lumen.

Another embodiment of the invention will be described with respect to FIGS. 26A-26D. A device for forming a port into a vessel (or for forming part of an anastomotic coupling) is indicated generally by the reference numeral 252 in FIG. 26A. The device 252 includes a member capable of producing a magnetic field, for example, permanent magnet 254, which preferably has an opening 256 adapted to communicate with a vessel lumen or other hollow body. The magnet 254 is received in a housing that, in this embodiment, comprises two elements configured for attachment to each other so as to enclose the magnet. One housing element 258 is generally dish-shaped with a rim 260 while the other housing element 262 is generally lid-shaped (as seen in FIG. 26A).

Figure 26B:
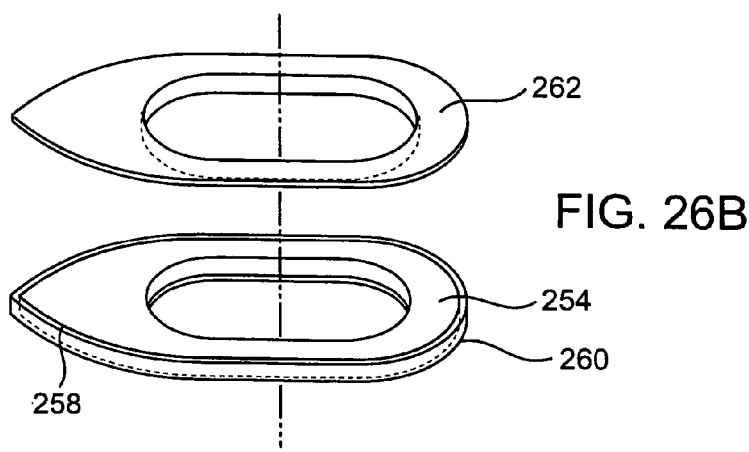
Figure 26C:
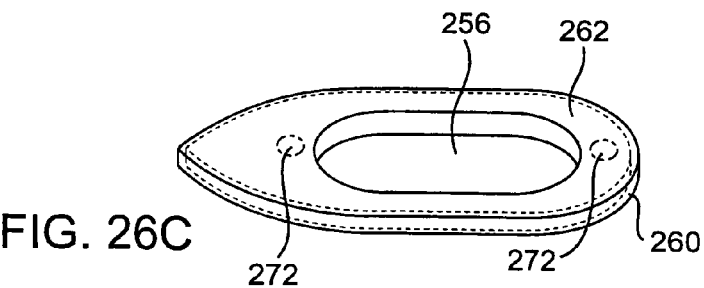
FIG. 26C is an assembled perspective view of the device shown in FIGS. 26A-26B.

FIG. 26B shows the magnetic member 254 disposed in the element 258 with the element 262 positioned above the assembly. FIG. 26C shows the element 262 affixed to the element 254 to form the housing and provide a sealed enclosure containing the magnetic member 254. This enclosure preferably forms a hermetically sealed environment that will protect the member 254 from external elements, e.g., blood or various bodily fluids, upon implanting the device 252 in a patient. The illustrated housing elements 258, 262 may be attached by any suitable means. For example, if constructed of metal laser welding may be used to join the housing elements. Other attachment means include adhesives, fasteners, etc.

Figure 27B:
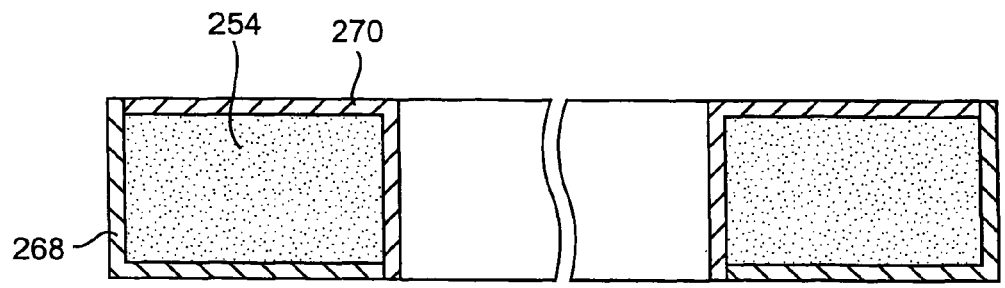
FIGS. 27A-27B are sectional views illustrating alternative constructions of the device shown in FIGS. 26A-26D.
Figure 27A:
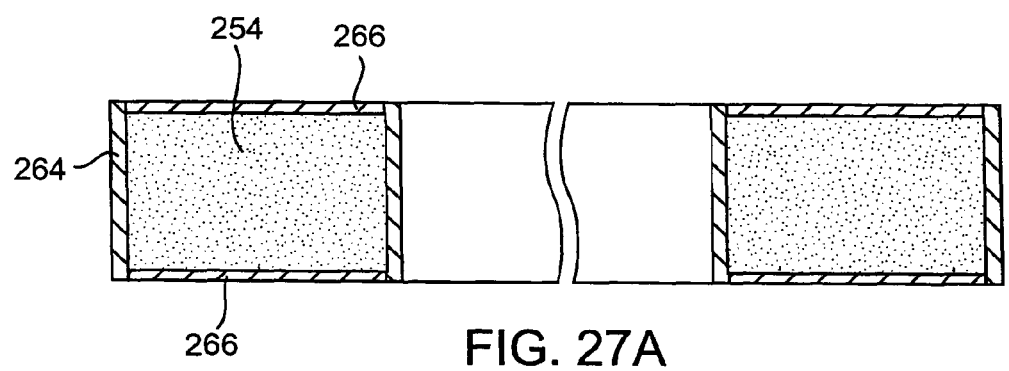
Figure 26D:
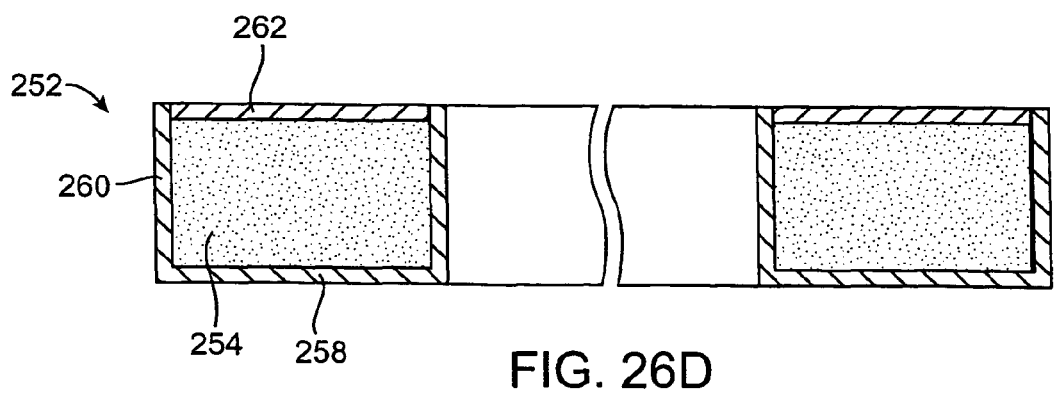
FIG. 26D is a sectional view taken along line D-D in FIG. 26C.

The housing enclosing the magnetic member may of course be formed of a unitary piece of suitable material, for example a metallic blank, or more than two pieces of material joined as described above. FIG. 26D is a sectional view of the device 252 shown in FIG. 26C illustrating the internal construction of the device, with lid element 262 resting on and secured to the rim 260 of dish element. FIG. 27A shows an alternative construction wherein the member 254 is enclosed in a housing defined by a spool-shaped element 264 and a pair of lid-shaped elements 266 secured thereto, for example as described above. FIG. 27B shows yet another construction wherein the member 254 is enclosed in a housing defined by mating channel-shaped elements 268, 270 which are secured together to form the enclosure for the member 254. The housing enclosing the magnetic member is preferably formed of a material that is a good to excellent conductor of magnetic flux. Exemplary materials are discussed above with respect to FIGS. 26A-26C and below in connection with FIGS. 28-31.

FIG. 26C also shows (in phantom) a schematic representation of means for indicating the polarity of the magnetic member 254. The illustrated indicator 272 may take the form of any suitable writing, color, etc., to indicate the polarity of the magnetic field produced by the member 254. For example, the indicator 272 may simply comprise the printed letters "N" or "S." This feature allows a user to confirm proper orientation of the device 252 relative to another device, thereby ensuring that the devices will attract each other (or repel each other, if that is desired). Other possible ways of ensuring proper orientation include pre-mounting the component(s) on a delivery instrument in a selected position, or providing a mechanism that automatically orients the component in the selected position. It may also be desirable to allow the component to be removed and remounted on the delivery device if its orientation is incorrect.

Turning to FIGS. 28-31, another embodiment of the invention will be described and includes methods and devices for increasing the magnetic attracting force between two components. FIG. 28 shows first and second components 274, 276 adapted to be coupled to a target vessel via magnetic attraction. The first and second components 274, 276 comprise, respectively, members 278, 280 which are capable of producing a magnetic field, as well as mechanisms 282, 284 for increasing the magnetic attraction force between the components. That is, when provided with the mechanisms 282, 284 and placed in proximity the components 274, 276 produce a higher magnetic force than when placed in proximity without the mechanisms.

FIG. 29 shows the components 274, 276 positioned on opposite surfaces of the wall W of a target vessel TV and coupled thereto by magnetic force. As shown, in order to form a port that communicates with the vessel lumen L, which is partially occluded at O, the components may have openings, such as respective openings 286, 288 in components 274, 276. These openings preferably are aligned with complementary openings in the mechanisms 282, 284 to form a port extending into the lumen. The mechanisms 282, 284 enhance the magnetic attraction between the components 274, 276, thereby more securely attaching the assembly to the vessel wall W than if the mechanisms were omitted.

Figure 30:
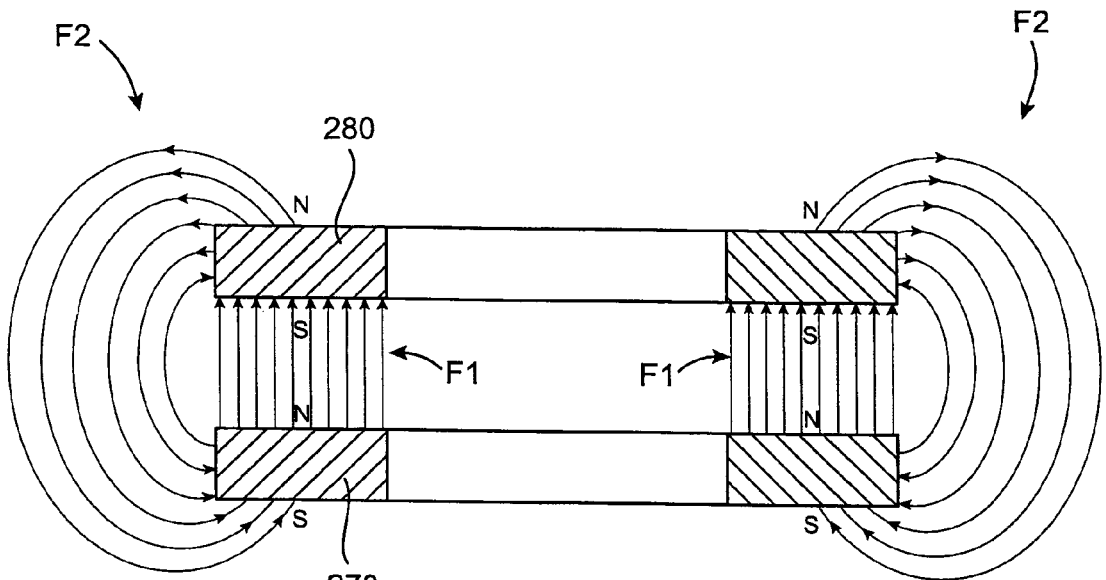
FIG. 30 is a sectional view of two magnets positioned in proximity to each other schematically illustrating the magnetic flux lines associated with the magnets.
Figure 31:
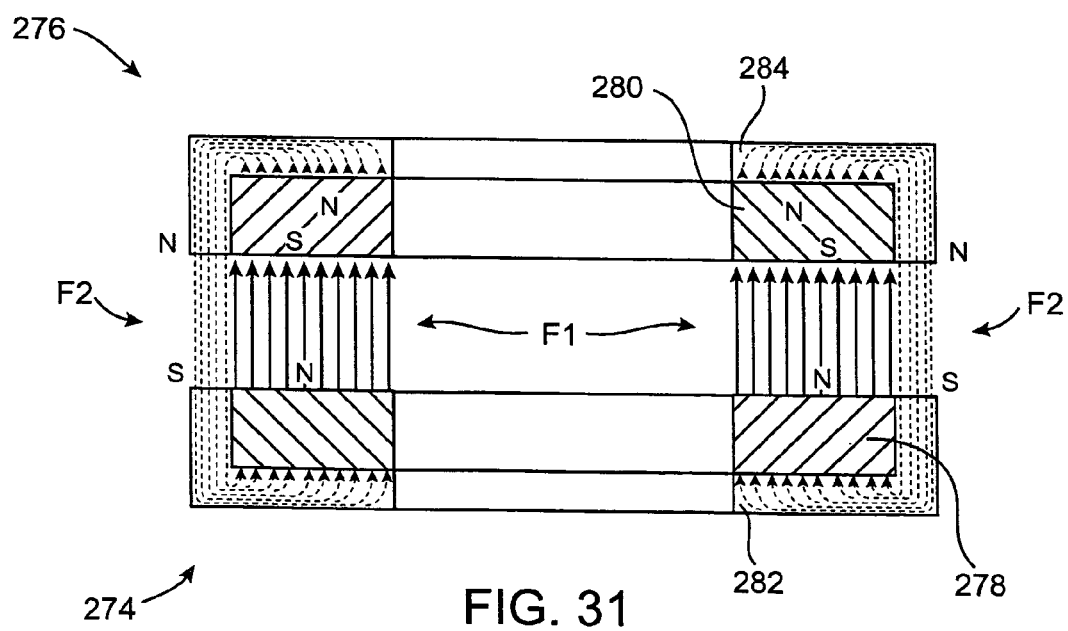
FIG. 31 is a sectional view showing the two magnets of FIG. 30 provided with flux concentration mechanisms constructed according to another embodiment of the invention and schematically illustrating the magnetic flux lines associated with the magnets of the invention.

Referring to FIGS. 30-31, the concept underlying this aspect of the invention will be described with respect to the specific embodiment of FIGS. 28-29. FIG. 30 shows the first and second members 278, 280 (which may be viewed as a pair of permanent bar magnets) in relatively close proximity, the poles of the magnetic members being oriented so that the components attract each other. FIG. 30 also schematically depicts the magnetic field produced by the magnetic members 278, 280. The magnetic field F1 located between the members 278, 280 is essentially uniform given the relatively large surface areas of and the small separation gap between the members. The number of lines present between the members 278, 280 is roughly indicative of the strength of field F1.

As shown, the magnetic field F2 located at the edges of the members 278, 280 fringes out, which dissipates or weakens the field F2. The field F2 fails to significantly increase the attraction force between the members 278, 280 due to its location and the fact that it is relatively weak (as it contains fewer, more spaced apart flux lines than the field F1). Put another way, the magnetic flux density or magnetic induction B (which is a measure of magnetic field strength) of field F1 is greater than the magnetic flux density of field F2. The invention provides means for utilizing the field F2 to increase the magnetic attraction force between two components. It will be noted that for sake of clarity FIG. 30 omits the portion of the magnetic field that would extend inward toward the center of each component.

FIG. 31 shows the members 278, 280 along with the mechanisms 282, 284 in fairly close proximity. The magnetic field F1 located between the members 278, 280 is essentially uniform as described above in connection with FIG. 30. As can be seen, though, the mechanisms 282, 284 alter the location and flux density of the magnetic field F2. Specifically, rather than fringing out as in FIG. 30, the field F2 is concentrated by the mechanisms 282, 284 between the components 274, 276. As such, the magnetic flux density increases, which in turn increases the attracting force between the components.

The specific manner of increasing the magnetic attraction force may vary from that shown. The illustrated mechanisms 282, 284 are configured to alter the construction of the magnetic members 278, 280 in order to increase magnetic flux density and hence raise the attraction force produced thereby. The mechanisms 282, 284 are separate elements coupled to the members 278, 280; however, means for increasing the magnetic force may comprise an integral portion of the magnetic member, a layer or coating applied to the member, etc. Further, the preferred mechanisms are channel-shaped to form an extension of the magnetic member that effectively channels the magnetic field F2 and concentrates the magnetic flux between the components 274, 276 (and more specifically, between the confronting edges of the mechanisms 282, 284). It will, however, be appreciated that this aspect of the invention may be practiced using mechanisms having alternative configurations.

The mechanisms 282, 284 have a magnetic permeability higher than air in order to concentrate the magnetic flux and increase the magnetic flux density and attracting force. That is, the mechanisms provide a path of least resistance as compared to air so that the magnetic flux flows into the mechanisms rather than the air. This in effect forms a magnetic circuit that captures a significant amount of the magnetic field F2 that otherwise would not contribute to the attracting force between the two components. One benefit of this aspect of the invention is that it allows a thinner magnetic member to be used for the component without sacrificing (or even increasing) magnetic field strength. In some applications, such as creating anastomoses on small vessels, it is typically desirable (e.g., for thrombogenecity reasons) to minimize the amount of foreign material located within or against the vascular tissue.

The material used to form the mechanism for increasing magnetic force preferably has a high magnetic permeability $\mu$ in order to concentrate a desired amount of magnetic flux in one or more desired areas. The mechanism is preferably formed of ferromagnetic material having a $\mu$ that is greater than the $\mu$ of air. More preferably, the material has a $\mu$ that is greater than 1.0, and even more preferably, significantly greater than 1.0 or as high as possible. Exemplary ranges of $\mu$ values include from about 1.0 to about 250,000, and from about 1.0 to about 1000. While ferromagnetic materials are preferably used to form the flux concentration mechanisms, other materials may be used instead. For example, ferrimagnetic, paramagnetic or diamagnetic materials may be used (although the results they achieve may be inferior to those obtained using a ferromagnetic material).

Tests have shown that, depending on the size, material and separation gap of the respective components having magnetic properties, the flux concentration mechanisms of the invention may be used to produce a magnetic attraction force that is from about 5% to about 75% higher than that obtained without flux concentration mechanisms. More preferable, though, is a flux concentration mechanism that increases the force from about 20% to about 75%. The exact amount of magnetic force used in practicing the invention, for example, to secure the components to a vessel, will depend on various factors, such as the sized of the vessel, the force limit prior to causing necrosis, etc.

It will be apparent that benefits provided by this feature of the invention include forming a firm attachment to tissue via magnetic force, the ability to alter the construction of a component to customize the amount or location of flux concentration, and the ability to reduce the size of the magnetic component while maintaining sufficient magnetic force to form the anastomosis.

Figure 32A:
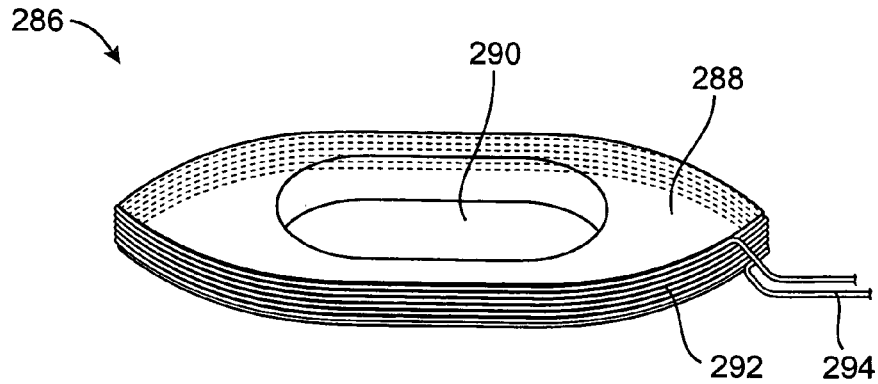
FIG. 32A is a perspective view of a device constructed according to another embodiment of the invention which is adapted to be coupled to tissue using electromagnetic force to form a magnetic port.
Figure 32B:
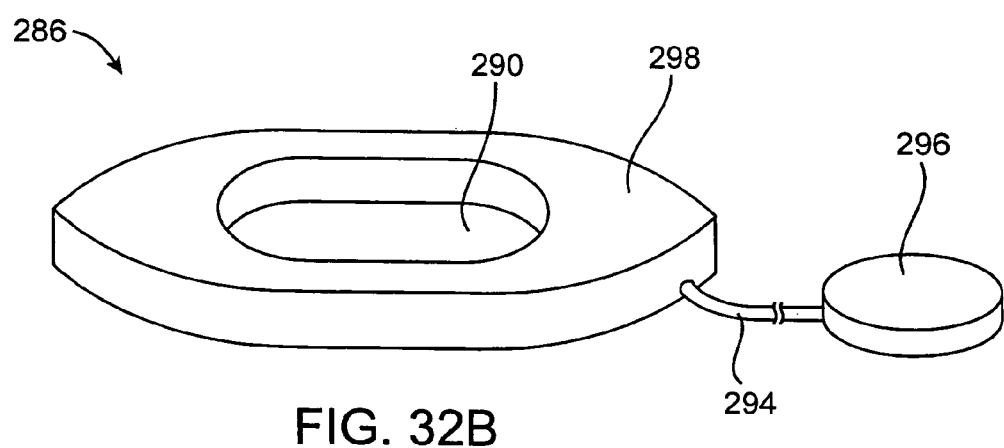
FIG. 32B is a perspective view of the device shown in FIG. 32A enclosed in a protective housing.

FIGS. 32A-32B show an anastomotic component 286 in the form of an electromagnet assembly including a core 288 having an opening 290. A coil 292 is wrapped around the side wall of the core 288 and has leads 294 running to a power source, such as battery 296 (FIG. 32B). FIG. 32B shows the component 286 after it has been placed in a protective housing 298 by suitable means, for example, a coating or structural enclosure as described above. The housing 296 is preferably formed of a strong, leak-tight biocompatible material.

Figure 33:
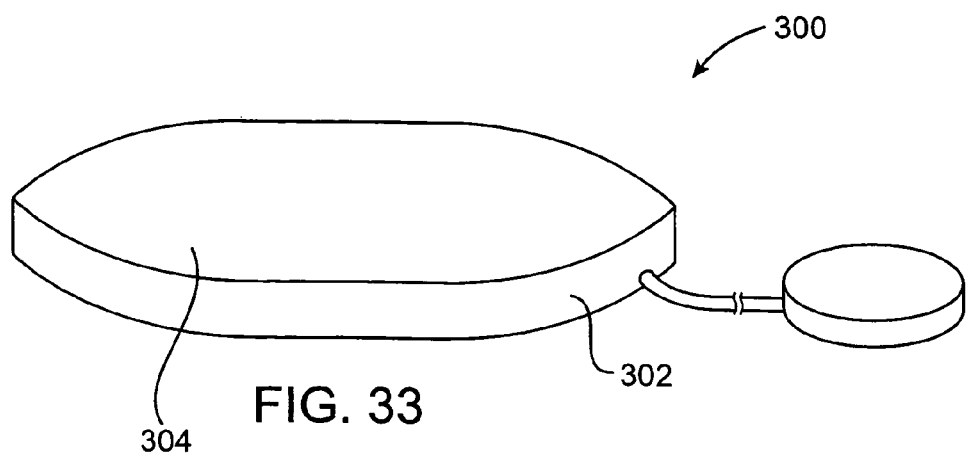
FIG. 33 is a perspective view of a device constructed according to yet another embodiment of the invention which is adapted to close an opening using electromagnetic force.

FIG. 33 shows an electromagnetic component 300 for use in closing an opening, for example, an opening in tissue such as an ASD, VSD, PDA, etc. As can be seen the component 300 includes a housing 302 with at least one occlusion surface 304 adapted to seal against tissue or an anastomotic component.

Figure 34A:
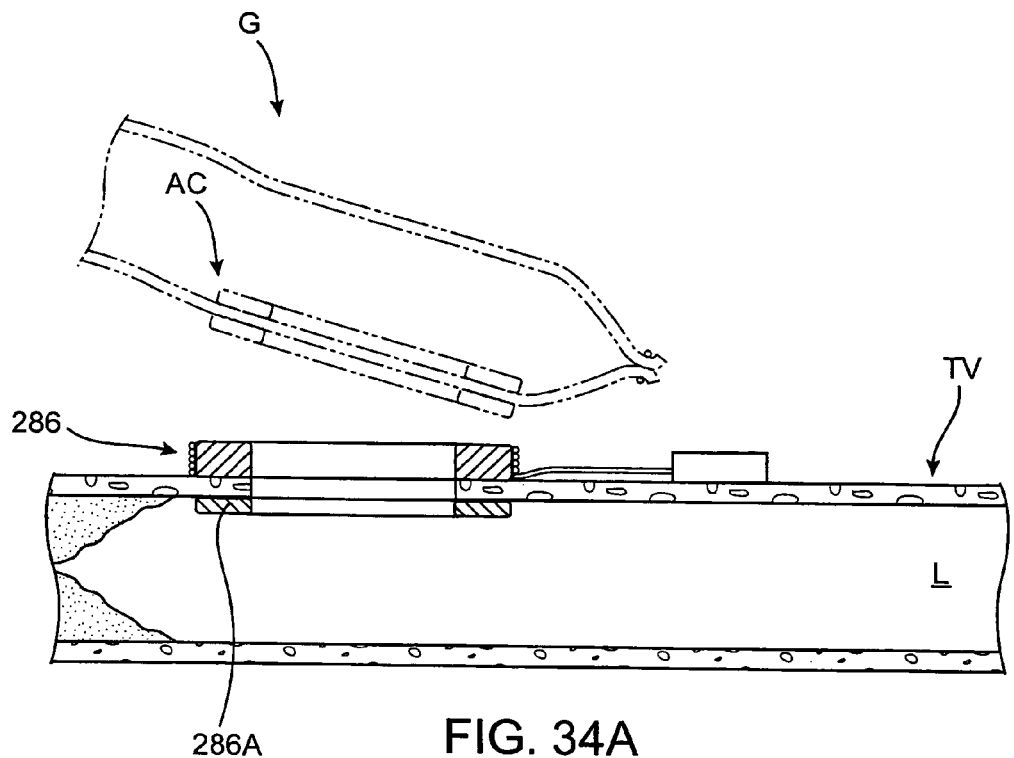
FIG. 34A is a sectional view taken through a target vessel having a lumen showing the device of FIG. 32B coupled thereto with a graft vessel shown (in phantom) prior to being anastomosed to the device.
Figure 34B:
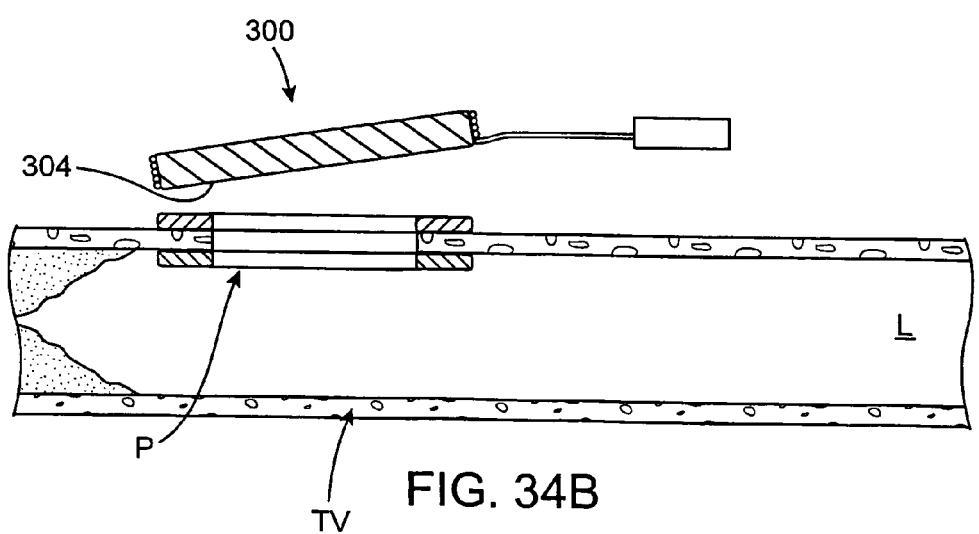
FIG. 34B is a sectional view taken through a target vessel having a port defined by an anastomotic component communicating with the vessel lumen with the device of FIG. 33 positioned above the port prior to being used to close the opening.

FIG. 34A is an example of the component 286 coupled to an anastomotic component 286A positioned on the opposite surface of the of a target vessel TV with a lumen L. A graft vessel G is shown (in phantom) just above the component 286 and includes an anastomotic component AC oriented to magnetically attract (or be attracted to) the electromagnetic assembly of component 286. FIG. 34B shows the occluding surface 304 of component 300 being used to close, either temporarily or permanently, a magnetic port P which communicates with the lumen L of the target vessel TV.

Figure 35A:
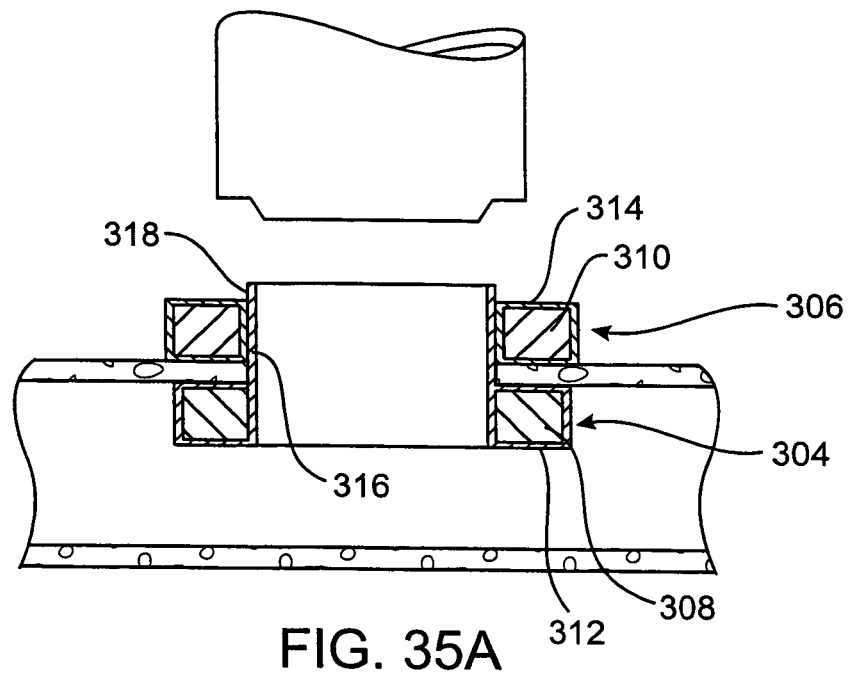
FIGS. 35A-35B are sequential sectional views taken through a target vessel having a lumen showing an anastomotic component constructed according to another embodiment of the invention being coupled to the wall of the vessel.
Figure 35B:
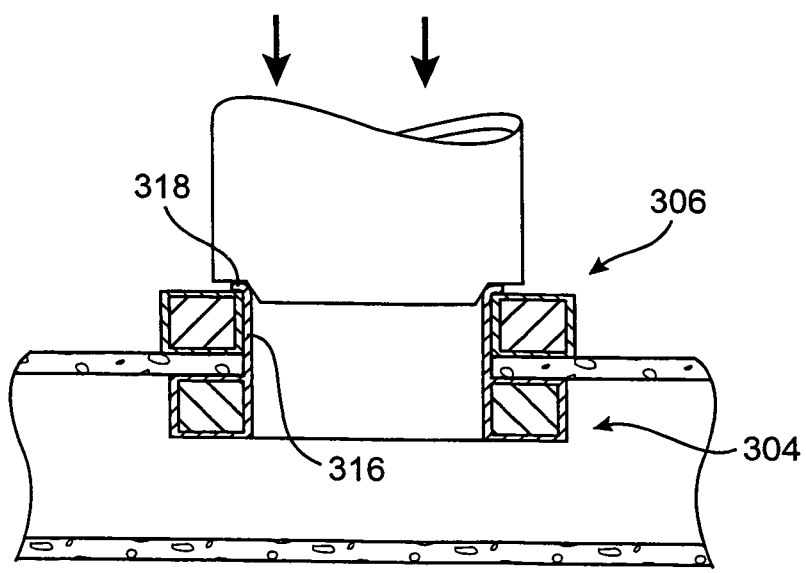
Figure 36A:
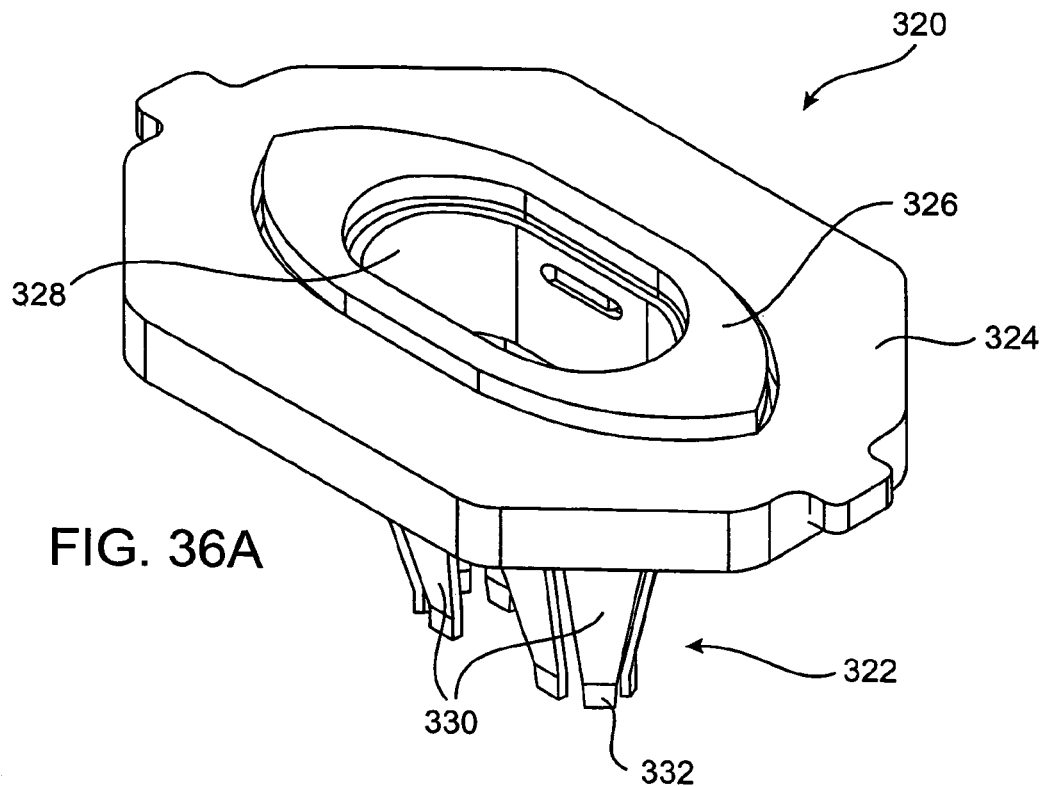
FIGS. 36A-36B are, respectively, upper and lower perspective views of a device constructed according to another embodiment of the invention for forming a port in a vessel having a lumen, wherein the device has a mechanical attachment portion shown in a low profile or collapsed orientation.
Figure 36B:
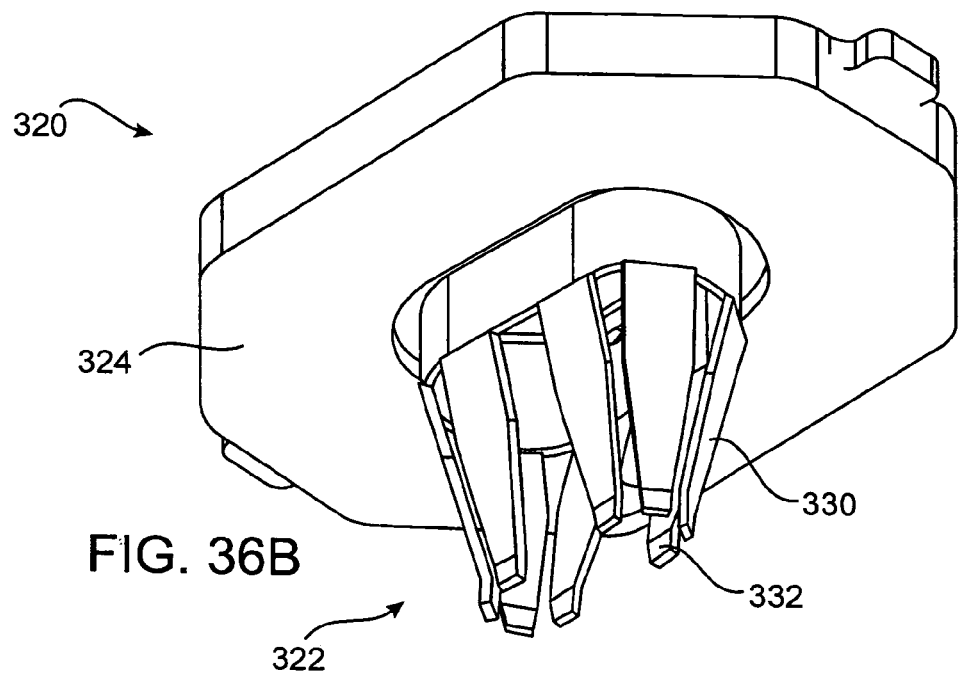
Figure 37A:
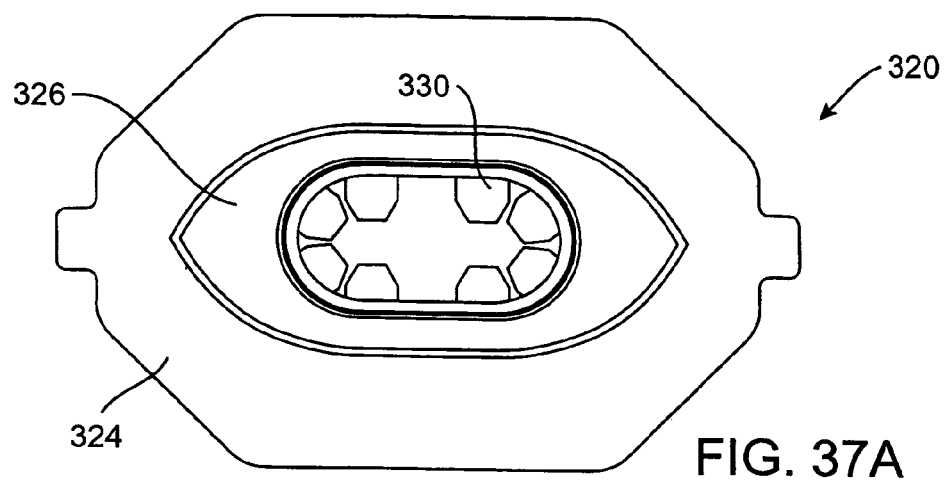
FIGS. 37A-37C are, respectively, upper plan, side elevation, and lower plan views of the device shown in FIGS. 36A-36B.
Figure 37B:
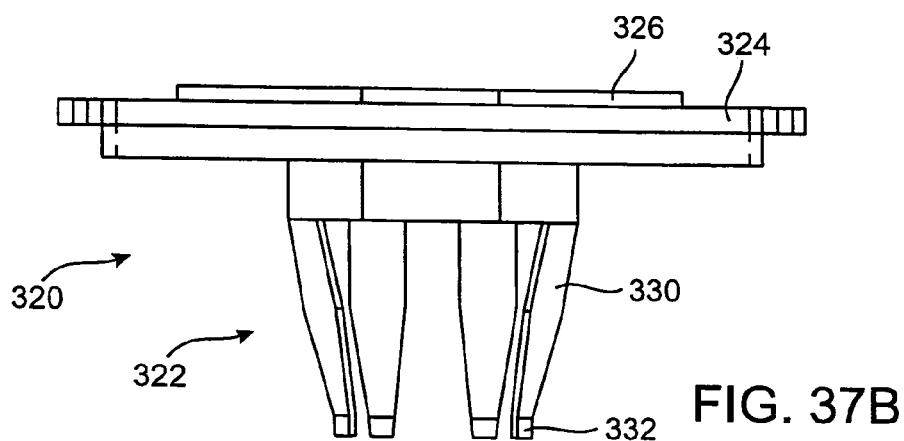
Figure 37C:
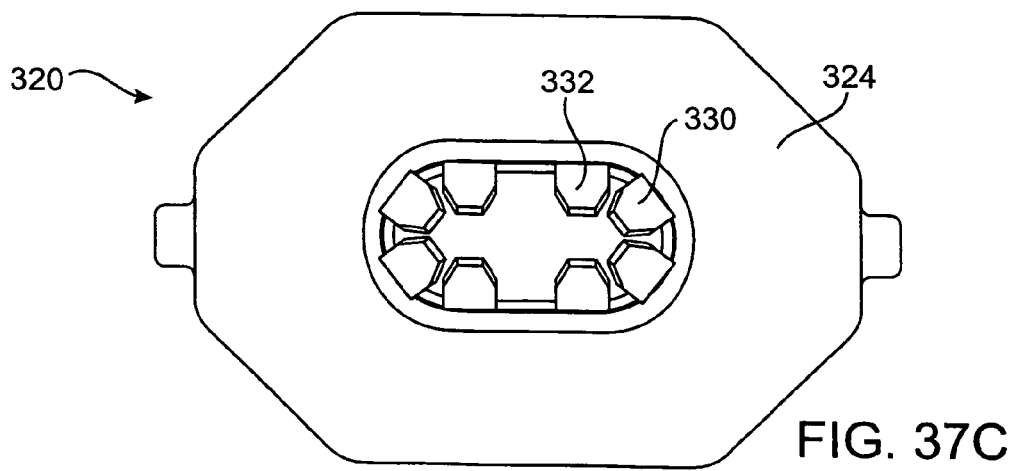
Figure 38A:
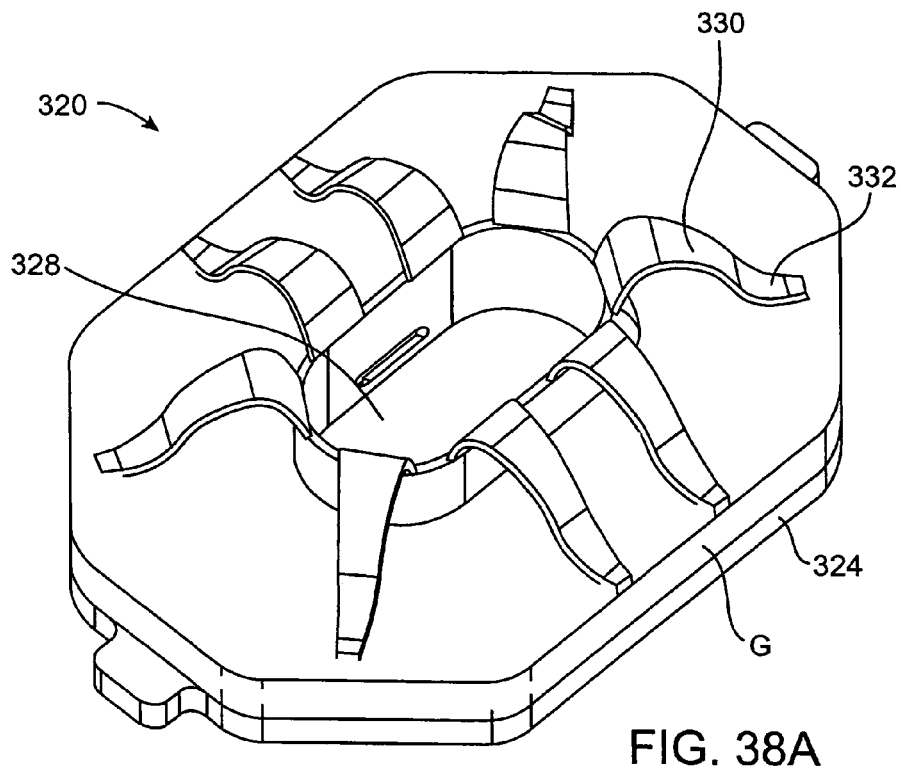
FIGS. 38A-38B are, respectively, upper and lower perspective views of the device shown in FIGS. 36A-36B, wherein the mechanical attachment portion of the device is shown in a wide profile or expanded orientation.
Figure 38B:
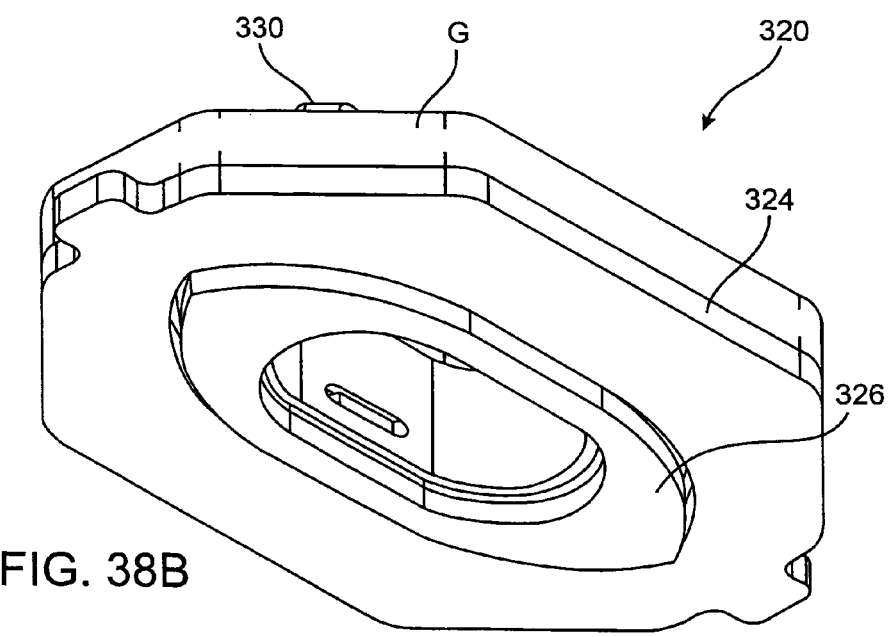

The invention may be practiced using magnetic, mechanical, or any other force-creating means to secure a component to tissue or to another component. FIG. 35A shows two anastomotic components 304, 306 including first and second magnetic members 308, 310 enclosed in housings 312, 314. The first component 304 has a sleeve portion 316 (which in FIG. 35A is an extension of the housing 314) having an end 318 that projects beyond the second component 306. Any suitable means may be used to collapse or other manipulate the end 318 relative housing 314 of second component 306, for example, the instrument represented schematically in FIG. 35A. As shown in FIG. 35B, the instrument is moved in the direction of the arrows to collapse the end 318 and mechanically couple the securing components 304, 206. As a result, this embodiment joins the components by both magnetic and mechanical forces.

FIGS. 36A-39C show another embodiment in the form of a component 320 to be coupled to tissue by a mechanical attachment portion 322. The component 320 includes a base 324 and a member 326 for producing a magnetic field. An opening 328 passes through the component 320 and is placed in communication with a target vessel, for example, a coronary or peripheral artery. FIGS. 36A-36B and 37A-37C show the component 320 in a low profile or collapsed configuration for delivery. The illustrated attachment portion 322 includes a plurality of arms 330 adapted to engage tissue of the target vessel wall, which results in the vessel wall being sandwiched between the ends 332 of the arms 330 and the base 324. The component 320 may comprise separate members, as in the illustrated embodiment, or it may comprise an integral structure with or without a magnetic portion.

Figure 39A:
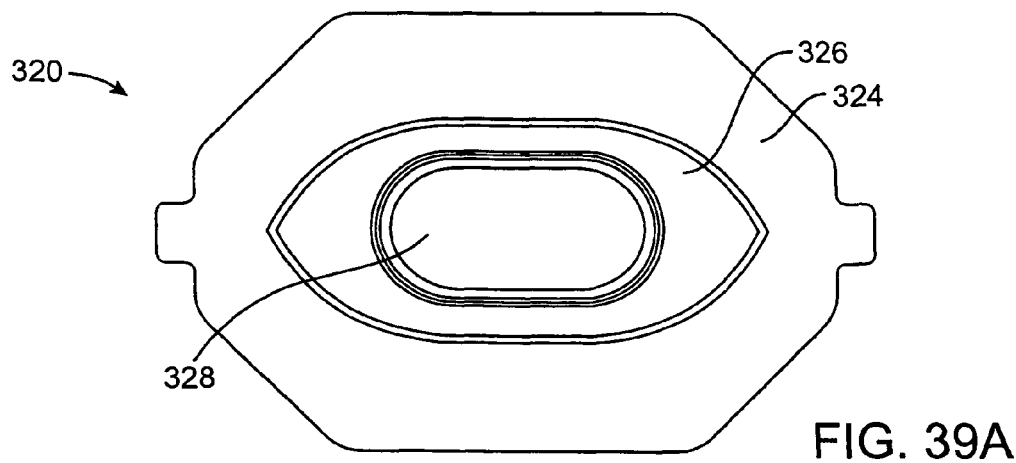
FIGS. 39A-39C are, respectively, upper plan, side elevation, and lower plan views of the device as shown in FIGS. 38A-38B.
Figure 39B:
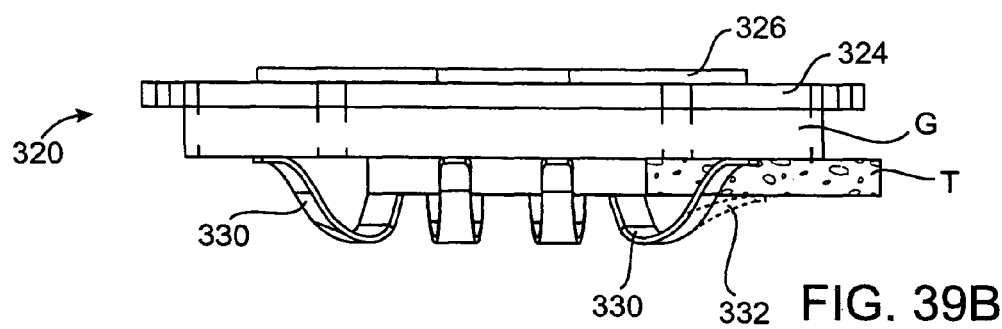
Figure 39C:
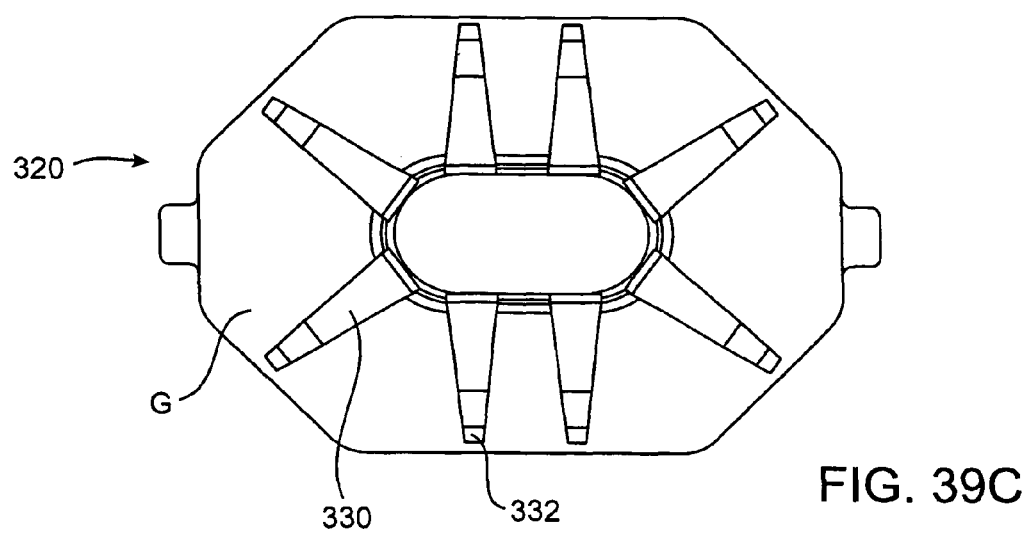

FIGS. 38A-38B and 39A-39C show the component 320 in a raised profile or expanded configuration corresponding to its deployed, tissue-engaging position. FIG. 39B shows (in phantom) tissue T engaged by the expanded arm 332. These Figures show, however, an optional feature of this embodiment, namely, a biocompatible layer G adapted to be placed in contact with the tissue. Exemplary uses for such as layer, which may be formed of any suitable material, include sealing the vessel opening and promoting tissue ingrowth at the site. This embodiment of the invention uses mechanical force to couple a component to the tissue but forms a magnetic port (via member 326) that may be anastomosed to another component having the same or a different construction. It will be recognized that the component 320, rather than presenting a magnetic port for docking a vessel, could present an alternative structure for attaching a graft, such as a stent, staples or fasteners, adhesive, etc.

FIGS. 40A-40C shows an exemplary use of the device illustrated in FIGS. 36A-39C. A delivery device 334 is schematically shown and includes a tip 336 which is preferably configured to incise and dilate tissue. The tip 336 may be mounted on a shaft 338 and has a recess that receives the ends 332 of the arms 330 (FIG. 40A) and retains them in their collapsed configuration. The delivery device 334 also has an end 340 for contacting the magnetic member 326 of the component 320 to prevent movement of the arms 330 relative to the delivery device.

FIG. 40A shows the device 334 after the tip 336 has cut through tissue of a vessel wall W and the component has been properly positioned against the surface of the wall. FIG. 40B shows the device 334 after the shaft 338 has been moved distally to release the ends 332 of component arms 330 and allow them to expand into contact with the tissue T. Next, as shown in FIG. 40C, the delivery device 334 with shaft 338 is removed proximally through the opening 328 of component 320.

It will of course be appreciated that this embodiment of the invention may take many constructions other than those specifically illustrated herein. For example, rather than having individual arms 330 which engage the tissue T, a continuous or semi-continuous surface could be used, the surface being planar, concave-convex, etc.

Figure 41A:
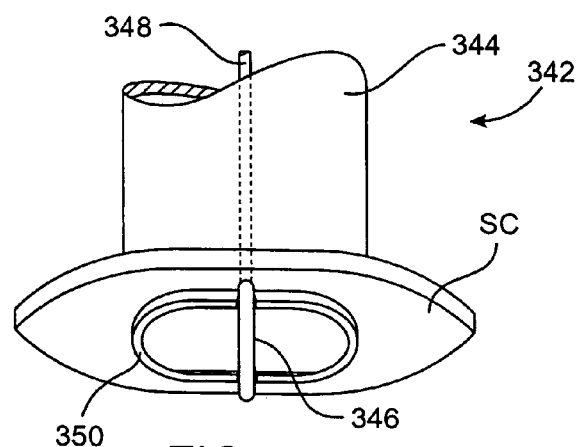
FIG. 41A is a perspective view of a delivery device constructed according to another embodiment of the invention, wherein the device has a retaining portion shown in a first position to retain an anastomotic component.
Figure 41B:
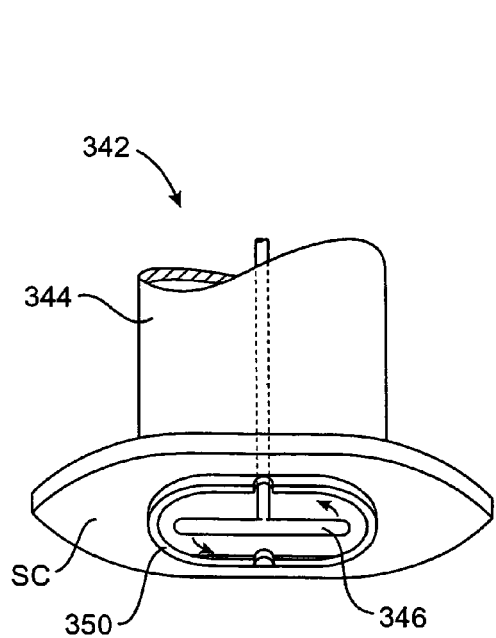
FIGS. 41B-41C are perspective views of the device shown in FIG. 41A but sequentially illustrating the retaining portion being moved to release the component.
Figure 41C:
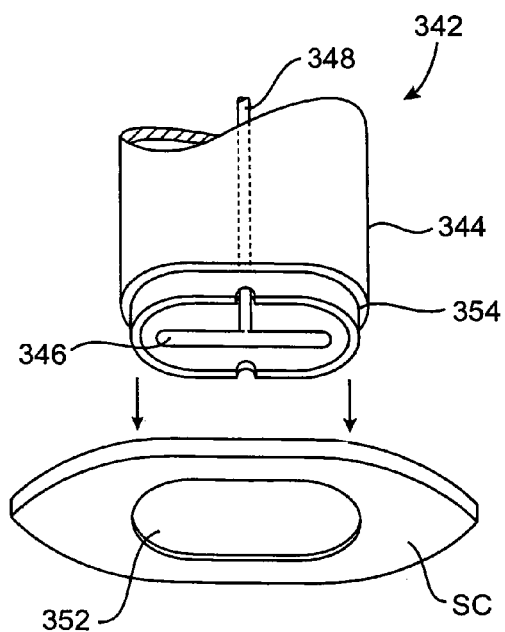

FIGS. 41A-41C show a delivery device constructed according to yet another embodiment of the invention. The delivery device 342 includes a support portion 344 and a retaining portion or mechanism 346 for retaining a securing component SC on the device. The illustrated retaining portion 346 is carried by a shaft 348 and engages a flange 350 formed on (or attached to) the securing component SC around its opening 352. The flanged securing component SC is preferably magnetic and may be constructed as described above regarding previous embodiments (e.g., FIGS. 19A-19C). FIG. 41A shows the delivery device 342 in a first position in which the retaining portion 346 is in its first position to retain the securing component SC. It will be noted that the device 342 may also be used to deliver a non-flanged securing component(s).

FIG. 41B shows the delivery device 342 after the retaining portion 346 has been moved out of the first position to release the securing component 342. In this embodiment the retaining portion is rotated 90° from the first position, although other motions may be used to release and engage the securing component. FIG. 41C shows the delivery device 342 after it has been withdrawn proximally through the opening 352 in the securing component 342. FIG. 41C also shows the particular construction of the support portion 344 of device 342. A step 354 is formed to receive the opening 352 of the securing component 342. The step 354 helps align the securing component and aids in even delivery to the tissue surface.

Figure 42A:
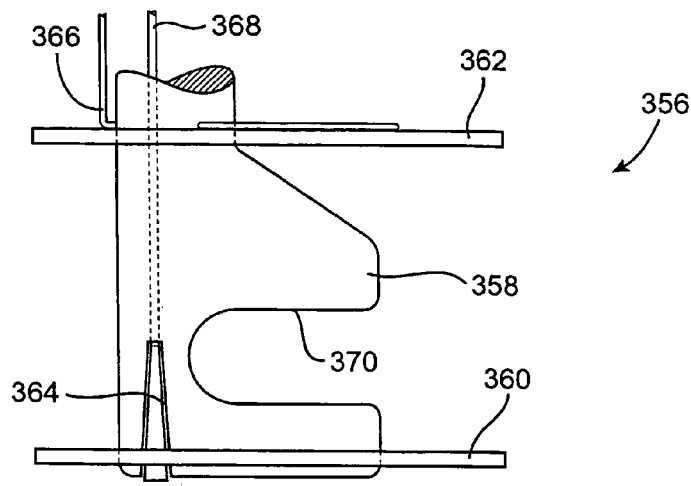
FIG. 42A is a perspective view of a delivery device constructed according to still another embodiment of the invention, wherein the device has a retaining portion shown in a first position to retain an anastomotic component.
Figure 42B:
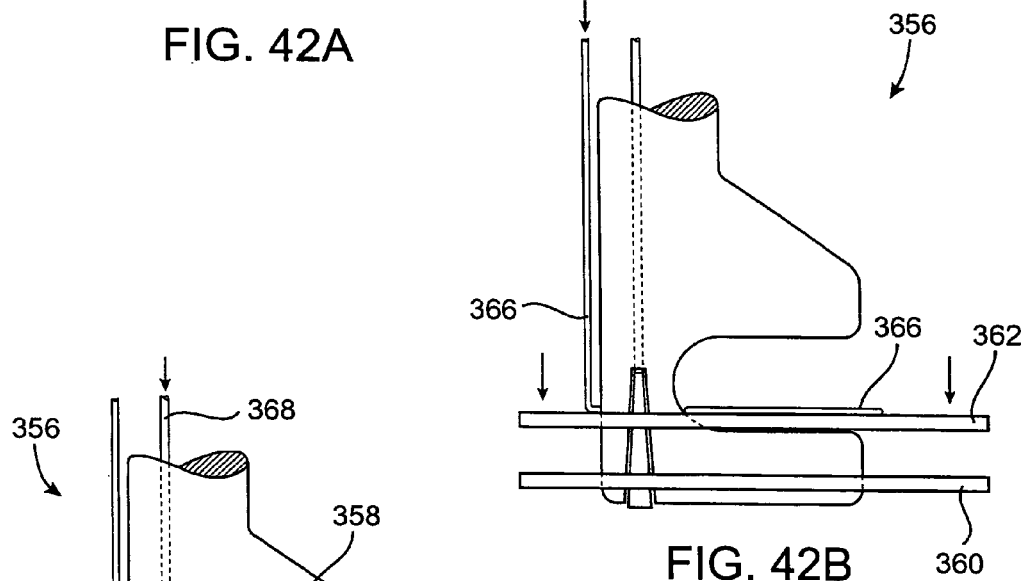
FIGS. 42B-42C are perspective views of the device shown in FIG. 42A sequentially illustrating the retaining portion being moved to release the component.
Figure 42C:
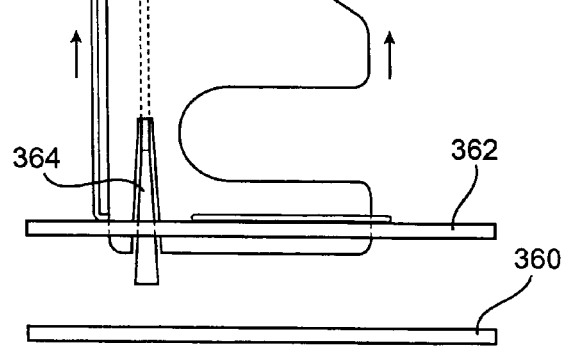

FIGS. 42A-42C show a delivery device 356 constructed according yet another embodiment of the invention. The device 356 includes a body 358 which to some extent acts as a support portion for first and second components 360, 362. A first retaining portion or mechanism 364 is movable relative the body 358 and engages the first component 360 to retain it in place prior to and during delivery. A second retaining portion or mechanism 366 is also movable and engages the second component 362 to retain it in place. A shaft 368 supports the first retaining portion 364, and the body 358 has a notch 370 which facilitates introducing the components into a vessel lumen, as described below.

FIG. 42B shows the device 356 after the second retaining portion 366 has been moved toward first component 360 to drive the second component 362 to its desired position, for example, against an opposite surface of the vessel wall. FIG. 42C shows the device 356 after the first retaining portion 364 has been moved distally relative to the body 358 of the device. The portion 364 is wedge-shaped and this motion moves the portion 364 out of contact with the first component 360, thereby releasing it from the device. Magnetic attraction maintains the two components 360, 362 in place.

Figure 43A:
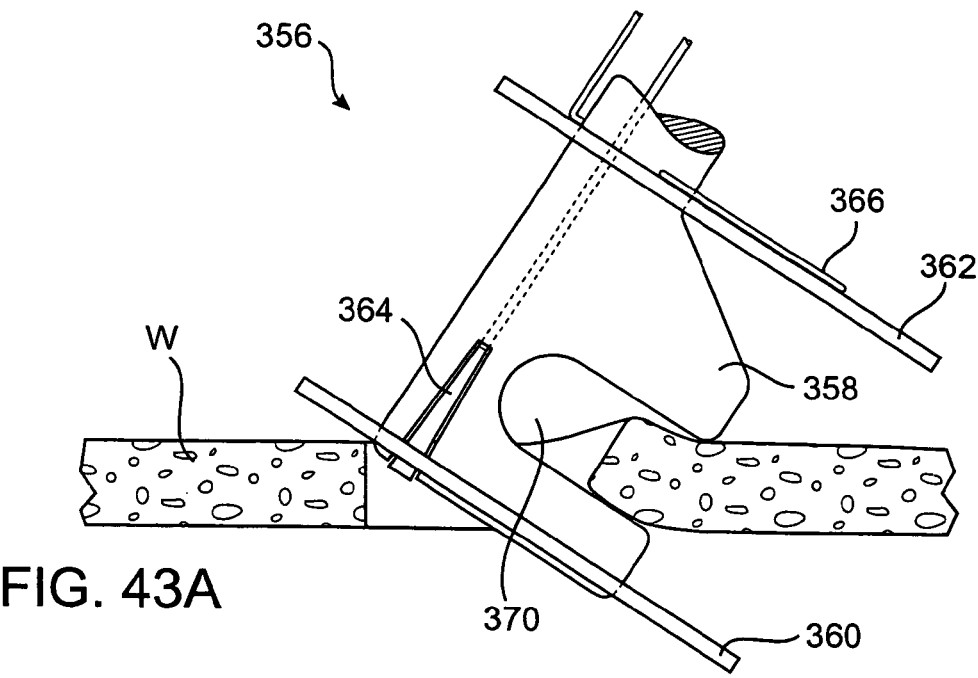
FIGS. 43A-43B are partial sectional views of the device shown in FIGS. 42A-42C sequentially illustrating the device being used to couple an anastomotic component to a vessel.
Figure 43B:
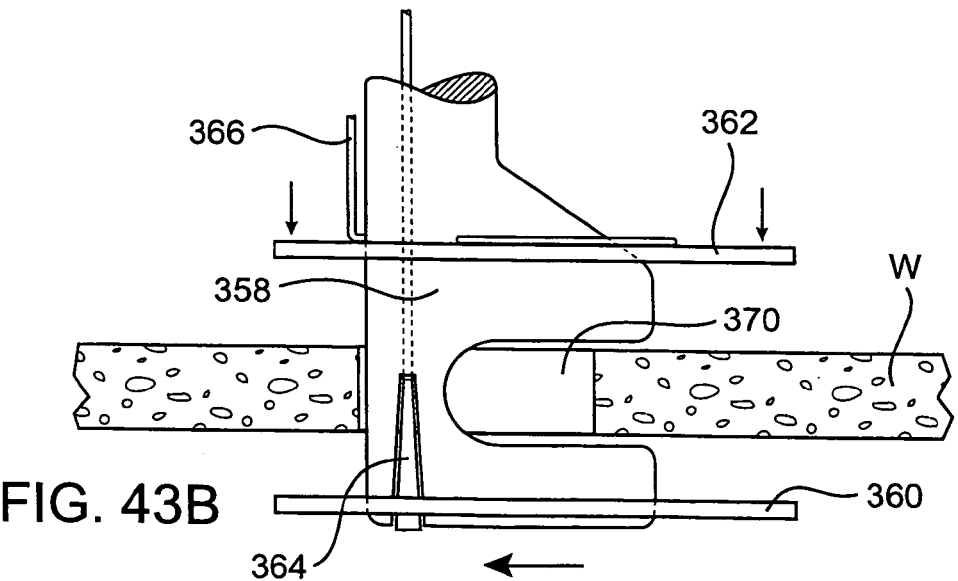
Figure 43C:
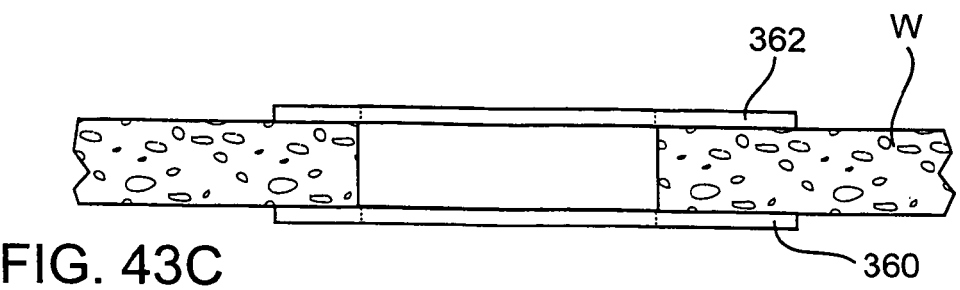
FIG. 43C is a partial sectional view showing the anastomotic component in its final position.

FIGS. 43A-43C show the delivery device 356 being used to couple the first and second components 360, 362 to a vessel wall W. As shown in FIG. 43A, the notch 370 can be used to guide the first component 360 through an incision in the wall W. It should be noted now that another aspect of this embodiment provides an offset structure for easier introduction of the leading end of a component. As can be seen in FIG. 43A, this feature allows the longer component 360 to be introduced through a shorter incision. The term offset means that the body 358, i.e., the delivery end of the device 356, extends laterally in one direction to give the device an asymmetrical configuration. For example, in the illustrated embodiment the body 358 extends to one side and defines the notch 370, but does not extend laterally in the opposite direction. Put another way, the delivery end of the device 356 is offset with respect to a longitudinal axis of the device.

FIG. 43B show the first component 360 passed through the incision and the second component 362 being lowered to a position that achieves the desired amount of magnetic attracting force. FIG. 43C shows the resulting position of the two components with their openings generally aligned with the incision in the wall W.

As mentioned above with respect to FIG. 5, the invention may be practiced using flexible components that are capable of producing a magnetic field. FIG. 44 shows another embodiment comprising a component 374 in the form of a foldable sheet being collapsed, for example, in order to deliver the component percutaneously. FIGS. 45A-45B show, respectively, expanded and collapsed orientations of a component 376 constructed according to another embodiment. FIGS. 46A-46B show, respectively, components 378, 380 having magnets 382 disposed partially therein so as to allow at least partial collapsing of the components in accordance with yet another embodiment.

FIG. 46C shows a component 384 constructed according to another embodiment in its expanded state. A frame 386 supports a web or body 388 and is capable of producing a magnetic field while being collapsible for easier delivery. The web 388 may be used to occlude an opening. FIG. 46D shows a collapsible component 390 that may be used to form a magnetic port or an anastomosis. The component 390 preferably comprises a magnetic core covered by a superelastic or shape memory housing and has ends 392 that permit the component to be delivered in a straight, low-profile configuration. FIG. 46E shows an exemplary catheter C retaining the component 390 in a low-profile orientation.

FIGS. 47A-47C show yet another embodiment of the invention that provides a device 394 for closing an opening in tissue, such as any of the cardiovascular defects mentioned above. The device 394 could be used in other applications as well. In FIG. 47A a sheath or catheter 396 houses a pair of magnetic components 398, 400 on a shaft 402. The components 398, 400 may take any of the previously described constructions and are configured to attract each other across a body of tissue with an opening to be closed. FIG. 47B shows the device 394 after relative movement has been imparted to the sheath 396 and the components 398, 400. The component 398 is out of the sheath 396 and fully expanded while the component 400 is partially out of the sheath and expanded. FIG. 47C shows the device 394 with the component 398 exploded from the shaft 402. The shaft 402 and component 398 have mating magnetic and/or mechanical interlocking means indicated at 404, such means securely holding the component 398 during delivery and then releasing it preferably via remote actuation upon reaching the target site.

FIGS. 48A-48C show an exemplary application of the embodiment illustrated in FIGS. 47A-47C wherein the device 394 is used to close a ventricular septal defect VSD in the septum S between the right and left ventricles RV, LV. FIG. 48 shows the device 394 introduced percutaneously into the right ventricle RV and the component 398 located and expanded in the left ventricle LV. The component 398 is forced against the septum S and the other component 400 is expanded as shown in FIG. 48B. Once expanded, component 400 is forced against the septum S (e.g., by using the sheath 396), attracts the component 398 to close the defect, and the device 394 is removed (FIG. 48C).

Turning now to FIGS. 49A-49C, an anastomotic component constructed according to another embodiment of the invention is indicated generally by the reference numeral 420 and includes a first portion 422 and a second portion 424 attached thereto. The second portion includes a tubular body adapted to be attached to a hollow body such as a blood vessel. The illustrated second portion 424 includes a plurality of openings 426 which may serve several purposes. For example, the openings may promote tissue ingrowth to enhance engagement of the component 420 with a vessel to which it is attached. The openings 426 may also serve to allow the tubular body of the portion 424 to flex or collapse during use easier, e.g., for delivery and deployment. The portion 424 may be formed from stainless steel, nitinol, etc., and is preferably tapered outwardly (not shown) to engage the interior of a vessel.

The first and second portions 422, 424 of the anastomotic component 420 are shown separated in FIG. 49A and assembled in FIG. 49B. According to the invention, the portions 422, 424 are provided with respective attachment structure to facilitate securing the portions together in fluid-tight fashion. The attachment structure in the embodiment of FIGS. 49A-49C comprises mating tabs and recesses 428, 430. As seen in FIG. 49C, the tabs 428 are formed on (or attached to) the second portion 424 and are received in the recesses 430 formed in the first portion 422. The result is a firm assembly that provides the anastomotic component with substantially flush continuous upper and lower surfaces.

FIGS. 50A-50B show another embodiment of the invention wherein an anastomotic component 432 includes a first portion 434 and a second portion 436, the second portion including openings 438. The first portion 434 has tabs 440 that are received in slots 442 formed in the second portion 434. FIG. 50A shows the two components separated while FIG. 50B shows them assembled. The tubular body of second portion 436 may be flexible (e.g., due to the presence of openings 438) to allow it to be bent in order to insert the tabs 440 into the slots 442. The anastomotic component of FIGS. 50A-50B may include structure in addition to that shown. For example, the tubular body of the second portion 436 may be provided with one or more fluid-impervious layers (such as ePTFE), additional structure to facilitate attachment to a tubular body, radiopaque markers, etc. Also, any desired number of tabs and slots may be used to interlock the first and second portions 434,436.

FIGS. 51A-51B show another embodiment of the invention comprising an anastomotic component 444 which includes a first portion 446 and a second portion 448. The first portion 446 is similar to that of the previous embodiments and the second portion 448 includes a tubular body in the form of a lattice or web-like structure with a plurality of openings 450. As shown in FIG. 51A, an end of the second portion 448 is received within the opening 452 of the first portion 446.

While the entire illustrated second portion 448 comprises a lattice-like structure, one or more portions may instead be solid, for example, the end that is secured to the first portion 456. The component portions 446, 448 may be attached by any suitable means. For example, an adhesive or thermal energy bond may be used to join the portions 446, 448.

FIGS. 52A-52C show another embodiment comprising an anastomotic component 454 having a first portion 456 and a second portion 458. The first portion 456 includes a rim or flange 460 that is adapted to be coupled to the second portion 458. The second portion 458 has one or more extensions (e.g., an end of a wire) 462 that is threaded through one or more openings 464 formed in the rim or flange 460 of the first portion 456. As in the previous embodiment, the attachment between the first and second portions 456, 458 may be fortified by additional means, such as adhesive, welding, clips, etc. FIG. 52C shows the assembled component 454 which is secured to a natural vessel or provided with synthetic vascular material (such as ePTFE or Dacron) to form a graft that may be attached to another component).

FIG. 53A shows a magnetic anastomotic component 466 constructed according to another embodiment of the invention. The component 466 includes a first portion 468 and a second portion 470 attached together at 472 by any of the means discussed above, such as adhesive or thermal bonding. As seen in FIG. 53A, the tubular body of the second portion 470 defines a lumen that communicates with an opening 474 defined by the first portion 468 (which itself communicates with a vessel lumen).

FIG. 53B shows the magnetic component 466 coupled to a hollow body 476 with the tubular body of the second portion 470 located inside of the hollow body 476. The second portion 470 may be in the form of a stent or other expandable structure (pressure or self-expanding) that exerts pressure against the interior surface of the wall of the hollow body 476, thereby securing the component 466 to the hollow body 476.

FIG. 53C shows the anastomotic component 466 of FIG. 53A mounted to a hollow body 478. In this embodiment, the second portion 470 of the component 466 is located on the exterior of the hollow body 478. The distal end of the hollow body 478 is passed through the opening 474 of the first component portion 468 and everted around the perimeter of the portion 468 in this embodiment. The end of the hollow body 478 may be secured to the component 466 by any suitable means, for example, adhesive, suture, etc. Additionally, the portion 470 of the component 466 may be constructed to engage the hollow body 478 and to secure the structures away from the distal end of body 478. It should be appreciated that the embodiments of FIGS. 53B-53C may be practiced using additional securing means disposed inside or outside of the hollow body.

FIGS. 54A-54F show a magnetic anastomotic component constructed according to another embodiment of the invention. The component is designated by the reference numeral 480 and includes first and second pluralities of tabs 482, 484 supported by an annular body 486. FIG. 54A shows the tabs 482, 484 in a restrained or biased orientation that aligns the tabs in a circumferential direction. FIG. 54B shows the tabs 482, 484 in an unbiased orientation in which they extend in alternate radial directions. Sleeves or layers 488A, 488B are respectively attached to the sets of tabs 482, 484, as shown in FIGS. 54C-54D. The sleeves 488A, 488B are moved from the position shown in FIG. 54D to the position shown in FIG. 54D and then restrained (for example, by a suitable instrument—not shown).

As shown in FIG. 54E, this creates an annular space between the sleeves 488A, 488B for receiving the end E of a hollow body. The tabs 482, 484 are released and sleeves 488A, 488B move toward each other to sandwich the end of the hollow body (FIG. 54F). This embodiment may be practiced using resilient, superelastic, malleable or deformable tabs.

FIGS. 55A-55C show another embodiment of the invention wherein an anastomotic component comprises an anastomotic component 494 includes a first portion 496 and a second portion 498. An end of the second portion 498 (which may be a natural or synthetic blood vessel) is secured to an exterior surface of the first component portion 496. The components may be attached by adhesive or any other suitable means such as those discussed above.

The magnetic anastomotic components shown in FIG. 49A through FIG. 55C may comprise permanent magnets, electromagnets, or materials having ferromagnetic properties. Suitable materials that may be used for the components are disclosed in the above-referenced, co-pending patent application Ser. No. 09/562,599. The magnetic anastomotic component has the ability to produce or be attracted by a magnetic field; that is, at least one of the first and second portions of the component include or are formed of a material that possesses such an ability. It will be recognized by those skilled in the art that many variations of magnetic anastomotic components illustrated herein will be possible without departing from the principles of the invention. For example, the material(s) used, the placement or disposition of material on or about the component, the size, shape and configuration of the component, etc., may be altered if desired.

Another aspect of the invention provides various attachment mechanisms between a magnetic anastomotic component and a hollow body. It will be appreciated that "hollow body" refers to any anatomical structure having a lumen. Exemplary structures include blood vessels, e.g., coronary or peripheral arteries or veins, as well as hollow bodies of the urological and gastrointestinal systems. In addition, it should be appreciated that the invention may be used in applications other than those involving a hollow body, e.g., to close an opening in tissue, attach a prosthesis, deliver a device or substance, etc.

The magnetic anastomotic components may be attached to the hollow body in different ways, including adhesively, mechanically and magnetically. FIGS. 56A-56B show the anastomotic component 466 of FIG. 53B in the process of being magnetically attached to a hollow body in the form of a blood vessel V. The first portion 468 of the component 466 is inserted through an opening in the wall of vessel V and positioned so that the upper surface of portion 468 abuts the interior surface of the vessel wall. As seen in FIG. 56B, a member 500 having an opening 502 sized to receive the tubular body 476 is slid down until it abuts the exterior of the vessel wall.

FIG. 56B shows the first component portion 468 and the member 500 (which may be viewed as part of the first component or a second anastomotic component) sandwiching the wall of vessel V. The anastomotic component 466 is wholly or partially capable of producing or being attracted by a magnetic field. In the illustrated embodiment, the first anastomotic component portion 468 and the member 500 are magnetically attracted to each other and compress the vessel wall, thereby ensuring a fluid-tight attachment between the hollow body 476 and vessel V.

FIGS. 57A-57B show the anastomotic component 466 and tubular body 478 of FIG. 53C being attached to a vessel V. The first component portion 468 is magnetically attracted to a member 504 secured to the exterior of the vessel V (FIG. 57B). The member 504 has an opening 506 that is aligned with an opening O formed in the side wall of vessel V. The opening 506 of the member 504 communicates with the tubular body 478 of the anastomotic component 466 once the anastomosis is complete (FIG. 57C).

FIGS. 58A-58C show another embodiment of the invention wherein an anastomotic component 508 includes a first portion 510 and a second portion 512. The first portion 510 includes a curved body 514 with optional openings 516. The member 510 is preferably magnetic or ferromagnetic. A tubular body 518 extends from the first component portion 510 and has a lumen 520 that communicates with an opening formed in the portion 510. The first portion 510 is positioned inside the lumen of the vessel V and pulled against the interior of the wall (FIG. 58B). The second portion 512 is slid down until magnetic attraction between the portions 510, 512 compresses the vessel wall and secures the magnetic anastomotic component 508.

FIGS. 59A-59B shown another embodiment of the invention wherein a magnetic anastomotic component 520 includes first and second portions 522, 524 which compress first and second vessels 526, 528. Magnetic attraction between the portions 522, 524 secures the vessels 526, 528 together; in addition, mechanical securing means is provided to further enhance the attachment. The mechanical means may take various forms, such as clips, hooks, staples, etc., the illustrated members 530 being in the form of suture loops.

Exemplary embodiments of the invention that utilize a mechanical attachment between a magnetic anastomotic component and a vessel will now be described. With reference to FIGS. 60A-60C, a magnetic anastomotic component 540 is shown positioned against the wall of a vessel V. The anastomotic component 540 includes an annular body 542 defining an opening 544 which communicates with an opening O formed in the vessel wall. The annular body 542 has a plurality of passageways 546 configured to receive attachment members 548 in order to secure the component 540 to the vessel V.

The attachment members 548 are carried in a delivery device 550 including a push rod 552 which, as shown in FIGS. 60A-60B, is used to move the attachment members 548 out of the distal end of the device 550. The attachment members 548 may be in any desired form and, in the illustrated embodiment, are superelastic hook-shaped elements. The attachment members 548 are constructed so that when unbiased they take the configuration shown in FIG. 60B. Therefore, upon exiting the delivery device 550, the attachment members 548 move from their biased straight configuration (FIG. 60A) to their unbiased hook-shaped configuration (FIG. 60B). As a result, the hooks engage the vessel wall and the annular body 542 of the component 540 and exert sufficient compressive force to securely attach the component to the vessel.

As seen in FIG. 60C, a plurality of the attachment members 548 are preferably used to secure the magnetic anastomotic component 540 to the vessel V. It will be understood though that the exact number and location of the attachment members may vary from the illustrated embodiment.

FIG. 60B shows, in phantom, an additional anastomotic component 552 secured to the magnetic anastomotic component 540. The additional component 552 (which may be attached to a second vessel—not shown—that will be anastomosed to the vessel V) is secured to the component 540 by magnetic attraction. The annular body 542 of the anastomotic component 540 preferably has recessed areas 554 that receive the ends of the attachment members 548. This provides a flush or substantially flush and continuous upper surface to mate with the additional component 552, thereby enhancing magnetic attraction and sealing.

It will be recognized that this embodiment of the invention may be practiced differently than illustrated in FIGS. 60A-60C. For example, rather than using separate attachment members to secure the annular body 542, a single annular attachment member with portions engaging the tissue and the component could be used. Also, while the figures show the attachment members being applied one at a time, they could also be applied simultaneously in a single delivery step by one or a plurality of push rods.

FIGS. 61A-61C show another embodiment in which a magnetic anastomotic component is mechanically secured to a vessel. The anastomotic component includes an outer portion 556 and an inner portion 558 that sandwich the end of a vessel V. As shown in FIG. 61B, the outer portion 556 is deformable, preferably by way of being resilient or elastic, which allows it to be expanded to receive the end of the vessel. The outer portion 556 is then released and compresses the vessel against the inner component portion 558. The component portions 556, 558 may or may not be magnetically attracted to each other. At least one of the portions is, however, preferably magnetic or ferromagnetic, in whole or in part, e.g., at its distal end, for attachment to another magnetic anastomotic component (not shown).

FIGS. 62A-62C show an embodiment of the invention similar to the previous embodiment but wherein an outer component 560 has a discrete portion 562 that is flexible, as shown in FIGS. 62B and 62C. This embodiment includes an inner anastomotic component portion 564 with a ledge 566 configured to support the end of the vessel V. (See FIG. 62C.) The ledge 566 may be a separate element or integrally-formed with the portion 560, and is preferably magnetic.

FIGS. 63A-63D show another embodiment of the invention wherein a magnetic anastomotic component is mechanically secured to a vessel. An anastomotic component 570 has the ability to produce or be attracted by a magnetic field and includes an annular body 572 defining an opening 574 and a plurality of movable coupling elements 576. The coupling elements 576 are restrained in a first position (FIG. 63A) and are delivered through an opening in the wall of a hollow body, such as blood vessel V (FIG. 63C). The coupling elements 576 are released and assume a second position (FIG. 63B) in which they are essentially parallel with the surface of the annular body 572, thereby capturing the vessel wall to secure the component 570 thereto (FIG. 63D).

FIGS. 64A-64B show a magnetic anastomotic component 580 constructed according to another embodiment of the invention. The component 580 includes an annular body 582 and a plurality of attachment members 584. The annular body 582 of the component 580 is formed with one or more recesses 586 that receive an end of an attachment member 584. Each attachment member 584 has a leg 588 that extends against the wall of a vessel V, a central portion 590 that extends longitudinally through an opening in the vessel wall, and another leg 592 that extends into the recess 586.

FIGS. 65A and 65B show an embodiment of the invention similar to the previous embodiment but wherein the anastomotic component 580 is secured to the wall of vessel V by a single attachment member 594. The attachment member 594 has an upper leg 596 that seats within a depression 586 formed in the annular body, the depression corresponding to the recesses 586 in the annular body 582 of FIGS. 64A-64B. It should be noted that in either embodiment, the leg 588 may be a continuous rim or flange also, or it may comprise one or more individual elements.

FIGS. 66A-66C show an exemplary device for deploying the anastomotic components shown in FIGS. 64A-64B and FIGS. 65A-65B. The device 600 includes an inner shaft 602 with an anvil at its distal end, a split intermediate shaft 604 and a split outer shaft 606. (For clarity, the distal ends(s) 588 of the attachment member 584 is shown already deformed by the anvil.) The intermediate shaft 604 is moved in the directions of the arrows which causes the ramped surfaces 608 thereon to abut corresponding ramped surfaces 610 on the outer shaft 606 (FIG. 66B). The ramped surfaces causes the arms of the outer shaft 606 to move outward in the direction of the arrows, which deflects the leg 592 of the attachment member 584 outward into the recess 586 in the annular body 582 of the anastomotic component 580 (FIG. 66B). The inner shaft 602 of the device 600 is rotated to position the anvil for removal through the anastomotic component 580 (FIG. 66C).

FIGS. 67A-67C show a magnetic anastomotic component 612 constructed according to another embodiment of the invention. The component 612 includes a body 614 defining an opening 616 and an annular depression 618. FIG. 67B shows the anastomotic component 612 attached to the end of a vessel V by passing the end of the vessel through the opening 616 and everting it around the exterior surface of the body 614. A suitable member 620, such as suture, may be provided to secure the end of the vessel to the component 612. Additionally, or alternatively, the vessel may be secured to the component by adhesive, clips, fasteners, etc.

FIG. 67C shows the magnetic anastomotic component 612 (with the body 514 slightly shortened) attached to the side wall of a vessel V. The tissue of the side wall is everted over the exterior surface of the body 614 of the component 612 and held as in the above embodiment. It should be appreciated that while in the illustrated embodiments the vessel is everted over the anastomotic component, this aspect of the invention may be practiced without everting the vessel, for example, by having the vessel terminate at the end of the body 614, or by securing the vessel wall to the inside of the component.

A number of embodiments of the invention that utilize adhesive to secure one or more anastomotic components to a hollow body will now be described. As used herein "adhesive" refers to any substance that may be used to bond an anastomotic component to a hollow body. The adhesive may be self-activating or activated by suitable means, for example, heat, light or chemical reaction (e.g., by providing the vessel and component with respective substances that are mixed, in an epoxy-like manner).

FIGS. 68A-68B show an anastomotic component 622 positioned against the exterior of the wall of a vessel V. A device for applying adhesive is schematically illustrated at 624 and is shown placing adhesive 626 between the component 622 and the vessel wall. As shown, the anastomotic component 622 has a flange 628 that defines a space configured to receive adhesive. FIG. 68B shows an alternative embodiment wherein a magnetic anastomotic component 630 includes a sloped surface 632 that defines a space for receiving adhesive 634 from the device 624. In each case the adhesive serves to bond the magnetic anastomotic components 622, 630 to the vessel wall in fluid-tight fashion FIGS. 69A-69B show an embodiment of the invention including an anastomotic component 636 defining an opening 638 and a surface 640 configured to be secured to the wall of a vessel V adjacent an opening O in the wall. An intermediate member 642, which may take the form of a blanket or sheet, is preferably positioned between the anastomotic component 636 and the vessel wall. FIG. 69A shows the blanket without an opening formed therein, as it may be desirable to first place the blanket and adhesively secure the component to the vessel, and then cut an opening through the member 642. An opening in the vessel wall may be formed at this time also, if desired. One benefit of this embodiment is that the intermediate member 642 can be used to carry the adhesive rather than specifically configuring the component 636 to carry the adhesive. The teachings of above-mentioned co-pending patent application 60/255,635 may be applied to this and other embodiments of the invention. It will be appreciated that the component 636, and specifically surface 640, may carry adhesive as well.

FIG. 70 shows an embodiment of the invention similar to that of FIGS. 69A-69B in that it uses an intermediate member 644 to secure a magnetic anastomotic component 646 to the wall of a vessel V. A second magnetic anastomotic component 648, which has an annular body secured to a tubular member 650, is magnetically attracted to the component 646. As can be seen, the mating surfaces of the components 646, 648 produce a fluid-tight seal when joined. In addition, an end 652 of tubular body 650 protrudes beyond the annular body of the component 648 and is received in an opening 654 defined by the component 646, enhancing alignment between the coupled components 646, 648 (and thus between the vessel V and the tubular body 650).

The anastomotic components 622, 630, 636 and 646 are adhesively secured to the exterior of the vessel wall in the previous embodiments. During attachment, the components may be held in place with respect to the vessel by any suitable means. For example, a placement member may be introduced into the vessel lumen to provide rigidity and/or alignment for the outer component. FIGS. 71A-71D illustrate, in somewhat schematic fashion, the use of an intraluminal placement member to secure a magnetic anastomotic component to a vessel.

Figure 71A:
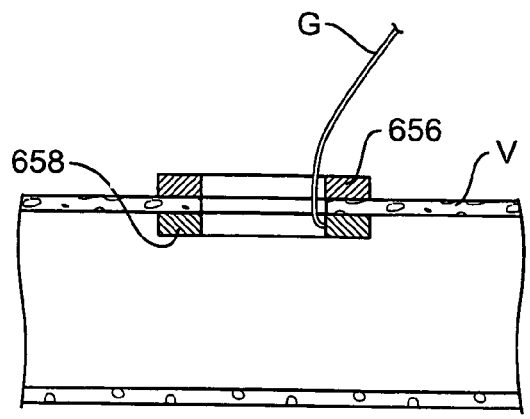

More specifically, FIG. 71A shows a magnetic anastomotic component 656 positioned on the exterior of the wall of a vessel V and a placement member 658 positioned on the opposite surface of the vessel wall. A wire G or other graspable structure is provided on the placement member 658. The component 656 and placement member 658 are magnetically attracted such that after positioning the member 658 at a desired location within the vessel, the component 656 may be guided and then secured. (For sake of example, the component 656 will be considered already attached to the vessel as viewed in FIG. 71A.)

Figure 71B:
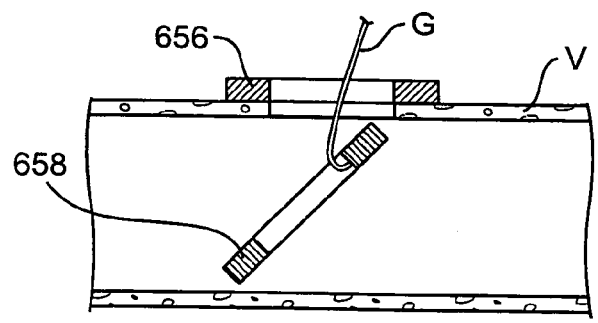
Figure 71C:
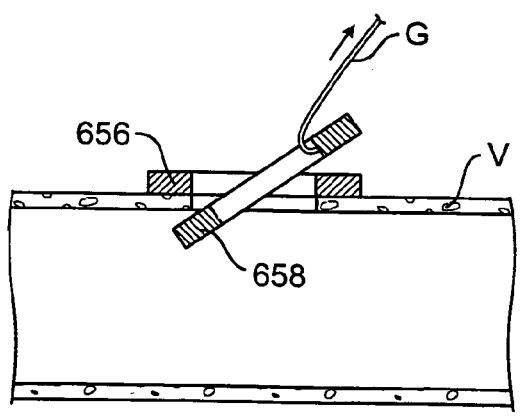

FIG. 71B shows the anastomotic component 656 attached to the vessel wall with the placement member 658 moved to overcome the magnetic attractive force. This can be done, for example, by manipulating the member 658 via the wire G. The placement member 658 is then removed through the opening of anastomotic component 656, as shown in FIG. 71C. It will be appreciated that removing the member 658 in this fashion will likely require some manipulation or repositioning thereof depending on the respective sizes and configurations of the anastomotic component 656 and member 658.

Figure 71D:
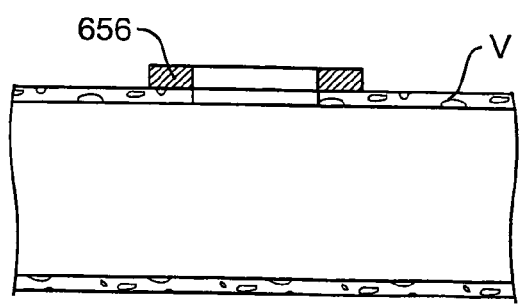

For example, the member 658 can be rotated in the plane of the drawing sheet in order to align its smaller dimension with the opening of the component 656. Alternatively or additionally, the placement member may be collapsible (either in whole or in part). FIG. 71D shows the magnetic anastomotic component 656 affixed to the wall of vessel V after the placement member 658 has been removed.

FIGS. 72A-72F show another embodiment of the invention wherein a magnetic anastomotic component is adhesively secured to a vessel. In this embodiment, a component 660 is secured to a vessel V, and more particularly, to an end 662 of the vessel V. Also, the illustrated component 660 is attached to the exterior of the vessel V, although it will be appreciated that the invention may be carried out by attaching a component to the interior of the vessel.

FIG. 72A shows the magnetic anastomotic component 660 positioned around the wall of the vessel V, while FIG. 72B shows (in phantom) a knife being used to cut the irregularly-shaped end of the vessel. FIG. 72C shows an internal support in the form of a balloon 664 being inserted into the lumen of vessel V, as well as an adhesive applicator 666 placing adhesive at the junction between the component 660 and the vessel V.

FIG. 72D shows the balloon 664 being inflated within the lumen of the vessel V. This forces the vessel V against the inner surface of component 660, thereby affixing the component to the vessel. The balloon 664 is then removed (FIG. 72E). The end 662 of the vessel is trimmed (after placing a mandrel or other internal support—not shown); or, alternatively, the end of the vessel may be everted over the component.

Figure 73A:
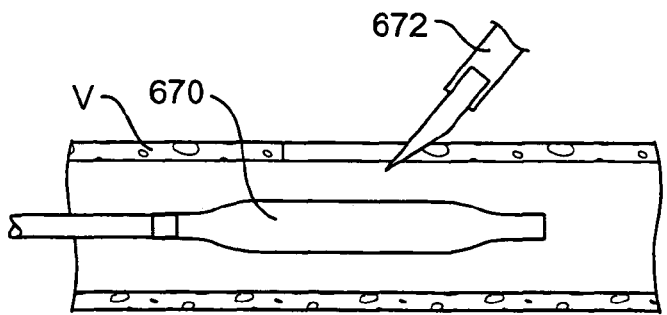
Figure 73B:
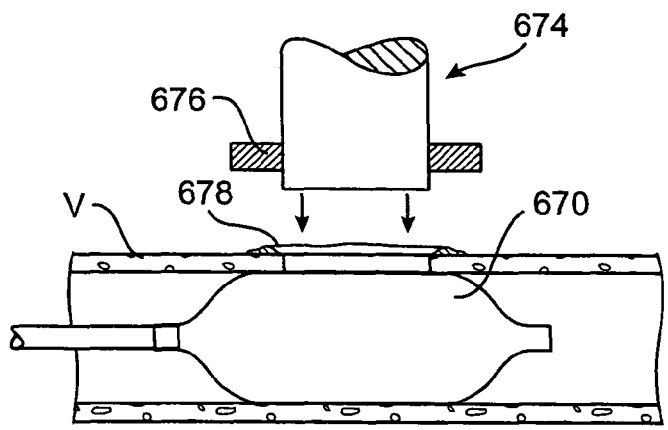
Figure 73C:
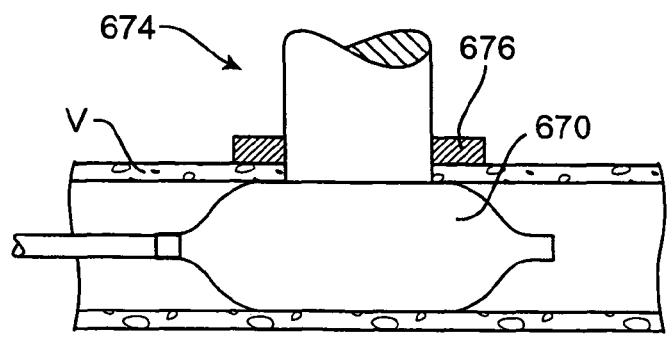
Figure 73D:
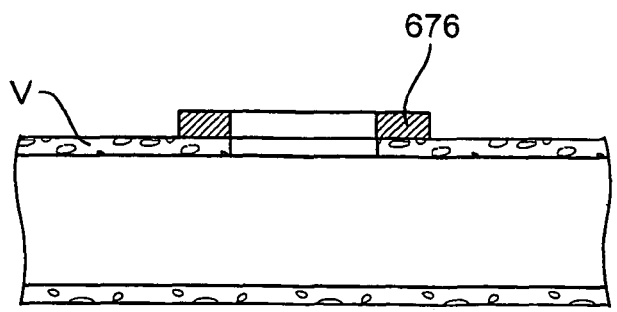

FIGS. 73A-73D show another embodiment of the invention wherein adhesive is used to secure a magnetic anastomotic component to a vessel. Unlike the previous embodiment, this embodiment secures a magnetic anastomotic component to the side wall of a vessel. As shown in FIG. 73A, an internal support in the form of a balloon 670 is inserted into the lumen of a vessel V. A knife, punch or other suitable instrument 672 is used to form an opening in the vessel side wall. FIG. 73B shows the balloon 670 inflated so as to support the wall of the vessel V with a delivery device schematically indicated at 674 supporting a magnetic anastomotic component 676. The device 674 is used to deliver the component 676 into contact with the wall of a vessel V, adhesive 678 having been applied to the vessel wall around the opening. The device 674 may protrude through the opening in the vessel wall against the balloon 670. FIG. 73D shows the magnetic anastomotic component 676 after it has been adhesively secured to the vessel V and aligned with the opening in the wall of the vessel.

Figure 74A:
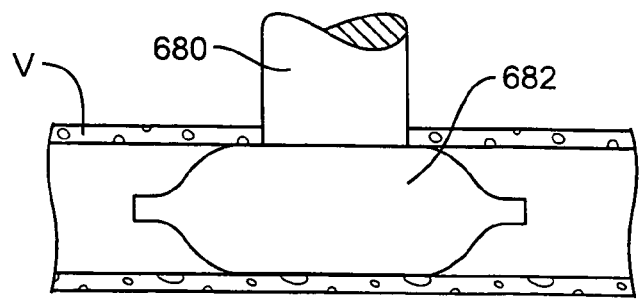
Figure 74B:
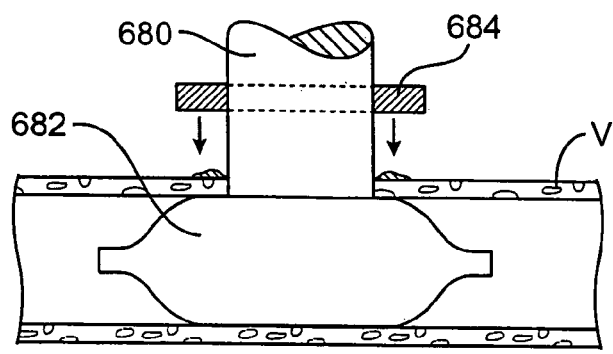
Figure 74C:
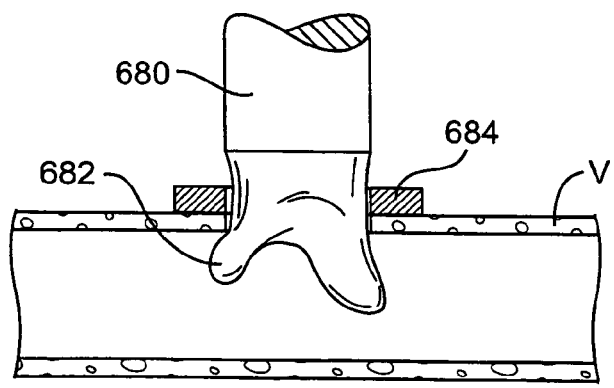
Figure 74D:
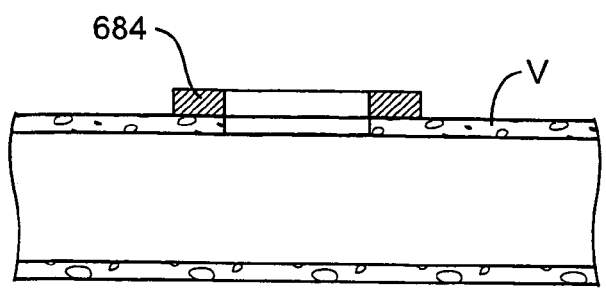

FIGS. 74A-74D show another embodiment of the invention wherein an internal support member is used to support a vessel while a magnetic anastomotic component is affixed to the vessel wall. FIG. 74A shows a device 680 with an expandable or inflatable structure, such as balloon 682, that is passed through an opening formed in the side wall and positioned in the lumen of a vessel V. FIG. 74B shows a magnetic anastomotic component 684 being slid over the device 680 into contact with adhesive 686 disposed on the vessel wall around the device 680. FIG. 74C shows the internal support structure 682 in a collapsed orientation as it is being removed through the vessel wall and the magnetic anastomotic component 684. FIG. 74D shows the magnetic anastomotic component 684 adhesively secured to the vessel.

FIGS. 75A-75D and 76A-76D show another embodiment of the invention wherein a magnetic anastomotic component is secured to a vessel by adhesive or other means. FIGS. 75A and 76A show a vessel V with a partially occluded lumen and an intraluminal placement member 690. The placement member is supported on a shaft 692 and is passed across the blockage in the vessel. FIGS. 75B-76B show the placement member 690 in an expanded state in contact with the interior of the wall of the vessel V. FIGS. 75C-76C show the magnetic anastomotic component 694 positioned against the exterior of the vessel V, with adhesive 686 having been applied to the vessel V (FIG. 75B, 76B). In this embodiment, the placement member 690 uses magnetic attraction to properly position the anastomotic component 694 on the vessel V. More particularly, the preferred placement member 690 may be in the form of a balloon that is inflated with magnetic fluid. Once inflated, as shown in FIGS. 75B and 76B, the anastomotic component 694 is guided to its desired location due to the magnetic attraction.

It will be noted that while adhesive is used to bond the illustrated magnetic anastomotic components to a vessel wall, alternative or additional means may also be used to secure the component and vessel.

In FIGS. 75C and 76C the magnetic anastomotic component 694 is secured to the wall of the vessel V with tissue remaining between the component and the vessel lumen. FIGS. 75D and 76D show the vessel after the portion of tissue circumscribed by the opening 698 of the anastomotic component 694 has been removed. As a result, the opening 698 in the component 694 communicates with the lumen of the vessel V. FIG. 77 is a perspective view showing the completed attachment of the magnetic anastomotic component 694 to the wall of the vessel V.

Turning now to FIGS. 78A-78C, yet another embodiment of the invention that uses adhesive to form an anastomosis between two vessels will be described. This embodiment uses magnetic attraction to hold vessels in a desired relative position while adhesive is used to form an anastomosis between the vessels. The illustrated embodiment forms a side-to-side anastomosis, however, it will be appreciated that this aspect of the invention may be used to form other types of anastomoses. FIG. 78A shows a first magnetic component 700 supported by a shaft 702 that runs through the lumen of a first vessel 704. A second magnetic component 706 is supported by a shaft 608 that extends through the lumen of a second vessel 710. As shown in the figures, the magnetic attraction between the components 700, 706 compresses the side walls of the vessels 704, 710 together.

FIG. 78B shows the components holding the walls in place while a cutting device 772 is introduced through the lumen of one of the vessels (in the figures, first vessel 704). The cutting device 712, which preferably has a seal 714 around its exterior, is sized to cooperate with the magnetic components 700, 706 to remove a desired amount of tissue T located between the components without damaging vessels walls or the components. FIG. 78C shows the anastomosis after the cutting device has formed an opening so that first and second vessels 704, 710 communicate with each other. Adhesive 716 (or other securing means) is applied around the periphery of the anastomosis to hold the vessels 704, 710 together. FIG. 78C shows the anastomosis after the magnetic components 700, 706 have been removed (after the adhesive 616 has cured or set sufficiently).

FIGS. 79A-79C illustrate first and second vessels 720, 722, respectively provided with magnetic anastomotic components 724, 726. FIG. 79B shows the vessels joined magnetically to form a side-to-side anastomosis, with blood leaking from the anastomosis, as indicated by 728. FIG. 79C illustrates an attempt to separate the magnetically attracted components 724, 726 in order to repair the leak 728. The magnetic force holding the components 724, 726 together is greater than the force that attaches component 726 to vessel 722. As a result, the component 726 remains magnetically coupled to the component 724 and separates from the vessel 722. Consequently, in view of the problems that may be associated with decoupling a magnetic anastomosis, it may be beneficial to determine the presence of any leaks between an anastomotic component and a vessel prior to completing the magnetic anastomosis.

FIGS. 80A-80C show a first embodiment of a device for checking the seal at an anastomotic junction. Designated generally by the reference numeral 730, the device includes a shaft 732 supporting a magnetic member 734. An expandable structure 736 is disposed between the shaft 732 and the member 734. A vessel V is shown to which is secured a magnetic anastomotic component 738. The anastomotic component 738 comprises two members magnetically attracted so as to sandwich the wall of a vessel, thereby holding the component in place.

Prior to joining another magnetic anastomotic component to the component 738, the device 730 is used to determine whether there are any leaks at the junction of component 738 and vessel V. As shown in FIG. 80B, the device 730 is placed against the magnetic anastomotic component 738 and magnetic attraction with the member 734 (due to their respective polarities) results in a tight seal. At this point, the vessel is pressurized and, if leaks are present, it may be surmised that they are due to an imprecise connection between the component 738 and the vessel V. Upon completing this step, the device is removed by expanding the expandable structure 736 which may be, for example, a balloon inflated with fluid. The expanding force is sufficient to overcome the magnetic attractive force between the member 734 of device 730 and the mounted component 738. The device 730 can then be removed by simply sliding it from the magnetic anastomotic component 738.

FIGS. 81A-81F show another embodiment of a seal-checking device comprising a device 740 with a magnetic member 742 contained within an expandable structure 744. This allows the magnet, which has two polarities, to be placed against a magnetic anastomotic component 746 mounted on a vessel V regardless of the polarity of the magnetic field produced by that component. In other words, the device 740 can be coupled to a mounted anastomotic component whether the north or south pole of that component is facing the device, simply by directing the opposite surfaces of the device 740 and member 742 toward the component. FIGS. 81B and 81C correspond to FIGS. 80B and 80C, with FIG. 81C illustrating the manner in which the magnet is preferably housed by an interference fit within the expandable structure 744 (which again may be a balloon).

FIGS. 82A-82F show another embodiment of a seal-checking device 750 including a magnetic member 752 enclosed in a mechanically expandable housing 754. FIG. 82B shows the device 750 mounted over and sealing an anastomotic magnetic component 756 secured to a vessel V. FIG. 82C shows the housing 754 being compressed longitudinally to flex the wall of the housing 754, which overcomes the magnetic attraction between the magnetic member 752 and the component 756.

It should be recognized that while the embodiments of FIGS. 80A-82C are described in connection with an anastomosis achieved by magnetic force, this aspect of the invention will apply to any anastomotic connection in which the coupling force between two components (once the anastomosis is completed) is or may be greater than the force attaching one of the components to a vessel, irrespective of whether the coupling and attachment forces are magnetic, mechanical, adhesive, etc.

FIGS. 83A-83B and FIGS. 84A-84B show a device which, among other functions, determines whether a magnetic anastomotic component is properly oriented prior to its use during a medical procedure. The illustrated device 770 comprises a fixture that slidably receives a delivery device 772 loaded with one or more magnetic anastomotic components 774, 776. The device 770 is preferably configured so that the delivery device 772 can be slid therein in the direction of the arrows to position the magnetic anastomotic components 774, 776 in proximity to one or more magnetized ledges 778, 780, 782.

The polarity of magnetized ledge 778 is selected so that the magnetic anastomotic component 774, when properly oriented, will remain in the lower position shown in FIGS. 83A-83B. When the anastomotic component 774 is incorrectly positioned, as shown in FIGS. 84A-84B, it is repelled upward by the magnetized ledge 778, forcing the component 774 against the second ledge 780 (which may or may not be magnetized). This is also true for a second magnetic anastomotic component 776 supported on an upper portion of the delivery device 772. Consequently, if the delivery device 772 is positioned on the fixture 770 with either anastomotic component incorrectly oriented, the component(s) will be moved so as to alert the user that the device needs to be adjusted.

In addition to ensuring proper loading of the anastomotic components, the device 770 also may be used as a loading tool that supports the delivery device 772 while one or more anastomotic components are loaded onto it. Finally, once the delivery device 772 has been loaded the device 770 may be used for storing and transporting it to the end user.

FIG. 85A is a sectional view of a magnetic anastomotic component 780 constructed according to another embodiment of the invention. The component 780 includes two portions 782, 784 that sandwich the end of a hollow body, such as blood vessel V, such that the vessel extends from the component at an angle θ. The illustrated angle is approximately 30°, although other angles may be used. The angle is preferably equal to or less than about 60°, and preferably equal to or less than about 45°. This directs flow more along the axis of the vessel lumen which may be desirable in some cases.

FIG. 85B is a sectional view of an anastomosis formed between the vessel V with magnetic anastomotic component 780 and a second anastomotic component 786 that is secured to the wall W of a second vessel. The second anastomotic component may take any configuration; the illustrated component 786 being constructed in accordance with the teachings of above-referenced, co-pending application Ser. No. 09/638,805.

FIG. 86A is a perspective view of a pair of closely positioned two-pole magnetic anastomotic components 790, 792 constructed according to the invention. The north and south poles (N, S) of each component 790, 792 are disposed on the ends thereof, with the magnetic field that attracts them indicated by the arrows.

FIG. 86B is a perspective view of a pair of closely positioned three-pole magnetic anastomotic components 794, 796 constructed according to another embodiment of the invention. In addition to the magnetic poles located at the ends of each component 794, 796, an additional pole is located at a central portion 798 of each component. As can be seen, this increases the pull force between the two components 794, 796, which, in the case of an anastomosis, enhances sealing while preventing migration of the components.

Referring to FIGS. 87-93, another embodiment of an anastomotic device is shown and designated by reference numeral 800. The device 800 has a first component 802 and a second component 804, which are magnetically attracted to one another. The particular manner the components are coupled may vary from that shown, for example, by changing the direction, location or amount of magnetic force.

FIG. 87 shows the two components mounted to vessels V1, V2, respectively, prior to coupling the components together. Although it is preferred that both the first and second components have magnetic properties, and most preferably comprise permanent magnets, only one of the components may be magnetic without departing from the principles and scope of the invention.

The first and second components 802, 804 are the same or substantially similar in construction and the following description of the first component applies to the second component. Although the first and second components are geometrically the same, the polarity of the components is different to provide magnetic attraction between the components, as described above with respect to previous embodiments. It can be appreciated, of course, that the present invention may be practiced with the first and second components having different geometric configurations. Also, as explained below, the first and second components may be attached to the vessels using magnetic and/or mechanical force.

The first component 802 has a first extravascular part 806 and a second intravascular part 808. The illustrated first part 806 includes a first portion 806A and a second portion 806B. The first and second portions 806A, 806B are preferably identical and are positioned so as to be magnetically attracted to the second component 804 (in FIG. 87 the two components 802, 804 have identical constructions). Although the first and second portions 806A, 806B are shown as separate elements that are not connected to one another some connecting structure (such as a connector bar 810 shown in FIG. 94) may be provided to mechanically join the first and second portions 806A, 806B together. Furthermore, it can be appreciated that the connector bar 810 or other suitable structure such as a spring may be used to provide a spring force to couple the first and second parts 806, 808 together mechanically rather than using magnetism as described below.

When the first and second components 802, 804 are coupled to form the anastomosis as shown in FIG. 90, the two portions 806A, 806B of the first part 806 of component 802 contact the two portions 812A, 812B. The second part 808 of the component 802 cooperates with a second part 814 of component 804 to compress the vessel walls together. The two components 802, 804 form a throughhole which provides fluid communication between the first and second vessels.

Referring to FIGS. 88 and 90, the throughhole 816 defines a longitudinal axis A. The throughhole 816 is somewhat oval shaped but may take on any other suitable shape. It should be noted that, longitudinal direction shall mean any direction generally parallel to the longitudinal axis, while the term radial direction shall mean any direction that is not parallel to the longitudinal axis such as perpendicular.

According to one aspect of the invention, the first exravascular parts of the two components are magnetically attracted to one another, while the second intravascular parts of the two components are also magnetically attracted to one another. The first parts of the two components contact one another while the second parts may contact one another or may be separated by the walls of the vessels (as shown in FIG. 90). The first parts of the two components are positioned outside the blood flow path by positioning them radially relative to their respective second part. In this manner, the first part of each component is not exposed to the blood flow path.

Referring to FIG. 90 again, the first and second components 802, 804 are generally attracted to one another along a longitudinal direction L. The first and second parts of each component 802, 804, on the other hand, are attracted to one another in a direction R which is not parallel to, and may be even perpendicular to, the longitudinal axis L. Stated another way, the first and second parts of the first component compress the wall in a substantially radial direction with respect to the throughhole whereas the first and second components are attracted to one another in a substantially longitudinal direction.

Referring to FIGS. 91-93, another embodiment of an anastomotic component is shown and designated by reference numeral 820. The component 820 includes a first part 822 with portions 822A, 822B, and a second part 824. As best illustrated in FIG. 91, the parts 822, 824 have complementarily-shaped portions 826 that serve to lock the parts together.

Referring to FIG. 94, another embodiment is shown wherein a first part 830 of an anastomotic component 832 has portions 830A, 830B connected by the connector bar 810. The bar 810 preferably provides a spring force to compress the vessel wall between the first and second portions 830A, 830B.

After attaching each of the components to their respective vessels, the first and second components are coupled together using magnetic attraction in the manner described herein. It should be appreciated that the first and second parts of each component may be secured or coupled to its vessel in any suitable manner. For example, the components may be coupled to the vessels using expandable arms, prongs, barbs, stent-like structures, etc., without departing from the spirit and teachings of the invention.

Figure 95:
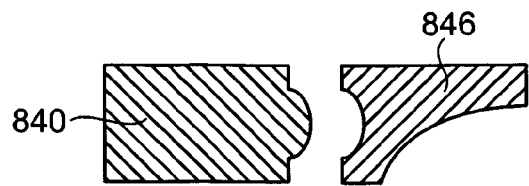
Figure 96:
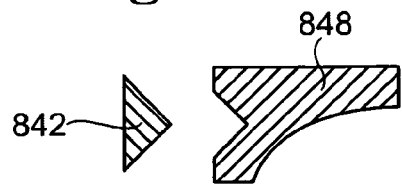
Figure 97:
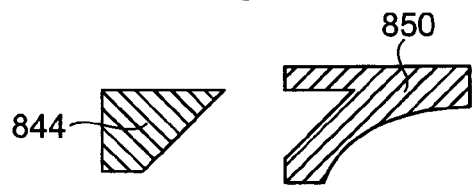

In the above embodiments, the wall of the vessel is compressed between first and second portions having two substantially flat surfaces. Referring now to FIGS. 95-99, various other cross-sectional configurations for the first (extravascular) and second (intravascular) parts are shown. FIGS. 95-97 show first parts 840, 842 having a protrusion 844 and second parts 846, 848 having a recess 850 which helps to mechanically interlock the first and second parts together when compressing tissue therebetween.

Figure 98:
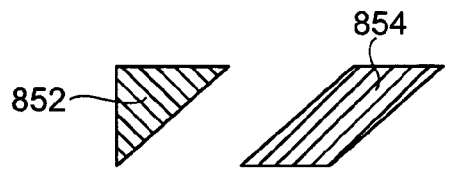
Figure 99:
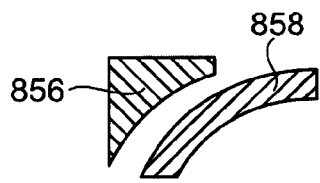
Figure 100:
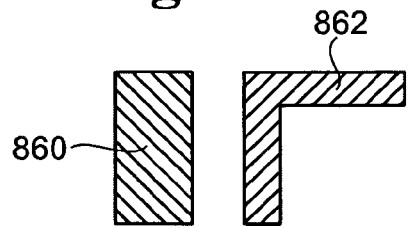

FIG. 98 shows first and second parts 852, 854 having complementary angled surfaces angled at 30-60 degrees, and preferably about 45 degrees, relative to the longitudinal axis A. FIG. 99 shows first and second parts 856, 858 having mating curved surfaces. FIG. 100 shows first and second parts 860, 862 with flat mating surfaces.

The magnetic attraction between the first and second components may be sufficient to securely couple the first and second components or, alternatively, additional attachment features may be provided. For example, an additional mechanical attachment, such as a latch, suture, adhesive, locking arm, tie, elastic band, etc. may be used to increase the strength of the anastomosis. Further, a mechanical attachment may be provided even if the magnetic attraction force is sufficient to provide an even greater level of safety.

Referring now to FIGS. 101-103, still another embodiment of an anastomotic component is shown and indicated by reference numeral 866. The anastomotic component 866 includes a first part 868 with portions 868A, 868B, and a second part 870. The anastomotic component 866 has means for being mechanically attached to a second component (not shown) having the same construction. The first part 868 of the component 866 has structure to hold a connecting element, such as a filament, wire, suture, etc. The holding structure, as shown, may be a recess, hole, hook or cleat 872, around which the filament is wound. As mentioned above, attachment features in addition to magnetic attraction may be used even if the magnetic force is sufficient to maintain the anastomosis. It will be recognized that any other suitable holder or attachment feature may be used, e.g., a clip, elastomeric band, latch, locking arm, tie, etc.

An exemplary use of the anastomosis devices shown in FIGS. 87-103 will now be described. The present invention may be practiced using end-to-side, side-to-side or end-to-end anastomosis techniques. To illustrate the invention, use of the device will be explained in connection with forming a side-to-side coronary anastomosis. An incision is made in a first vessel, such as a coronary artery, and the second intravascular part of a first component is introduced into the artery lumen. Once the second part is in the desired position within the lumen, the first part of the first component is then moved toward the artery to trap and compress the vessel wall. FIGS. 87-89 show a first component coupled to a first vessel.

The above process is repeated for a second vessel (such as a graft) and a second component. The graft is then moved toward the artery so that the first and second components are magnetically attracted to one another to hold the first and second components together, as shown in FIG. 90. An additional attachment step, such as securing sutures around the suture holders of FIGS. 100-103, may then be performed if desired.

The devices described herein may be introduced in any suitable manner without departing from the scope of the invention. One such manner will now be described in connection with an exemplary delivery device shown in FIGS. 104-110. FIG. 104 shows the delivery device 880 with the first and second parts 868, 870 of anastomotic component 866 mounted on a distal end 882 of the device. The distal end 882 of the device 880 has a first retainer 884 that holds the first part 868 and a second retainer 886 that holds the second part 870. The first retainer 884 includes two arms 884A, 884B with ends 888A, 888B configured to hold the two portions 868A, 868B of the first part 868 of the anastomotic component 866, as shown in FIG. 105. The second retainer 886 has a pair of retaining portions 890A, 890B that are biased away from each other (as indicated by the arrow in FIG. 8) to hold the second part 870 of the anastomotic component 866.

The two arms 884A, 884B are movable in order to release the two portions 868A, 868B of the first component part 868 once they have been moved into proximity with the second component part 870. In the illustrated embodiment, the arms 884A, 884B pivot about points 892A, 892B, for example, from the position of FIG. 109 to the position of FIG. 110. Any suitable actuation means may be used to move the retainer arms 884A, 884B in the desired manner. As for the second retainer 886, the retaining portions 890A, 890B also may be moved in the desired manner by any suitable actuation means. It will be appreciated that the specific configuration illustrated herein is only one possible delivery device which may be used to practice the invention.

Other features, aspects and advantages of the invention beyond those specifically discussed will be apparent to those skilled in the art. Many modifications, alterations and variations of the illustrated embodiments may be made without departing from the scope and spirit of the invention as defined by the claims.

What is claimed is:

1. An anastomotic device comprising:
   a first component; and
   a second component magnetically attracted to the first component, the first and second components forming a throughhole to provide fluid communication between a first vessel and a second vessel, the throughhole having a longitudinal axis;
   the first component having a first part and a second part, wherein the first part is positionable outside the first vessel and the second part is positionable within the first vessel, the first and second parts being configured to compress a wall of the first vessel between the first and second parts, the first part being forced toward the second part in a first direction;
   the second component being magnetically attracted to the first component in a second direction in order to couple the first and second components, wherein the first and second directions are generally non-parallel.

2. The anastomotic device of claim 1, wherein:
   the first and second parts of the first component are magnetically attracted to one another along the first direction.

3. The anastomotic device of claim 1, wherein:
   the first and second directions are transverse and form an angle of at least about 45 degrees.

4. The anastomotic device of claim 1, wherein:
   the first and second directions are substantially perpendicular to one another.

5. The anastomotic device of claim 1, wherein:
   the first direction extends radially from the longitudinal axis of the throughhole formed by the first and second anastomotic components.

6. The anastomotic device of claim 1, wherein one of the first and second parts of the first components is made of at least two portions.

7. The anastomotic device of claim 6, wherein the two portions are separate and unconnected.

8. The anastomotic device of claim 1, wherein:
   the second anastomotic component also has a first part and a second part, the first and second parts being configured to compress a wall of the second vessel.

9. The anastomotic device of claim 1, further comprising:
   means for mechanically coupling together the first and second components.

10. The anastomotic device of claim 9, wherein:
    the coupling means includes suture holders for holding a suture extending between the first and second components.

11. The anastomotic device of claim 1, wherein:
    at least one of the first and second parts of the first component has a protrusion and the other of the first and second parts has a recess to compress and hold the first vessel.

12. The anastomotic device of claim 1, wherein:
    the first part has a curved surface and the second part has a curved surface positioned opposite the curved surface of the first part to compress the first vessel.

* * * * *